US012746122B2

(12) United States Patent
Wallace et al.

(10) Patent No.: US 12,746,122 B2
(45) **Date of Patent: *Sep. 29, 2026**

(54) SYSTEMS, DEVICES AND METHODS FOR DELIVERY SYSTEMS

(71) Applicant: Capstan Medical Inc., Santa Cruz, CA (US)

(72) Inventors: Daniel T. Wallace, Santa Cruz, CA (US); Peter W. Gregg, Santa Cruz, CA (US); Jeremy J. Boyette, Santa Cruz, CA (US); Evelyn N. Haynes, Santa Cruz, CA (US); Spencer C. Noe, Santa Cruz, CA (US); Diana L. Chu, Santa Cruz, CA (US)

(73) Assignee: Capstan Medical Inc., Santa Cruz, CA (US)

( * ) Notice: Subject to any disclaimer, the term of this patent is extended or adjusted under 35 U.S.C. 154(b) by 524 days.

This patent is subject to a terminal disclaimer.

(21) Appl. No.: 18/264,626

(22) PCT Filed: Feb. 10, 2022

(86) PCT No.: PCT/US2022/016042
§ 371 (c)(1),
(2) Date: Aug. 8, 2023

(87) PCT Pub. No.: WO2022/173997
PCT Pub. Date: Aug. 18, 2022

(65) Prior Publication Data

US 2024/0081991 A1 Mar. 14, 2024

Related U.S. Application Data

(63) Continuation-in-part of application No. 17/179,308, filed on Feb. 18, 2021, now Pat. No. 11,246,726.

(Continued)

(51) Int. Cl.
*A61F 2/95* (2013.01)
*A61F 2/24* (2006.01)

(52) U.S. Cl.
CPC .......... *A61F 2/2436* (2013.01); *A61F 2/2418* (2013.01); *A61F 2/9517* (2020.05); *A61F 2002/9534* (2013.01)

(58) Field of Classification Search
CPC .... A61F 2/2436; A61F 2/2439; A61F 2/9517; A61F 2/243; A61F 2/2427;
(Continued)

(56) References Cited

U.S. PATENT DOCUMENTS

| | | | |
|---|---|---|---|
| 5,476,510 | A | 12/1995 | Eberhardt et al. |
| 5,904,667 | A | 5/1999 | Falwell |

(Continued)

FOREIGN PATENT DOCUMENTS

| | | | |
|---|---|---|---|
| EP | 3316804 B1 * | 12/2023 | ..... A61B 17/320758 |
| WO | 2022094001 | 5/2022 | |

(Continued)

OTHER PUBLICATIONS

International Preliminary Report on Patentability issued in International Application No. PCT/US2024/020288, mailed on Sep. 25, 2025, 6 pages.

(Continued)

*Primary Examiner* — Seema Mathew
(74) *Attorney, Agent, or Firm* — Dorsey & Whitney LLP

(57) ABSTRACT

Delivery systems for expandable and stented implants include adjustable tensioning members that control the expansion of the implant along the length of the implant. The tensioning members are wound onto one or more rotors located on the distal segment of the delivery system, which are rotated to unwind the tensioning members and incrementally expand the implant. Positioning mechanisms are
(Continued)

also provided to adjust the position and orientation of the implant during delivery.

45 Claims, 79 Drawing Sheets

Related U.S. Application Data

(60) Provisional application No. 63/178,390, filed on Apr. 22, 2021, provisional application No. 63/150,518, filed on Feb. 17, 2021, provisional application No. 63/148,124, filed on Feb. 10, 2021.

(58) Field of Classification Search
CPC ............ A61F 2002/9505; A61F 2/9522; A61F 2/966; A61F 2/2433; A61F 2/2409; A61F 2/2466; A61F 2/2418; A61F 2/95; A61F 2002/9665; A61F 2/958; A61F 2/97; A61F 2002/9583; A61M 2025/1056; A61M 25/10
See application file for complete search history.

(56) References Cited

U.S. PATENT DOCUMENTS

| | | | | |
|---|---|---|---|---|
| 5,941,849 | A | 8/1999 | Plassche, Jr. | |
| 6,511,768 | B1 | 1/2003 | Trapp et al. | |
| 6,817,974 | B2 | 11/2004 | Cooper et al. | |
| 7,550,001 | B2 * | 6/2009 | Dorn | A61F 2/95 623/1.12 |
| 8,475,366 | B2 | 7/2013 | Boulais et al. | |
| 8,500,792 | B2 | 8/2013 | Berra | |
| 8,608,648 | B2 | 12/2013 | Banik et al. | |
| 8,622,894 | B2 | 1/2014 | Banik et al. | |
| 9,149,372 | B2 | 10/2015 | Kasprzak et al. | |
| 9,421,071 | B2 | 8/2016 | Smith et al. | |
| 9,572,957 | B2 | 2/2017 | Osypka et al. | |
| 10,028,826 | B2 | 7/2018 | Yohanan et al. | |
| 10,231,827 | B2 | 3/2019 | Mulvihill | |
| 10,433,961 | B2 | 10/2019 | Mclean | |
| 10,555,825 | B2 | 2/2020 | Gong et al. | |
| 10,743,992 | B2 | 8/2020 | Krans et al. | |
| 10,765,513 | B2 | 9/2020 | Mendelson et al. | |
| 10,772,727 | B2 | 9/2020 | Vaughan | |
| 10,772,749 | B2 | 9/2020 | Gloss et al. | |
| 10,799,676 | B2 * | 10/2020 | Khuu | F16C 11/06 |
| 11,083,583 | B2 | 8/2021 | Kirk et al. | |
| 11,197,755 | B1 | 12/2021 | Wallace et al. | |
| 11,246,726 | B1 * | 2/2022 | Wallace | A61F 2/2439 |
| 11,793,541 | B2 * | 10/2023 | Shen | A61B 17/320725 |
| 12,048,639 | B2 | 7/2024 | Wallace et al. | |
| 2002/0095204 | A1 * | 7/2002 | Thompson | A61F 2/95 623/1.12 |
| 2003/0236567 | A1 | 12/2003 | Elliot | |
| 2005/0149159 | A1 * | 7/2005 | Andreas | A61M 25/0136 623/1.11 |
| 2005/0273151 | A1 * | 12/2005 | Fulkerson | A61F 2/966 623/1.11 |
| 2007/0142906 | A1 | 6/2007 | Figulla et al. | |
| 2010/0049313 | A1 * | 2/2010 | Alon | A61F 2/2436 623/2.11 |
| 2011/0257719 | A1 * | 10/2011 | Argentine | A61F 2/95 623/1.11 |
| 2011/0282425 | A1 * | 11/2011 | Dwork | A61F 2/966 623/1.11 |
| 2012/0041537 | A1 * | 2/2012 | Parker | A61F 2/95 623/1.11 |
| 2012/0053671 | A1 * | 3/2012 | McHugo | A61F 2/966 623/1.12 |
| 2012/0191183 | A1 | 7/2012 | Rzany et al. | |
| 2012/0197376 | A1 * | 8/2012 | Heidner | A61F 2/966 623/1.11 |
| 2012/0330401 | A1 * | 12/2012 | Sugimoto | A61F 2/915 623/1.12 |
| 2013/0197629 | A1 | 8/2013 | Gainor et al. | |
| 2013/0204357 | A1 | 8/2013 | Thill et al. | |
| 2013/0204360 | A1 | 8/2013 | Gainor | |
| 2013/0304200 | A1 | 11/2013 | Mclean et al. | |
| 2013/0310928 | A1 | 11/2013 | Morriss et al. | |
| 2014/0005778 | A1 | 1/2014 | Buchbinder et al. | |
| 2014/0303719 | A1 | 10/2014 | Cox et al. | |
| 2014/0330370 | A1 | 11/2014 | Matheny et al. | |
| 2014/0371844 | A1 | 12/2014 | Dale et al. | |
| 2015/0328002 | A1 | 11/2015 | Mclean et al. | |
| 2016/0030167 | A1 | 2/2016 | Delaloye et al. | |
| 2016/0030169 | A1 | 2/2016 | Shahriari | |
| 2016/0074188 | A1 | 3/2016 | Ryan et al. | |
| 2016/0213826 | A1 | 7/2016 | Tanner et al. | |
| 2017/0100236 | A1 | 4/2017 | Robertson et al. | |
| 2017/0128203 | A1 | 5/2017 | Zhang et al. | |
| 2017/0156859 | A1 * | 6/2017 | Chang | A61F 2/2439 |
| 2017/0216027 | A1 | 8/2017 | Marchand et al. | |
| 2017/0231761 | A1 | 8/2017 | Cohen-Tzemach et al. | |
| 2017/0325945 | A1 | 11/2017 | Dale et al. | |
| 2017/0325948 | A1 | 11/2017 | Wallace et al. | |
| 2018/0021129 | A1 | 1/2018 | Peterson et al. | |
| 2018/0116689 | A1 | 5/2018 | Nakano | |
| 2018/0206983 | A1 | 7/2018 | Noe et al. | |
| 2018/0256241 | A1 | 9/2018 | Cohen et al. | |
| 2018/0256331 | A1 | 9/2018 | Vaughan | |
| 2018/0333259 | A1 | 11/2018 | Dibie | |
| 2019/0099267 | A1 | 4/2019 | Tubishevitz et al. | |
| 2019/0125534 | A1 * | 5/2019 | Arcaro | A61F 2/2436 |
| 2019/0183642 | A1 | 6/2019 | Tegels et al. | |
| 2019/0192289 | A1 | 6/2019 | Levi et al. | |
| 2019/0262129 | A1 | 8/2019 | Cooper et al. | |
| 2019/0307588 | A1 * | 10/2019 | Tran | A61F 2/966 |
| 2019/0321171 | A1 | 10/2019 | Morriss et al. | |
| 2019/0336262 | A1 * | 11/2019 | Duffy | A61F 2/0095 |
| 2019/0365538 | A1 | 12/2019 | Chambers et al. | |
| 2020/0078167 | A1 | 3/2020 | Quijano et al. | |
| 2020/0113683 | A1 | 4/2020 | Dale et al. | |
| 2020/0197175 | A1 | 6/2020 | Chang et al. | |
| 2020/0246527 | A1 | 8/2020 | Hildebrand et al. | |
| 2020/0352717 | A1 * | 11/2020 | Kheradvar | A61F 2/2418 |
| 2020/0352753 | A1 * | 11/2020 | Giasolli | A61F 2/86 |
| 2020/0405926 | A1 | 12/2020 | Alexander et al. | |
| 2021/0000593 | A1 | 1/2021 | Rahmig et al. | |
| 2021/0186693 | A1 | 6/2021 | Vidlund et al. | |
| 2021/0275297 | A1 | 9/2021 | Berndt et al. | |
| 2021/0307943 | A1 | 10/2021 | Gupta et al. | |
| 2021/0346153 | A1 | 11/2021 | Metmeier et al. | |
| 2021/0369257 | A1 | 12/2021 | Huddleston | |
| 2022/0079762 | A1 * | 3/2022 | Serina | A61F 2/2445 |
| 2022/0249265 | A1 | 8/2022 | Wallace et al. | |
| 2022/0323213 | A1 | 10/2022 | Wallace et al. | |
| 2024/0081991 | A1 * | 3/2024 | Wallace | A61F 2/2418 |
| 2024/0382329 | A1 | 11/2024 | Wallace et al. | |
| 2025/0228679 | A1 * | 7/2025 | Gregg | A61F 2/9524 |

FOREIGN PATENT DOCUMENTS

| | | | | |
|---|---|---|---|---|
| WO | 2022173997 | A1 | 8/2022 | |
| WO | WO2022/173997 | | 8/2022 | |
| WO | WO-2023034144 | A1 * | 3/2023 | A61B 17/0401 |
| WO | 2024192413 | A2 | 9/2024 | |
| WO | WO-2025008042 | A1 * | 1/2025 | A61B 17/320725 |

OTHER PUBLICATIONS

International Preliminary Report on Patentability issued in International Application No. PCT/US2022/056915, mailed on May 11, 2023, 7 pages.

International Search Report and Written Opinion Issued in International Application No. PCT/US2022/016042 mailed on May 3, 2022, 17 pages.

International Search Report and Written Opinion received in PCT App. No. PCT/US2021/056915 dated Dec. 1, 2021.

Extended European Search Report issued in European Application No. 22753382.5, mailed on Dec. 6, 2024, 8 pages.

(56) References Cited

OTHER PUBLICATIONS

International Preliminary Report on Patentability issued in International Application No. PCT/US2022/016042, mailed on Aug. 24, 2023, 13 pages.
International Search Report and Written Opinion issued in International Application No. PCT/US2024/020288, issued on Jul. 31, 2024, 7 pages.
First Office Action issued in Chinese Patent Application No. 202280020414.3, mailed on May 20, 2026, 11 pages including 6 pages of English translation May 20, 2026.

* cited by examiner 300
302
304
306
308
310
312
314
316
318
320

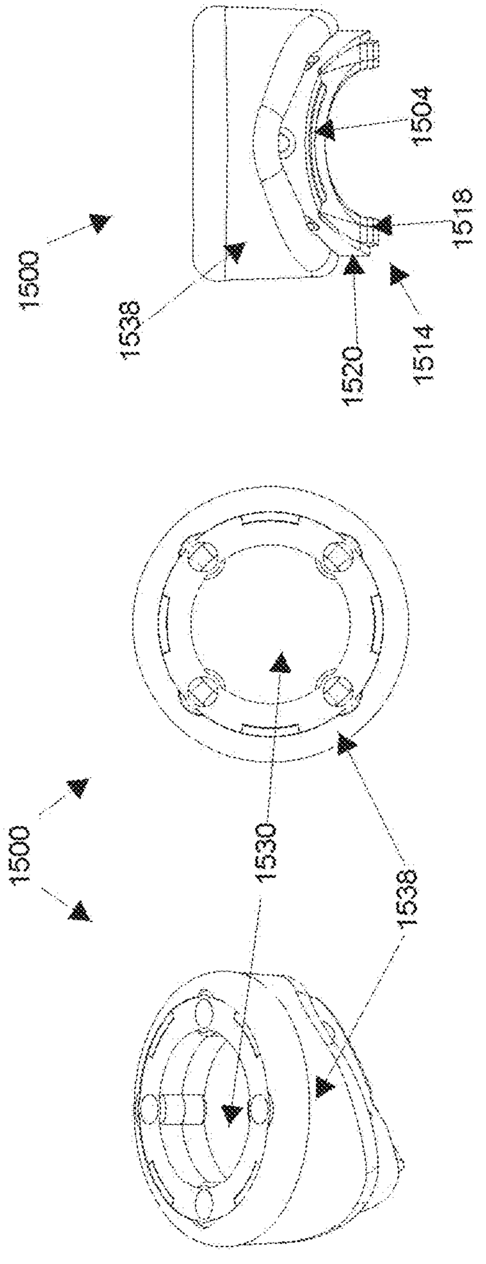
FIG. 15E
FIG. 15C
FIG. 15A
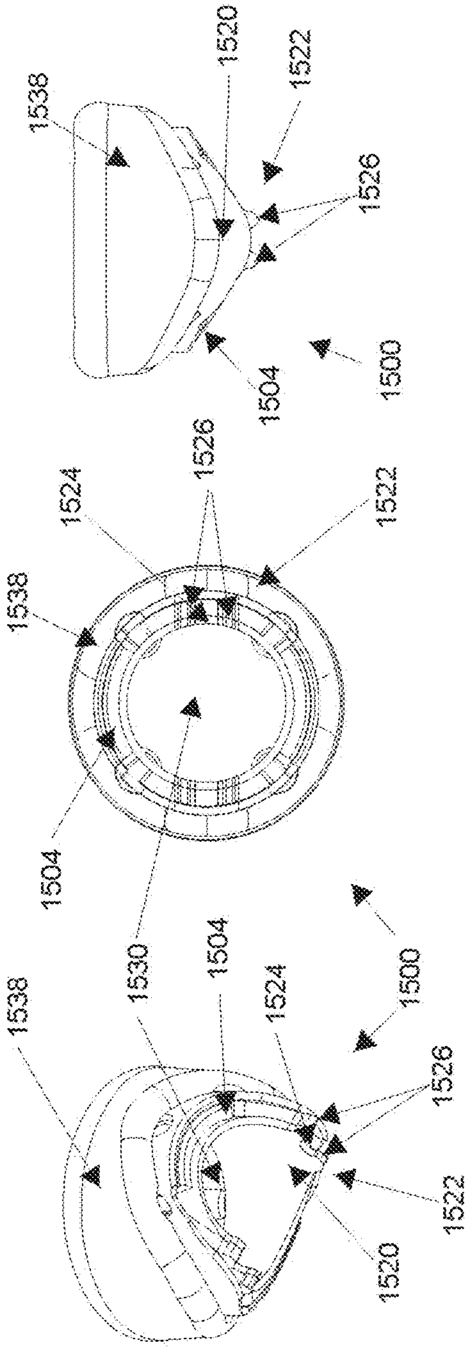
FIG. 15F
FIG. 15D
FIG. 15B

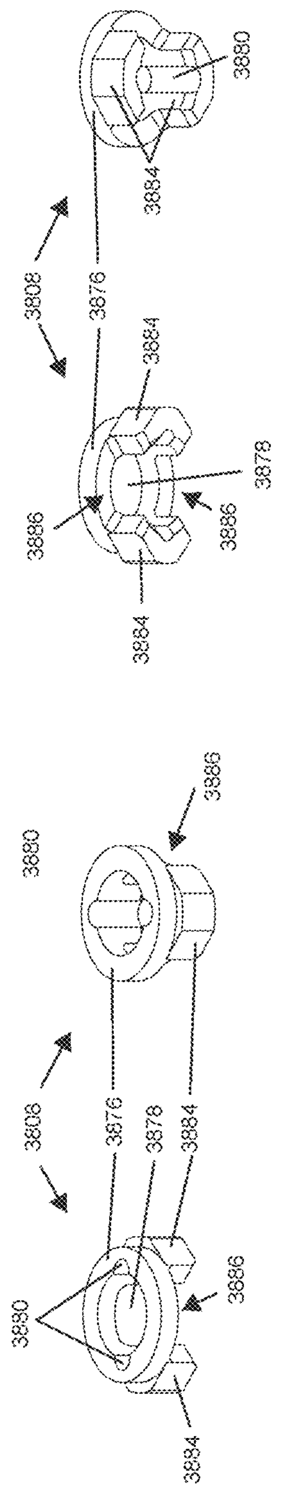
FIG. 45A
FIG. 45B
FIG. 45C
FIG. 45D
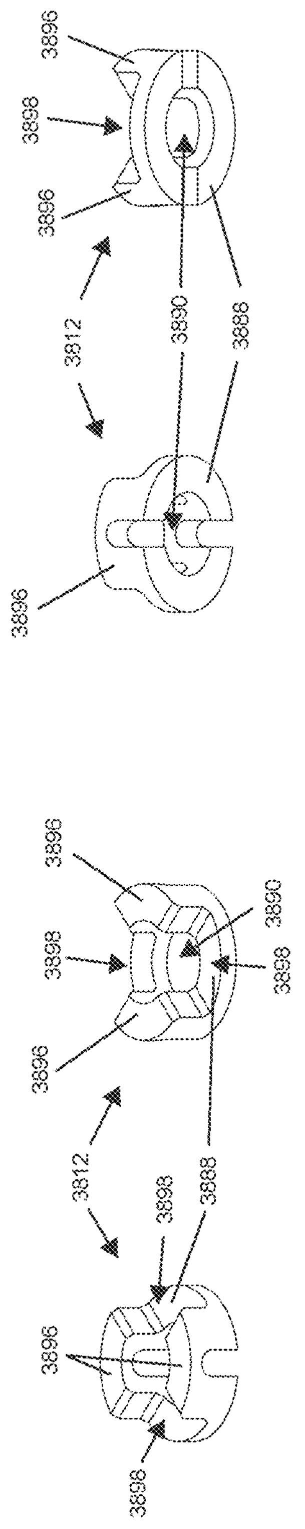
FIG. 46A
FIG. 46B
FIG. 46C
FIG. 46D

SYSTEMS, DEVICES AND METHODS FOR DELIVERY SYSTEMS

CROSS-REFERENCE TO RELATED APPLICATION(S)

This application is a 371 national phase entry of International Application No. PCT/US2022/016042, which a) claims priority to U.S. Provisional Application No. 63/148,124, filed Feb. 10, 2021, U.S. Provisional Application No. 63/150,518, filed Feb. 17, 2021, and U.S. Provisional Application No. 63/178,390, filed Apr. 22, 2021, and b) is a continuation-in-part of U.S. application Ser. No. 17/179,308, filed Feb. 18, 2021, issued as U.S. Pat. No. 11,246,726 on Feb. 15, 2022. This application is related to U.S. Provisional Application No. 63/148,124 filed Feb. 10, 2021, U.S. Provisional Application No. 63/106,871 filed Oct. 28, 2020, and U.S. application Ser. No. 17/083,266 filed Oct. 28, 2020, which are incorporated herein by reference, in their entirety, for any purpose.

BACKGROUND

This patent application relates generally to the delivery of expandable and stented devices diseases, and more specifically to methods and apparatus for minimally invasive delivery of expandable or stented implants, such as into the cardiovascular system, such as heart valve replacement.

Valvular heart disease is a significant burden to patients and healthcare systems, with a prevalence of 2-3% worldwide, and with an increasing prevalence in aging populations. Valvular disease may result from a variety of etiologies, including autoimmune, infective and degenerative causes. The epidemiology of valvular disease also varies with the affected valve, with rheumatic heart disease being the cause worldwide of primary mitral regurgitation and mitral stenosis, but with secondary mitral disease from left ventricular dysfunction being more common in developed countries.

While surgical repair and valve replacement remains a mainstay of many mitral valve therapies in the current clinical guidelines by the American Heart Association and American College of Cardiology, transcatheter mitral repair is recommended for certain patient populations. In the 2017 Focused Update and the 2014 Guidelines for Management of Patients with Valvular Disease, the AHA/ACC recommended percutaneous mitral valve balloon commissurotomy for severe mitral valve stenosis, and transcatheter mitral valve repair in certain severely symptomatic patients with severe primary mitral regurgitation with a reasonable life expectancy who are non-surgical candidates due to comorbidities.

BRIEF SUMMARY

Further growth of transcatheter mitral valve therapies is challenged by the difficulty by mitral valve anatomy and physiology, compared to more established transcatheter aortic valve therapies. The tortuous anatomical pathways between the remote anatomical location and the target anatomical location often exerts stresses and strains on the delivery system that can affect the concordance between the controls on the proximal end of the delivery system and the effectors on the distal end of the device.

To facilitate the expansion and release at the target location, the delivery system may include an adjustable radial tensioning system that provides control of implant expansion via extension of the tensioning members. The tensioning members are contained within the distal region of the delivery system and therefore are not subject to stretching or slippage over the distances between the proximal control and distal region of the delivery system, or from spring-out effects of expandable heart valves maintained in a collapsed configuration solely by a retention sheath.

In some further embodiments, the delivery system may also comprise one or more steering or positioning mechanisms to facilitate final positioning and orientation of the implant at the target location, before and/or during expansion and release of the implant. The positioning mechanisms may include extension mechanisms which are configured to adjust the longitudinal position of a distal segment of the delivery system, without repositioning the entire delivery system relative to the patient's anatomy. Single axis and multi-axis steering mechanisms may also be included to facilitate the insertion and navigation of the delivery system through the anatomy, and to adjust the pose of distal segment of the delivery system and the implant during the delivery procedure.

In one embodiment, a delivery system is provided, comprising a proximal handle comprising a handle housing and a first actuator, a catheter body coupled to the handle, the catheter body comprising a distal section, a proximal section and a middle section therebetween, a rotatable drive shaft coupled to the first actuator and located in the catheter body, a first stator housing attached to the catheter body, the first stator housing comprising an internal opening and an external opening, a first rotor attached to the rotatable drive shaft and located in the first stator housing, the first rotor comprising at least one tension line attachment site, and a movable sheath located over the catheter body. The delivery system may further comprise a self-expanding implant, the implant comprising a contracted configuration and an expanded configuration, and a first tensioning member releasably coupled to the self-expanding implant and fixedly coupled to the attachment site of the first rotor. The first tensioning member may be further wound around the first rotor, and may be wound around the first rotor at least three times. The delivery system may also further comprise a second stator housing attached to the catheter body and spaced apart from the first stator housing, the second stator housing comprising an internal opening and an external opening, a second rotor attached to the rotatable drive shaft and located in the second stator housing, the second rotor comprising at least one tension line attachment site. The delivery system may also further comprise a third stator housing attached to the catheter body and spaced apart from the first and second stator housings, the third stator housing comprising an internal opening and an external opening, a third rotor attached to the rotatable drive shaft and located in the third stator housing, the third rotor comprising at least one tension line attachment site. The first stator housing may be larger than the second stator housing and the first rotor is larger than the second rotor. The first stator housing may be larger than both the second and third stator housings and the first rotor is larger than the second and third rotors. The proximal handle may further comprise a first actuator lock, wherein the first actuator lock comprises locked and unlocked configurations and is biased to the lock configuration. The delivery system may further comprise a catheter extension assembly configured to reversibly adjust a longitudinal spacing between the distal section and the middle section of the catheter body. The catheter extension assembly may comprise a proximal housing with a proximal threaded lumen, a distal housing and a threaded extension shaft located in the proximal threaded lumen and coupled to the distal housing. The proximal housing and distal housing may comprise a slotted interface therebetween to resist rotational displacement therebetween. The proximal handle may further comprises a second actuator coupled to the threaded extension shaft. The delivery system may further comprise a first steering assembly comprising a first segmented tubular body and a first plurality of elongate steering wires. The first steering assembly may be located proximal to the catheter extension assembly. The first segmented tubular body may comprise a laser-cut tubular body. The delivery system may further comprise a second steering assembly comprising a second segmented tubular body and a second plurality of steering wires. The second steering assembly may be located distal to the catheter extension assembly. The first steering assembly and second steering assembly may comprise different bending configurations. For example, the first steering assembly may comprise a two-way steering assembly and the second steering assembly may comprise a four-way steering assembly. The first segmented tubular body may comprise segments attached by living hinges. The second segmented tubular body may comprise a plurality of discrete segments. Each of the plurality of discrete segments may comprise one or two non-planar end openings. The non-planar end openings comprise a hyperbolic paraboloid shape. Each of the plurality of discrete segments may comprises a perimeter bumper configured to slidably within a lumen of the distal section of the catheter body. The delivery system may further comprise a first guide structure located on the first stator housing. The first guide structure may be a first guide ring. The delivery system may also further comprise a second guide structure located on the catheter body. The second guide structure comprises a second guide ring and a ring support. The first guide ring and the second guide ring may have the same inner diameter.

In another embodiment, a delivery system is provided, comprising a proximal handle comprising a handle housing and a first actuator, a catheter body coupled to the handle, comprising a first rotatable drive shaft coupled to the first actuator and located in the catheter body, the first rotatable drive shaft comprising a first mechanical interfit interface at a distal end of the first rotatable drive shaft, and a first locking structure coupled to the catheter body, an implant delivery body, comprising a first stator housing attached to the implant delivery body, the first stator housing comprising an internal opening and an external opening, and a second rotatable drive shaft located in the implant delivery body, the second rotatable drive shaft comprising a second mechanical interfit interface at a proximal end of the second rotatable drive shaft and configured to form a mechanical interfit with the first mechanical interfit interface of the first rotatable drive shaft, a first rotor attached to the second rotatable drive shaft and located in the first stator housing, the first rotor comprising at least one tension line attachment site, and a second locking structure coupled to the implant delivery body, the second locking structure configured to attach to the first locking structure, and a movable sheath located over the catheter body. The first and second locking structures may be configured to attach via a threaded interface. The first locking structure may comprise a threaded lumen, and the second locking structure comprises a complementary threaded tubular body. The first and second locking structure may be configured to attach via a bayonet mount interface. In other variations, the first locking structure may comprise an L-shape slot, and the second locking structure may comprise a radial pin configured to movably reside in the L-shape slot. The first rotor may be a rotor plate, and the rotor plate may comprise at least one elongate projection and/or at least one aperture. In further variations, the rotor plate may comprise a plurality of identical sets of elongate projections and/or apertures.

In another embodiment, a minimally invasive implant delivery system is provided, comprising a handle comprising first, second, third and fourth controls, a tubular catheter body attached to the handle, the catheter body comprising a distal section, a middle section and proximal section, a catheter extension assembly configured adjustably extend the distal section of the catheter body relative to the middle section, a first steering assembly located proximal to the catheter extension assembly, and a second steering assembly located distal to the catheter extension assembly. The implant delivery system may further comprise a main drive shaft coupled to the first control and extending through the first steering assembly, catheter extension assembly and second steering assembly, and an extension drive shaft extending through first steering assembly and terminating at the catheter extension assembly, the extension drive shaft coupled to the second control. The first and second controls may comprise rotary dials. The first steering assembly may be coupled to the third control and the second steering assembly is coupled to the fourth control. The third control comprise a pivot handle. The fourth control may comprise a joystick. The first steering assembly may be attached to a proximal end of the catheter extension assembly and the second steering assembly is attached to a distal end of the catheter extension assembly. The first steering assembly may be located within the middle section of the catheter body and wherein the second steering assembly may be located within the distal section of the catheter body.

In still another embodiment, a method of delivering an expandable implant is provided, comprising navigating an expandable implant to a target location using a delivery catheter, using at least one of a steering assembly and a catheter extension assembly of the delivery catheter to set the expandable implant in a target pose, withdrawing a catheter sheath to expose the expandable implant, and actuating at least one rotor of the delivery catheter to unwind and extend at least one tensioning member from the delivery catheter to permit expansion of the expandable implant, the at least one tensioning member attached to the expandable implant. The method may further comprise further actuating the at least one rotor of the delivery catheter after expansion of the expandable implant to permit separation of the at least one tensioning member from the deliver catheter. The method may further comprise unlocking a rotor lock before or during the actuation of the at least one rotor. Unlocking a rotor lock may comprise squeezing a rotor lock release of a delivery catheter handle and wherein actuating the at least one rotor comprises rotating a rotor dial of the delivery catheter handle. The squeezing of the rotor lock release and rotating the rotor dial may be performed with a single hand.

In another embodiment, a method of loading an expandable stent structure onto a delivery catheter is provided, comprising providing an expanded stent structure attached to a plurality of tensioning members at different locations of the expanded stent structure, inserting a delivery catheter through the expanded stent structure, attaching the plurality of tensioning members to a plurality of rotors located at a distal section of a delivery catheter, collapsing the stent structure onto the delivery catheter, rotating the plurality of rotors to wind the plurality of tensioning members onto the plurality of rotors, and extending a catheter sheath over the collapsed stent structure. Collapsing the stent structure may be performed by tensioning the tensioning members by rotating of the plurality of rotors, or by collapsing the stent structure by pushing or pulling the expanded stent structure through a tapered structure, for example.

In still another variation, a method for performing mitral valve replacement is provided, comprising positioning a delivery device containing a collapsed heart valve assembly in an orthogonal, centered pose across the native mitral valve, wherein the heart valve assembly comprises a self-expandable stent and attached valve leaflets, retracting a sheath of the delivery device to expose the collapsed heart valve, rotating a first rotor to unwind and extend a first tensioning member to permit expansion of a first end of the stent located in a left atrium, and rotating a second rotor to unwind extend a second tensioning member to permit expansion of a second end of the stent located in a left ventricle. Rotating the first and second rotors are attached to a common drive shaft but unwind the first and second tensioning members at different lengths per rotation. The method may further comprise accessing a femoral vein, inserting a transseptal puncture device through the femoral vein and to the right atrium, puncturing the intraatrial septum, and inserting the delivery device with a collapsed heart valve assembly through the femoral vein and into the left atrium. Expanding the first end of the stent and expanding the second end of the stent may occur simultaneously but wherein the diameters of the first and second rotors are different. The method may further comprise dilating the intraatrial septum. The method may also further comprise accessing the left thoracic cavity through the chest wall, puncturing the cardiac tissue at an apex of the left ventricle, and inserting the delivery device with a collapsed heart valve assembly though the chest wall and transapically into the left ventricle, or may further comprise accessing a femoral artery, and inserting the delivery device with a collapsed heart valve assembly through the femoral artery and aortic arch and into the left ventricle.

BRIEF DESCRIPTION OF THE DRAWINGS

FIGS. 15A to 15F are top perspective, bottom perspective, top plan, bottom plan, side elevational and front/rear elevational views, respectively, of the distal segment of the distal steering assembly in FIG. 12, with perimeter bumpers.

FIGS. 31A to 31D but with a displacement tube coupled to the tension line.

FIGS. 45A to 45D are various perspective views of the distal rotor connector.

FIGS. 46A to 46D are various perspective views of the proximal rotor connector.

DETAILED DESCRIPTION

Figure 1A:
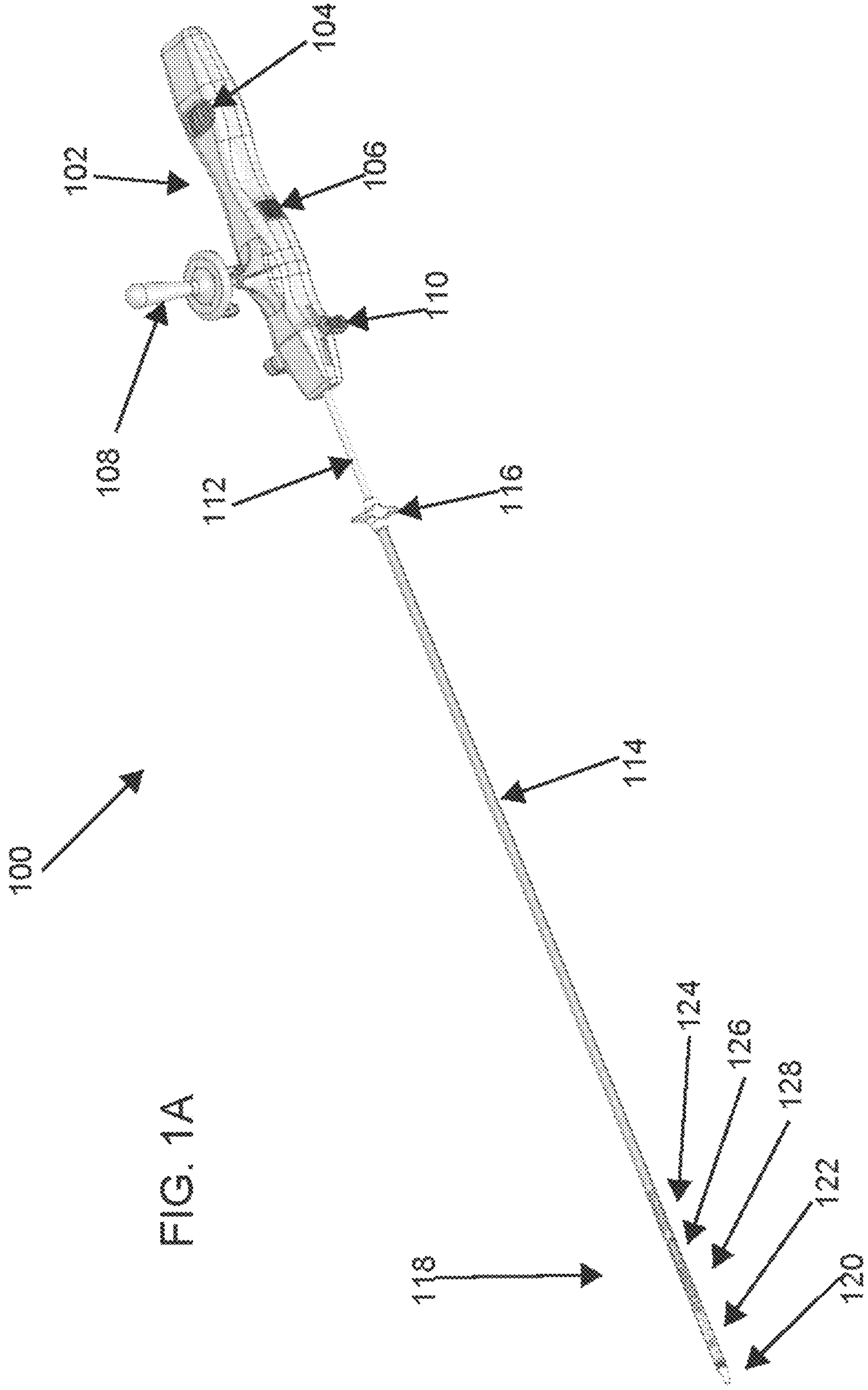
FIGS. 1A, 1B and 1C are top perspective, top plan and side elevational views, respectively of one exemplary embodiment of delivery system for an expandable implant.

FIG. 1 depicts one exemplary embodiment of a delivery system for a transcatheter heart valve replacement or other self-expanding stent structure. The delivery system 100 comprises a handle 102 with one or more actuators or user controls 104, 106, 108, 110, 130 and a catheter body 112 extending distally. The catheter body 112 is located inside an outer sheath 114 which can be moved by the user via a sheath handle 116 to sheath or expose a distal catheter section 118 with an atraumatic tip or nosecone 120 located at the distal end of the distal catheter section 118.

The distal catheter section 118 comprises an implant deployment section 122 that is configured to releasably retain a self-expanding implant (not shown) for delivery. The implant deployment section 122 includes a rotor/stator assembly, described in greater detail below, that is used to maintain the implant in a contracted or compressed configuration, and that can be adjusted to incrementally permit implant expansion toward its expanded configuration. The length of the catheter body 112 exposed between the sheath handle 116 and the main handle 102 will correspond generally to the length of the implant deployment section 122. In some further variations, depending on the physical characteristics of the implant and/or the delivery system, the rotor/stator assembly may also be used to contract or compress the implant back toward to the contracted or compressed configuration. One or more tensioning members that are attached to the implant and wound around the rotors are used to control the expansion and/or contraction of the implant. To facilitate the positioning and/or orientation of the implant deployment section 122 during the procedure, one or more steering or positioning mechanisms 124, 126, 128 may be provided along the catheter body 112, and are described in greater detail below.

Once the implant is expanded to the desired size and location, the delivery system may be separated from the implant in any of a variety of ways. For example, the one end or a middle portion of a tensioning member may be adhered, knotted or coupled by a friction fit to a rotor, while the other end or both ends of the tensioning member may be releasably attached to a clamp or other retention member located in the distal catheter section or in the handle of the delivery system. In other examples, the end(s) of the tensioning member may be severed by a cutting mechanism to separate the tension line from the implant or from the delivery system, e.g. where the tension line is retained on the implant after separation. In still other examples, the tensioning member may be transiently coupled to the rotor via one or more windings of the tensioning member that hold the tensioning member against the rotor. Upon further unwinding of the tensioning member, the end(s) of the tensioning member may be released, to allow the tensioning member to be pulled out of the implant for removal along with the delivery system.

Figure 1B:
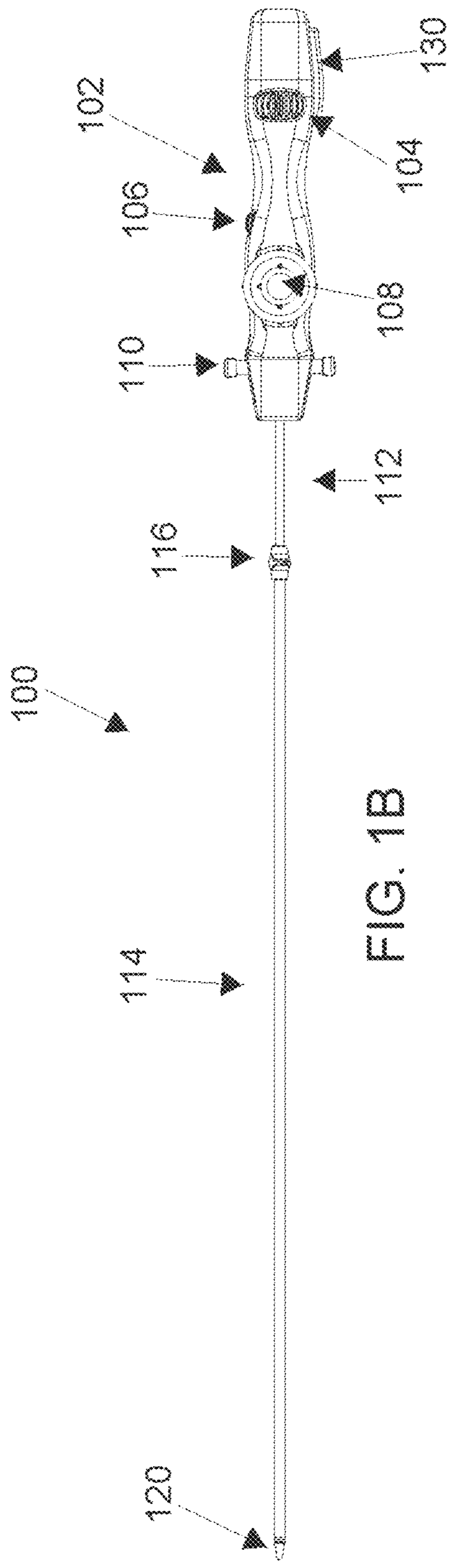
Figure 1C:
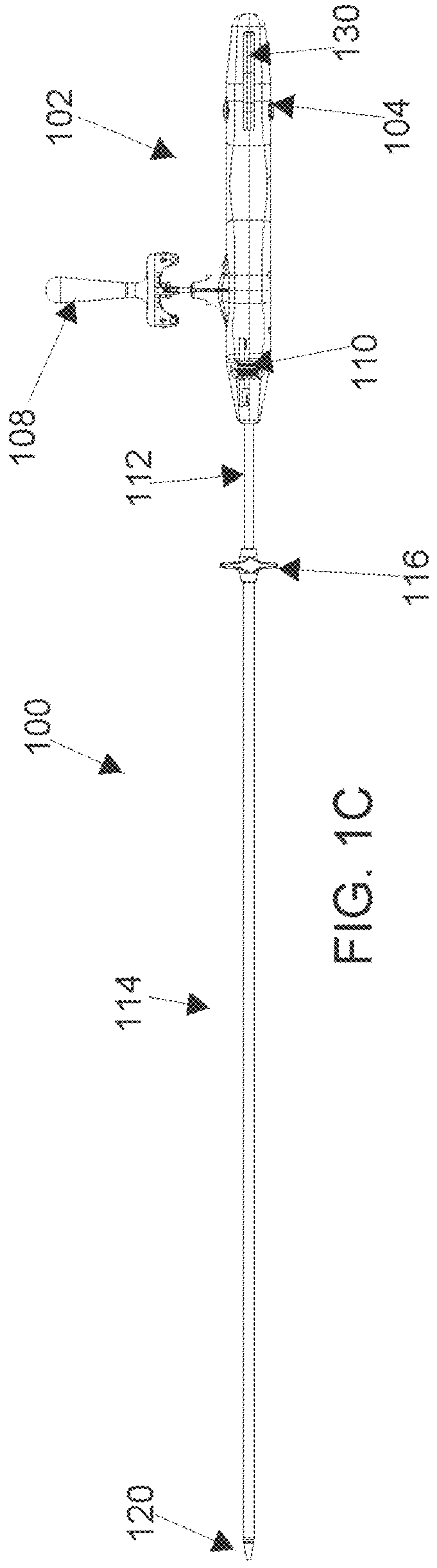
Figure 2A:
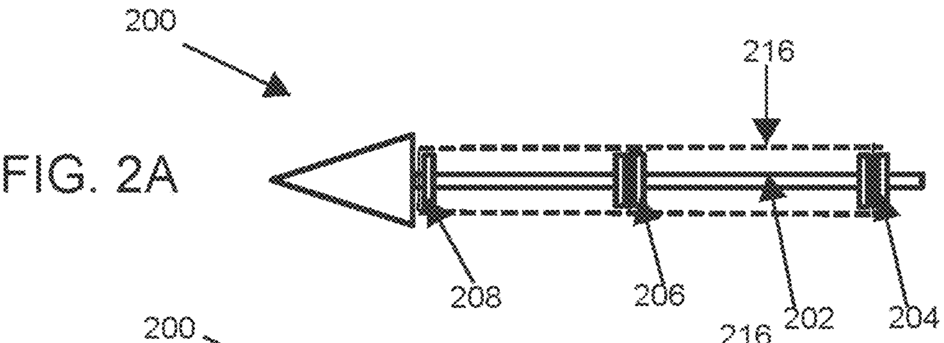
FIGS. 2A to 2D schematically depict one configuration of a delivery system which simultaneously extends tensioning members at three rotors of the delivery system.
Figure 2B:
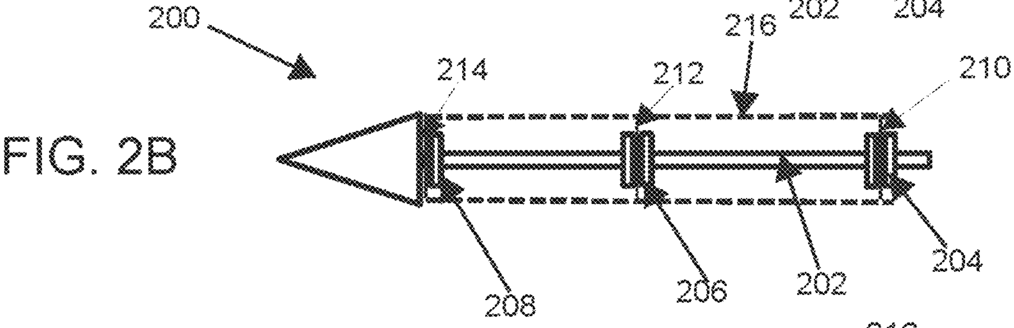
Figure 2C:
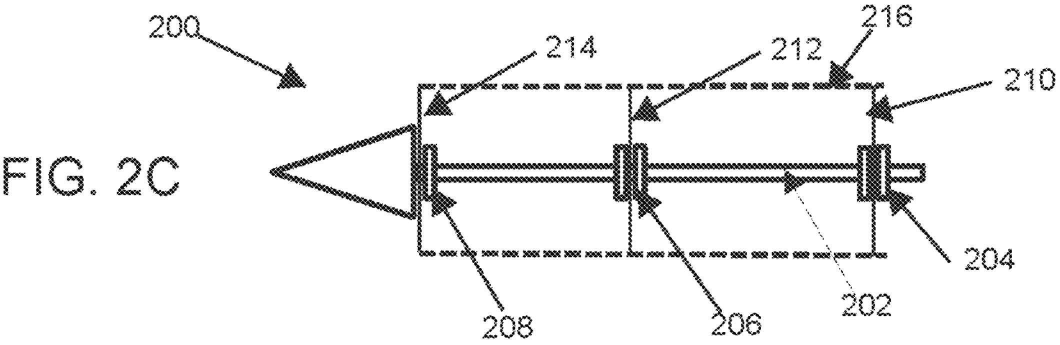
Figure 2D:
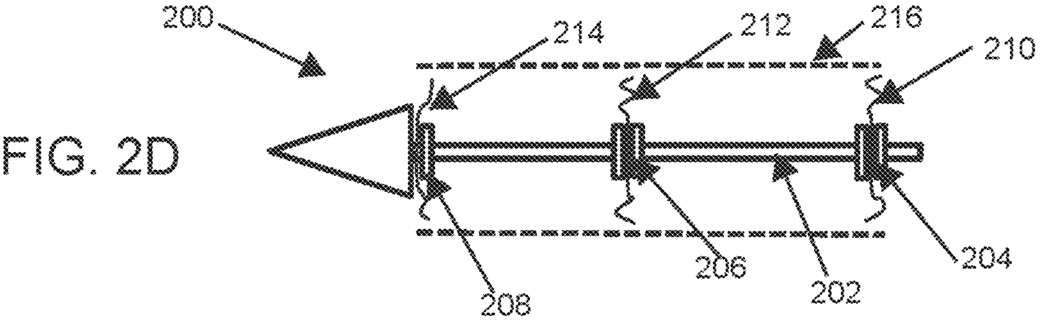
Figures 3A, 3B, 3C, 3D:
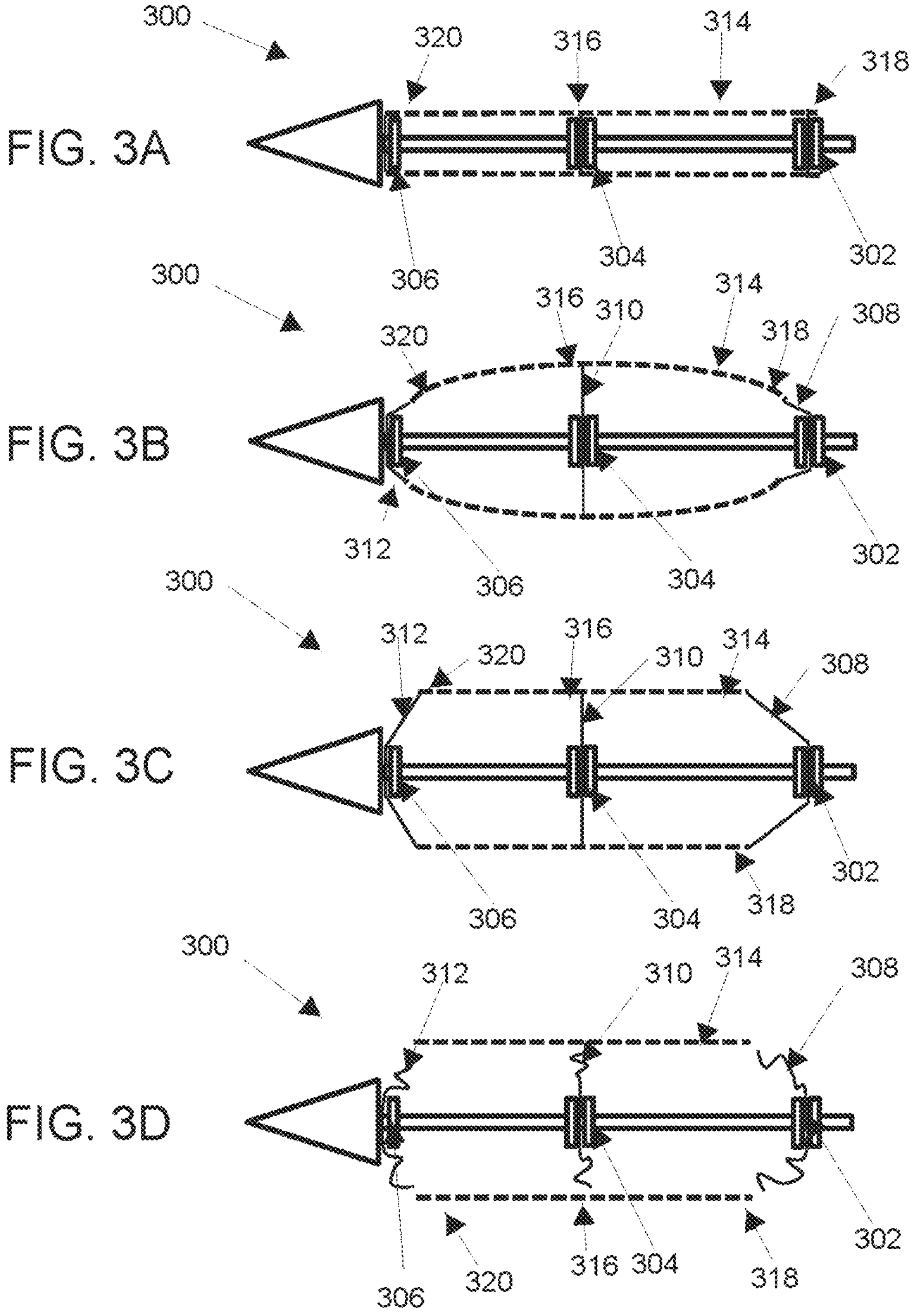
FIGS. 3A to 3D schematically depict another configuration of an exemplary delivery system where a middle rotor is actuated first or to a greater degree than a proximal and distal rotor.

The rotor/stator assembly may comprise any of a variety of configurations. In one embodiment, depicted in FIGS. 2A to 2D, the implant deployment section 200 of the delivery system includes distal elongate body 202 from which the implant or stent 216 is released. The distal elongate body 202 includes multiple rotors/stators 204, 206, 208 spaced along the longitudinal length of the implant deployment region 202. As a drive shaft inside distal elongate body 202 is rotated, the tension lines 210, 212, 214 are unwound from the rotors/stators 204, 206, 208 in generally equal tension line lengths/rotation. The rotation of the drive shaft may be manipulated by the user at a control or knob 104 located in handle 102, as depicted in FIGS. 1A to 1C. The handle may also include a user releasable lock 130 that is holds the control of knob 104 in place, to avoid inadvertent release or expansion of the implant. In other examples, the knob 104 may comprise an auto-locking mechanism, e.g. a knob that is biased to the lock position by a spring that and must be pushed longitudinally to disengage and rotate the knob. Description of the exemplary knob 104 and the lock 130 are provided in greater detail below. This results in the stent implant 216 expansion in FIGS. 2B and 2C occurring equally along the length of the implant 216. Once expanded against the surrounding anatomical structure, the tension lines 210, 212, 214 may be separated from the implant 216 by further unwinding of the tension lines 210, 212, 214 until the tensioning members 210, 212, 214 are freed from self-binding to the rotors/stators 204, 206, 208, as schematically depicted in FIG. 2D. Although the depicted embodiment in FIGS. 2A to 2D includes three equally spaced apart rotors/stator 204, 206, 208, in other variations, a different number of rotors/stators may be provided and the spacing may be different between them, depending on the implant configuration and the target location. In other variations, number of rotors/stators may be in the range of 2 to 4, 1 to 3 or 2 to 3, for example.

FIGS. 3A to 3D depict another variation of the delivery system, wherein the implant deployment region 300 comprises a distal includes multiple rotors/stators 302, 304, 306, which may be configured to either unwind the tensioning members 308, 310, 312 at different rates per unit rotation, or in a sequential manner. In the depicted embodiment, the middle rotor/stator 304 on the implant deployment region 300 is configured to unwind a greater length of tensioning member 310 than either proximal or distal rotors/stators 302, 306, to allow the middle section 316 of the implant 314 to expand first or to a greater degree than the ends 318, 320 of the implant 314. This may facilitate positioning of the implant 314 in some procedures at the target location by aligning the expansion of the middle section 316 implant 314 rather than the ends 318, 320, which may be more difficult to align due to foreshortening of the implant 314. This may be provided by configuring the middle rotor/stator 304 with a larger diameter for wrapping around the tensioning members compared to the proximal or distal rotors/stators 302, 206, which increases the length of tensioning member per rotation of the rotor. The length per rotation may also be altered by providing a different number of tensioning members at each rotor/stator. A greater number of tensioning members as they are wrapped around the rotor will result in a larger diameter from all of the coiled tensioning members, which will provide an increased initial length per rotation during deployment. In other examples, multiple drive shafts (not shown) may be provided to independently drive one or more rotors/stators with different amount of rotation relative to one or more other rotors/stators. The multiple drive shafts may comprise a concentric configuration with a solid inner drive shaft for one or more distal rotors/stators, a tubular drive shaft for one or more proximal rotors/stators, for example, or multiple parallel drive shafts, each terminating at a different rotor/stator, for example.

FIGS. 4A to 4D depict still another embodiment of a delivery system 400, wherein the implant deployment region 420 of the catheter includes multiple rotors/stators 422, 424, 426 used to deliver a double-wall stented structure, such as the unibody folded stent heart valve implant 804 as described in U.S. application Ser. No. 17/083,266, which is hereby incorporated by reference in its entirety. In this configuration, the distal rotor/stator 426 is actuated first, before the middle and proximal rotors/stators 422, 424.

Figures 4A, 4B, 4C:
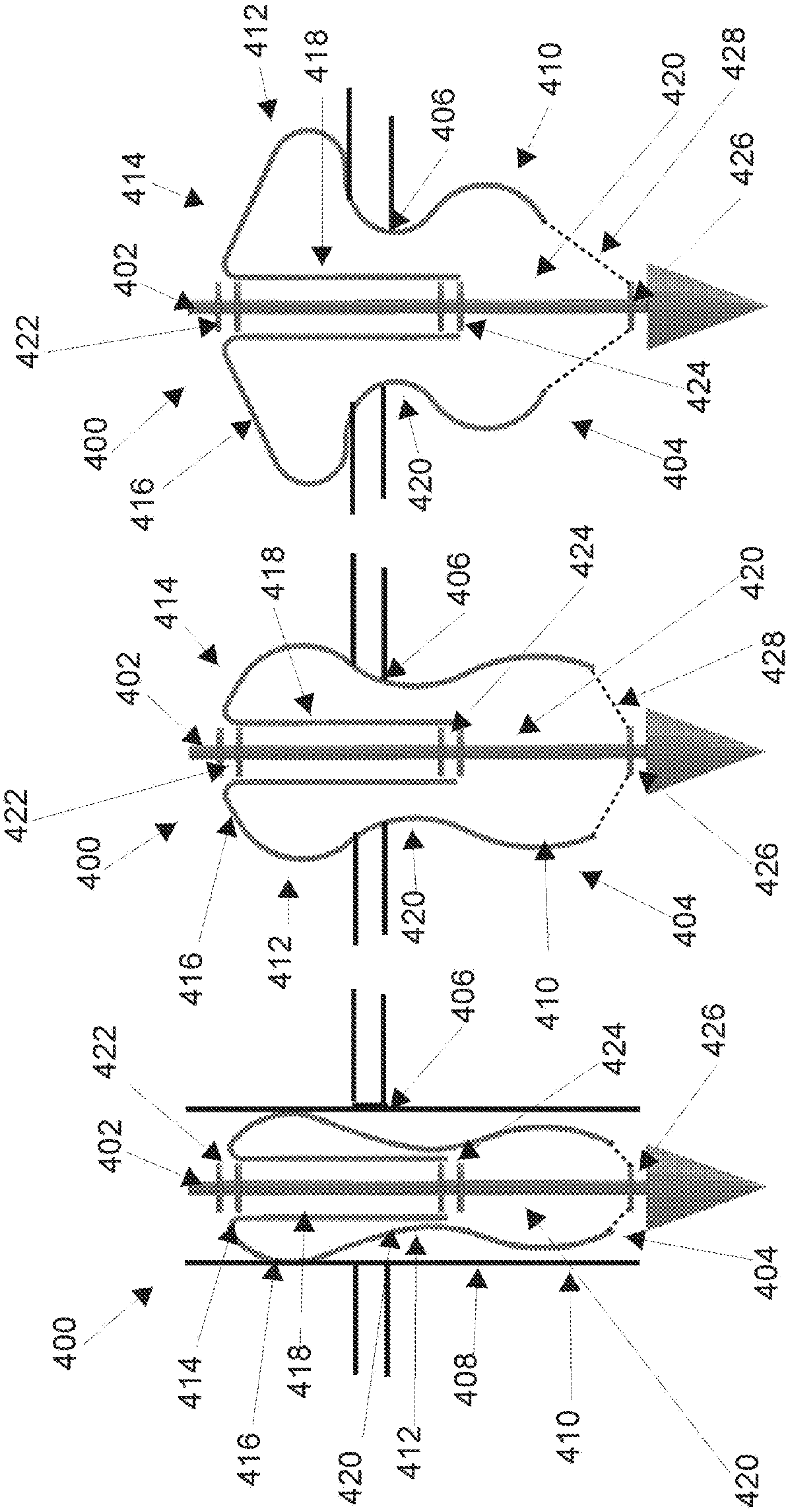
FIGS. 4A to 4E schematically depict another configuration of an exemplary delivery system for a double-wall stent in which the outer wall is expanded before the inner wall.

Referring to FIG. 4A, the delivery system 400 with the delivery catheter 402 and valve 404 is positioned across the mitral valve opening 406. The delivery system 400 may also be further manipulated to adjust the angle of entry through the mitral valve opening 406 to be roughly orthogonal to the native valve opening and/or to be centered with the mitral valve opening 406. Once the desired catheter pose is achieved, the delivery sheath 408 is withdrawn proximally, to expose the collapsed valve 404.

In FIG. 4B, the first set of tension lines 428 controlling the release of the downstream or ventricular end 410 of the outer wall 412 of the valve 404 is partially released, while the tension lines 430, 432 controlling the inner wall 416 remain tensioned. Next, in FIG. 4C, ventricular end 410 of the outer wall 412 of the valve 404 is further released, allowing the ventricular end, the middle region and more of the atrial end 414 of the outer wall 412 to expand further, thereby allowing the transition wall 416 of the valve 402 to at least partially expand outward. The partial expansion of the atrial end 414 and the ventricular end 410 of the valve 402 helps to further center and orient the middle region 422 of the valve 402 orthogonally prior to complete release. While the initial expansion of the atrial end 414 of the outer wall 412 in this embodiment is a secondary effect from the partial release of the ventricular end 410 of the valve 402 as longitudinal tension is released, in other examples, independent tension line control of the atrial end 414 may be provided.

Figure 4E:
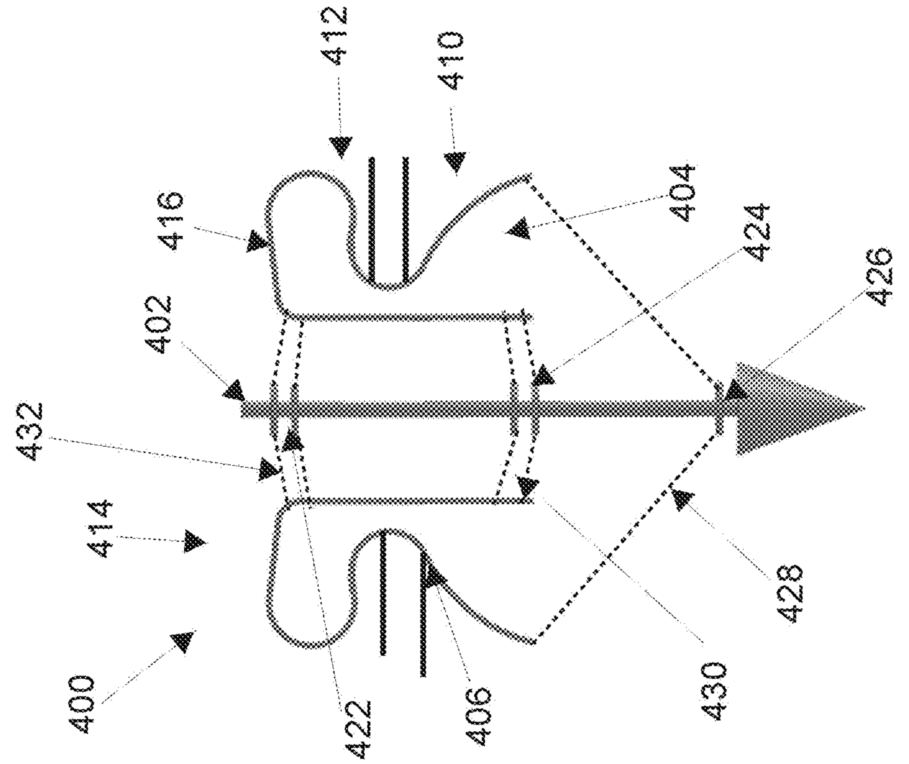
Figure 4D:
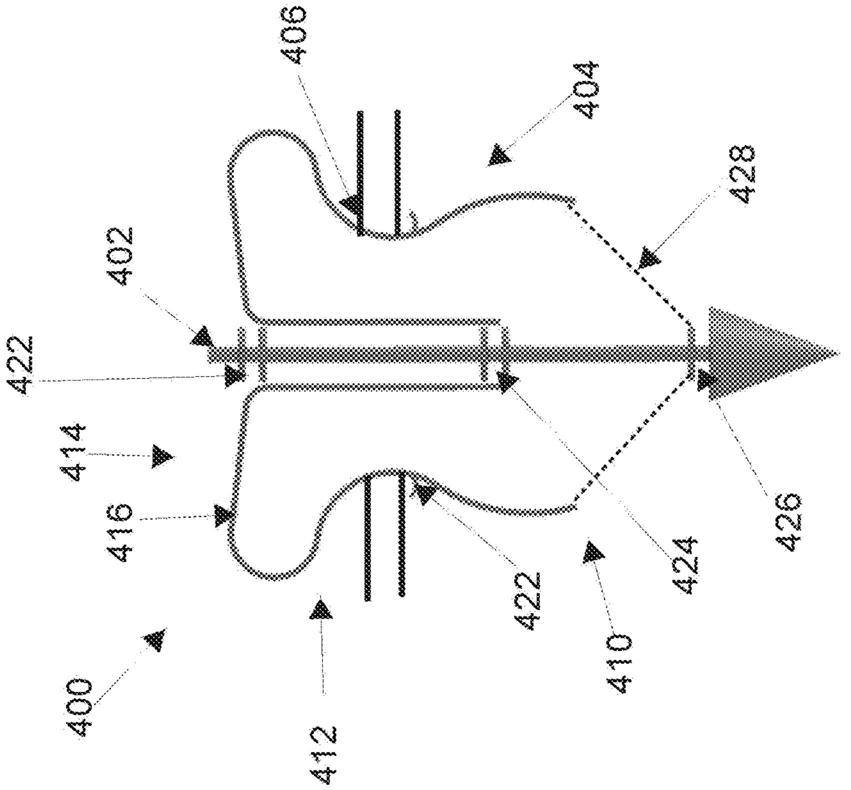

In FIG. 4D, the tension lines of the ventricular end 410 and atrial end 414 are further released, either simultaneously or singly in a stepwise fashion, further engaging the middle region 420 of the outer wall 412 against the valve opening 406. This further expansion of the outer wall 412 also exposes the retention barbs or projections 422 on the outer wall 412. Proper centering and orientation of the valve is reconfirmed, to make sure the valve has not been deployed in a skewed or partially disengaged pose with respect to the mitral valve annulus. In some variations, the tension lines may be re-tensioned to re-collapse the valve 404, to facilitate re-positioning and/or re-orienting of the valve 404. Once confirmed, the tension lines 430, 432 of the inner wall 418 may be released, as shown in FIG. 4E, which also allows the outer wall 412 to achieve its untethered expansion against the mitral valve opening 806. The outer wall 412 may also be expanded first against the valve opening 806, with the tension lines 430, 432 released afterwards. The tension lines 428, 430, 432 can then be cut or otherwise released or separated from the valve implant as described herein and the tension lines 428, 430, 432 may be withdrawn into the catheter and optionally out of the proximal end of the catheter. The delivery catheter and guidewire can then be withdrawn from the patient and hemostasis is achieved at the femoral vein site.

FIGS. 5A to 5D depict still another embodiment of a delivery system 500, wherein the implant deployment region 520 of the catheter includes multiple rotors/stators 522, 524, 526 that are located on the same drive shaft (not shown) and used to deliver a double-wall stented heart valve structure. In this configuration, all three rotors/stators 522, 524, 526 are configured to rotate simultaneously and with equal degrees of rotation, though the length of the tensioning member 428, 430, 432 that is extended or retracted per unit of rotation may be different, depending on the diameter of the rotor and/or the number of tensioning members.

Figure 5C:
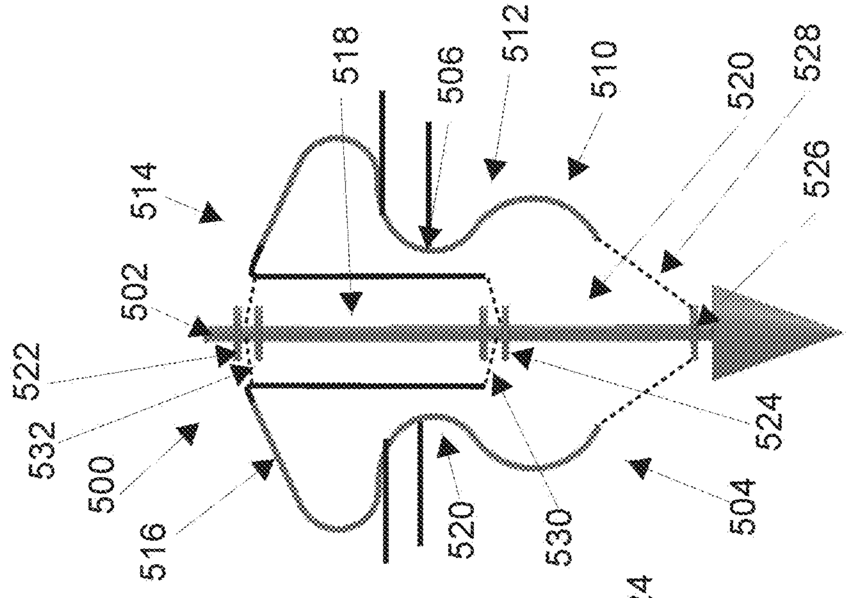
FIGS. 5A to 5E schematically depict another configuration of an exemplary delivery system for a double-wall stent in which the inner and outer walls are expanded simultaneously but at different rates.
Figure 5B:
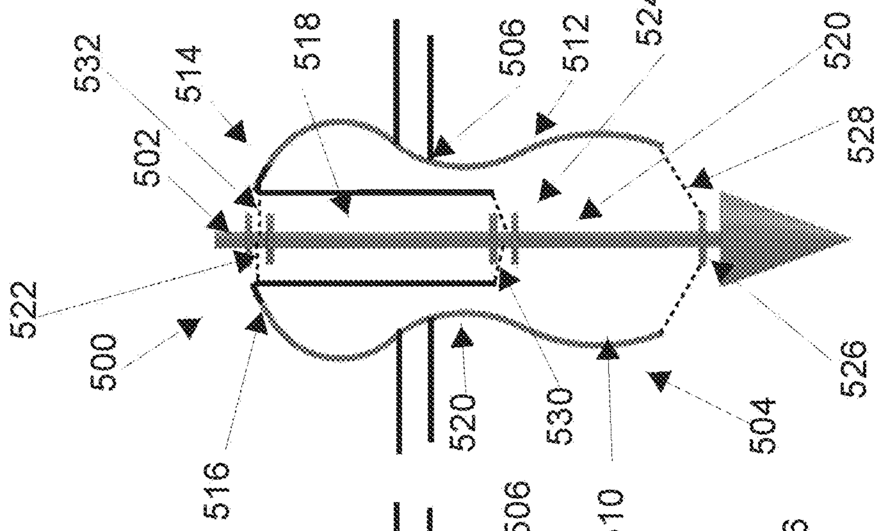
Figure 5A:
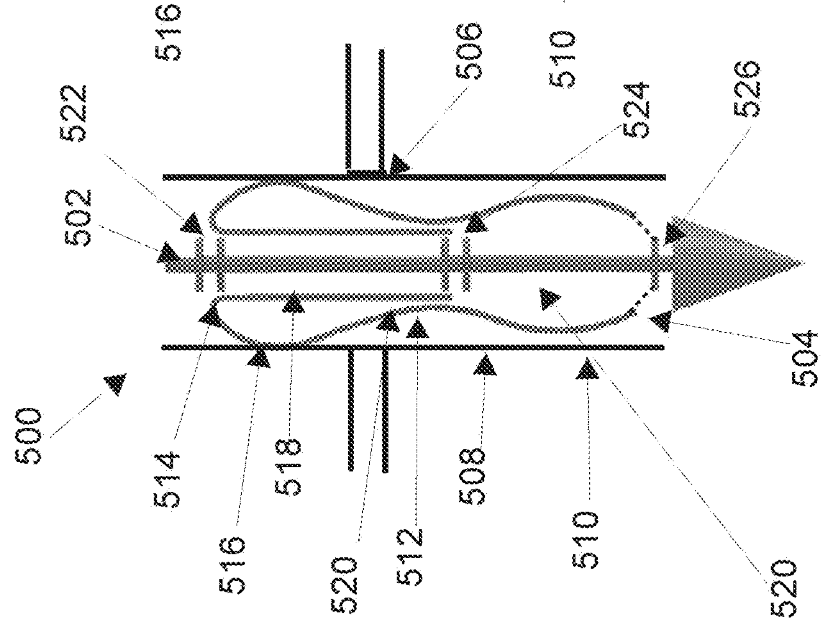

Referring to FIG. 5A, the delivery system 500 with the delivery catheter 502 and valve 504 is positioned across the mitral valve opening 506. The delivery system 500 may also be further manipulated to adjust the angle of entry through the mitral valve opening 506 to be roughly orthogonal to the native valve opening and/or to be centered with the mitral valve opening 506. Once the desired catheter pose is achieved, the delivery sheath 508 is withdrawn proximally, to expose the collapsed valve 504.

Figure 5E:
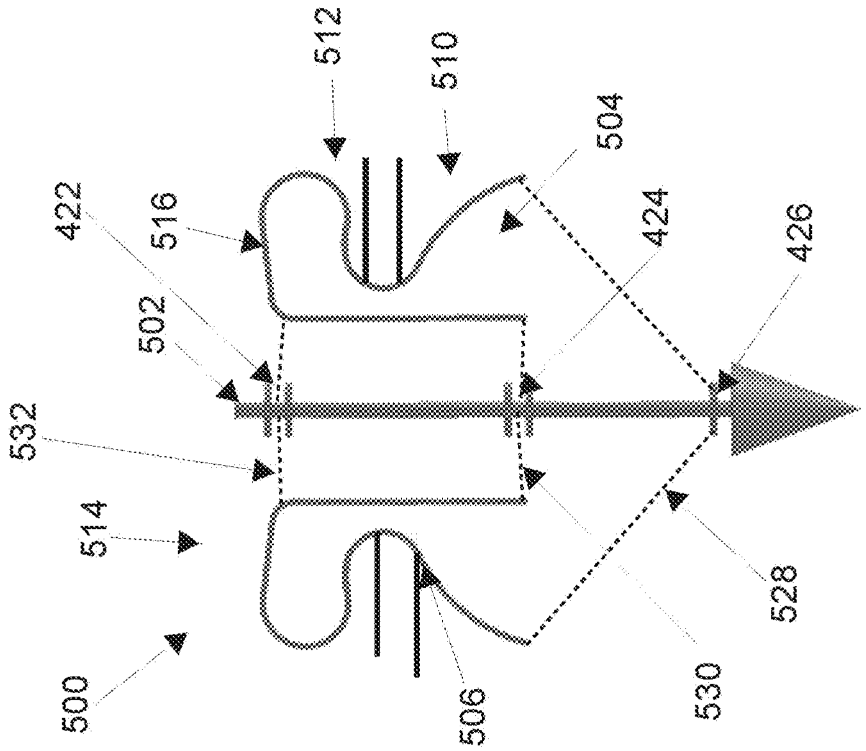
Figure 5D:
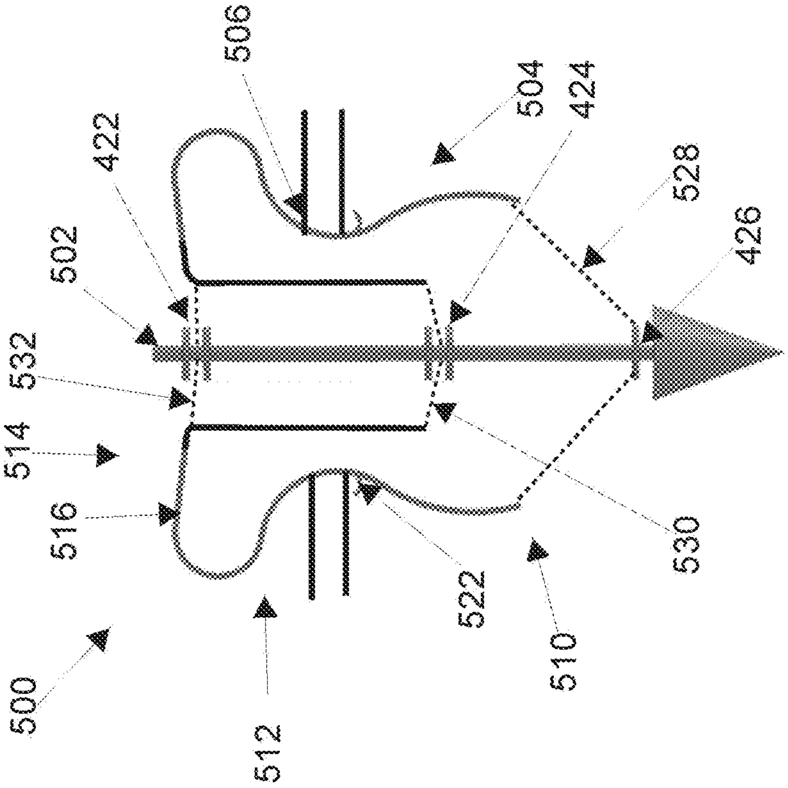

In FIGS. 5B to 5D, all three sets of tension lines 528, 530, 532 controlling the release of the downstream or ventricular end 510 of the outer wall 512 and the inner wall 518 of the valve 504 are simultaneously incrementally released, although tension lines 528 may be configured to release at a greater rate than tension lines 530, 532 due to the greater amount of travel of the ventricular end 510 of the outer wall 512 exhibited during expansion compared the inner wall 518. Next, in FIG. 5C, ventricular end 510 of the outer wall 512 of the valve 504 is further released, allowing the ventricular end, the middle region and more of the atrial end 514 of the outer wall 512 to expand further, thereby allowing the transition wall 516 of the valve 504 to at least partially expand outward. The partial expansion of the atrial end 514 and the ventricular end 510 of the valve 504 in conjunction with the partial expansion of the inner wall 518 helps to further center and orient the middle region 520 of the valve 504 orthogonally prior to complete release. While the initial expansion of the atrial end 514 of the outer wall 512 in this embodiment is a secondary effect from the partial release of the ventricular end 510 of the valve 504 as longitudinal tension is released, in other examples, independent tension line control of the atrial end 514 may be provided.

In FIG. 5D, the tension lines 528, 530, 532 of the ventricular end 510 and inner wall 518 are further released simultaneously, further engaging the middle region 520 of the outer wall 512 against the valve opening 506. This further expansion of the outer wall 512 also exposes the retention barbs or projections 522 on the outer wall 512. Proper centering and orientation of the valve is reconfirmed, to make sure the valve has not been deployed in a skewed or partially disengaged pose with respect to the mitral valve annulus. In some variations, the tension lines may be re-tensioned to re-collapse the valve 504 may be performed, to facilitate re-positioning and/or re-orienting of the valve 504. Once confirmed that the outer wall 512 has achieved its desired expansion against the mitral valve opening 506, as shown in FIG. 5E, the tension lines 528, 530, 532 can then be cut or otherwise released or separated from the valve implant as described herein and the tension lines 528, 530, 532 may be withdrawn into the catheter and optionally out of the proximal end of the catheter. The delivery catheter and guidewire can then be withdrawn from the patient and hemostasis is achieved at the femoral vein site.

Figure 26A:
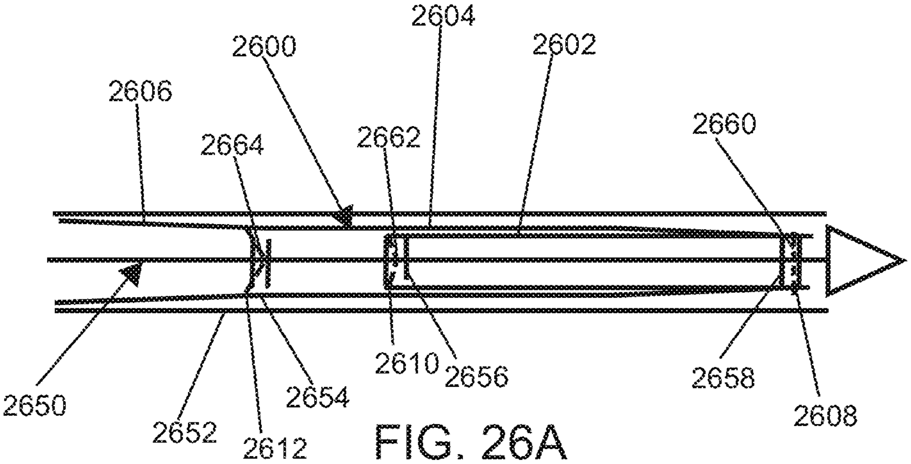
FIGS. 26A to 26D depict another configuration of an exemplary three-capstan delivery system for a valve stent with an atrial brim or flange.
Figure 26B:
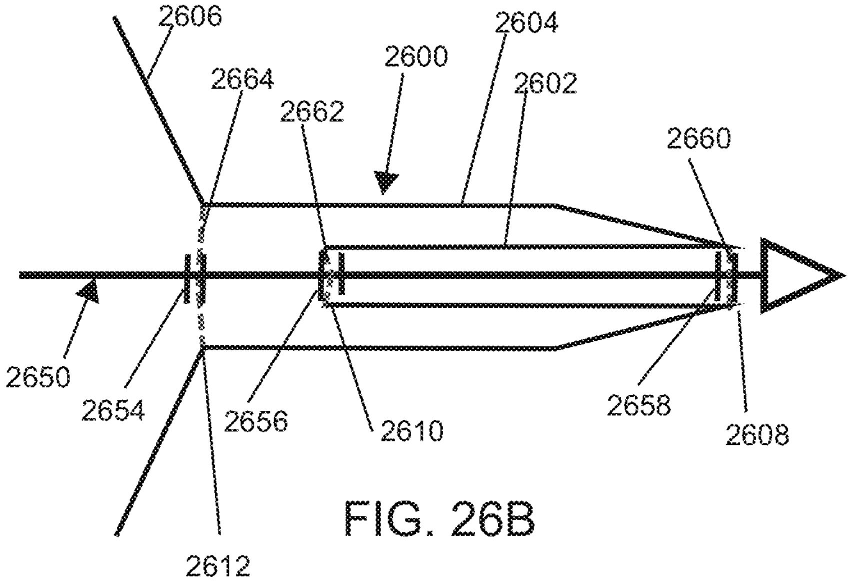

FIGS. 26A to 26D schematically illustrates another embodiment of the valve delivery system configured for delivery of a flanged stent valve. The flanged stent valve 2600 may comprise a mitral valve prosthesis supported by an inner valve stent 2602 with a fixation ring 2604 with an atrial flange or brim 2606. The stent core and flange may comprise a unibody design, or may comprise a two component design with a separate valve stent and a separate fixation ring or structures that are pre-attached for delivery. An example of the latter valve design is described for example, in U.S. Pat. No. 10,792,151 to Mauch et al. The prosthesis 2600 may be compressed or collapsed onto the delivery system 2650 and covered by a retractable sheath 2652. The delivery system comprises three rotor/stator assemblies 2654, 2656, 2658, with the distal assembly 2658 attached by tension members 2660 to the valve or ventricular outflow opening 2608 of the prosthesis 2600. The middle assembly 2656 is attached by tension members 2662 to a valve inflow opening 2610 of the prosthesis 2600 and the proximal assembly 2654 is attached by tension members 2664 to an inner atrial opening 2612. In this embodiment, the perimeter of the atrial brim 2606 is not coupled to a tension member or rotor/stator assembly, and is permitted to at least partially expand upon withdrawal of the retractable sheath 2652, as depicted in FIG. 26B. Because the inner atrial opening 2612 is held in a constrained configuration by tension members 2664, the atrial brim 2606 is not yet fully expanded against the surrounding anatomy.

Figure 26C:
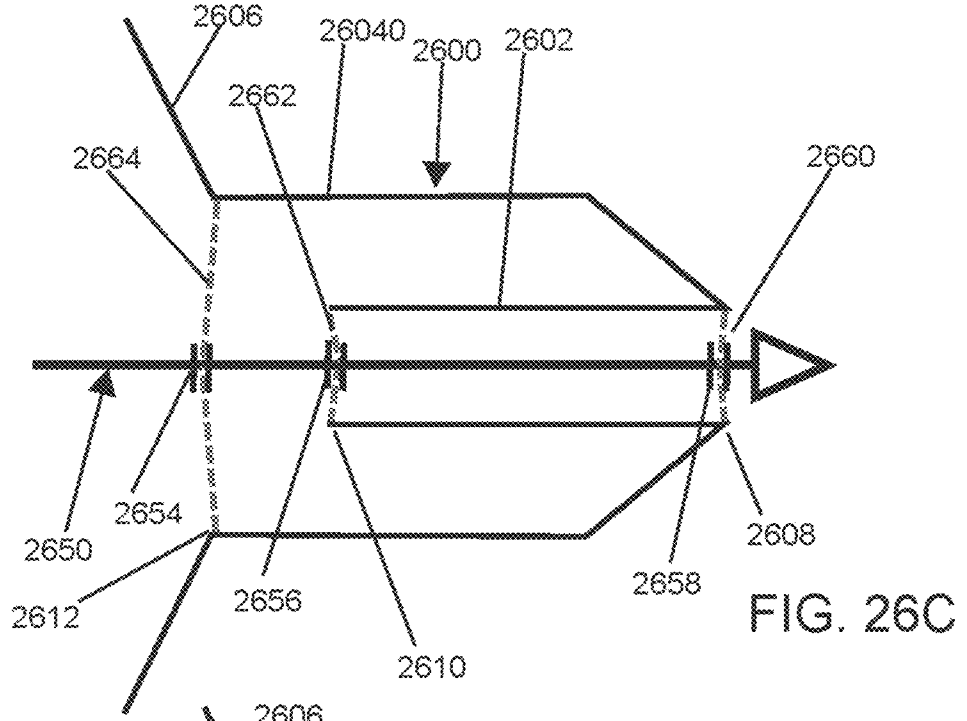
Figure 26D:
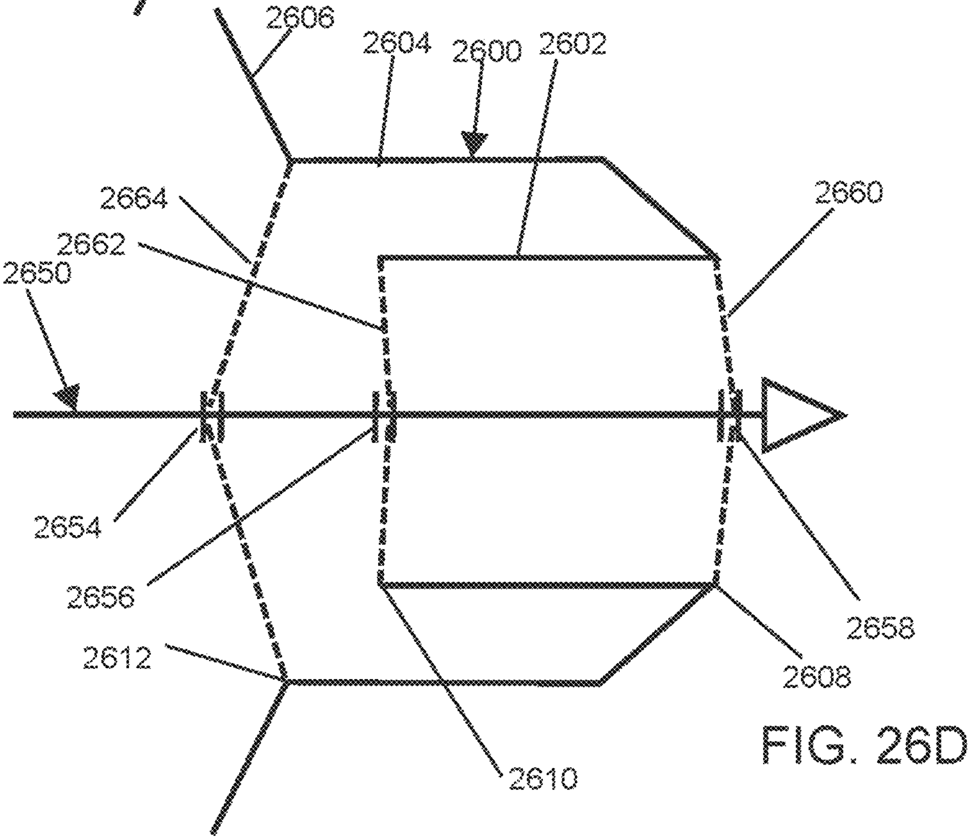
Figure 27A:
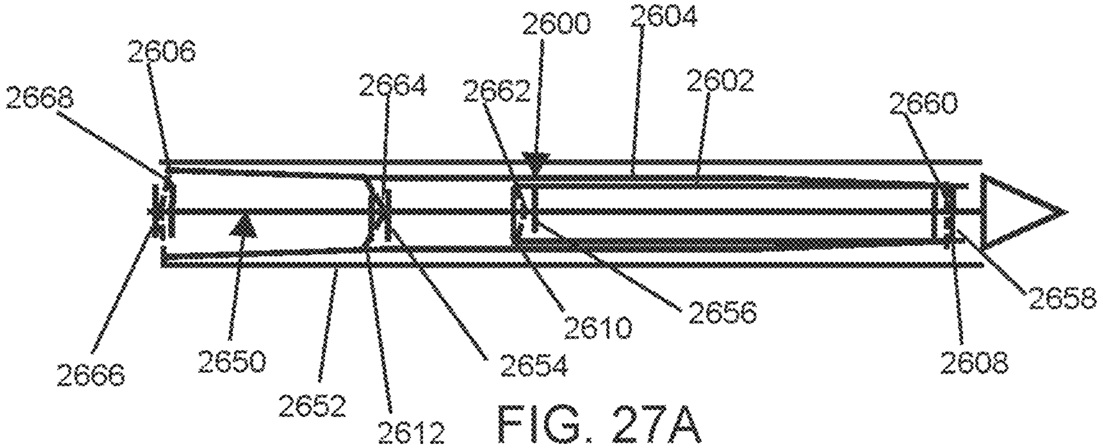
FIGS. 27A to 27D depict an exemplary four-capstan delivery system for the valve stent depicted in FIGS. 26A to 26D.
Figure 27B:
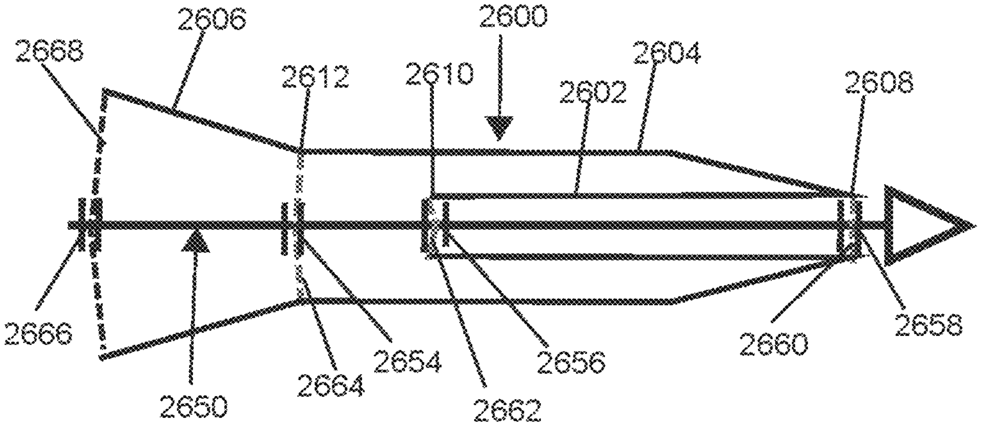
Figure 27C:
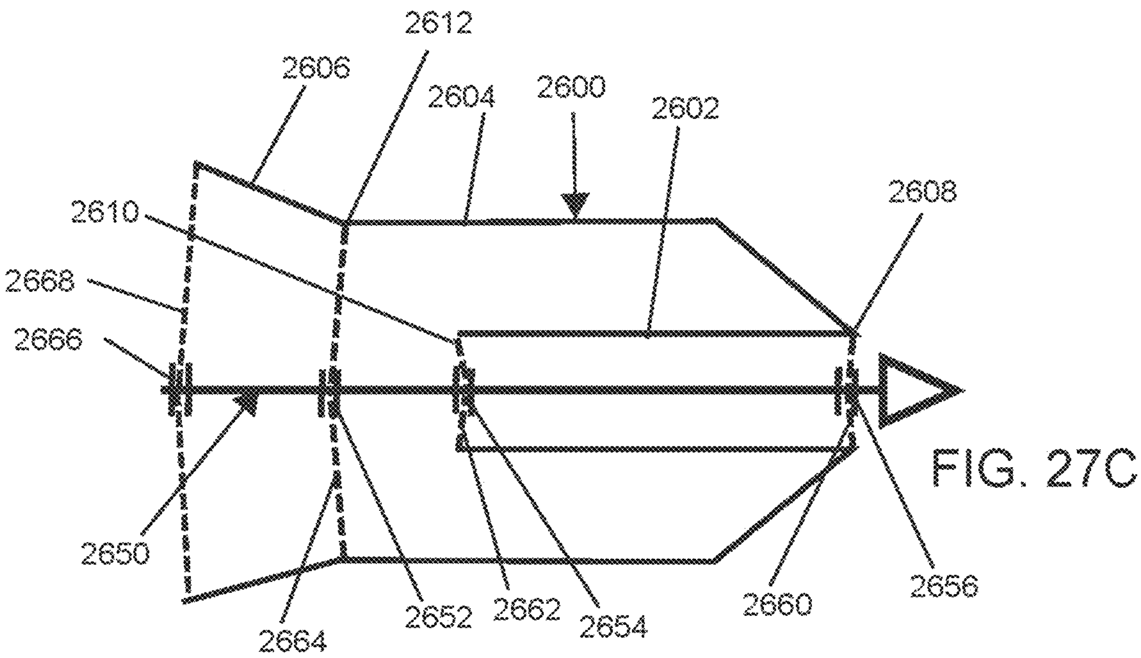
Figure 27D:
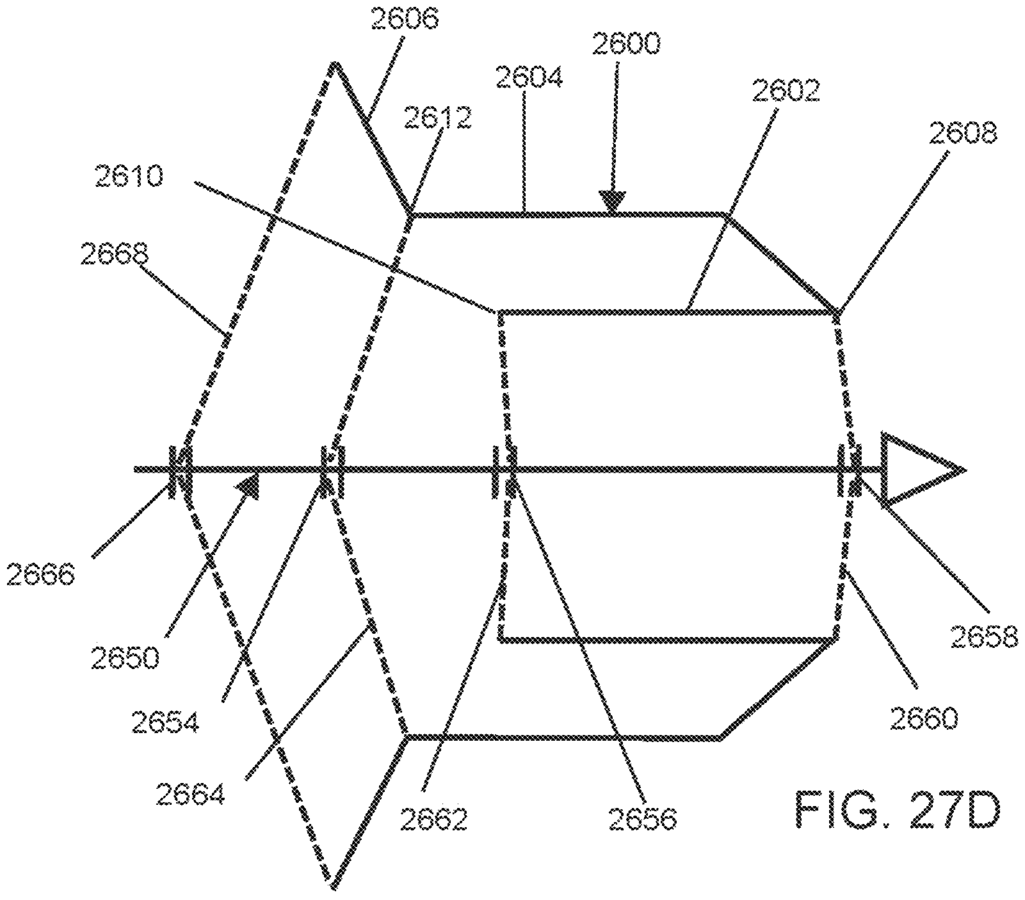

After the withdrawal of the sheath 2652, the location and orientation of the prosthesis 2600 may be further adjusted by the delivery system 2650 until it is centered in the valve orifice and the desired axial station of the prosthesis 2600 is confirmed. Once confirmed, the tension members 2660, 2662, 2664 may be unwound by the rotor/stator assemblies 2654, 2656, 2658 until the prosthesis 2600 is engaged to the surrounding anatomy, as shown in FIGS. 26B to 26D. As depicted, as the fixation ring 2602 of the prosthesis 2600 is further released, the angle of tension member 2664 becomes more acute, due to the foreshortening of the fixation ring 2602, while the tension members 2660, 2662 that are attached to the inner valve stent 2602 extend out but exhibit minimal if any angular change as a result of the non-foreshortening design of the inner valve stent 2602. The rotor/stator assemblies 2654, 2656, 1658 may then be further unwound until the tension members 2660, 2662, 2664 are released from the prosthesis 2600.

FIGS. 27A to 27D depict another variation of the delivery system 2650 for delivering prosthesis 2600, except that the delivery system 2650 includes an additional rotor/stator assembly 2666 located proximal to the proximal rotor/stator assembly 2654 and attached to the atrial brim 2604 by additional tension members 2668. This configuration of the delivery system 2650 may help to redistribute the intrinsic expansion forces exerted by the prosthesis 2600 on the proximal tension member 2660 and the proximal rotor/stator assembly 2654, which in turn may allow for smoother, more incremental manipulation of the rotor/stator assemblies 2654, 6656, 6658, 2666 and tension members 2660, 2662, 2664 and 2668.

In the preceding examples of delivery systems and valves, the delivery systems and valves are configured for transseptal delivery, but spacing and orientations of the rotor/stator assemblies and the nosecones may be reconfigured for retrograde delivery via the arterial system, or for transapical delivery.

Figure 6B:
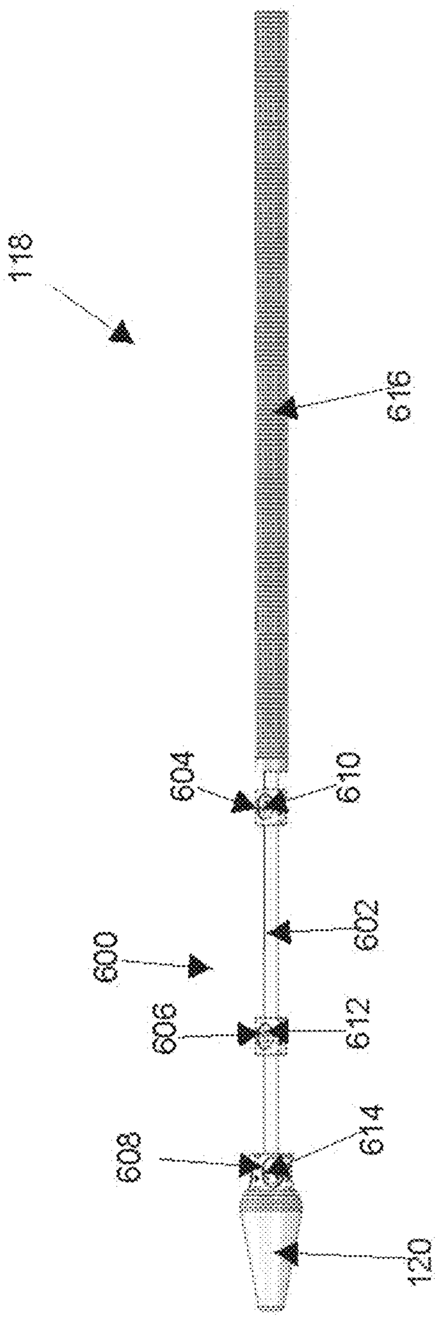
FIG. 6B is a side view of the distal region of the delivery system in FIG. 6A, without the sheath or the combination steering and extension assembly.
Figure 6A:
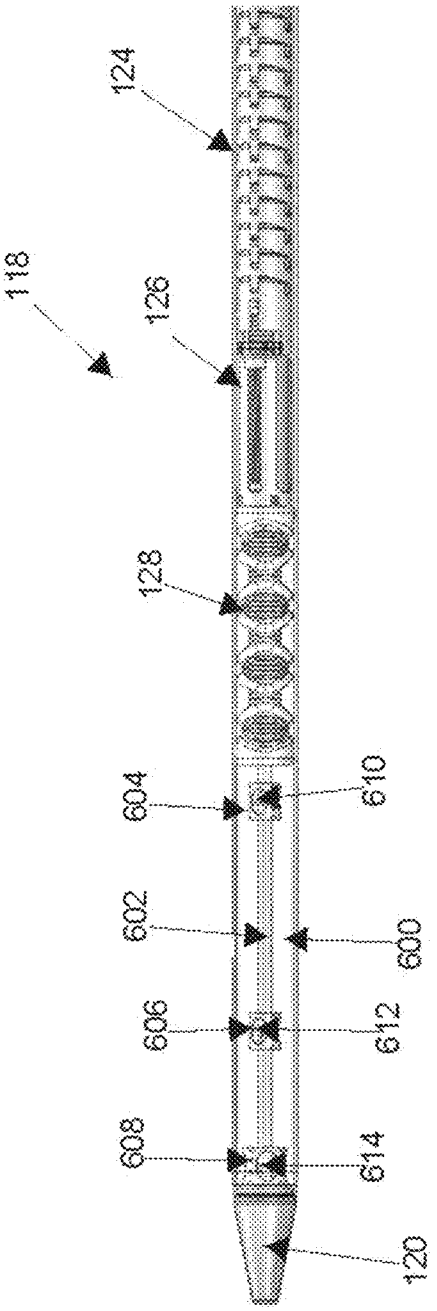
FIG. 6A is a side cut-away view of the distal region of the delivery system in FIG. 1.

FIGS. 6A and 6B depict an exemplary detailed configuration of the distal catheter section 118 of the distal delivery system 100 in FIGS. 1A to 1C. As noted previously, the distal catheter section 118 includes a nose cone 120 to facilitate insertion and navigation of the delivery system 100 along the anatomical pathway. The nose cone 120 may include a guidewire lumen and distal opening (not shown) and may comprise a soft atraumatic material such as nylon, polyurethane, or silicone, for example. The nose cone 120 is attached to the stator assembly 600 with at least one stator housing 604, 606, 608 spaced along the stator body 602. Inside the tubular stator body 602 and the stator housings 604, 606, 608 is a rotor body (not shown) with a rotors 610, 612, 614, upon which the elongate tension lines are attached and wound around. Openings in the stator housings 604, 606, 608 permit the tension lines to extend and optionally retract as the rotor body is rotated.

Figure 7B:
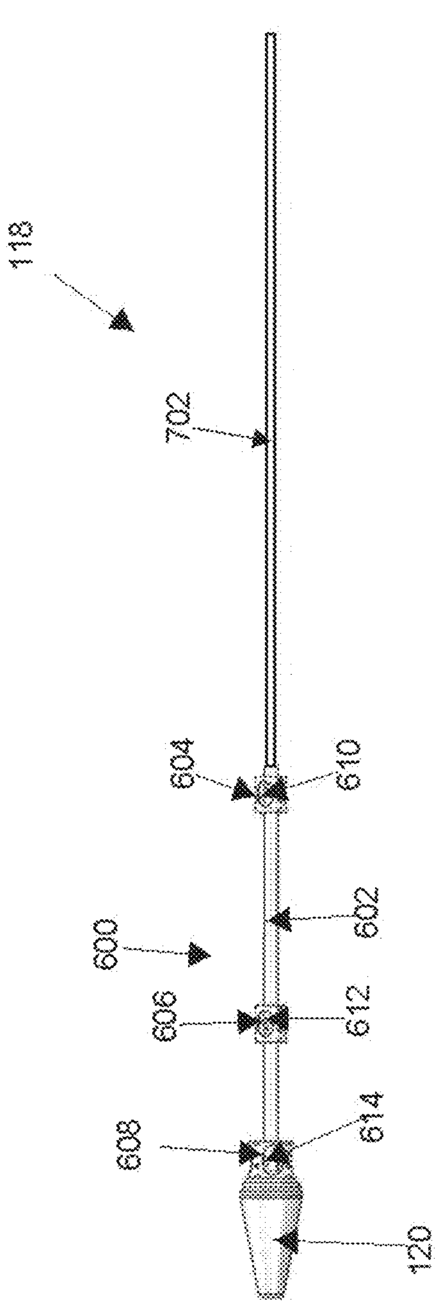
FIG. 7B is a cross sectional view of the distal region of the delivery system in FIG. 7A.
Figure 7A:
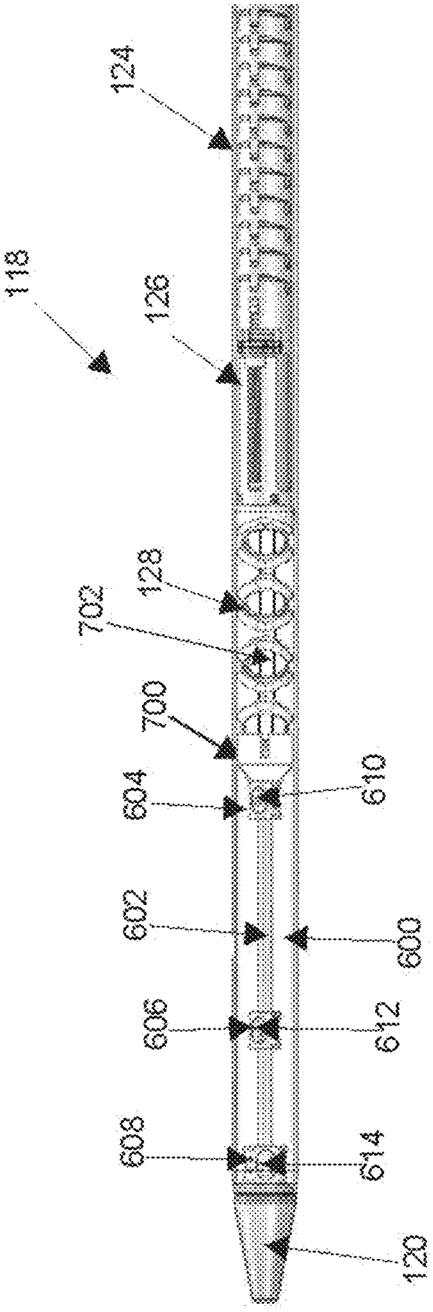
FIG. 7A is a side cut-away view of the distal region of another embodiment of a delivery system, without a torque tube.
Figure 7C:
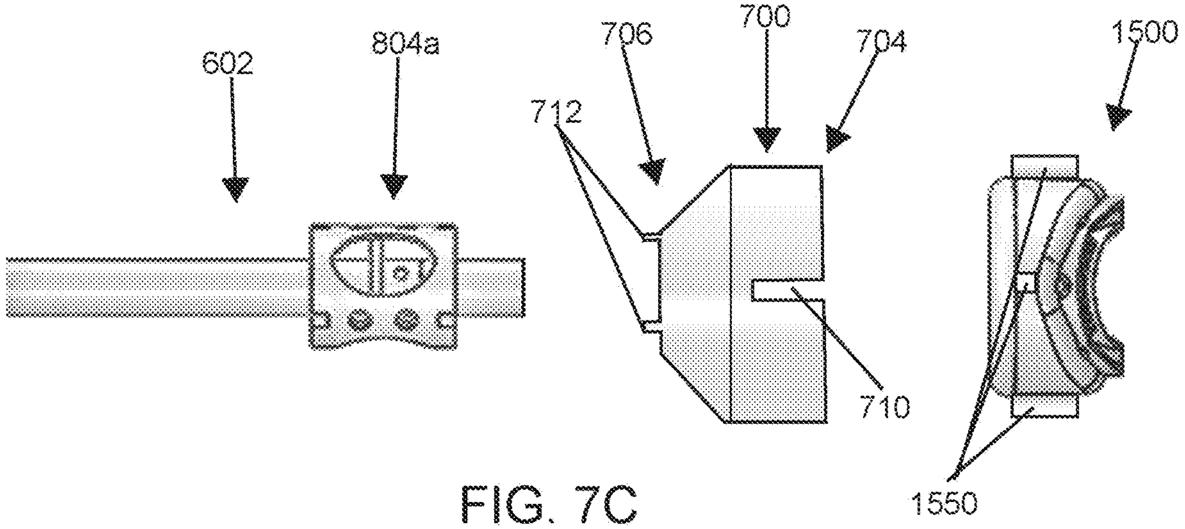
FIG. 7C is an exploded view of the interface between the steering and stator sections.
Figure 7D:
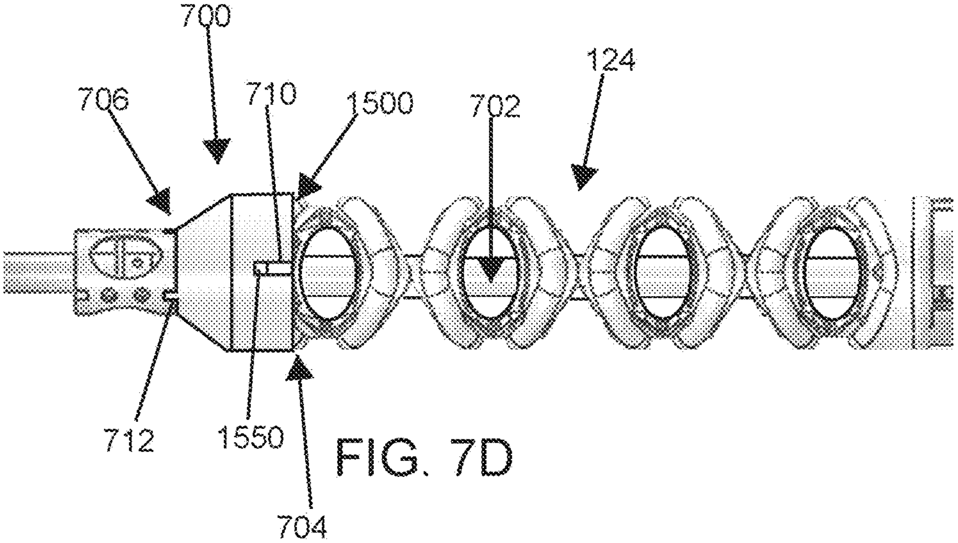
FIG. 7D is a cut-away view of the steering/stator interface region.
Figure 7E:
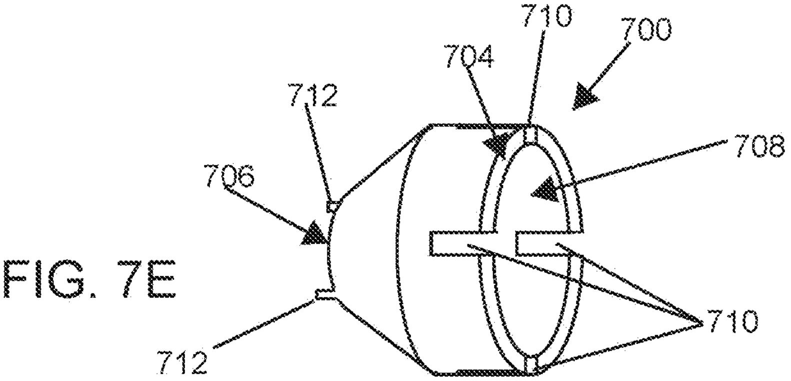
FIG. 7E is a perspective view of the adapter between the steering and stator structures.

The proximal end of the tubular stator body 602 is attached to a flexible tubular drive shaft casing 616 in which a flexible drive shaft resides. The drive shaft casing 616 may be located within one or more steering and/or positioning assemblies 124, 126, 128 that may be provided in the delivery system 100. In this particular embodiment, a proximal steering assembly 124 is directly coupled at its distal end to a proximal end of a catheter extension assembly 126. In turn, the distal end of the catheter extension assembly 126 is directly coupled to a distal steering assembly 128. The drive shaft casing 616 may also act as a torque tube to resist rotation of the stator body 602 as the rotor shaft is rotated. The drive shaft casing 616 may comprise, for example, a helical hollow strand torque tube. In other examples, however, as depicted in FIGS. 7A to 7D, the stator body 602 may be attached or coupled to the proximal steering assembly 124, without the drive shaft casing. In this case, the structure of the proximal steering assembly 124 serves to resist rotation of the stator body 602 as the rotor shaft 702 is rotated, as no torque tube or drive shaft casing is provided. The stator body 602 may be inserted and/or directly welded to the distal segment of the steering assembly, such as the central opening 1530 of the exemplary distal segment 1500 depicted in FIGS. 15A to 15L. In other variations, as depicted in FIGS. 7B to 7E, an adapter 700 may be used to augment the attachment between the stator body 602 and the steering assembly 124. The adapter 700 may comprise a tubular, frusto-conical or ring shape that is configured to engage and mechanically couple to the stator body 602 and steering assembly 124 at locations about the periphery of these structures, which may better resist the torque forces by extending the torque arm distance from the central longitudinal axis of the delivery system. In the particular example depicted in FIGS. 7C to 7E, the adapter 700 comprises a steering end 704, a stator end 706, and a cavity 708 therebetween to receive the stator body 602 and the distal segment 1500 of the steering assembly 124. Each end 704, 706 of the adapter may further comprise one or more mechanical interfaces 710, 712, respectively, to increase the mechanical interfit of the components. The mechanical interfaces 710, 712 may comprise openings, recesses, slots, flanges and/or tabs that form a mechanical interfit with complementary structures located on the stator and/or steering assembly. These may include end openings 830*a* of the stator proximal stator housing 804*a*, or optional complementary structures such as peripheral flanges 1550 that may be provided on the distal segment 1500 of the steering assembly, as depicted in FIG. 7C. These interfit structures may be provided in addition to any bonding or welding provided between the stator body, adapter and distal segment. Examples of the steering and extension assemblies are described in greater detail below.

Figure 8A:
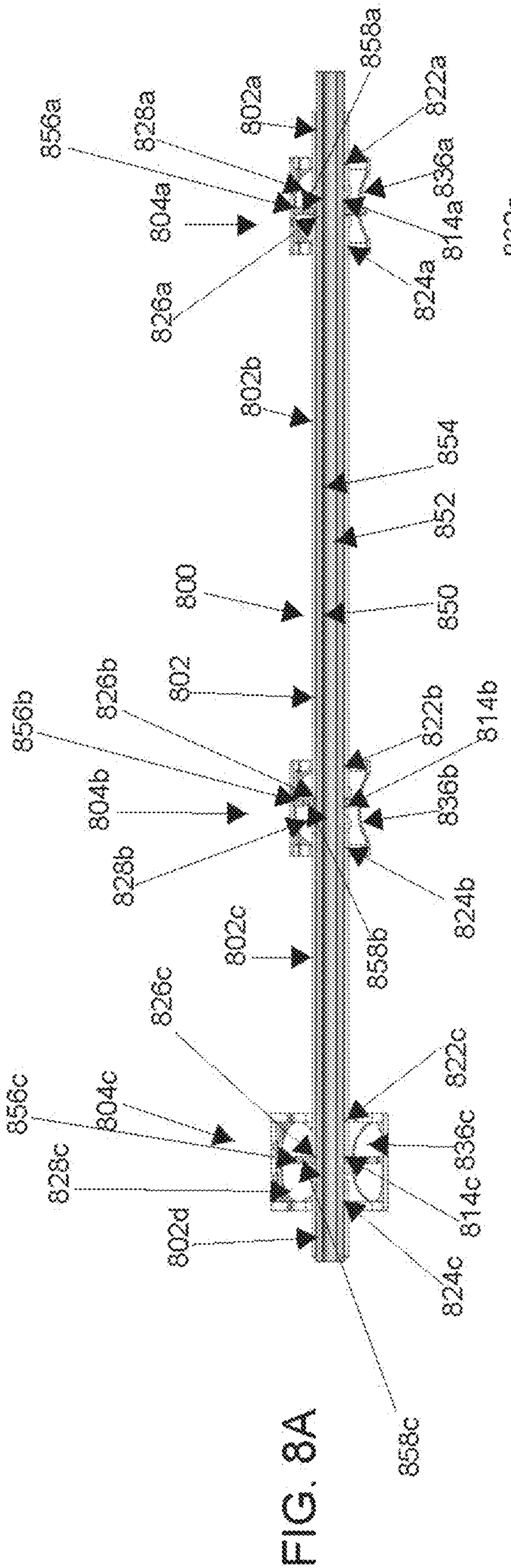
FIGS. 8A and 8B are a side cross sectional views of the rotor and stator region of the delivery system, without and with an exemplary stent structure, respectively.
Figure 8B:
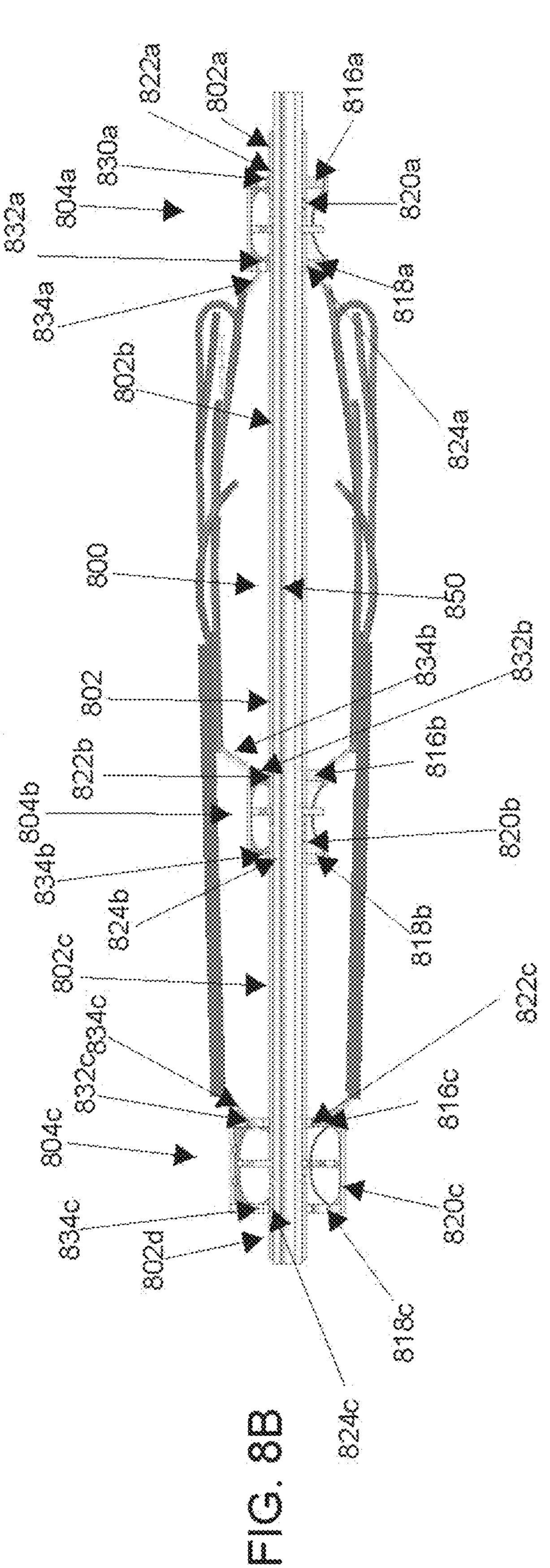
Figures 9A, 9B, 9C, 9D, 9E, 9F:
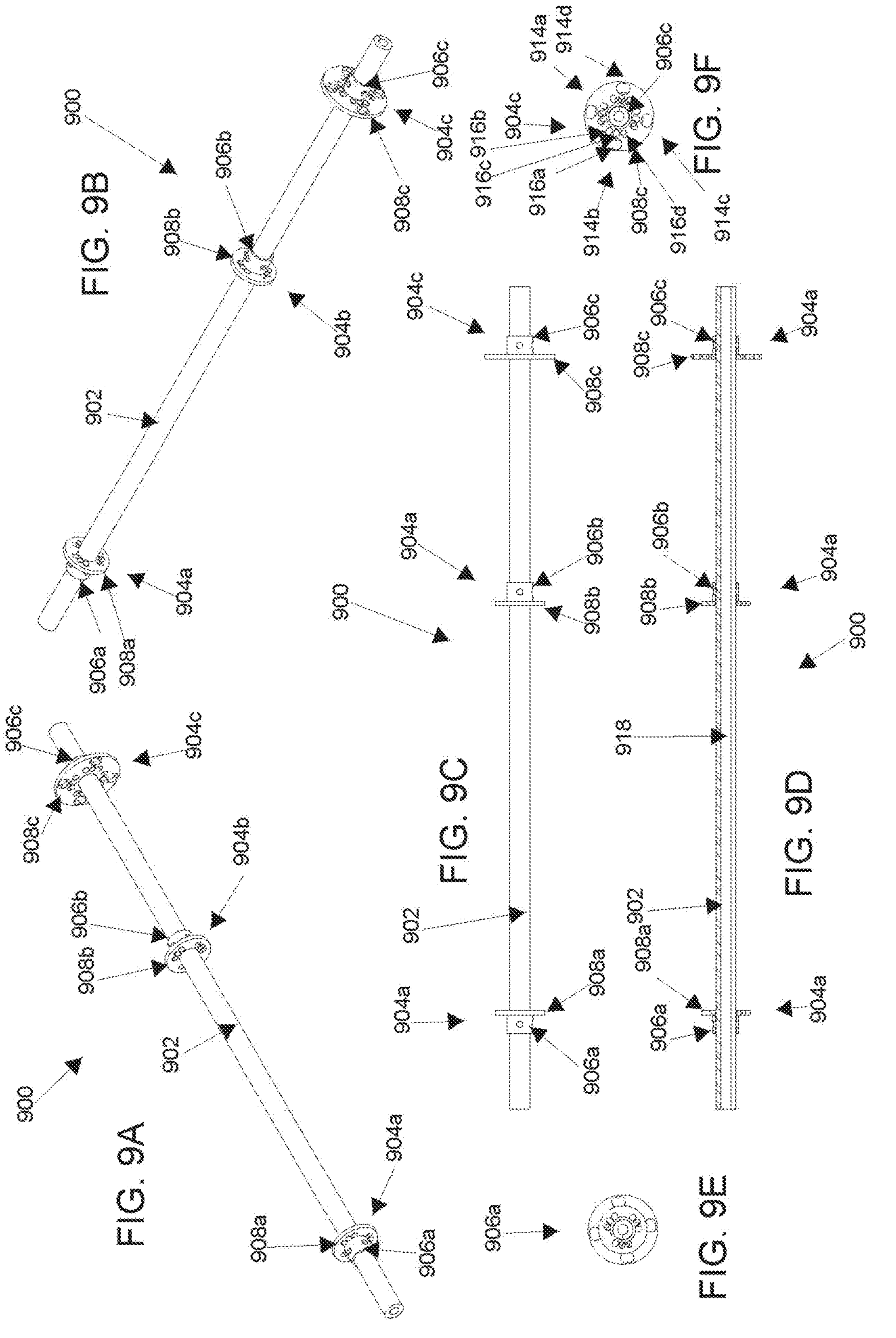
FIGS. 9A and 9B are front and rear perspective views of the rotor shaft.
FIGS. 9C and 9D are side elevational and side cross-sectional views of the rotor shaft in FIGS. 9A and 9B.
FIGS. 9E and 9F are front and rear elevational views of the rotor shaft in FIGS. 9A and 9B.

Referring now to FIGS. 8A and 8B, exemplary embodiments of a stator assembly 800 and a rotor assembly 850 are depicted in greater detail. The stator assembly 800 comprises a tubular stator body 802, comprising a plurality of tubular body segments 802*a-d* that are connected by stators 804*a-c*. The lengths of the segments 802*a-d* may be the same or different. In this particular embodiment, the end segments 802*a*, 802*d* have a similar length, while the middle segments 802*b*, 802*c* are each longer than the end segments 802*a*, 802*d* and with the proximal middle segment 802*b* having a greater length than the distal middle segment 802*c*. The segments 802*a-d* form a longitudinal lumen 812 along the length of the stator assembly 800 in which the rotor assembly 850 resides.

Each of the stators 804*a-c* comprises a housing that is generally cylindrical in shape, but may also be configured with other three-dimensional shape shapes, e.g. frustoconical, square box, rectangular box, trapezoidal box, etc. Each stator 804*a-c* comprises a proximal end wall 816*a-c*, a distal end wall 818*a-c*, and a lateral wall 820*a-c*. The proximal end walls 816*a-c* and distal end walls 818*a-c* may include a central opening 822*a-c*, 824*a-c*, respectively, configured to receive a stator body segment 802*a-d*, and an inner opening 826*a-c* through which the rotors of the rotor assembly may project from and into the stator cavities 828*a-c*. As depicted in FIG. 8B, the proximal and distal end walls 816*a-c*, 818*a-c* may also comprise peripheral openings 830*a-c*, 832*a*-c through which the tension lines 834*a-c* may be routed through. The lateral walls 820*a-c* may also comprise one or more lateral openings 836*a-c*.

The rotor assembly 850 comprises a rotor shaft 852 with a longitudinal lumen 854 through which a guidewire may be inserted. Spaced apart on the rotor shaft 852 are rotors

856*a-c* that extend out radially from the rotor shaft 852 at the stator body gaps 814*a-c* located between the stator body segments 802*a-d*. The rotors 856*a-c* may comprise a circular shape as depicted herein, but in other variations, may comprise an oval shape or polygonal shape. Each of the rotors 856*a-c* may comprise one or more attachment structures 858*a-c* for attaching a tension line 834*a-c*. The attachment structures 858*a-c* may comprise an opening through the rotor 856*a-c* that allows the tension line 832*a-c* to be wound around or to be unwound from the rotor 856*a-c*, rotor shaft 852 or tubular body segment 802*b*, 80*c*. The radial distance from the longitudinal axis of the delivery system to the attachment structures 858*a-c* and/or to the peripheral end openings 830*a-c*, 832*a-c* may be configured, depending on the implant configuration and/or angle of the tension lines 832*a-c* as they exit the peripheral end openings 830*a-c*, 832*a-c* during implant expansion. Each of the rotors 856*a-c* and stators 804*a-c* may have more than one tension line 832*a-c* attached to it, and each of the tension lines may have a different length. For example, rotor 856*c* may have four tension lines 832*c* attached, which each tension line 832*c* exiting the stator 804*c* at a different end opening 830*c* and spaced 90 degrees apart from each other, while rotors 804*a* and 804*b* may be configured with three tension lines 832*a*, 832*b* each, spaced 120 degrees apart but wherein tension lines 832*a* and 832*b* have a different line length, which may result from different degrees of expansion along the implant. In other variations of the delivery system, the one, two or four rotors/stators may be provided, and the number of tension lines for each rotor/stator may be one, two, five, six, seven, eight, nine, twelve or any range therebetween. The lengths of each tension line or tension loop may be 10 mm to 70 mm, 15 mm to 60 mm, or 20 mm to 40 mm. The diameter of a stator body may be in the range of 2 mm to 8 mm, 3 mm to 5 mm or 6 mm to 8 mm. As noted previously, the distal stator may comprise different diameter than the other stators, in the range of 5 mm to 10 mm, 6 mm to 8 mm, or 6 mm to 7 mm. The proximal and/or middle stator may comprise a diameter in the range of 3 mm to 8 mm, 4 mm to 6 mm, or 4 mm to 5 mm. The radial distance from the longitudinal axis to the attachment structure of a rotor may be in the range of 0.7 mm to 3.75 mm, 1 mm to 2.9 mm, or 1.5 mm to 2 mm.

FIGS. 9A to 9F illustrates another variation of a rotor assembly 900, comprising a tubular shaft 902, a proximal rotor 904*a*, a middle rotor 904*b* and a distal rotor 904*c*. Each rotor 904*a-c* comprises a mount, ring or tubular body 906*a-c* to couple to the shaft 902, with a disc-like flange 908*a-c*. Each mounting ring 906*a-c* includes a central opening 910*a-c* to receive the shaft 902 and may include one or more optional sidewall openings 912*a-c* which may be used to facilitate the bonding of the rotors 904-*ac*. The distal rotor 904*c* has a larger flange 908*c* than the flanges 908*a*, 908*b* of the proximal and middle rotors 904*a-b*. The larger size allows a greater number of tension lines to be attached. Each flange 908*a-c* comprises one or more attachment structures for the attachment of the tension lines. The attachment structures may comprise projections or openings on the flange 908*a-c*. In the particular embodiment depicted in FIGS. 9A to 9F, the distal flange 904*c* comprises four sets of apertures 914*a-d*, with each set comprising a larger oblong opening 916*a* along the outer diameter of the flange 908*c*, and along with three smaller openings 916*b-d* along the inner diameter of the flange 908*c*, with the larger opening 916*a* symmetrically radially aligned with the smaller openings 916*b-d*. Each of the aperture sets 914*a-d* is equally spaced 90 degrees apart around the flange 908*c*, but in other examples may have a non-uniform spacing, or spacing that is bilaterally symmetrical but not circumferentially symmetrical.

In this particular embodiment, the proximal and middle flanges 908*a*, 908*b* of the rotors 904*a*, 904*b* have the same shape but are mounted on the rotor shaft 902 with their mounting rings 906*a*, 905*b* away from the other, with the proximal rotor mounting ring 906*a* located proximal of its flange 908*a*, while the middle rotor 904*b* has a mounting ring 906*b* that is distal to its flange 908*b*. The distal mounting ring 906*c* is also distal to its flange 908*c*. In other examples, however, one or more of the rotors may have the opposite orientation. In still other variations, the rotor may comprise a different configuration, e.g. with two flanges, or two or more mounting ring sections on each side of each flange.

The length of the rotor shaft 902 may be in the range of about 10 mm to 80 mm, 20 mm to 65 mm or 35 mm to 45 mm. The distance between any two adjacent rotors may be in the range of about 5 mm to 60 mm, 10 mm to 50 mm or 20 mm to 30 mm. In embodiments with a middle rotor, the distance between the proximal rotor and middle rotor may be in the range of about 5 mm to 40 mm, 7 to 30 or 10 mm to 15. The distance between the middle rotor and the distal rotor may be in the range of about 25 mm to 30 mm, 20 mm to 40 mm or 10 mm to 60 mm. The thickness of each rotor may be in the range of about 0.35 mm to 0.40 mm, 0.3 mm to 0.5 mm or 0.2 mm to 0.6 mm.

The outer diameter of the rotor shaft 902 may be in the range of about 1 mm to 3 mm, 1.2 mm to 2 mm or 1.4 mm to 1.8 mm, while the diameter of the internal lumen 918 of the rotor shaft 902, if provided, may be in the range of about 0 mm to 1.5 mm, 0.5 mm to 1.2 mm or 0.80 mm to 1.0 mm. The diameter of the mount or ring 904*a-c* may be in the range of about 1.2 mm to 3.5 mm, 1.6 mm to 3.0 mm or 2.0 mm to 2.4 mm. The diameter of the rotor flange 908*a-c* may be in the range of about 2 mm to 9 mm, 4 mm to 7 mm or 2 mm to 5 mm, 3.5 mm to 4.5 mm, 5 mm to 6 mm, 4.5 mm to 7 mm.

In the exemplary flanges or rotor plates 908*a-c* of FIGS. 9A to 9F, the plates 908*a-c* comprise a closed circular perimeter with a three or four groups of tension line engagement structures, comprising circular or oval closed apertures located therethrough for attachment to a tension line. In other variations, however, the rotor plate may comprises different engagement structures, including but not limited one or more open perimeter apertures which are confluent with the perimeter of the rotor plate, and/or one or more projections. FIGS. 37A to 37D depict various alternative rotor plates that may be used with any of the various delivery system embodiments described herein.

Figure 37A:
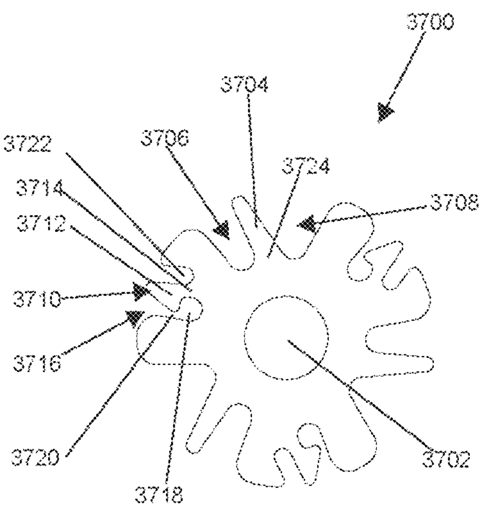
FIGS. 37A to 37D depicts various embodiments of a rotor flange that may be used with the rotor assembly.

FIG. 37A depicts an embodiment of a rotor plate 3700 comprising a central opening 3702 for mounting to the rotor shaft, and also three symmetric groups of attachment structures. Here, the attachment structures of each group include a first elongated, straight projection 3704, which has a length in the range of about 2 mm to 15 mm, 2 mm to 10 mm, or 3 mm to 6 mm, or a length that is in the percentage range relative to the radius (center to maximum perimeter distance) in the range of about 10% to 80%, 20% to 70%, or 25 to 60%. The projection may also be characterized by the absolute distance from center of the plate to the base 3724 of the projection 3704, or the relative location of the base of the projection, as a percentage of the radial distance from the center to the maximum perimeter distance of the rotor plate. This relative location may be in the range of 10% to 90%, 20% to 80%, 40% to 80%, for example. The absolute distance may be in the range of 1 mm to 12 mm, 2 mm to 8 mm, or 2 mm to 6 mm, for example. The longitudinal axis of the projection may be aligned, parallel or at an angle to a radius or diameter of the rotor plate intersecting the center of the base of the projection. In the example depicted in FIG. 37A, the projection 3704 may be at an offset angle to the radius or diameter of the rotor plate 3700 intersecting the base of the projection, in the range of 0 to 90 degrees, 15 to 45 degrees, 15 to 90 degrees, or 25 to 45 degrees. In still other variations, the projection may be at an offset angle in the range of between 91 and 180 degrees, i.e. projecting radially inward from the perimeter toward the center of the plate. In some variations, the angle of the projection with an offset from the radius or diameter of the plate may facilitate retention/engagement of a tension line in one rotational direction, and release/disengagement of a tension in in the other rotational direction. The straight projection 3704 is flanked on each side by gaps 3706 and 3708 that is open or confluent with the perimeter of the rotor plate 3700. In this particular example, the gaps 3706 and 3708 have different shapes and sizes, with gaps 3706 being smaller in size than gaps 3708. The one or both lateral sides of the gaps 3706 and 3708 may also be aligned, parallel or at an angle to the closest radius or diameter of the rotor plate 3700. Rotor plate 3700 also comprises a second set of projections 3710 which comprise a one-sided barb shape with a triangular enlarged region or head 3712 and a narrower region or neck 3714. Likewise, the gap 3716 on one side of the projections 3710 comprises an enlarged region or head 3718 and a narrower region or neck 3722, and gap 3722 of uniform width on the other side of the projection 3718.

Figure 37B:
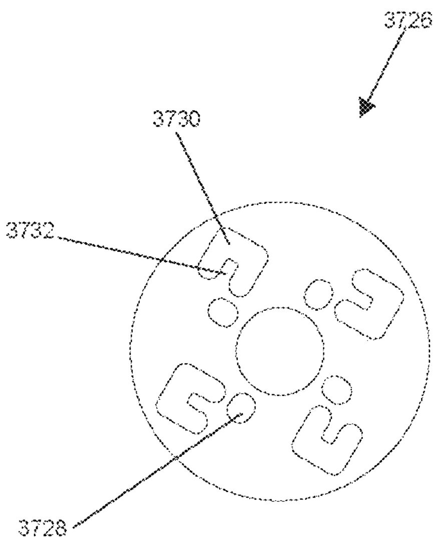

FIG. 37B depicts another variant of a rotor plate 3726, comprising a circular perimeter and four pairs of engagement structures spaced around the plate 3726. Here, the engagement structures include a closed smaller aperture 3728 and a closed larger aperture 3730 that partially surrounds a projection 3732. Here, the smaller aperture 3728 is located closer to the central aperture 3734 of the plate 3726, but in other variations may be equidistant or farther than the closest larger aperture 3730. In this particular variant, the smaller aperture 3728 may be circular or oval, and the larger aperture 3730 or the aperture with the projection may polygonal or square, though in still other variations, each of the apertures may instead be circular, oval, polygonal, square, rectangular, and the like, and/or may be closed or open in configuration, relative to the perimeter of the plate. The projection 3732 may comprise a length that that may be similar to the length as describes for projections of FIG. 37A, or may comprise a length that extends into the center of the surrounding aperture, or a length that is a percentage of the distance from the base of the projection 3732 to the farthest edge of the surrounding aperture 3730 along the longitudinal axis of the projection 3732. This percentage may be in the range of 10% to 90%, 20% to 80%, 30% to 70% or 40% to 60%, for example. As depicted, the offset angle of the projection 3732 is about 45 degrees to the radius or diameter of the rotor plate that intersects the base of the projection 3732, but in other variations, the offset angle may be in the other ranges as described above. The larger aperture 3730 may be characterized as comprising a U-shape surrounding the projection 3732, or may be characterized nominally to its general shape notwithstanding the projection 3732, e.g. a square with rounded corners. In other variations, the larger aperture may be rectangular, polygonal, circular or oval, for example.

Figure 37C:
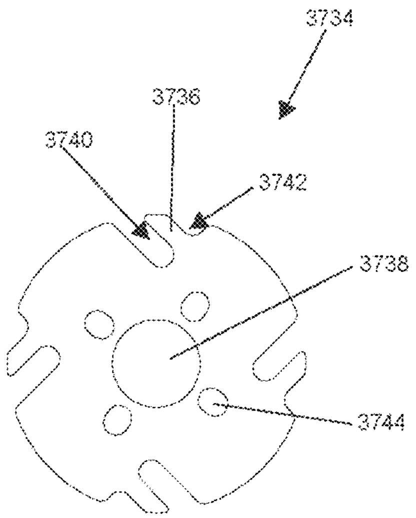
Figure 37D:
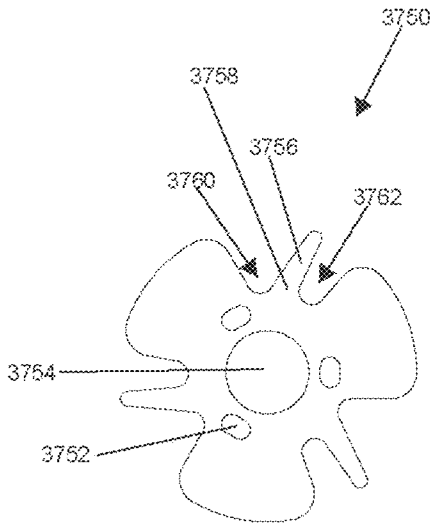

FIGS. 37C and 37D depict still other variations of a rotor plate, respectively, comprising a single configuration of projections, compared to FIG. 37A. In FIG. 37C, the base of the projections 3736 of the rotor plate 3734 lies closer to the perimeter of the plate 3734 than the center opening 3738, but extends to an asymmetric distal end with a gap 3740 on one side of the projection 3736 that has a region of uniform width and extends to the plate center less than 50% of the radius of the plate, and a shallow gap 3742 with v-shaped sides on the other side of the projection 3736 that extends less than 20% of the radial distance toward the center. Also provided in plate 3736 are a group of closed oval apertures 3744 that are close to the center opening 3738. In In FIG. 37D, the rotor plate 3750 comprises three oblong closed apertures 3752 near the center opening 3754, along with three projections 3756 with a base 3758 that is in the range of about 3 mm to 10 mm from the center opening 3754, and has a length of 3 mm to 8 mm, and has angle of about 10 degrees to 45 degrees from the radius or diameter intersecting the base 3758. The projections 3756 each may have an average width in the range of 0.5 mm to 3 mm. In other variations, the distance of the base for the center opening may alternatively be in the range of 4 mm to 10 mm, or 5 mm to 10 mm, comprise a length of 4 mm to 8 mm, or 3 mm to 5 mm and/or have an angle in the range of 10 degrees to 30 degrees, or 15 degrees to 40 degrees. Flanking the projection are a larger gap 3760 with acutely angled lateral sides, and a smaller gap 3762 with generally parallel sides.

Referring now to FIGS. 10A to 10F, the stator assembly 1000 may comprise a tubular stator shaft 1002, which itself may comprise one or more tubular shaft segments 1002*a-d*, which are connected in a spaced apart fashion by corresponding proximal, middle and distal stator housings 1004*a-c*, respectively. In this particular embodiment, the proximal and middle stator housings 1004*a*, 1004*b* have the same size and configuration, while the distal stator housing 1004*c* comprises a larger size and a different configuration. Each stator 1004*a-c* may comprise a generally cylindrical shape, with a proximal or first end wall 1006*a-c*, distal or second end wall 1008*a-c* and cylindrical or lateral wall 1010*a-c* therebetween, but in other variations may comprise a frustoconical shape, oval or oblong shape, square box shape, rectangular box shape, triangular box shape or other polygonal box shape. The end walls 1006*a-c*, 1008*a-c* each comprise three or four oval or oblong openings 1014*a-c*, 1016*a-c*, respectively, that are equally spaced around the center openings 1018*a-c*, 1020*a-c* in which the stator shaft segments 1002*a-d* are located. The cylindrical walls 1010*a-c* of the housings 1004*a-c* comprise three or four larger oval openings 1018*a-c* with two longitudinally aligned smaller circular openings 1020*a-c* located between each of the larger oval openings 1018*a-c*. The number of openings may correspond with the number tensioning members provided at each location, e.g. three tensioning members at each of the smaller stator housings with three openings, and four tensioning members at the larger stator housing with four openings. The larger oval openings 1018*c* are equally spaced apart at 90 degrees, and each of the smaller pairs of openings 1020*c* are also equally spaced apart at 90 degrees. Of course, in other variations, a different number of the end and cylindrical wall openings may be provided on each wall 1006*a-c*, 1008*a-c*, 1010*a-c*, e.g. one, two, three four, or five of each type of opening, and the openings may or may not equally spaced apart. Each of the stator housings 1004*a-c* is configured with a cavity 1022*a-c* that is of a sufficient size to allow receive and to permit rotation of the corresponding rotor, and manufactured with shaft segment gaps 1024*a-c* to also receive and to permit rotation of the corresponding rotor. The end walls 1006*a-c*, 1008*a-c* and the cylindrical walls 1010*a-c* may also comprise one more projections 1026*a-c* and/or recesses 1028*a-c* to provide a mechanical or friction fit to facilitate assembly of the stator housings 1004*a-c*.

The length of the stator shaft 1002, including the shaft segment gaps 1024*a-c*, may be in the range of about 25 mm to 80 mm, 40 mm to 70 mm or 55 mm to 65 mm. The stator shaft 1002 length may be longer or shorter than the rotor shaft length, and the difference in rotor/stator shaft length may be in the range of about 0.2 mm to 3 mm, 0.4 mm to 2 mm or 0.4 mm to 0.8 mm. The outer diameter of the stator shaft may be in the range of about 1.6 mm to 3.3 mm, 1.7 mm to 3 mm or 1.8 mm to 2.5 mm, while the diameter of the stator internal lumen may be in the range of about 1.6 mm to 3.3 mm, 1.7 mm to 3 mm or 1.8 mm to 2.5 mm. The various distances between the stators may otherwise be similar to the various distance ranges as recited above for the distances for the corresponding rotors. The outer length of the stator housings may be in the range of about 3 mm to 8 mm, 4 mm to 7 mm or 5 mm to 6 mm, and the outer diameters of the stator housings may be in the range of about 4 mm to 5 mm, 6 mm to 7 mm, 2 mm to 8 mm, 5 mm to 9 mm, or 3 mm to 8 mm. The internal cavities of the stator housings may have a length in the range of about 3 mm to 5 mm, 3 mm to 6 mm or 4 mm to 5 mm, and a diameter in the range of about 4 mm to 6 mm, 3 mm to 5 mm, 5 mm to 7 mm, 4 mm to 7 mm, 3 mm to 8 mm, 4 mm to 9 mm. The shaft segment gaps lengths may be in the range of about 1 mm to 4 mm, 1 mm to 3 mm or 1.5 mm to 2.5 mm.

Figures 10A, 10B, 10C, 10D, 10E, 10F:
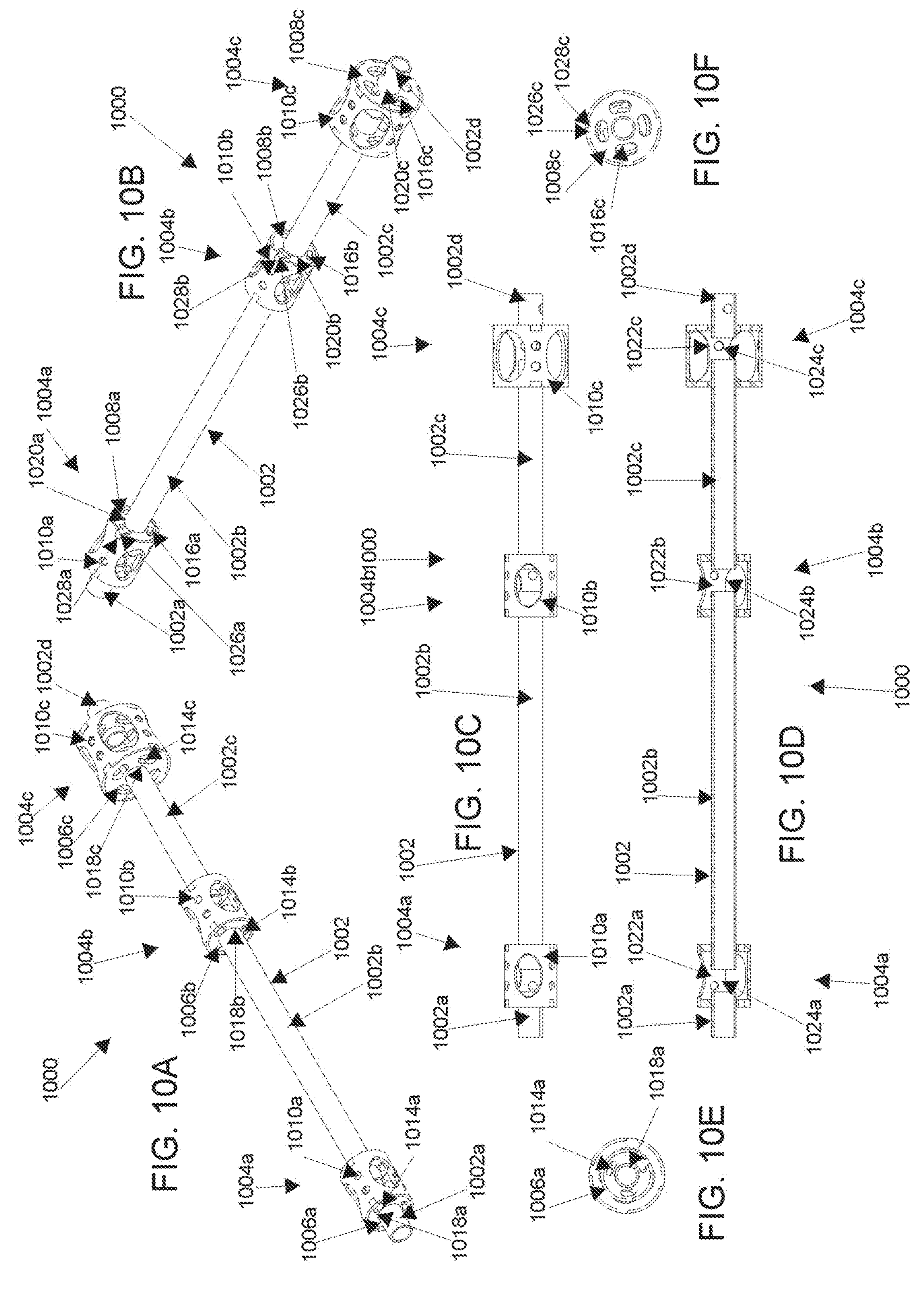
FIGS. 10A and 10B are front and rear perspective views of the stator shaft.
FIGS. 10C and 10D are side elevational and side cross-sectional views of the stator shaft in FIGS. 10A and 10B.
FIGS. 10E and 10F are front and rear elevational views of the stator shaft in FIGS. 10A and 10B.
Figure 10G:
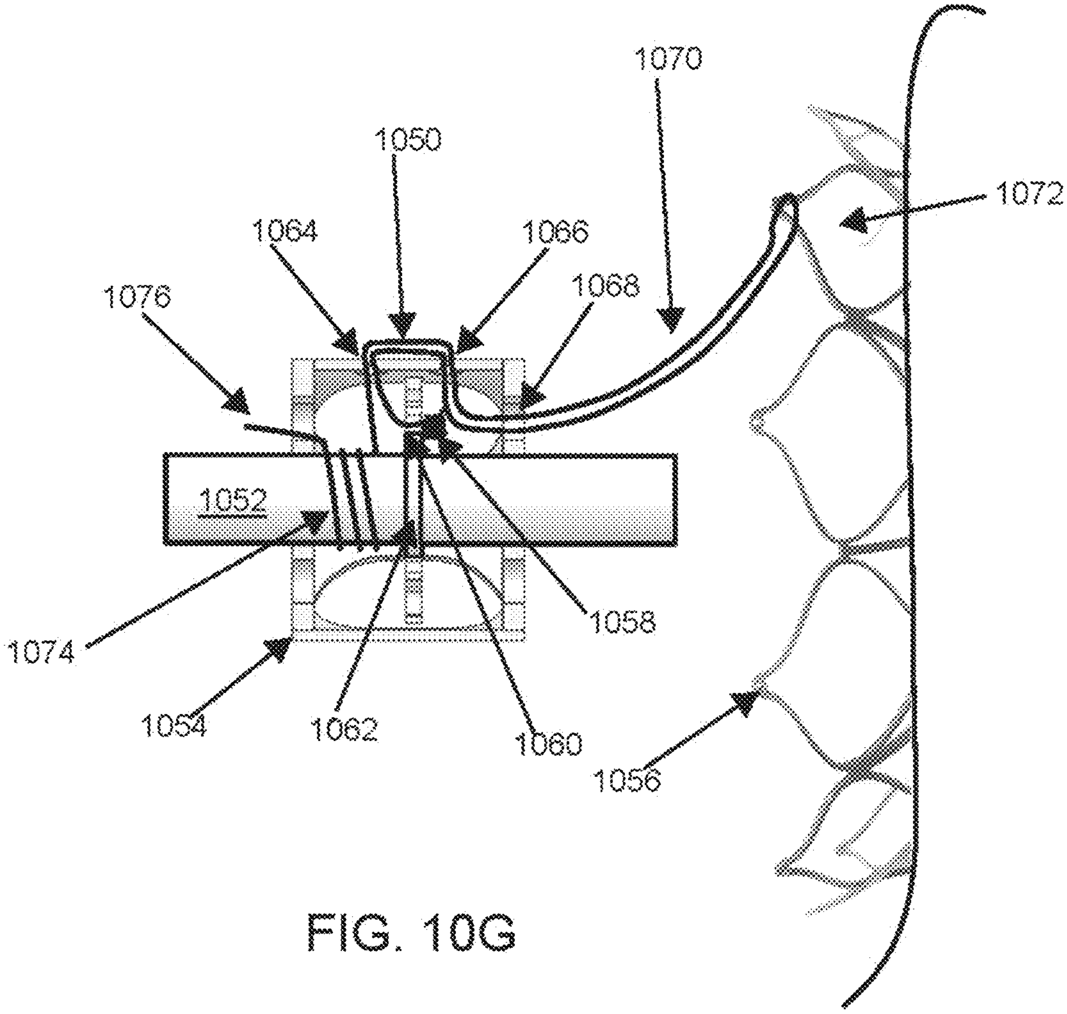
FIGS. 10G and 10H are schematic cutaway views of a rotor/stator structure depicting an exemplary configuration of the routing of a tensioning member in an engaged and released configuration to a rotor/stator and a stent structure.

FIG. 10G is a schematic illustration of the routing configuration for a tensioning member 1050 about a rotor 1052, stator housing 1054 and a stent 1056. For clarity, only one of the multiple tensioning members that would be spaced around at different angular positions of the rotor/stator location is shown. A first end 1058 of the tensioning member 1050 is knotted or otherwise attached to an opening 1060 of the rotor flange 1062 to resist separation from the rotor 1052. The tensioning member 1050 is then routed out of a first stator opening 1064 and into a second stator opening 1066 on the other side of the rotor flange 1062 and out of an end opening 1068 of the stator 1056.

The tensioning member 1050 would then extend out and as a loop segment 1070 through an opening 1072 of the stent 1056, or multiple such openings and then route back into the end opening 1068, the second stator opening 1066 and the first stator opening 1064. The tensioning member 1050 would then be wrapped around the rotor 1052 two, three, four, five or more times forming coils 1074, along with the other tensioning members at that location, even wrapping around itself and/or other tensioning members. This number of wrapped loops or coils provides sufficient frictional resistance so to resist unwrapping or slippage from the expansion force of the stent 1056, depending on the tensioning member material. The other, free end 1076 of the tensioning member 1050 may extend out of the opposing end opening 1076 of the stator 1054.

Figure 10H:
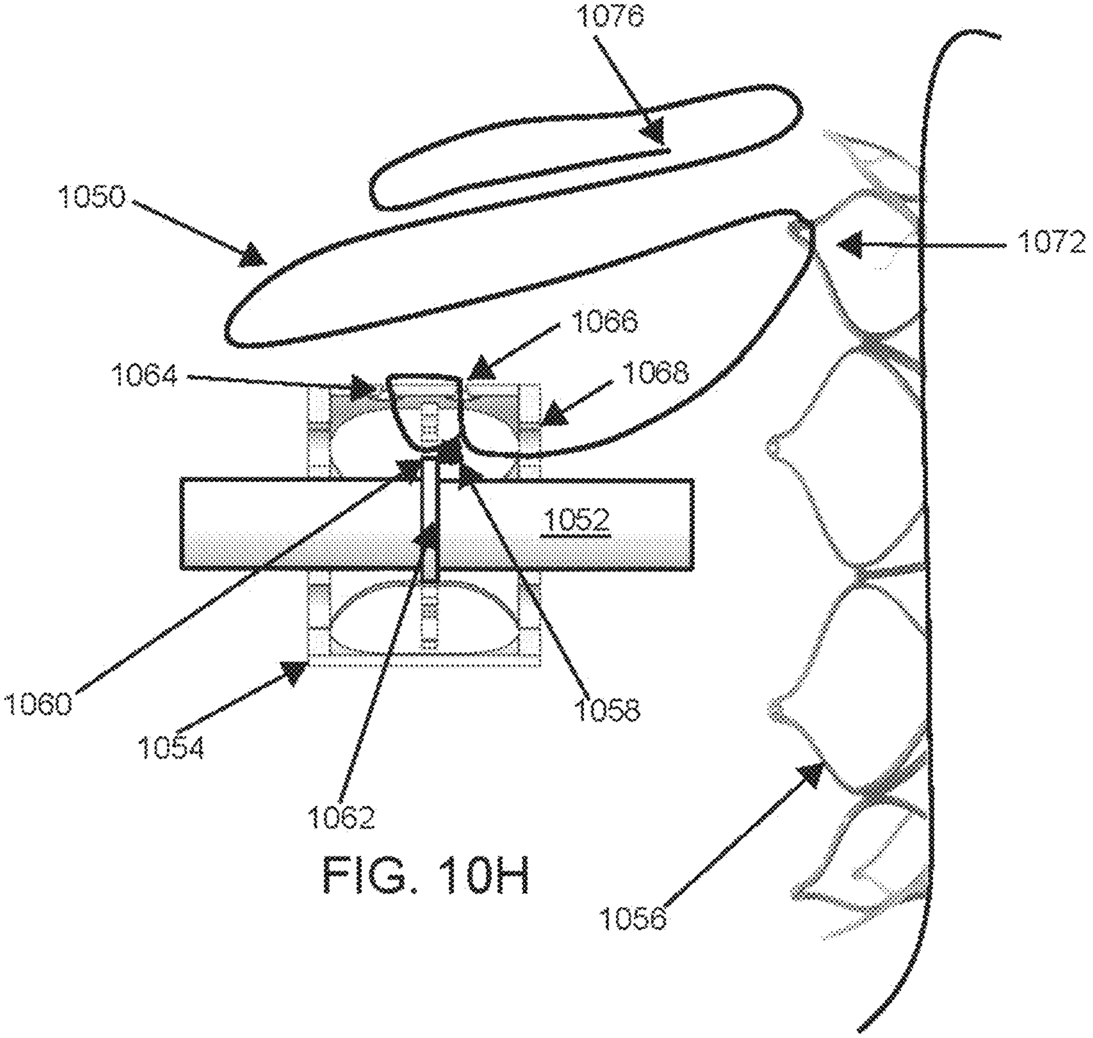

When the stent 1056 is in a collapsed state, most of the tensioning member 1050 will be within the stator 1054 or in contact with the stator 1054, wrapped around the rotor 1052. As the rotor 1052 is rotated to unwind or unwrap the tensioning member 1050 from the stator 1052, the tensioning member 1050 will slide along its routing path to extend the loop segment 1070 through the end opening 1068, which permits the stent to further expand. In FIG. 10H, as the tensioning member 1050 further unwraps from the rotor 1052, the friction between the rotor 1052 and the coils 1074 of the tensioning member 1050 will decrease to a point where the free end 1076 of the tensioning member 1050 is able to disengage and be pulled out of from the rotor 1052 and out of the stator 1054. Further rotation of the rotor 1052 will begin to recoil or rewrap the tensioning member 1050 beginning at the attached or knotted end 1058 of the tensioning member 1050 until the free end 1076 is pulled out of the stent 1056. In other variations, as long as the free end 1076 has been released from the rotor 1052 and stator 1054, the further rotation of the rotor 1052 is not performed to partially recoil or fully recoil the tensioning member 1050 before the delivery system is withdrawn. Instead, the tensioning member 1050 can be fully separated from the stent 1056 by withdrawing the delivery system with the tensioning member 1050 still extending out from the stator 1054.

Figure 10I:
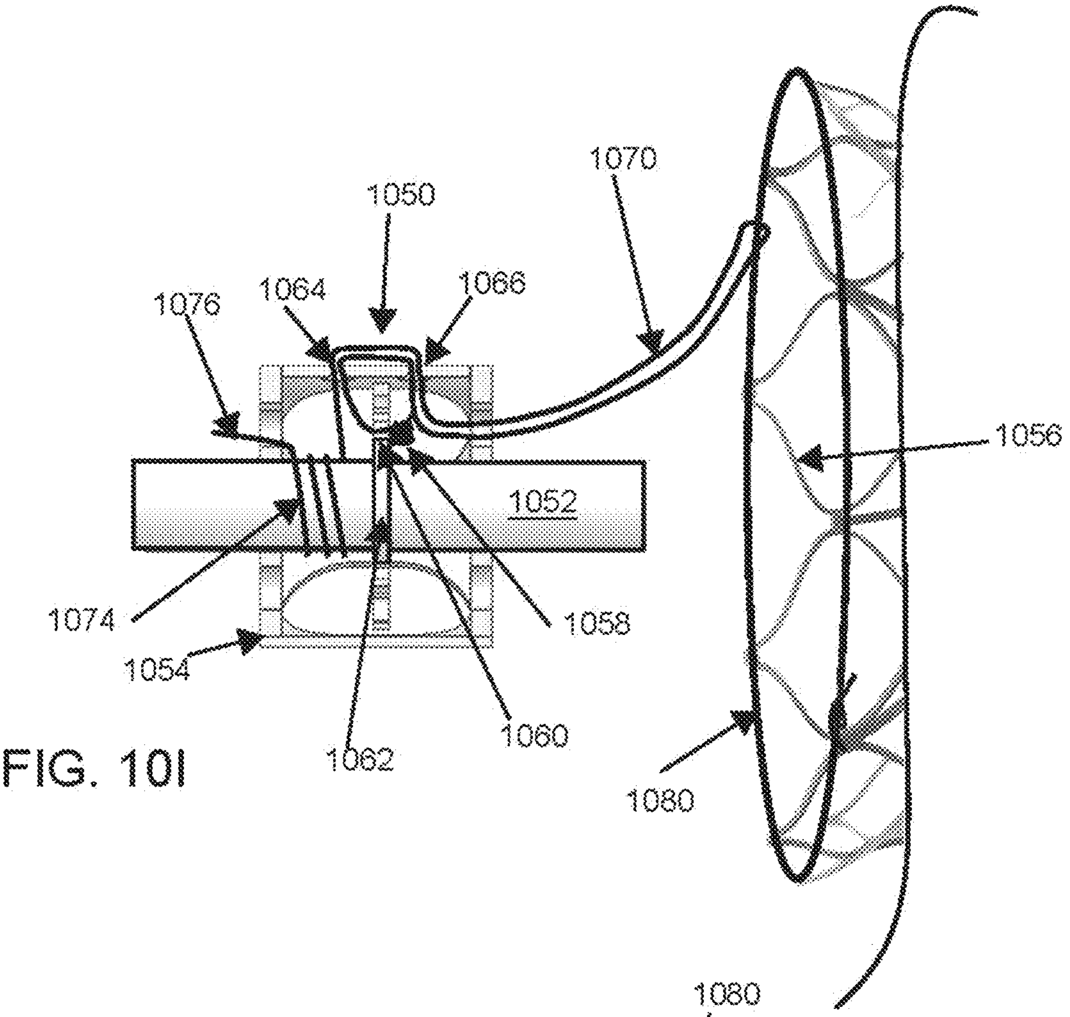
FIGS. 10I and 10J are schematic cutaway views depicting another configuration of the routing of a tensioning member to a rotor/stator structure and a suture loop attached to a stent structure, in an expanded and collapsed state.
Figure 10J:
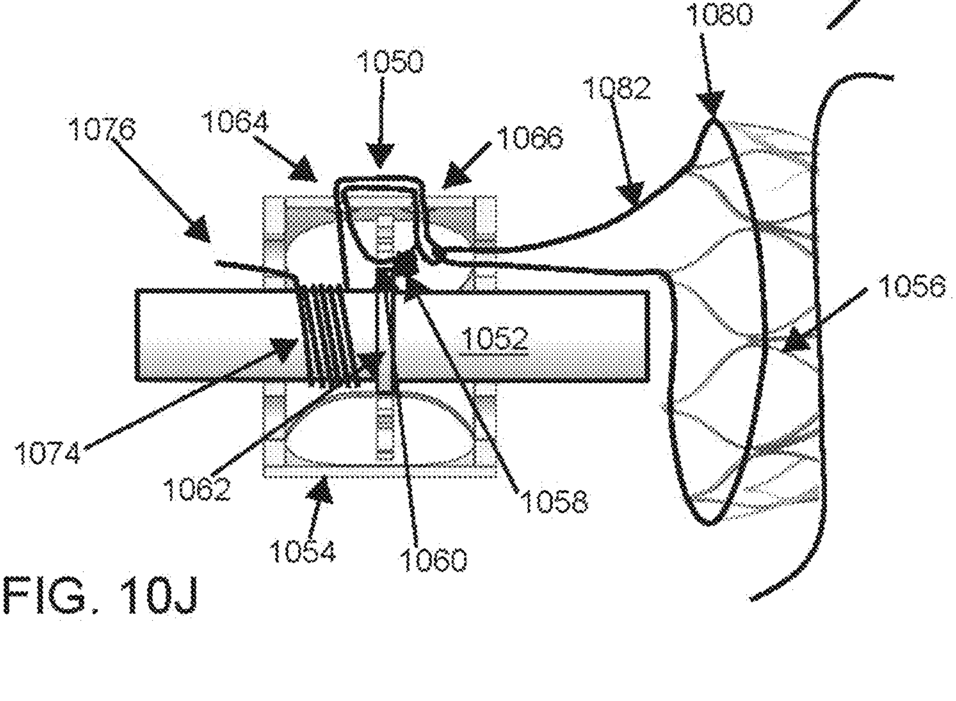

FIGS. 10I and 10J depicts another variation of the attachment of the tensioning member 1050 to the stent 1056. This variation is similar to the prior variation in FIGS. 10G and 10H, except that instead of the tensioning member 1050 looping through an opening 1072 of the stent 1056, the stent 1056 further comprises a flexible suture or attachment loop 1080 located around one or more circumferences of the stent 1056. The attachment loop 1080 is permanently attached to the stent 1056 and is left with the stent 1056 after the delivery system is withdrawn. The attachment loop 1080 may comprise the same or different material as the tensioning member 1050. The tension members and the attachment loop may comprise a monofilament or a multifilament man ultra high molecular weight polyethylene, including but not limited to nylon, polyethylene, FORCE FIBER® suture (TELEFLEX MEDICAL, Gurnee, IL), liquid crystal polymer suture, including but not limited to VECTRAN™ (KURARAY AMERICA, Tokyo, Japan), braided aramid fiber, including but not limited to KEVLAR® (DUPONT™, Wilmington, DE), multi-strand metal wire, including but not limited to stranded stainless steel wire rope and tungsten wire rope, for example. The attachment loop 1080 may be configured with a net length that is or corresponds to the circumference of the stent 1056 when at its full expansion size, within 5%, 10%, 15%, 20% or 25% of the circumference. As shown in FIG. 10J, as the stent collapses into its delivery configuration, the a portion 1082 of the attachment loop 1080 that is attached to the loop 1070 of the tensioning member 1050 is able to be pulled away from the stent 1056 and can invaginate or be pulled into the stator housing 1056 or even coiled around the rotor 1052. In some variations, the use of an attachment loop 1080 on the stent 1056 may provide a more predictable coiling, release or other interactions with the tensioning member 1050, by allowing the tensioning member 1050 to slide along the circumference of the loop, rather than restricting its attachment at a specific location of the stent 1056. This may reduce the risk of unintended snagging or cutting or the tensioning members during loading or delivery, and/or uneven tensioning forces between different tensioning members during loading or delivery.

Figure 28A:
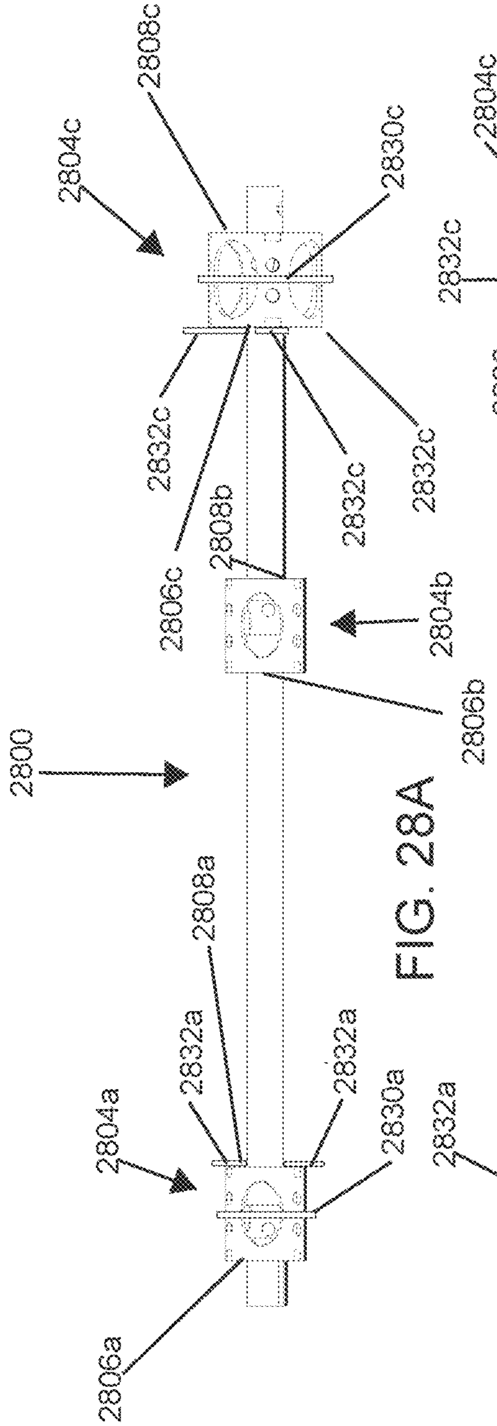
FIGS. 28A to 28C depicts a stator shaft with optional wire loop structures to alter the tension member routing.
Figure 28B:
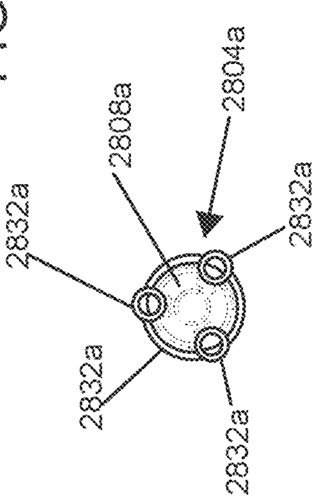
Figure 28C:
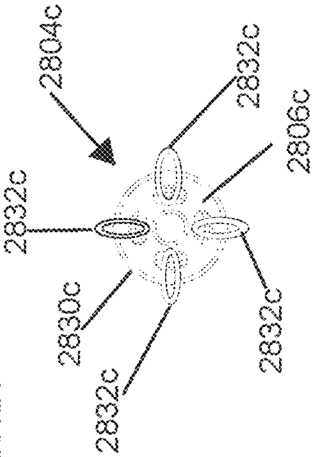

In some embodiments, to further configure the tension member routing, one or more control structures may be provided on the stator assembly. The control structures may comprise one or more wire loops that are welded to the stator housing for the tension members to slide over during loading and delivery. The wire loops may provide more rounded sliding surfaces for the tensioning members to reduce friction and suture degradation, may reduce the number of corners that the tensioning members are routed around, and may and/or can be used to alter the angle of the tensioning member between the stator assembly and the stent structure, by altering the location and distance from which a tensioning member extends from the stator assembly. FIGS. 28A to 28C depicts one embodiment of a stator shaft 2800 that is similar to stator shaft 1000 in FIGS. 10A-10J but wherein one or more stator housings, such as stator housings 2804*a* and 2804*c* each comprises a main control ring 2830*a*, 2830*c* that provides a curved structure to facilitate smoother sliding of the tension members as the tension members exit the circumferential wall of the stator housings 2804*a*, 2804*c*. Rather than routing the tension members through the end openings of the stator housings 2804*a*, 2804*c*, a plurality of secondary control rings 2832*a*, 2832*c* may be provided about the end walls 2806*a-c*, 2808*a-c* of the stator housings 2804*a*, 2804*c* so that the tension members are kept closer to the stator housing and has a smooth sliding surface as the tension members extend out toward the stent 285.

Figure 28D:
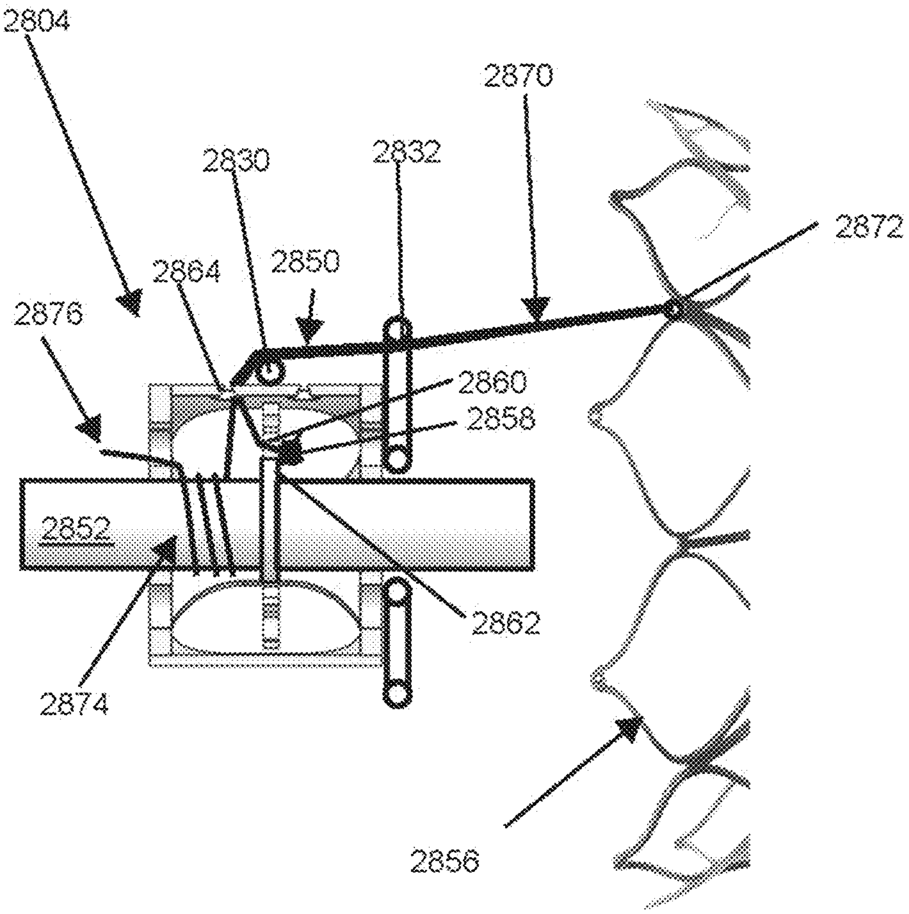
FIG. 28D is a schematic cutaway view of the stator shaft in FIGS. 28A to 28C in an assembly and tension member routing

FIG. 28D depicts one exemplary routing of a tension member 2850 with a stator housing 2840 that includes the main and secondary control rings or structures 2830, 2832. As with the earlier depictions, for clarity, only one of the multiple tensioning members that would be spaced around at different angular positions of the rotor/stator location is shown. A first end 2858 of the tensioning member 2850 is knotted or otherwise attached to an opening 2860 of the rotor flange 2862 to resist separation from the rotor 2852. The tensioning member 2850 is then routed out of a first stator opening 2864 and over the main control ring 2830 and then through the corresponding secondary control ring 2832. The tensioning member 2850 would then extend out and as a loop segment 2870 through secondary control ring 2832 to an attachment site 2872 on the stent 2856, and then loop back through the secondary control 2832 over the main control ring 2830 and back through the first stator opening 2864 and wound around the rotor 2852 two, three, four, five or more times forming coils 2874, along with the other tensioning members at that location, even wrapping around itself and/or other tensioning members. As noted previously, this number of wrapped loops or coils provides sufficient frictional resistance so to resist unwrapping or slippage from the expansion force of the stent 2856, depending on the tensioning member material. The other, free end 2876 of the tensioning member 2850 may extend out of the opposing end opening 2876 of the stator 2854.

The control rings or guide structures typically comprise a curved surface along which the tension lines or members may slidably extend or retract, and may be used to set the location and/or angle of the tension line path or a portion of the tension line path between the rotor/stator and attachment to the implant. Based on the longitudinal location and/or radial distance of the guide structure with respect to the delivery system, the tension vector of the tension member may be altered to suit the desired control/release characteristics of the implant. In some examples, the relative allocation of the longitudinal and/or radial components of the tension force acting on the implant at a stage or point of implant expansion is adjusted to provide improved control, e.g. relatively greater radial tension vs. longitudinal tension early in the expansion process. The rings may have an inner diameter in the range of 1 mm to 12 mm, 2 mm to 8 mm or 3 mm to 7 mm, and an outer diameter in the range of 2 mm to 15 mm, 3 mm to 12 mm or 4 mm to 10 mm.

Figure 31A:
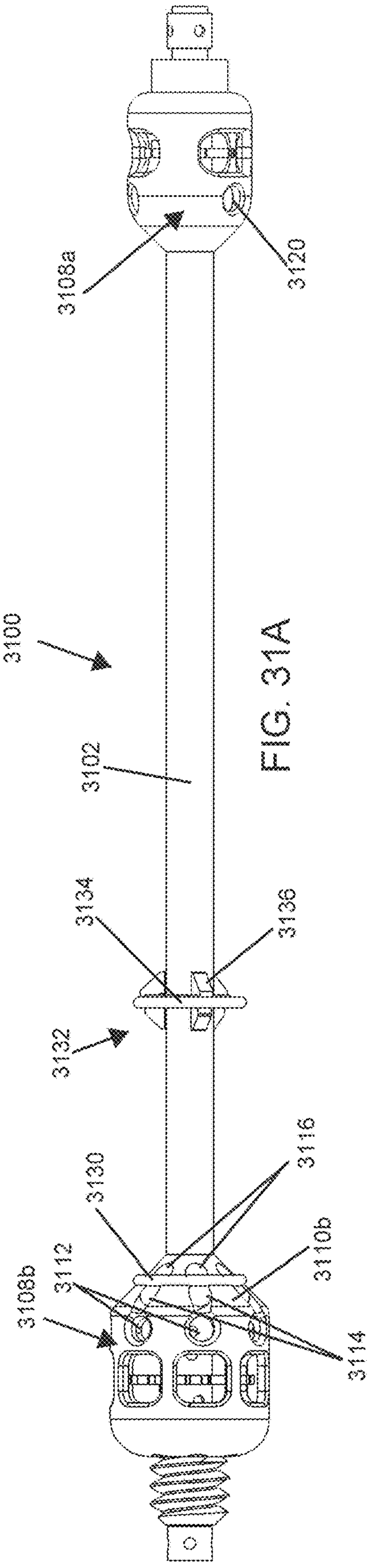
FIGS. 31A and 31B are side and cross-sectional views of a stator/rotor assembly comprising tension line guide structures on the stator housing and stator shaft.
Figure 31B:
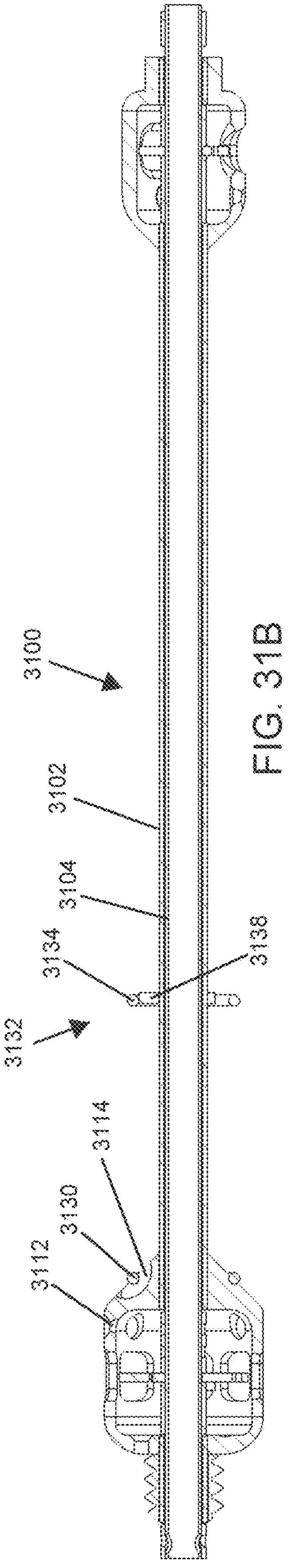
Figure 31C:
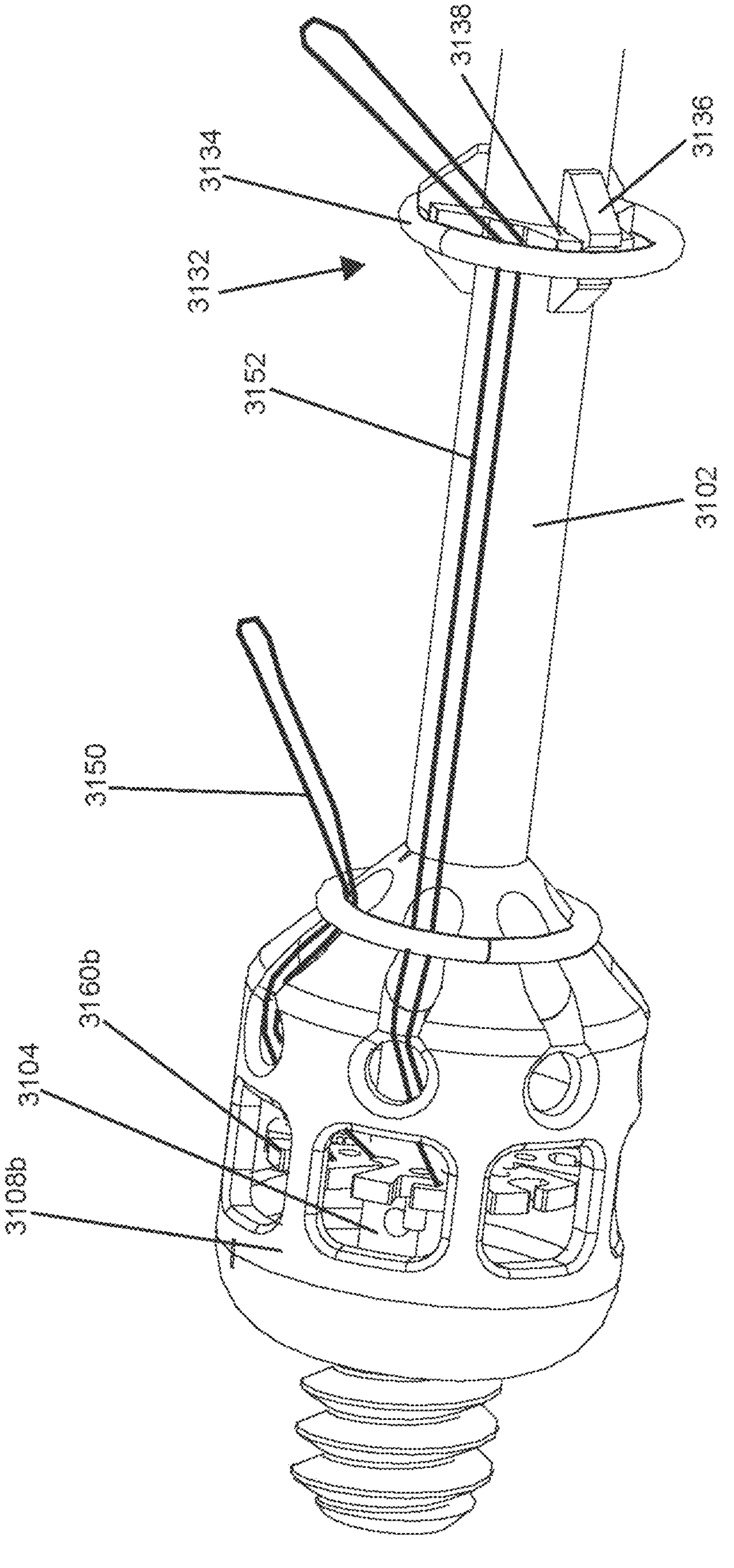
FIGS. 31C and 31D are perspective views of the distal and proximal regions of the assembly, respectively, depicting exemplary tension line routing paths.

In another embodiment of the delivery system, the stator assembly 3100, depicted in FIGS. 31A to 31D, comprises a tubular stator shaft 3102 with a tension line guide structure or control ring 3130 located about the exterior surface 3110*b* of the distal stator housing 3108*b*. In this particular variation, the control ring 3130 is located between a tension line opening 3112 of the stator housing 3108*b* and the proximal end 3116 of a tension line guide channel or recess 3114 in continuity or communication with the tension line opening 3112. Although the guide structure 3130 comprises a single ring structure directly attached or welded to a perimeter along the exterior surface 3110*b* of the housing 3108*b* to affect a plurality of openings 3112 and a plurality of guide channels 3114, but in other variations, separate control rings or guide rails may be provided, and/or may be offset from the exterior surface of the stator housing by one or more supports. The guide structure 3130 here is a complete ring, but in other variations, a partial ring or separate arcuate or linear segments may be provided. In still other variations, the ring may be an oval, square, triangle or rectangle in shape, and may be concentrically or eccentrically configured relative to the center of the stator housing 3108*b*. As depicted in FIGS. 31A to 31C, the openings 3112, channels 3114 and ring 3130 comprise rounded or chamfered edges or surfaces to facilitate sliding or translation of a tension line along those structures.

Figure 31D:
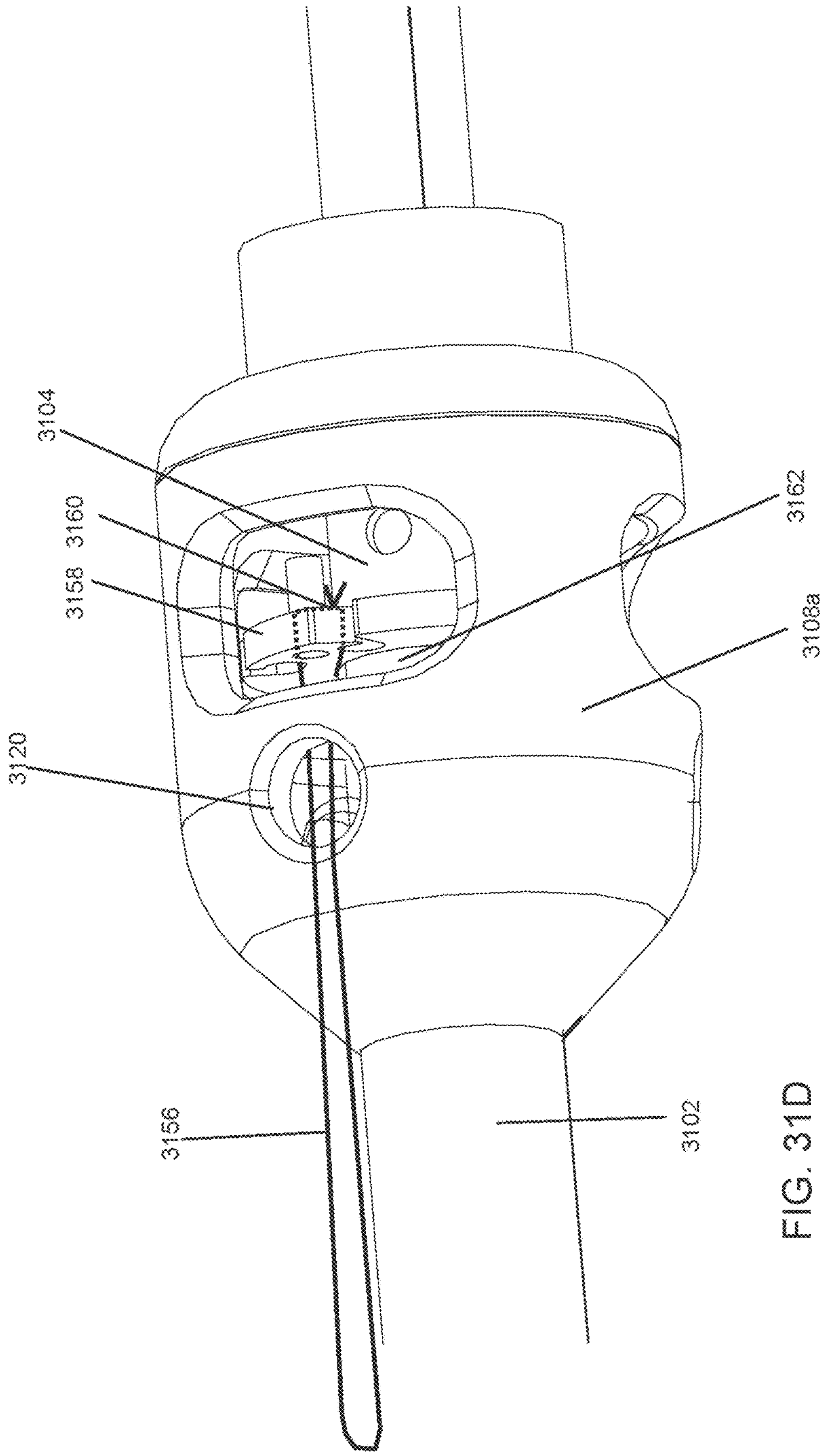
Figure 32:
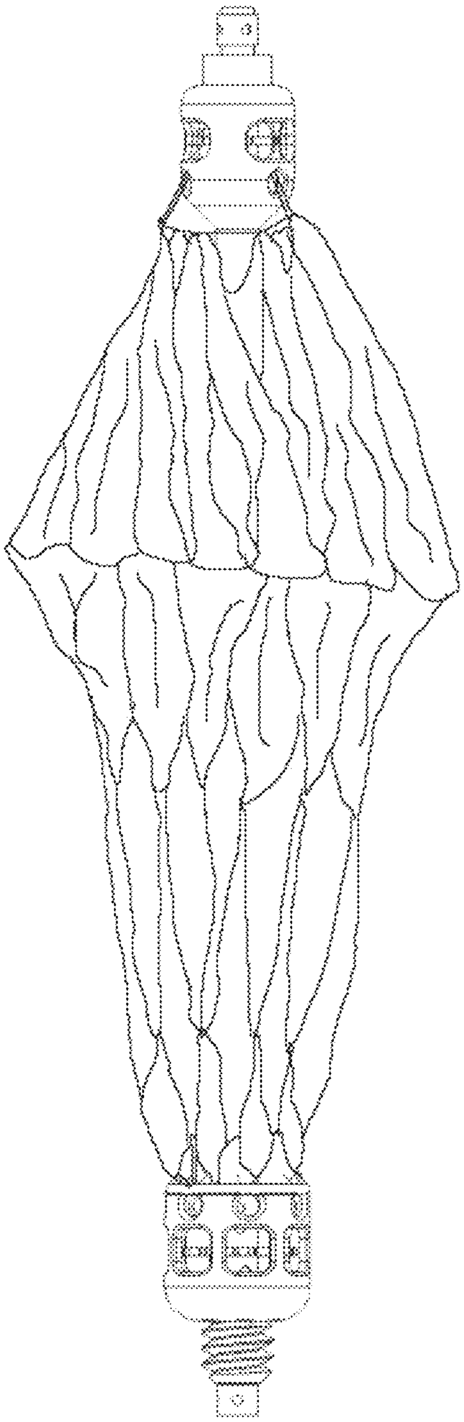
FIG. 32 depicts the stator/rotor assembly of FIGS. 31A to 31D with a covered valve stent.

Referring to FIGS. 31A, 31B and 31D, in this particular example, the proximal stator housing 3108*a* includes tension line guide openings 3120 but does not include a guide structure or guide channels. With implants that do not require tension lines to be routed closer to the tubular stator shaft 3102, the tension lines may extend from the opening 3120 direct to its attachment on the implant, without any guide structure or guide channel.

Referring back to FIGS. 31A to 31C, the tubular stator body 3102 may optionally comprise one or more stator shaft guide structure 3132 to facilitate routing of tension lines spaced apart from the stator housings 3108*a* and/or 3108*b*. In this particular example, the guide structure comprises a guide ring 3134 located concentrically around the tubular stator body 3102 and held in place by one or more supports 3136, 3138. The supports here comprises a triangular or trapezoidal support projections 3136 with the base oriented along the longitudinal axis of the stator body, with an upper notch or recess in which the ring 3134 is seated. Adjacent projections 3136 are in turn supported by circumferential supports 3138. The support projections 3136 and circumferential support 3138 may be heat or ultrasonically welded, adhered or form a mechanical or interlocking interfit. The support projections 3136 and the circumferential support 3138 may also be integrally formed as a ring-like structure. In other variations, the support may comprise a more rounded shape, and/or may be integrally formed with the control ring or guide structure. As depicted in FIGS. 31A to 31C, this guide ring 3134 may have the same size as the control ring 3130 that may be provided on the stator housing 3108*b*, but in other variations, the rings 3130, 3134 may have different sizes, e.g. different inner diameter, outer diameter, overall shape (as recited previously), or cross sectional shape. The cross-sectional wire shapes of rings 3130 and 3134 are circular, but in other variations, the cross-sectional wire shapes may be oval, square or rectangular, and each ring may have a different overall shape or cross-sectional shape. Also, more than one guide ring may be provided on the stator body. The gap distance between the outer surface of the tubular stator body and an inner diameter of the ring 3134 may be in the range of about 1 mm to 6 mm, 2 mm to 5 mm, or 2 mm to 4 mm, or 2 mm to 3 mm. The distance between a ring and the proximal or distal stator housing may be in the range of 5 mm to 50 mm, 10 mm to 40 mm, 20 mm to 30 mm, 2 mm to 20 mm, 4 mm to 10 mm, or 5 mm to 15 mm. This distance may also be characterized as a percentage of the length of the inner or outer wall of the implant in the expanded or compressed configuration, e.g.

between 60% and 180%, 80% and 150%, 90% and 120%, or 90% and 150%, or 60% and 110 for example.

FIG. 31C schematically depicts how a tension loop or line 3150, 3152 may be routed using the control rings 3130, 3134. One tension loop or line 3150, for example, may be looped around or tied to the rotor attachment structure or rotor plate 3160*b* of the rotor shaft 3104, routed out one of the guide openings 3118 of the distal stator housing 3108*b*. As the line 3150 exits the opening 3118, it passes into the guide channel 3114 and under the ring 3130 of the stator housing 3108*b* before extending out to attach to the implant. Tension line 3152 follows a similar path, but after extending under the ring 3130, the line 3152 continues along the stator shaft 3102 and under the stator control ring 3134 before attaching to the implant. Here, there are four supports 3136 for the control ring 3134, spaced equally apart. It is noted that the tension line 3152 to slidably move between support projections 3136, which may accommodate some relative movement between the delivery system and the implant. The range of movement may be altered based on the number of support projections 3136 of the stator body guide structure 3132.

FIG. 31D schematically depicts how a tension loop or line 3156 in the same delivery system may not need any guide channel on the stator housing 3108*a* or any stator housing ring or stator shaft guide structure. Here, the tension line 3156 is attached to the rotor attachment structure or rotor plate 3160*a*, and extends out of a guide opening 3120 to attach to the implant. As noted elsewhere herein, The tension line 3156 may be initial secured to the rotor plate 3158 via a knot 3160, and after several rotations to wrap the tension line 3156 around itself several times, the tension line 3156 may be severed or cut near the knot 3160 but still maintained on the rotor 3162 via the friction from the wraps. When unwound during the implantation procedure, the cut free end of the tension line 3156 may be freed and pulled away from the attachment line or other implant structure from which it was looped around.

In the embodiment depicted in FIGS. 31C and 31D, tension line 3150 may be used to attach and control the expansion of the distal outer wall, ventricular opening or ventricular loop of the implant, while tension line 3152 may be used to attach and control the expansion of the inner wall, outflow opening or outflow loop of the implant. Tension line 3156 may be used to attach and control the expansion of the proximal outer wall, atrial opening, atrial loop, or inflow opening of the implant. These relationships may be reversed if the implant has the opposite orientation relative to the delivery system.

Figure 33:
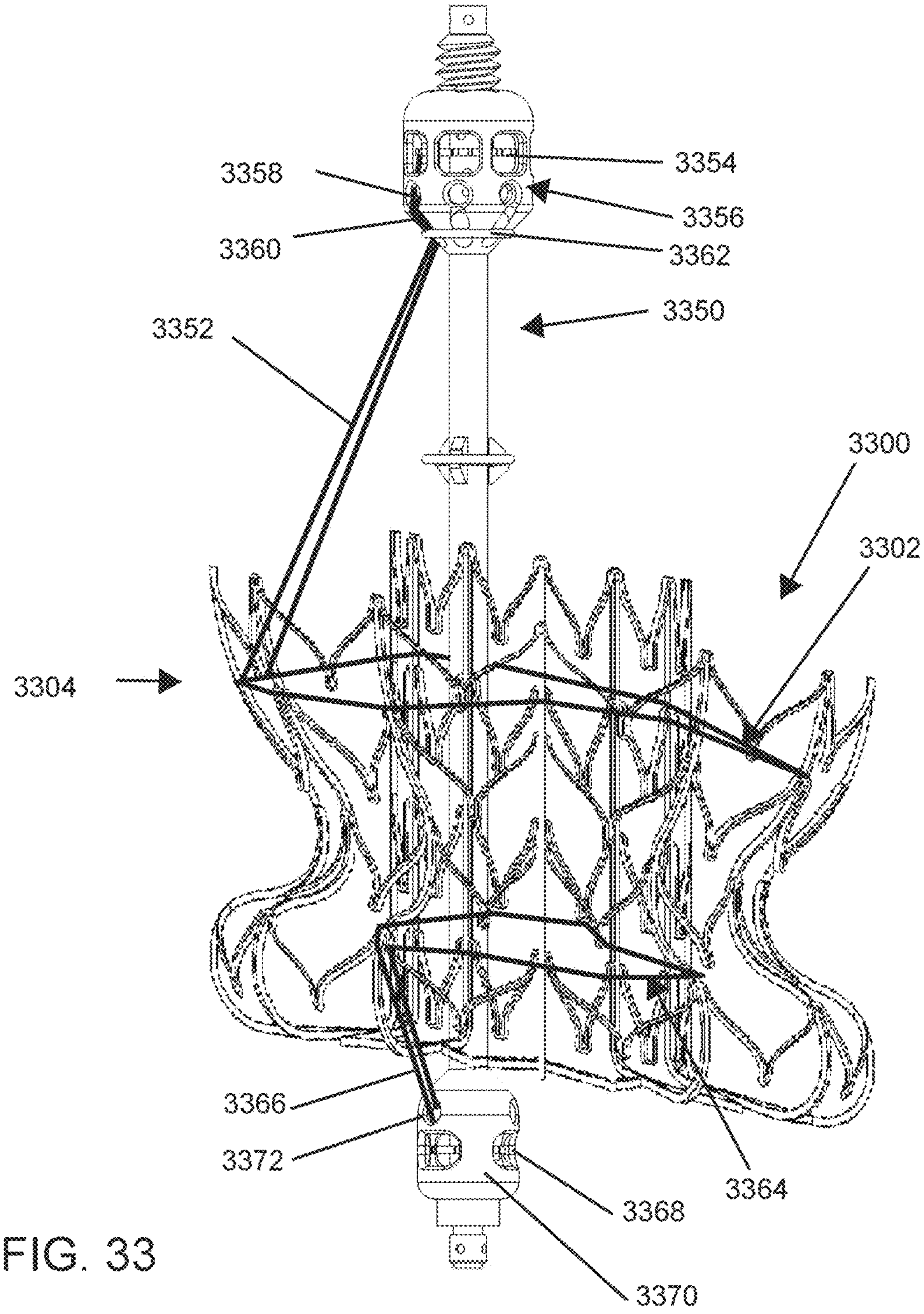
FIG. 33 depicts the stator/rotor assembly of FIGS. 31A to 31D with a valve stent that is asymmetrically coupled to the stator/rotor assembly.

Although several of the exemplary embodiments of the delivery system and implant described herein utilize multiple tension lines spaced around the perimeter of the implant to provide generally uniform control of the implant expansion, in other variations, a single tension line may be used. In FIG. 33, for example, the implant 3300 comprises a flexible attachment loop 3302 coupled to the distal outer wall 3304 of the implant 3300 to facilitate attachment of the tension line 3352 of the delivery system 3350. The tension line 3352 is attached to the rotor plate 3354 in the distal stator housing 3356 and extends out of the guide opening 3358 of the housing 3356, into the guide channel 3360 and under the housing guide structure 3362 and then out to loop around or couple to the attachment loop 3302 of the implant 3300. Another attachment loop 3364 is also attached through the proximal inner wall of the implant 3300, with a second tension line 3366 provided that is attached to the rotor plate 3368 located in the proximal stator housing 3370 through a guide opening 3372. Because the tension lines 3352, 3366 coupled to their respective attachment loops 3302, 3364 are not symmetrically distributed around the attachment loop 3302, the portions of the implant 3300 and the attachment loops 3302, 3364 nearest the tension lines 3352, 3366 are pulled closer to the proximal and distal stator housing 3356, 3370, which may result in a tilted, asymmetric implant configuration relative to the delivery system or stator drive shaft, as shown in FIG. 33. In some embodiments of the implant and delivery system, this asymmetric expansion may be provide in order to simplify the assembly, release and/or reliability of the implant due to having fewer tension lines to control the implant expansion.

Figure 34A:
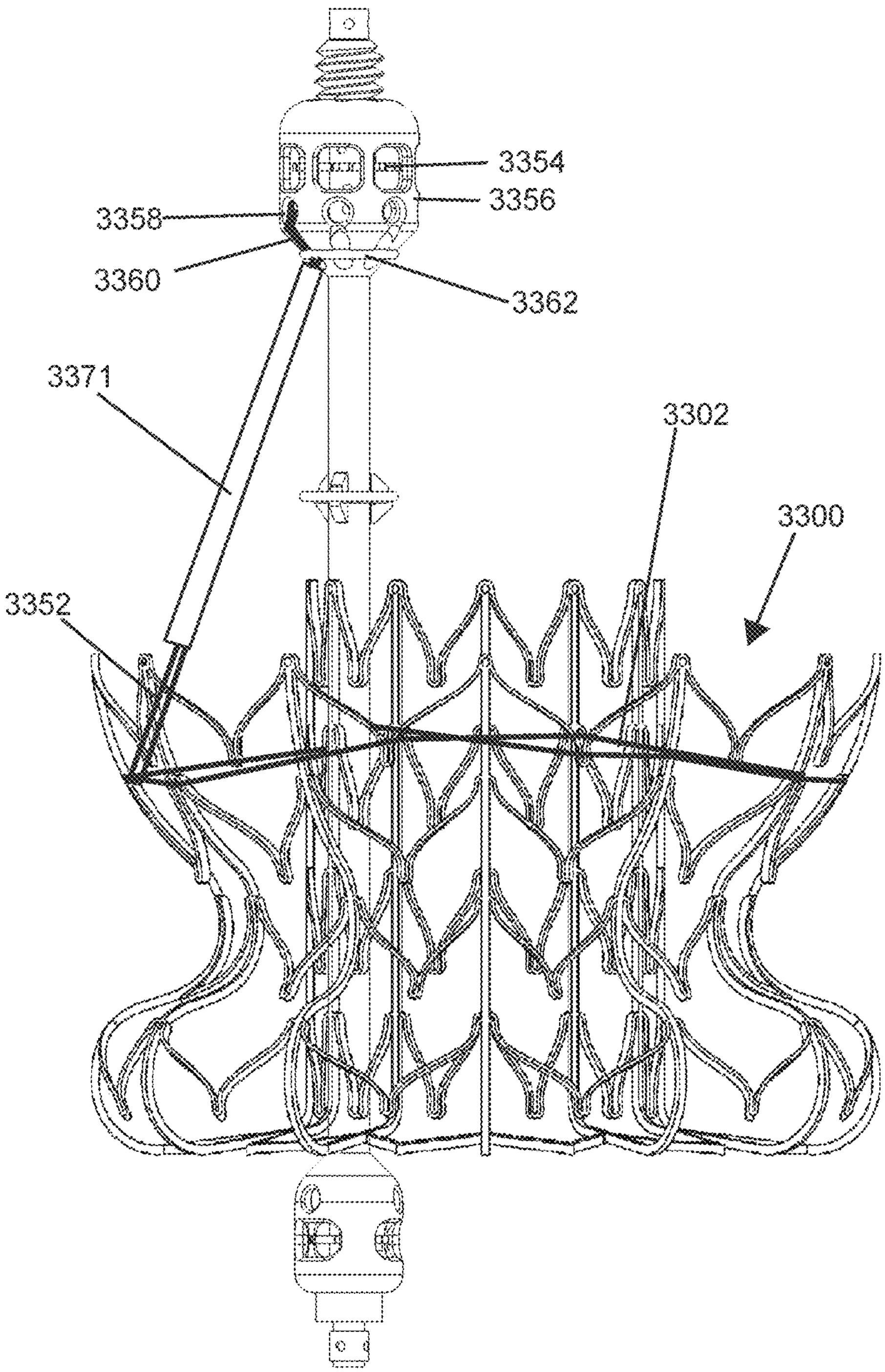
FIGS. 34A and 34B are side and end views of the stator/rotor assembly of FIGS.
Figure 34B:
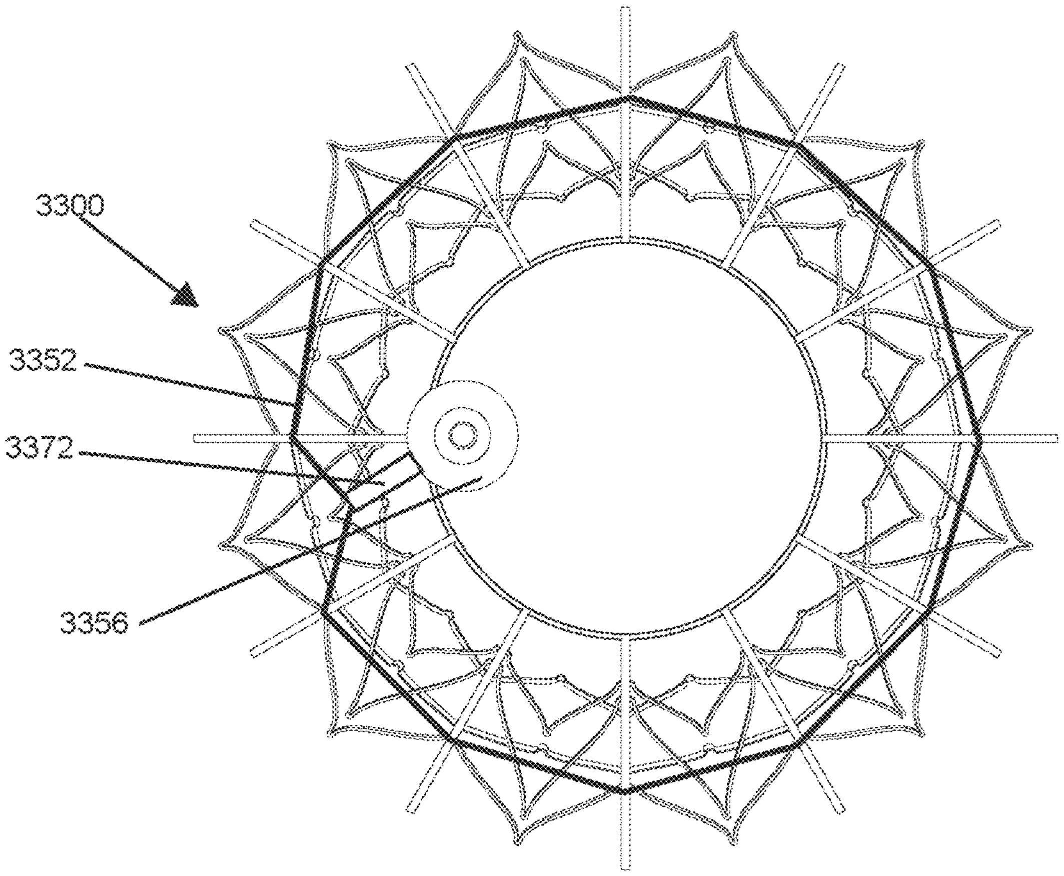

This asymmetry may be reduced by providing a rigid guide tube 3370 between the stator housing and the implant 3300. The tube 3370 effectively displaces or translates the tension line source point from the exit location about the stator housing guide structure 3362 to the proximal end of the tube 3370 closer to the attachment loop 3302 of the implant 3300. This single tension line configuration may still result in an eccentric position of the implant 3300 relative to the delivery system or drive shaft, but reduces the tilting, angulation or asymmetric deformation of the implant 3300 during expansion, as depicted in FIGS. 34A and 34B.

Figure 29A:
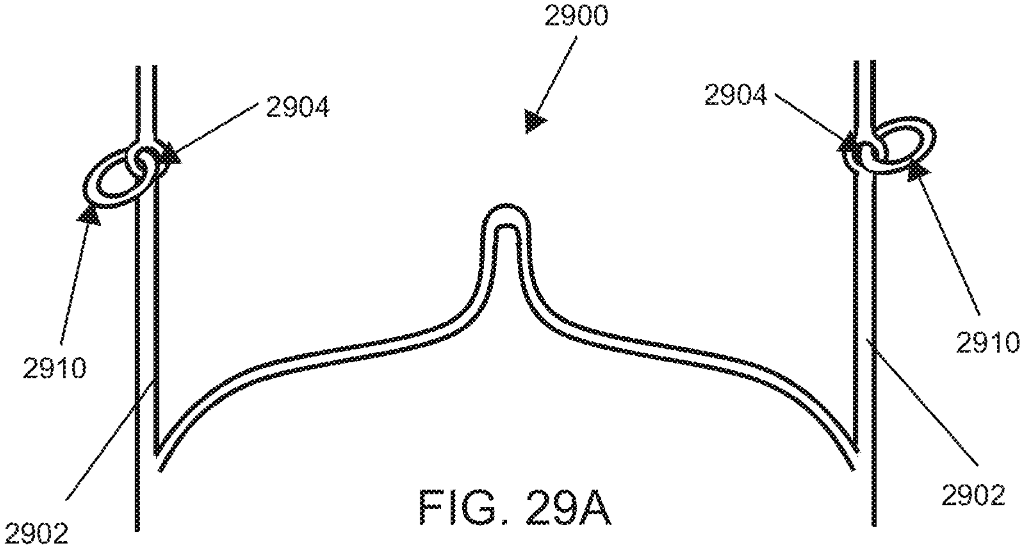
FIGS. 29A to 29C depict various attachment rings located in openings of a stent structure.
Figure 29B:
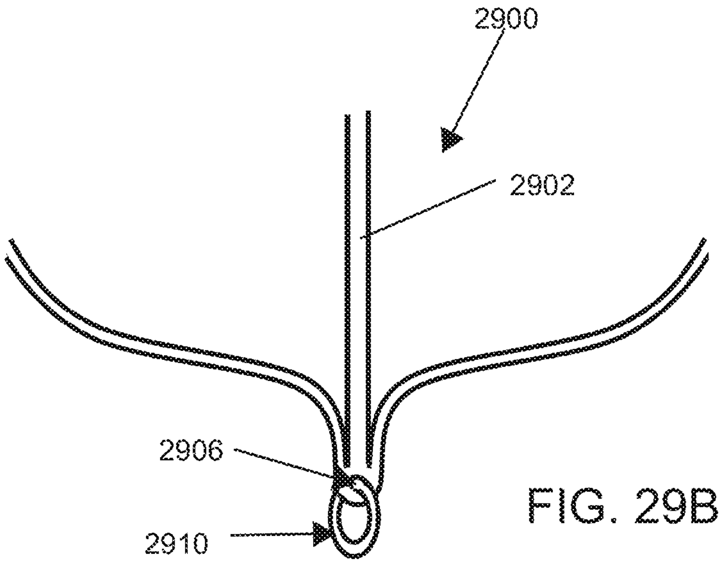
Figure 29C:
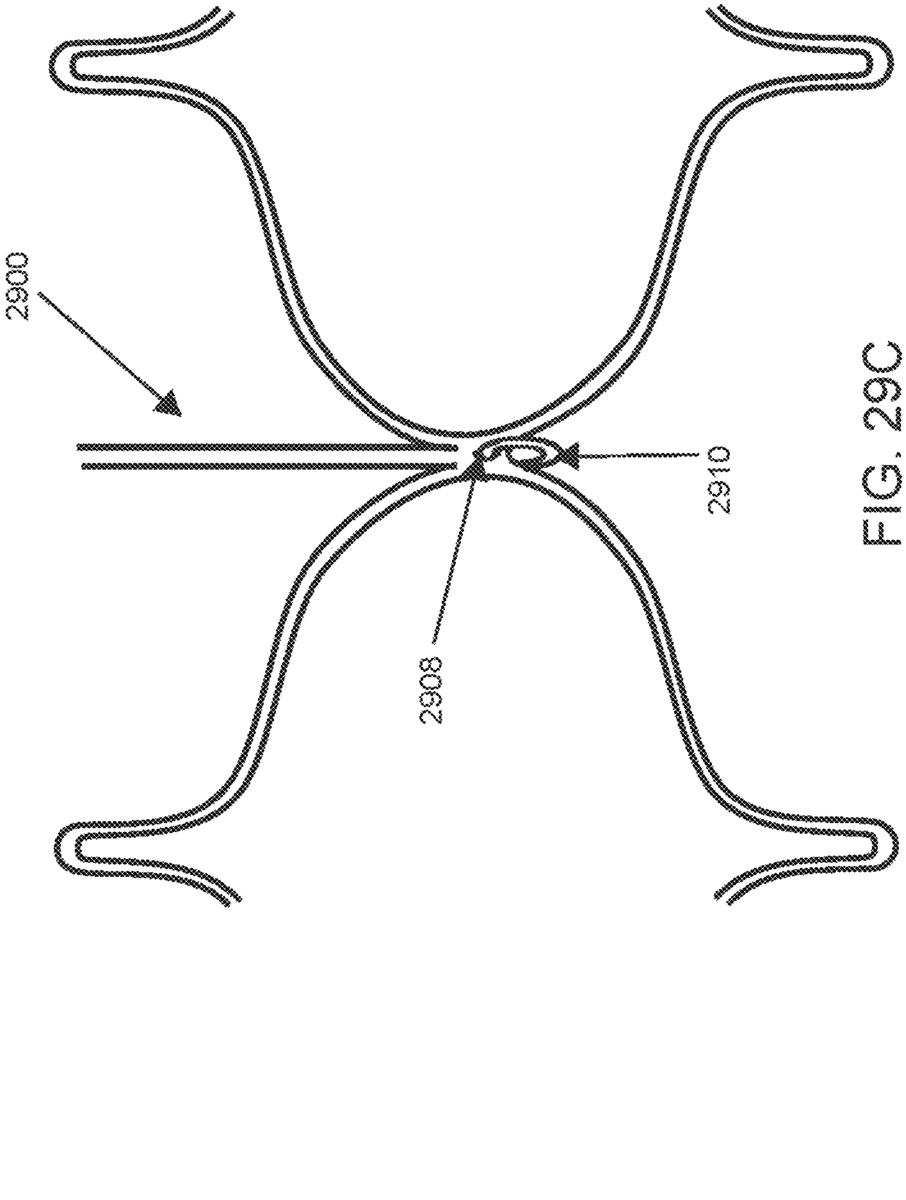
Figure 30:
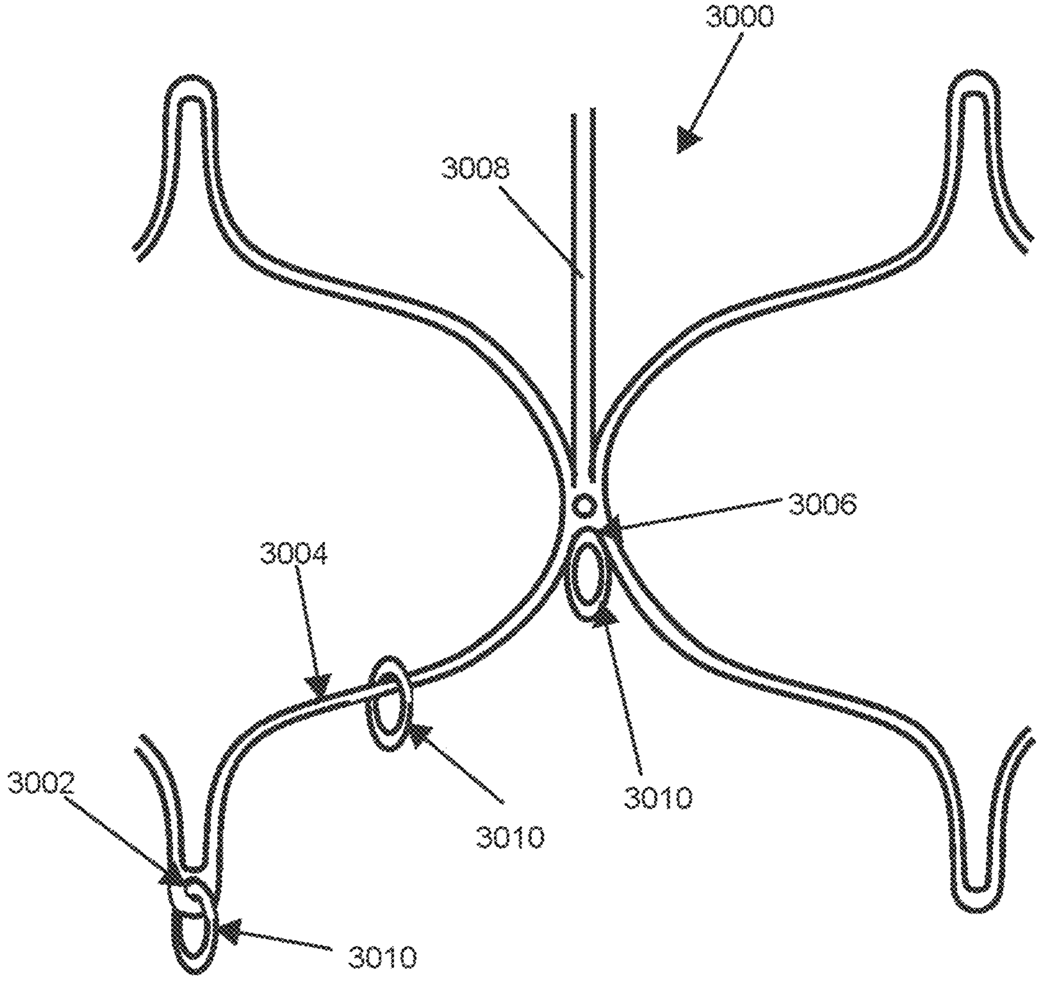
FIG. 30 depicts other exemplary attachment rings coupled to a stent structure.

In some further variations, one or more rings or wire loops may be attached to the stent structure to facilitate attachment of the tensioning members. The rings, in contrast to the stent struts, may comprise a more rounded surface for the tensioning members can slide over. The rings may be directed fixed to the stent structure, or may be provided in an opening of the stent structure. The latter configuration permits the rings to move or rotate in the opening, which may help to orient the tensioning direction between tensioning member and the attachment region of the strut. FIGS. 29A to 29C depict various openings 2904, 2906, 2908 that may be provided on the stent 2900. In these particular examples, the openings 2904, 2906, and 2908 are located on the longitudinal struts 2902 of the stent 2900, but in other variations, as depicted in FIG. 30, the opening 3002 may be located along the lateral or circumferential struts 3004 of the stent 3000. The rings or wire loops 2910, 3010 may comprise a circular shape as depicted in FIGS. 30A to 30C, but in other variations, may be oval, square, rectangular or other polygonal or curvilinear closed shape. The rings or wire loops may round wire with a diameter in the range of 0.001" to 0.100", 0.005" to 0.050", or 0.010" to 0.020", for example, and may comprise a ring or other shape with a diameter or maximum internal opening dimension in the range of 0.010" to 0.5", 0.020" to 0.2", 0.30" to 0.1", 0.030" to 0.060", 0.030" to 0.040", 0.040" to 0.50", 0.50" to 0.60", for example. In some variations, the rings attached to a stent structure may have different sizes, depending on size constraints at a particular location, to provide greater changes to the orientation of the tensioning member. The wire may comprise titanium, stainless steel, nitinol, cobalt-chromium, or other biocompatible wire. The wire may be square cut to provide flat end faces for joining them together. The wire may be crimped into the opening and the ends of the wire may be joined by laser welding a butt joint. The stent structure and the rings may be further processed together, e.g. passivation.

FIG. 30 schematically depicts other embodiments of the stent rings, including a ring 3010 welded to an end 3006 of a longitudinal strut 3008 of stent 3000 in a fixed manner, a ring 3010 slidably located along a circumferential strut 3004, and a ring 3010 located in an opening 3002 of the circumferential strut 3010.

In some other embodiments, the implant and the delivery system may be configured for delivery without the use of tension lines and/attachment lines. In FIGS. 35A to 35E, for example, delivery system 3500 comprises a distal unsheathing mechanism to release a contracted implant 3550. The system comprises a distal assembly 3502 with a retention sheath 3504 and a sheath cavity 3506. The sheath 3504 is coupled to a distal retention cap 3508, which is attached to a hollow threaded rod 3510 either directly or via a sheath washer 3512. A lumen 3514 in the rod 3510 and a distal opening 3516 of the cap 3508 permits the use of a guidewire, infusion of materials or a saline flush through the distal assembly 3502. The threaded rod 3510 is fixedly attached to the distal end of a tubular rotor drive shaft 3518 located within the lumen 3520 of a stator tube 3522. Threads located in the lumen 3520 of the stator tube 3522 form a complementary threaded drive interface with the threaded rod 3510 so that rotation of the tubular rotor drive shaft 3518 causes the distal advancement of the sheath 3504 via the threaded rod 3510. The advancement of the sheath 3504 occurs without rotation of the sheath 3504 as a result of a rotational interface between the threaded rod 3510 and the sheath cap 3508, which allows the threaded rod 3510 and optionally the sheath washer to rotate freely relative to the sheath cap 3508 and sheath 3504 while still transferring longitudinal translation motions to the sheath 3504 resulting from the interaction of the threaded rod 3510 and the stator tube 3522.

Figure 35A:
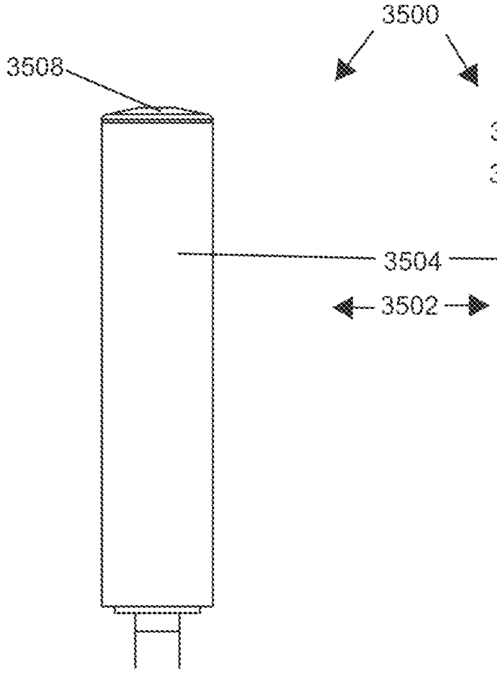
FIGS. 35A and 35B are side elevational views of an alternate delivery system with a distal implant sheath and locking system configured to releasably couple to a stent valve with corresponding or complementary attachment structures.
Figure 35C:
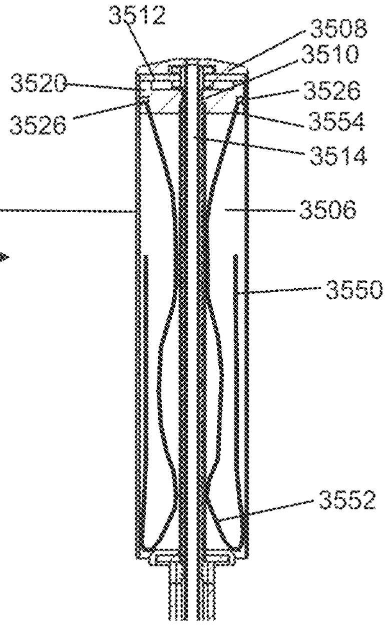
FIGS. 35C and 35D are cross-sectional views of the corresponding structures depicted in FIGS. 35A and 35B.
Figures 35B, 35D:
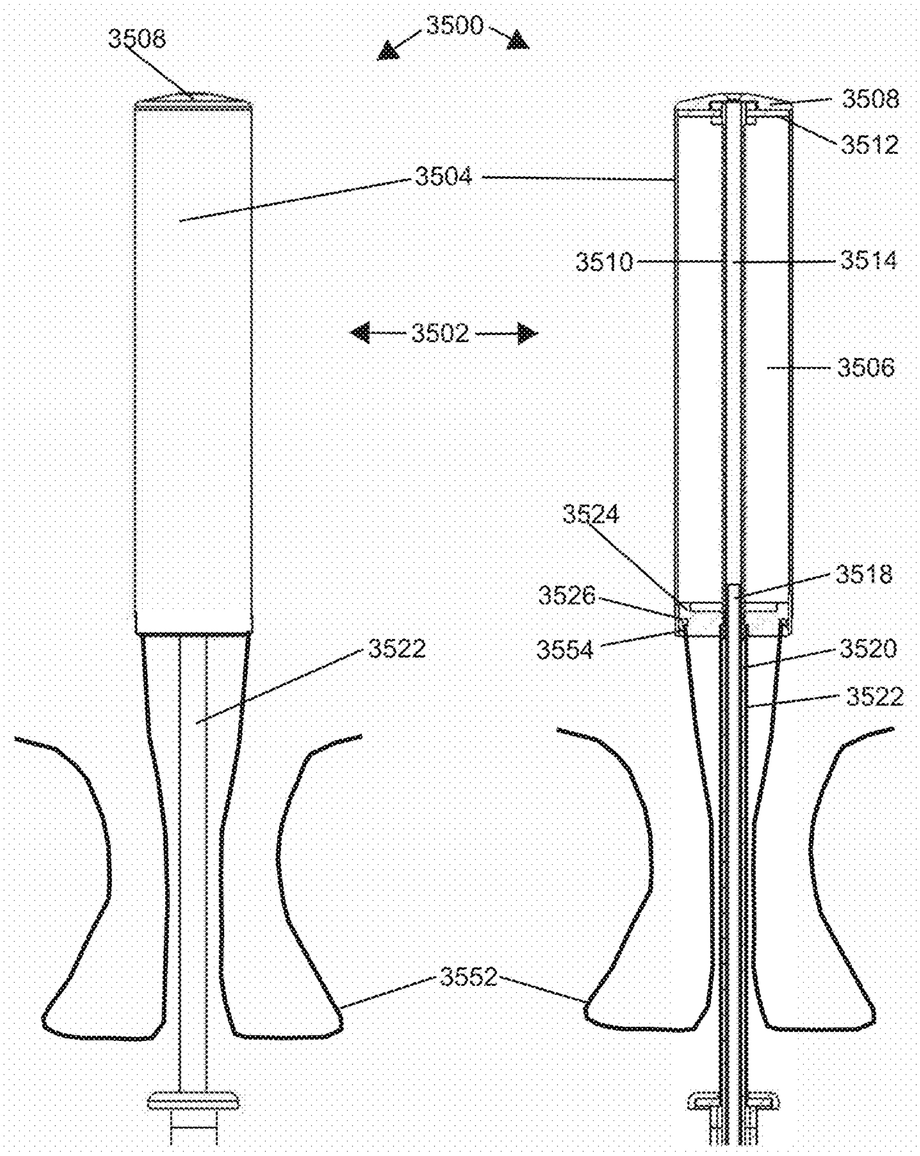
Figure 35E:
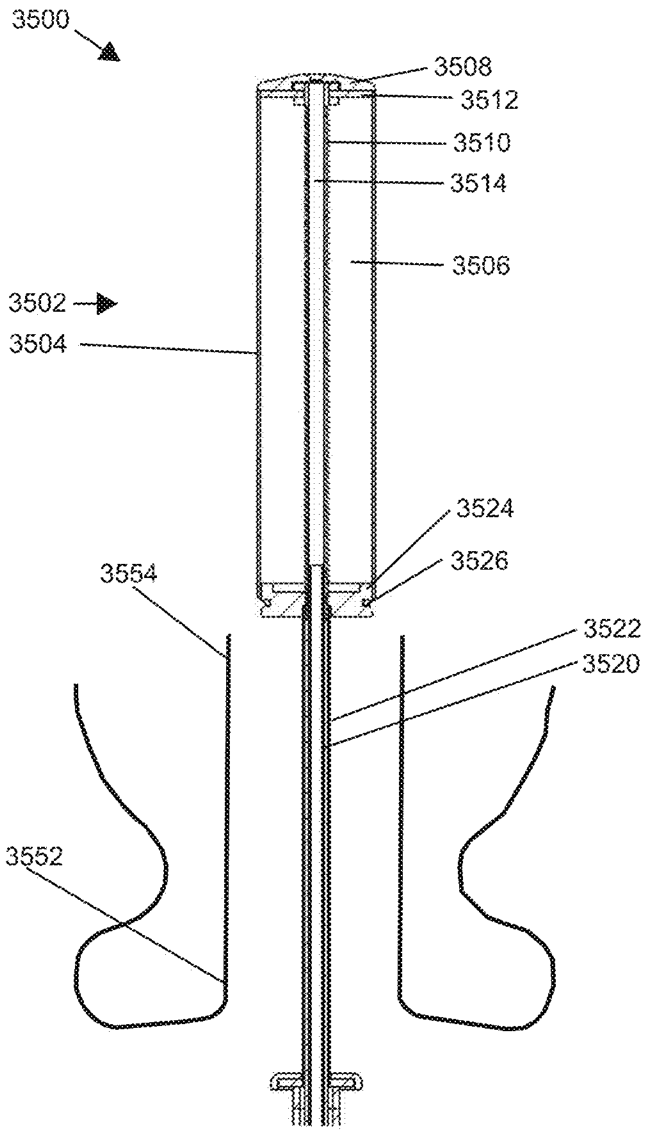
FIG. 35E is a schematic depiction of implant self-expansion and separation from the delivery system.
Figure 35F:
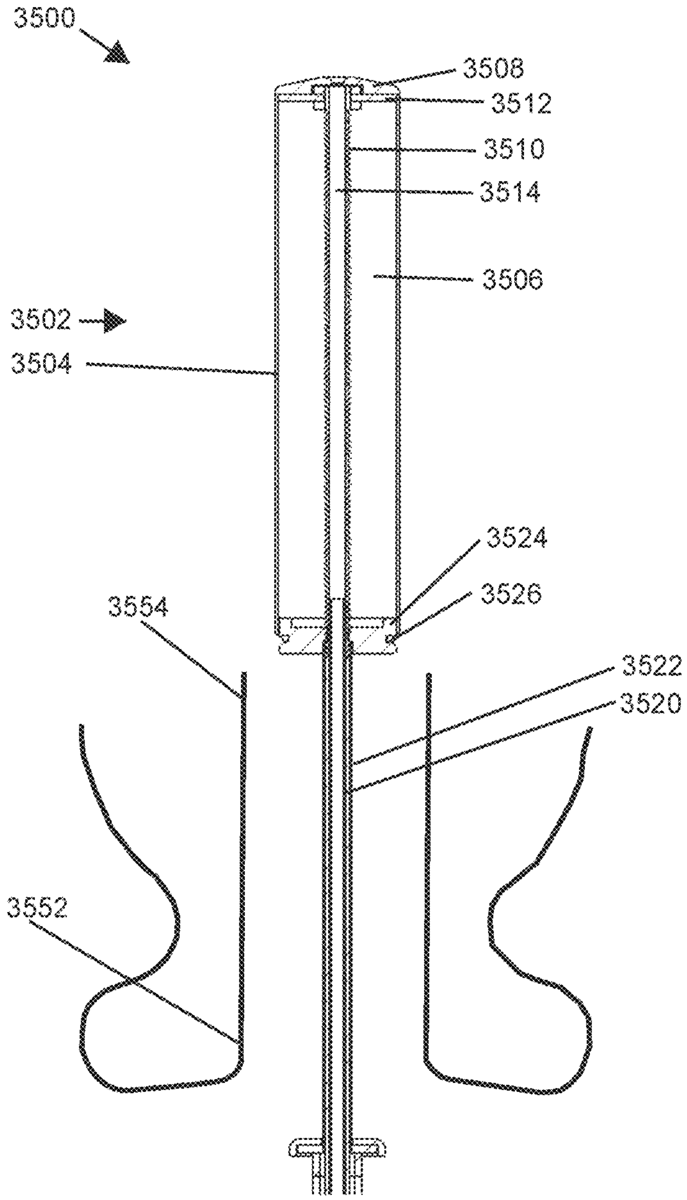

The stator tube 3522 is also fixedly attached to a distal implant attachment structure 3524, which includes one or more implant recesses 3526 that are configured to releasably retain one or more structures of the implant. The recesses 3526 are further configured to receive and release the implant structure in the radial axis, while resisting displacement of the implant structure in the longitudinal axis. The retention sheath 3504 is configured to fully retain the implant in the sheath cavity 3506, when sheath 3504 is in its proximal position, as depicted in FIG. 35C. As the rotor shaft is rotated, the sheath 3504 will advance distally, to expose the proximal end 3552 of the implant 3550, as depicted in FIGS. 35B, thereby allowing the proximal end of the implant 3550 to expand outward, while still retaining the distal end 3554 of the implant 3550 by virtue of the sheath 3504 still covering the recesses 3526 with the implant structures therein, as shown in FIGS. 35B and 35D. Once the sheath 3504 is advanced distally past the recesses 3526, the distal end 3554 of the implant 3550 can then self-expand radially, to separate from the recesses 3526 and to be released from the delivery system, as depicted in FIG. 35E.

Figure 36:
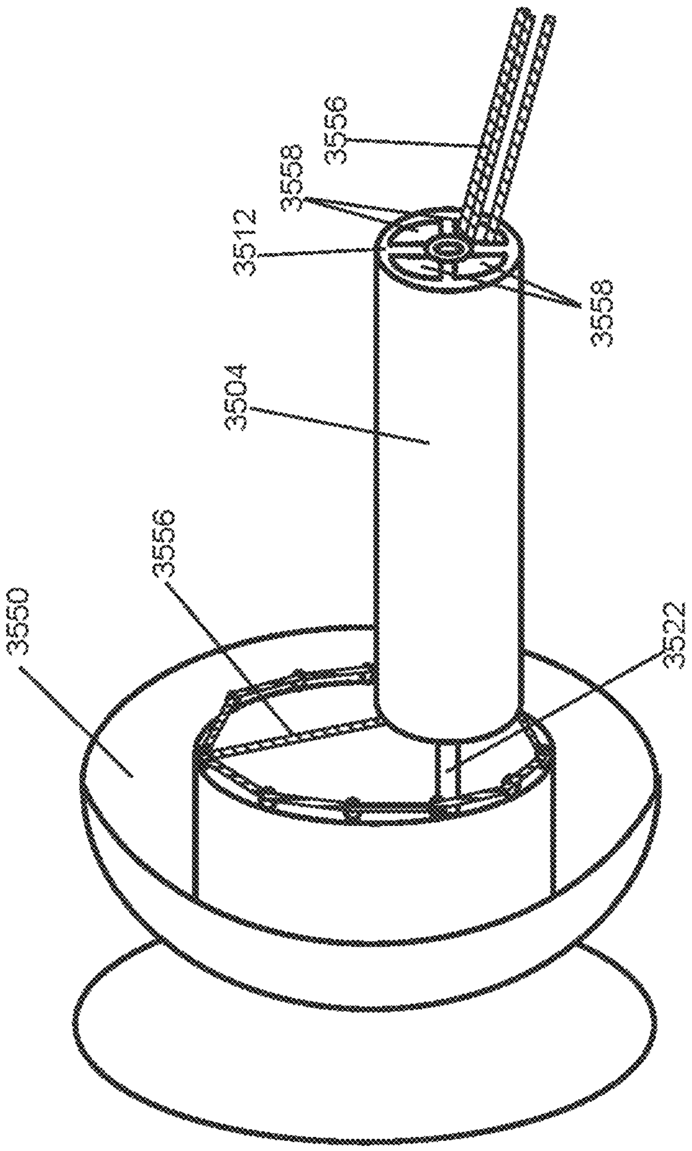
FIG. 36 depicts one exemplary embodiment for loading a valve implant into the delivery system with the distal implant sheath and locking system.

As depicted in FIG. 36, during the manufacturing process or the implant loading process at the point-of-use, loading sutures or lines 3556 may be temporarily attached to the implant 3550 and threaded through the sheath 3504 and through an opening 3558 of the sheath washer 3512. By pulling on the loading lines 3556, the implant 3550 may be collapsed into the sheath cavity 3506. This may be performed in an ice bath in order to deformably maintain the implant 3550 in the contracted configuration during the loading procedure. The implant 3550 may also be optionally crimped down prior to facilitate the loading process, so as to not having to achieve the radial collapsing force acting on the implant 3550 solely via the loading lines 3556 and the constraint from the sheath 3504.

Figure 11:
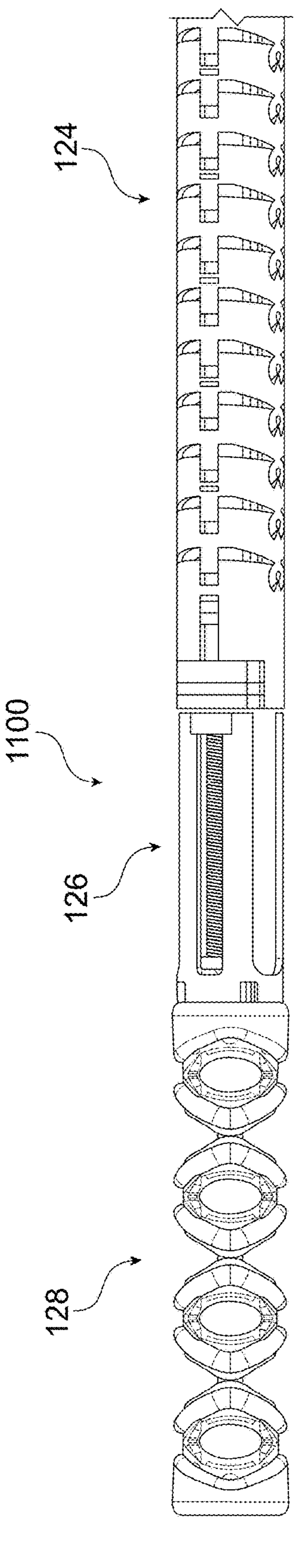
FIG. 11 is a side elevational view of the steering and extension assembly of the delivery system in FIG. 1.
Figure 12:
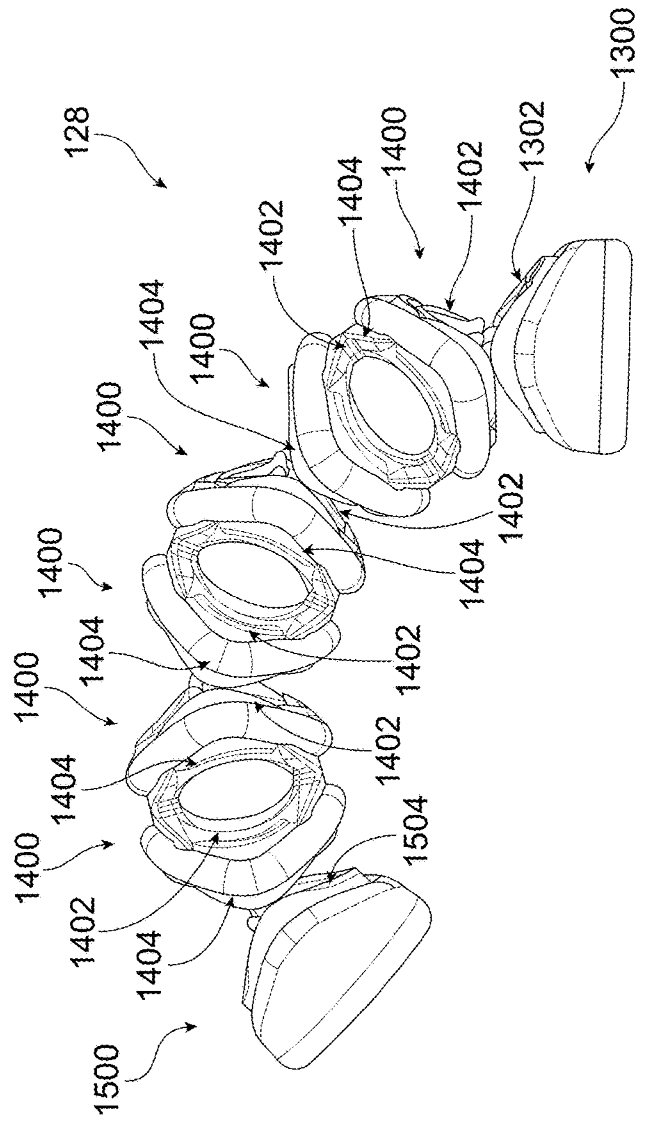
FIG. 12 is a side elevational view of the distal steering assembly of FIG. 11, in a bent configuration.
Figures 13A, 13B, 13C, 13D, 13E, 13F:
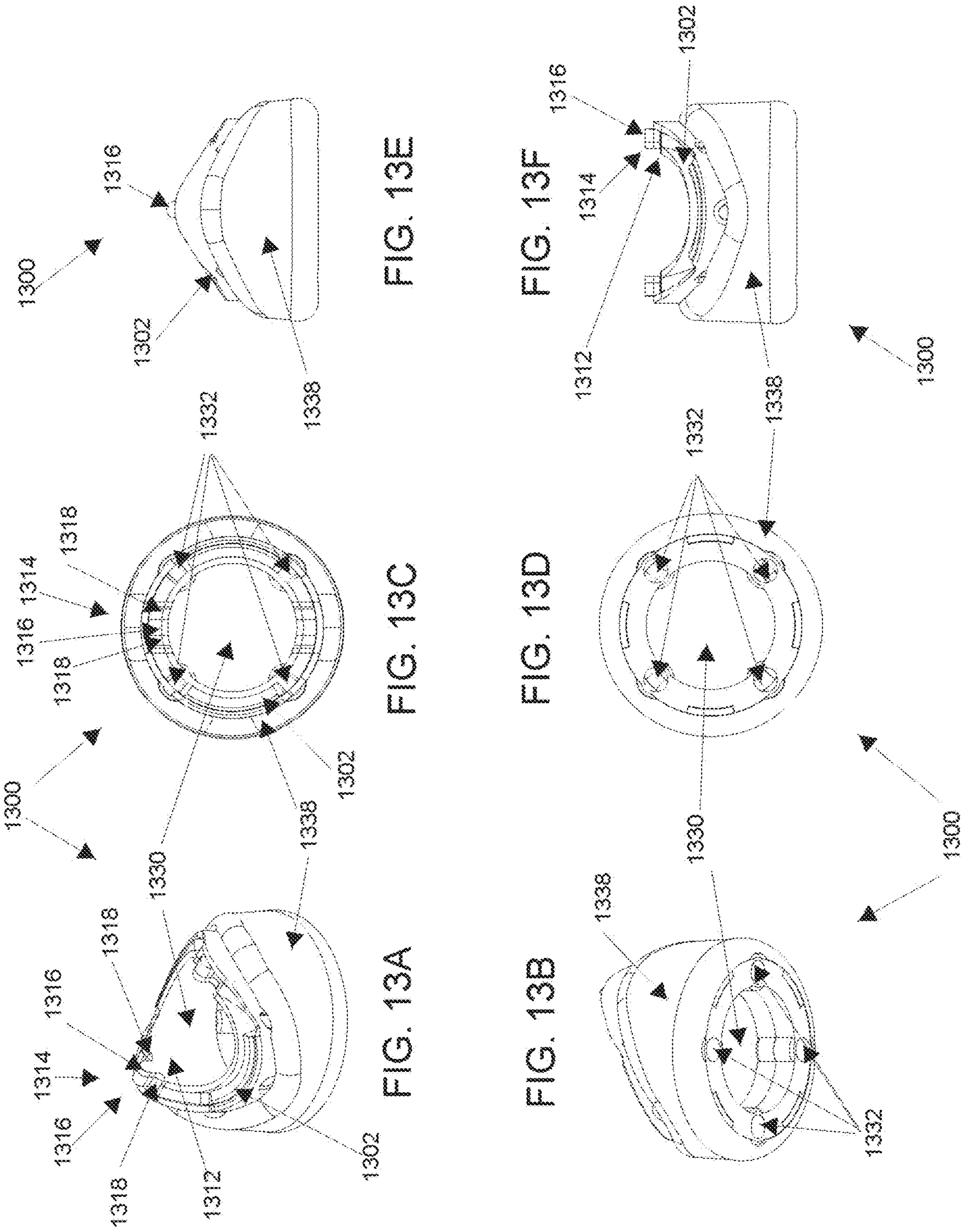
FIGS. 13A to 13F are top perspective, bottom perspective, top plan, bottom plan, side elevational and front/rear elevational views, respectively, of the proximal segment of the distal steering assembly in FIG. 12, with perimeter bumpers.
Figure 13K:
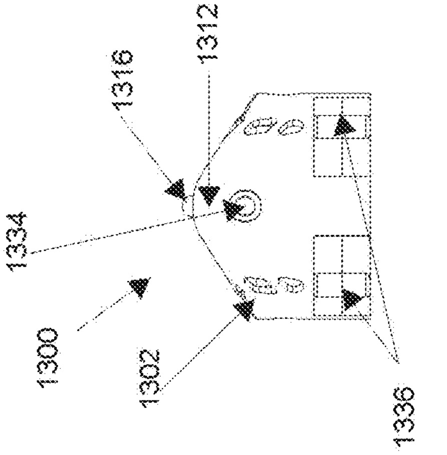
FIGS. 13G to 13L are top perspective, bottom perspective, top plan, bottom plan, side elevational and front/rear elevational views, respectively, of the proximal segment of the distal steering assembly in FIG. 12, without perimeter bumpers.
Figure 13I:
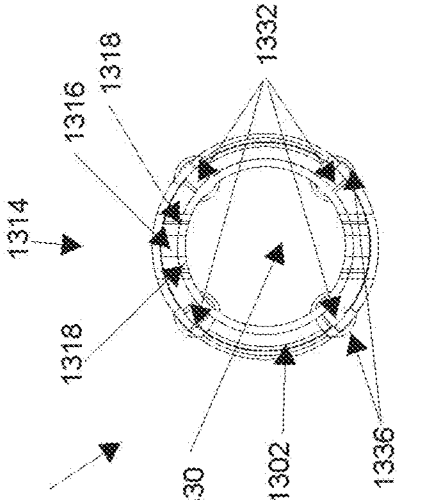
Figure 13G:
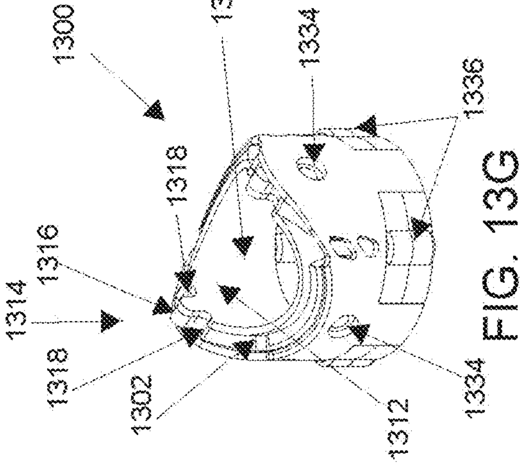
Figure 13L:
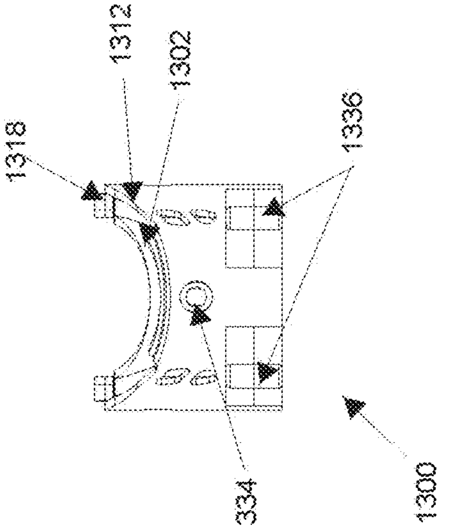
Figure 13J:
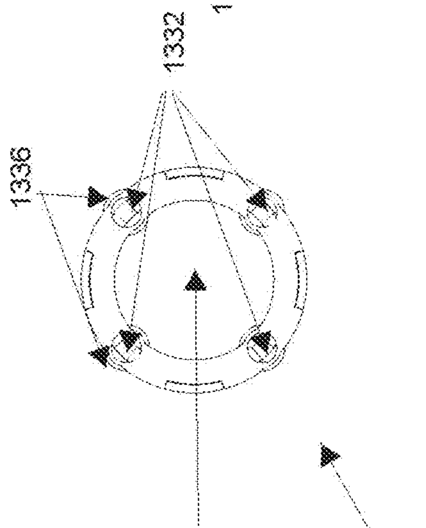
Figure 13H:
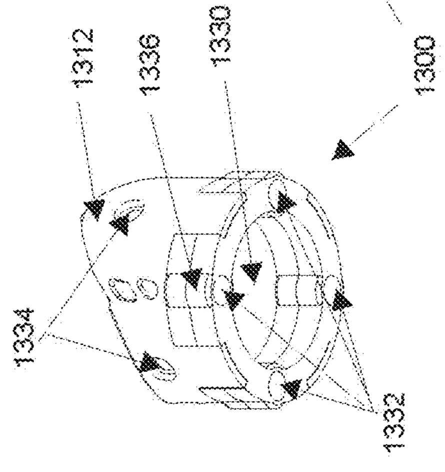
Figure 14E:
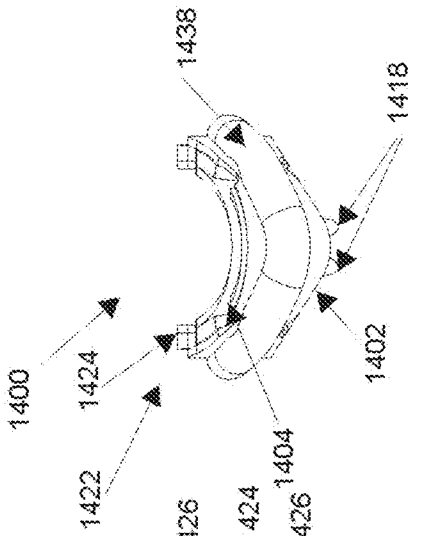
FIGS. 14A to 14F are top perspective, bottom perspective, top plan, bottom plan, side elevational and front/rear elevational views, respectively, of the middle segments of the distal steering assembly in FIG. 12, with perimeter bumpers.
Figure 14F:
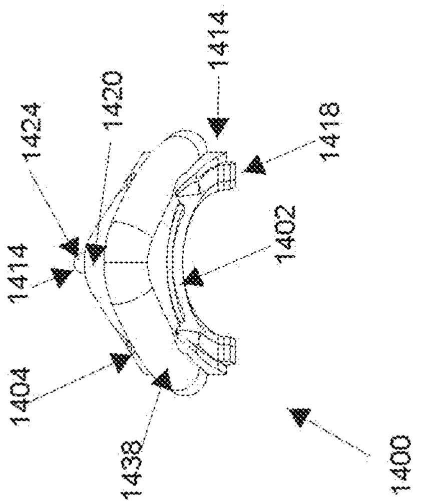
Figure 14C:
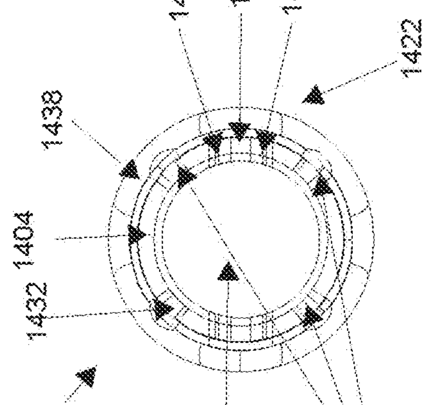
Figure 14D:
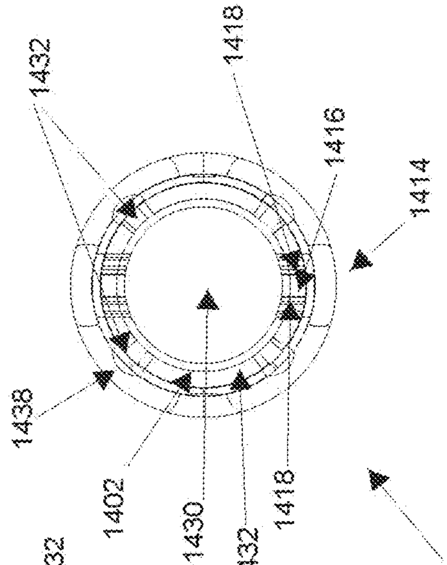
Figure 14A:
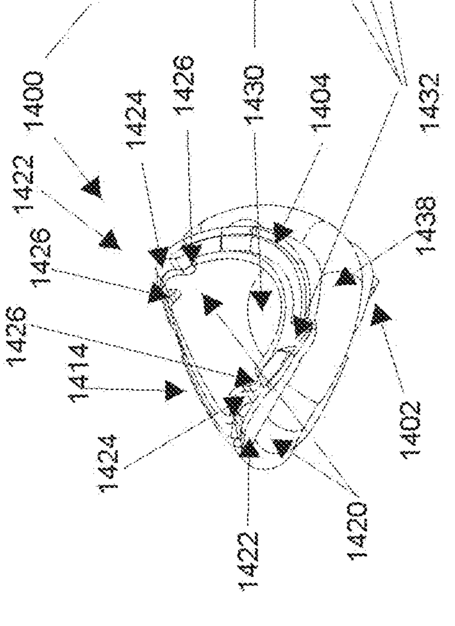
Figure 14B:
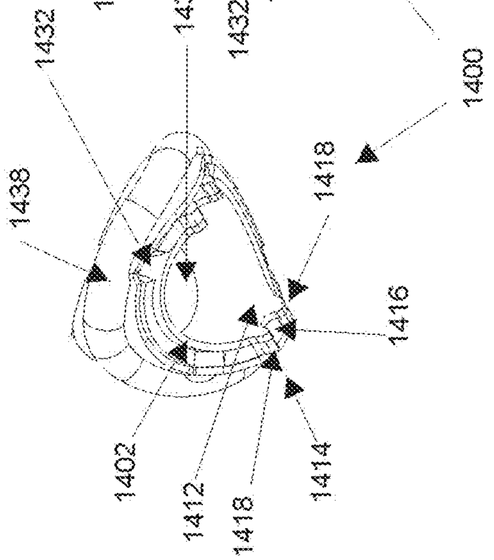
Figures 14G, 14H, 14I, 14J, 14K, 14L:
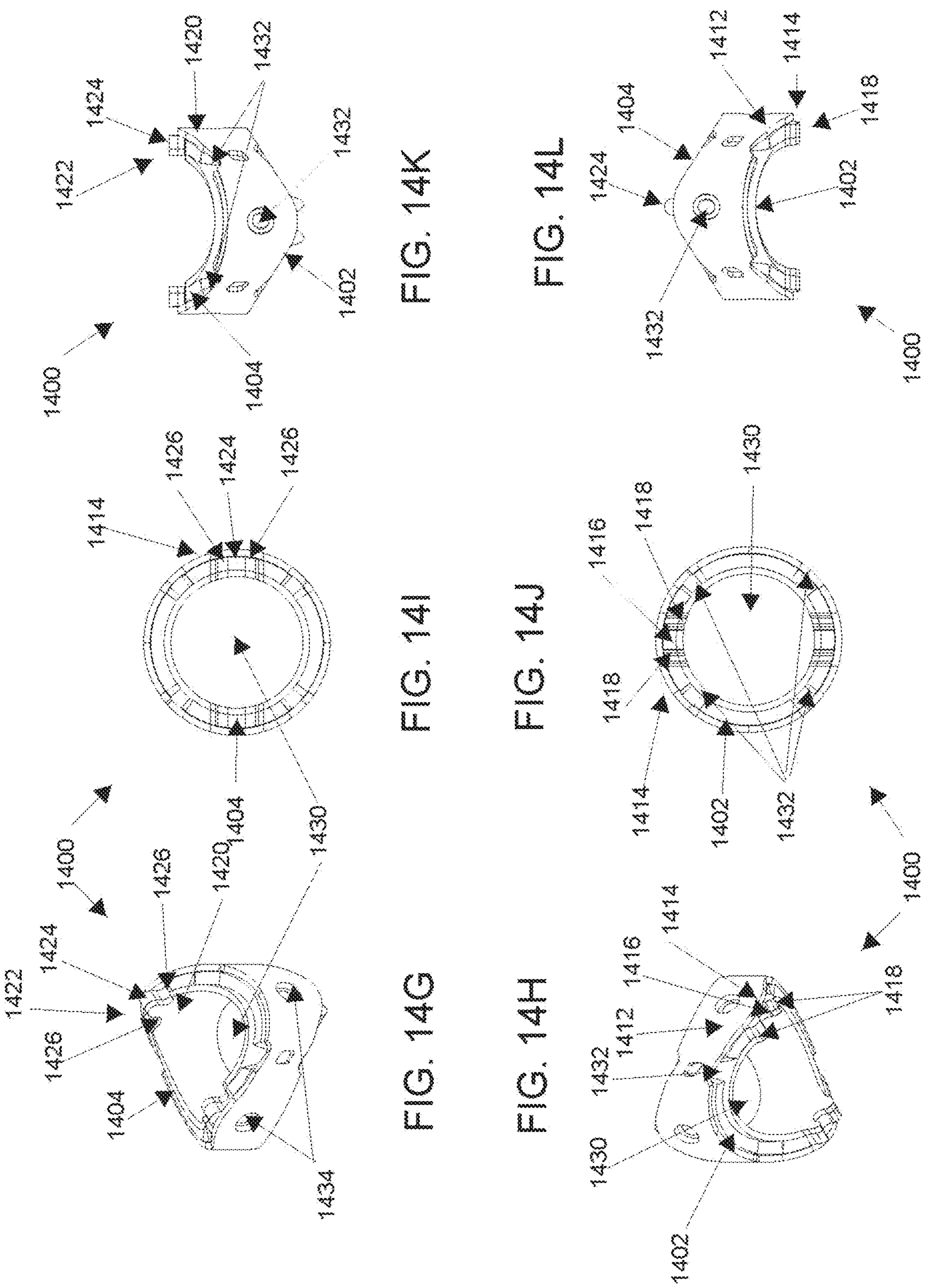
FIGS. 14G to 14L are top perspective, bottom perspective, top plan, bottom plan, side elevational and front/rear elevational views, respectively, of the middle segments of the distal steering assembly in FIG. 12, without perimeter bumpers.
Figures 15G, 15H, 15I, 15J, 15K, 15L:
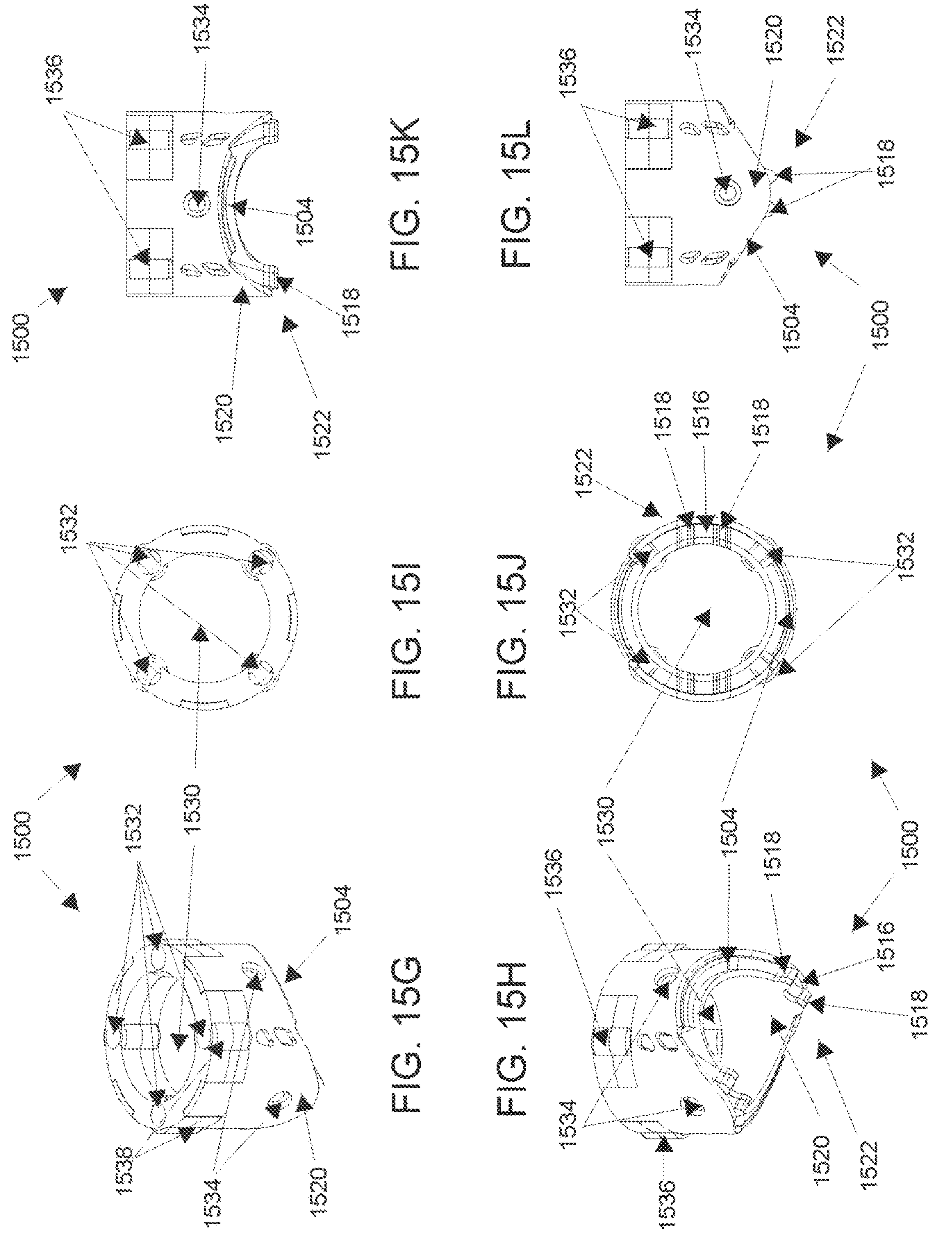
FIGS. 15G to 15L are top perspective, bottom perspective, top plan, bottom plan, side elevational and front/rear elevational views, respectively, of the distal segment of the distal steering assembly in FIG. 12, without perimeter bumpers.

As noted previously, in some variations, one or more steering or catheter extension assemblies may be provided to facilitate navigation of the delivery system and/or positioning and orienting the delivery section or implant during the procedure. In embodiments with two or more of such assemblies, the assemblies may be spaced apart along the delivery system, or as shown in FIG. 11, the assemblies 124, 126, 128 may be subassemblies that are directly attached end-to-end, as a single assembly 1100. In this particular embodiment, assemblies 124, 128 are bending or steering assemblies that are configured to bend the delivery system along one or multiple axes. In this example, the proximal bending assembly 124 is a two-way bending assembly that it is configured to bend in a single plane in two opposite directions, while the distal bending assembly 128 is a four-way bending assembly in that it is bends in at least two planes and optionally in combinations of the bends in the two planes, e.g. multi-axial steering/bending. Between the two steering assemblies 124, 128 is an extension assembly 126 that is configured to reversibly adjust its length or spacing between its proximal and distal ends. This allows the user to make incremental changes to the longitudinal positioning of the distal region of the delivery system, without requiring longitudinal displacement of the entire delivery system. Although this particular configuration comprises two different configurations of steering assemblies, in other variations, the steering assemblies may comprise the same configuration, or the order of the steering assemblies may be reversed, and/or the extension assembly may be located before or after the two steering assemblies.

Referring to FIGS. 12-15L, the distal steering assembly 128 may comprise a segmented tubular or ring configuration, with each segment 1300, 1400, 1500 comprising one or two segment interface ends, depending on the location of the segment 1300, 1400, 1500 in the assembly 128. In the depicted example of FIGS. 1A-IC, the distal steering assembly 128 may be controlled by a joystick controller 108 on the handle 102, as described in greater detail below. Referring back to FIGS. 12 to 15L, the proximal and distal segments 1300, 1500 each comprise a segment interface end 1302, 1504 which is configured to interface with a segment interface end 1402, 1404 of a middle segments 1400. The interface ends 1402, 1404 are also configured to interface with the complementary other configuration of end 1402, 1404 of another middle segment 1400. The segment interface ends 1302, 1402, 1404, 1504 are configured as a single-axis, two-way bend at each articulation between the interface ends 1302, 1402, 1404, 1504 but with the distal steering assembly 128 comprising interfaces with different orientations, e.g. one set of interfaces 1302, 1402 having an orthogonal orientation to the other set of interfaces 1404, 1504, the assembly 128 as a whole is configured as a four-way, two axis bending assembly.

Referring to FIGS. 13A-13F, 14A-14F, and 15A-15F, the proximal and distal segments 1300, 1500 comprises a non-planar end 1302, 1504 that has a hyperbolic paraboloid shape that is configured to interface with a complementary non-planar end 1402, 1404 of a middle segment 1400 that also has a hyperbolic paraboloid shape. The non-planar end 1402 of the middle segment 1400 is also configured to interface with the non-planar end 1404 of another middle segment 1400. At the upper regions 1312 of the end 1302, an alignment structure 1314 may be provided to interface with an alignment structures 1414 at the upper regions 1412 of the complementary end 1402 of the middle segment 1400. In this particular variation, the alignment structure 1314 comprises a middle protrusion 1316 flanked by indents or recesses 1318 which forms a complementary interface with the alignment structure 1416 of the middle segment 1400, which comprises a middle recess 1418 flanked by protrusions 1418. Likewise, the upper regions 1420 of the other end 1404 of the middle segment 1400 comprises an alignment structure 1422 with a middle protrusion 1424 flanked by indents or recesses 1426 that can also form a complementary interface with the alignment structure 1404 of the middle segment 1400, and also the alignment structure 1522 in the upper regions 1520 of the non-planar end 1504 of the distal segment 1500. The alignment structures 1522 on the distal segment 1500 are the same or similar to the alignment structure 1422 of the middle segment 1400, with a middle recess 1524 flanked by two protrusions 1526. The alignment structures 1314, 1414, 1422, 1522 are configured to still provide a limited amount of pivoting between the segments 1300, 1400, but do not lock the two segments 1300, 1400 together. In other variations, however, the alignments structures 1314, 1414, 1422, 1522 may comprise complementary ball-in-socket structures or other type of complementary interference structures that does lock the segments 1300, 1400 together. Also, in other variants, instead of a hyperbolic paraboloid shape, the non-planar ends 1302, 1402, 1404, 1504 may comprise two planar sections that are non-orthogonal to the longitudinal axis of the bending assembly 128.

Referring still to FIGS. 13A-13F, 14A-14F, 15A-15F, each of the segments 1300, 1400, 1500 comprises a center or primary opening 1330, 1430, 1530 through which the drive shaft of the delivery system may reside. Segments 1300, 1400 further comprise bending openings 1332, 1432, 1532 in which a steering wire or element may reside. In other examples, however, the distal segment 1500, may comprise attachment structures to which the steering wires or elements attach, rather than pass through to attach to structures distal to the distal segment. The bending openings 1332, 1432, 1532 may be orientated such that they are spaced 90 degrees apart, and spaced 45 degrees apart from an adjacent alignment structure 1314, 1414, 1514.

As depicted in FIGS. 13G-13L, 14G-14L, 15G-15L, each of the segments 1300, 1400, 1500 may also comprise one or more openings 1334, 1434, 1534 and protrusions 1336, 1436, 1536. In some examples, the protrusions 1436, 1536 may reinforce the segments 1300, 1400, 1500 where the bend openings 1332, 1432, 1532 are located, and/or may facilitate the coupling or attachment of the segment 1300, 1400, 1500 to the other components of the delivery system. In the variants depicted in FIGS. 13A-13F, 14A-14F, 15A-15F, polymeric jackets or bumpers 1338, 1438, 1538 are provided around the segments 1300, 1400, 1500. These jackets or bumpers 1338, 1438, 1538 may help to disperse or redistribute the bending forces acting on the catheter body 112. This may reduce the risk of tearing and/or kinking of the catheter body 112, as well as the sheath 114. The bumper 1438 may have an overall hyperbolic paraboloid shape as depicted in FIGS. 14A-14F, or a hyperbolic paraboloid end configuration on their interface ends as depicted in FIGS. 13A-13F and 15A-15F. The jackets or bumpers 1338, 1438, 1538.

The proximal and distal segments 1300, 1500 may comprise a planar end 1340, 1540 to attach or interface with other components of the delivery system. The jackets or bumpers 1338, 1538 may comprise a non-planar end and a planar or circular end, corresponding their ends 1302, 1402, 1404, 1504. The jackets or bumpers 1338, 1438, 1538 may comprise any of a variety of materials, including silicone, polyurethane, styrenic co-block polymers, PEEK, nylon, PTFE, HDPE, and the like.

Figures 16A, 16B, 16C, 16D:
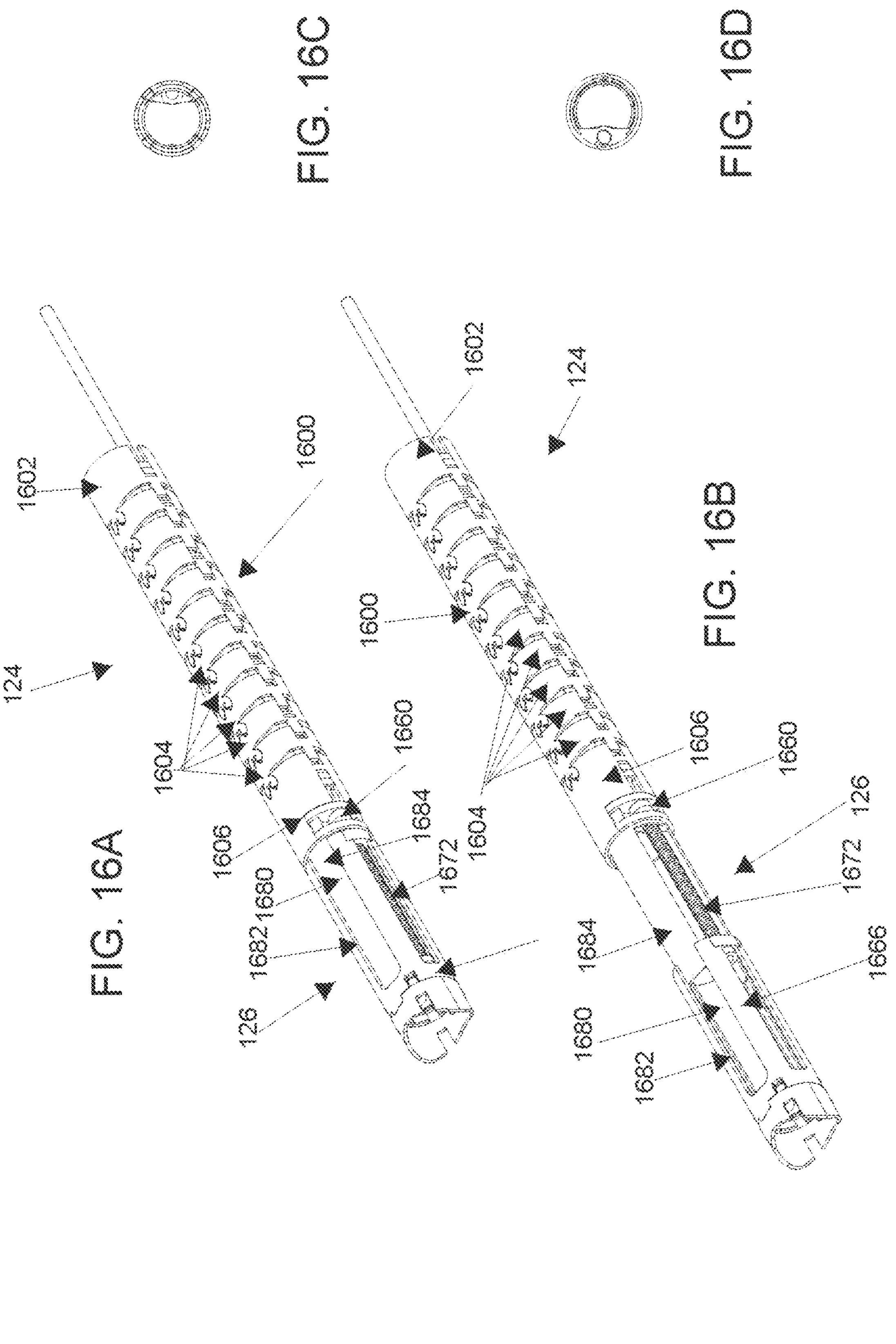
FIGS. 16A and 16B are top perspective views of the combined proximal steering and extension assembly, in a retracted and extended configuration, respectively.
FIG. 16C is a front elevational view of the extension assembly in FIGS. 16A and 16B.
FIG. 16D is a rear elevational view of the proximal steering assembly in FIGS. 16A and 16B.
Figures 16E, 16F, 16G, 16H:
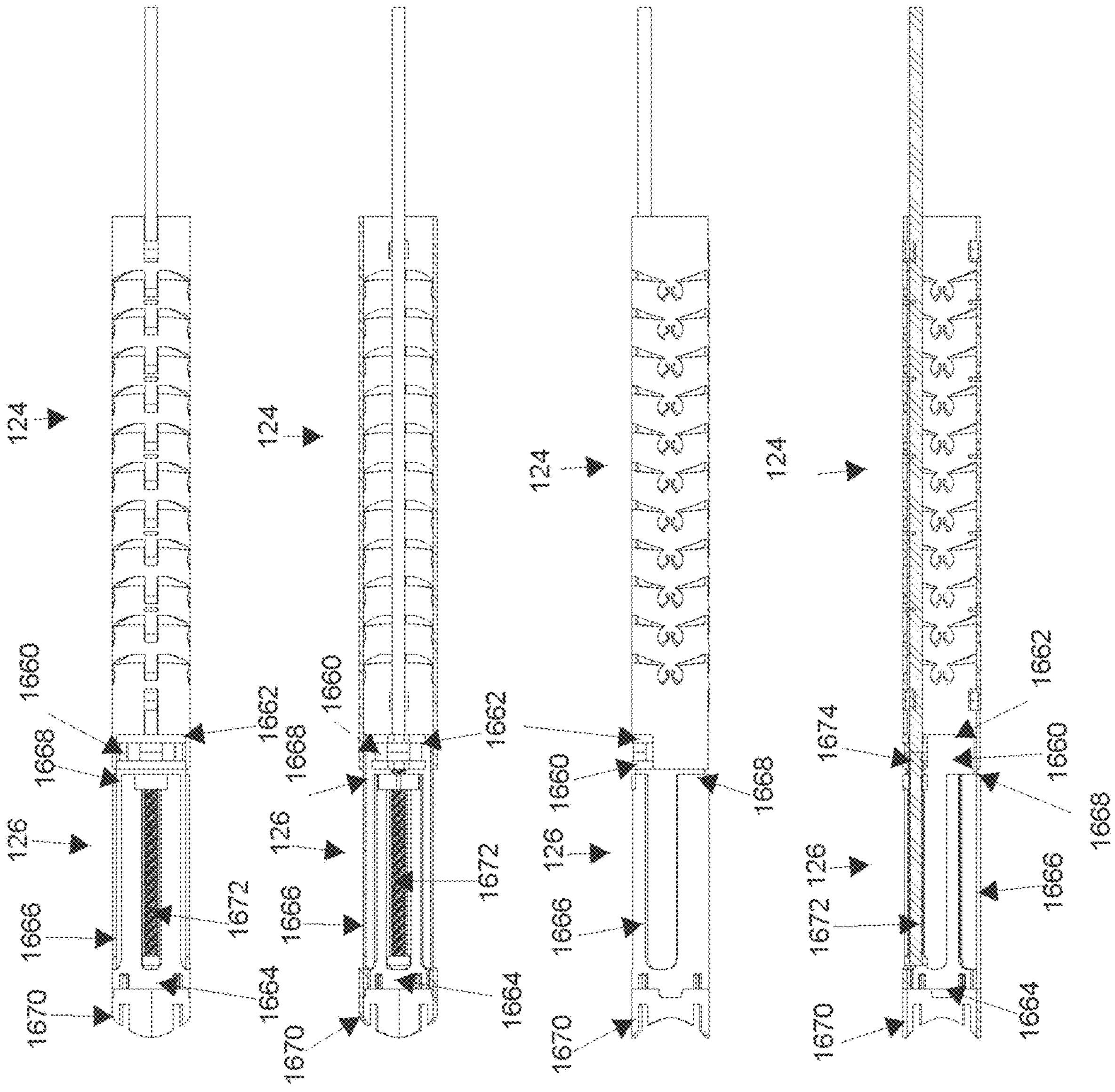
FIGS. 16E to 16H are top plan, top cross-sectional, side elevational and side cross-sectional views, respectively, of the combined proximal steering and extension assembly of FIG. 16A in a retracted configuration.
Figure 16I:
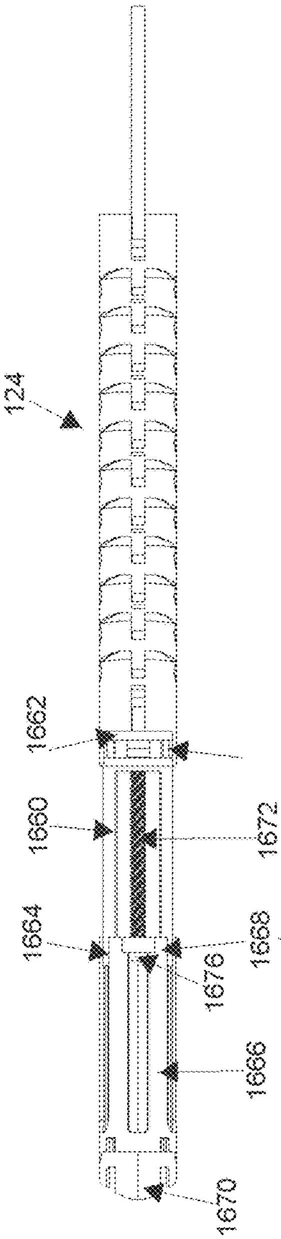
FIGS. 16I to 16L are top plan, top cross-sectional, side elevational and side cross-sectional views, respectively, of the combined proximal steering and extension assembly of FIG. 16B in an extended configuration.
Figure 16J:
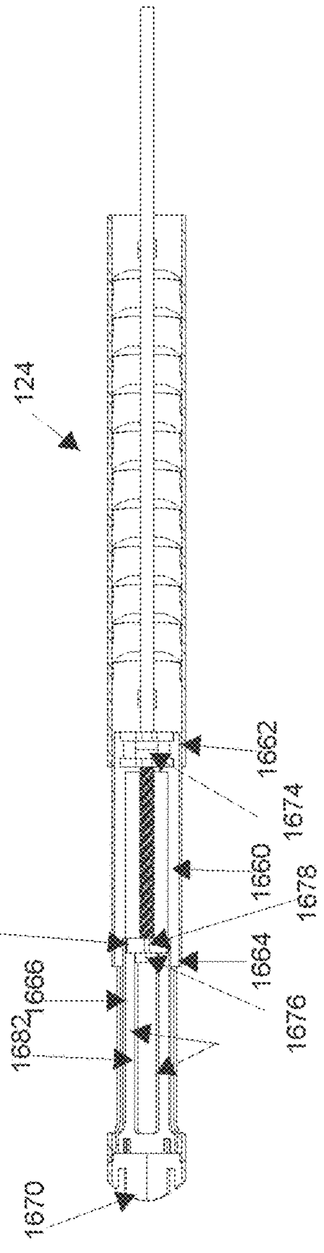
Figure 16K:
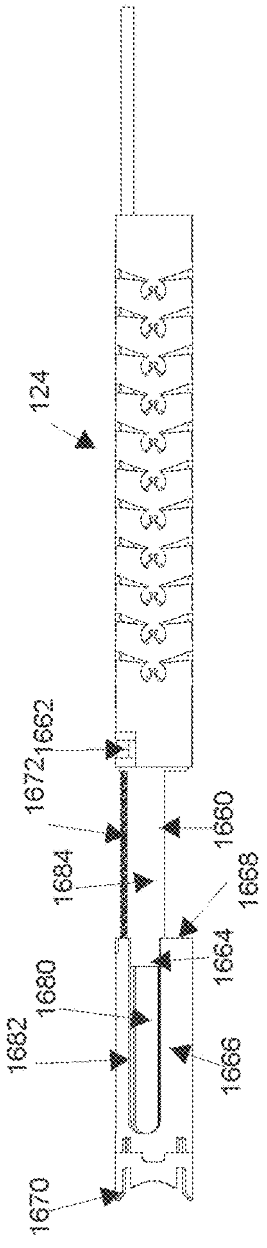
Figure 16L:
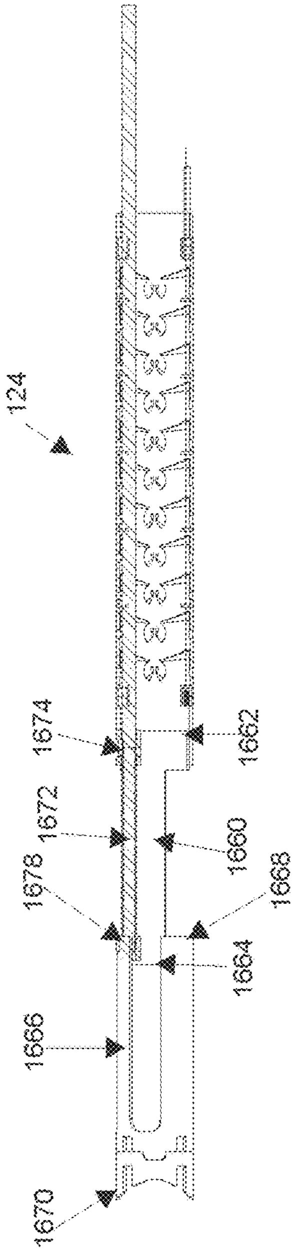

FIGS. 16A to 16L depicts an exemplary embodiment of the proximal steering and extension assemblies 124, 126 as shown in FIG. 1A. In this particular embodiment, the proximal steering assembly 124 comprises a flexible segmented tubular body 1600, but instead of discrete segments as in the distal steering assembly 128, the flexible segmented tubular body 1600 is a lasercut, unibody flexible segmented tubular body 1600 comprising segments 1602, 1604, 1606. Referring to FIG. 16M, the segments 1602, 1604, 1606 are interconnected by a pair of living hinge struts 1608 and a pair of neck regions 1610 on opposite sides of the tubular body 1600. To each side of neck region 1610 is a wedge opening 1614, which is configured to allow limited flexion between the segments 1602, 1604, 1606. The wedge opening 1614 is formed by a tapered or angular gap between the proximal ends 1616 and distal ends 1618 of the segments 1602, 1604, 1606. The maximum longitudinal separation along the opening 1614 may be in the range of 0.6 mm to 0.9 mm, 0.4 mm to 1 mm, or 0.2 mm to 1.2 mm. The angle formed by the proximal and distal ends 1616 and 1618 may be in the range of 5 degrees to 30 degrees, 8 degrees to 20 degrees, or 10 degrees to 15 degrees. The wedge openings 1614 may be in continuity with narrower arcuate slits 1620 from the apex 1622 of the wedge openings 1614 to the wide end 1624 of the strut 1608. A smaller wedge opening 1626 is provided between the wide end 1624 and the middle of strut 1608 and is also in communication with a smaller opening 1630 at the narrow end 1632 of the interconnect 1608. The smaller opening 1630 may comprise a teardrop shape, wherein the tip of the teardrop is in continuity with the tip of the smaller wedge opening 1632. Together, the larger wedge arcuate slit 1620, smaller wedge opening 1626 and teardrop opening 1630 form a partially circular configuration with a partially circular opening 1640 of one segment attached to a bifid pivot head 1642 that is able to pivot or bend within the partially circular opening 1640. The maximum bending angle between each segment 1602, 1604, 1606 may in the range of 10 degrees to 45 degrees, 15 degrees to 35 degrees, or 20 degrees to 30 degrees, and the maximum total bending angle of the segmented tube 1600 may be 75 degrees to 150 degrees, 90 degrees to 130 degrees, or 100 degrees to 120 degrees.

Figure 16N:
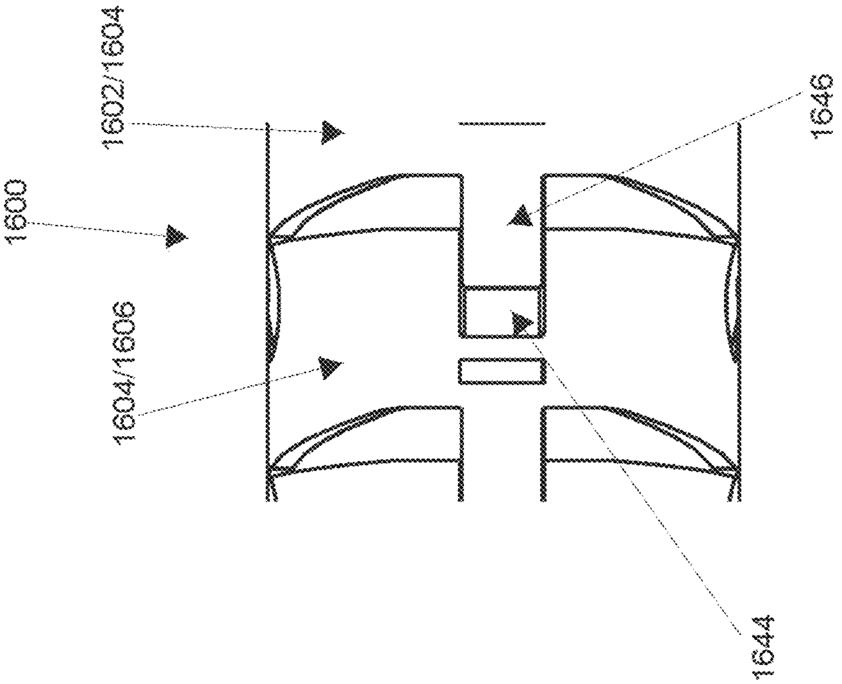
FIGS. 16M and 16N are detailed schematic views of various regions of the extension assembly.
Figure 16M:
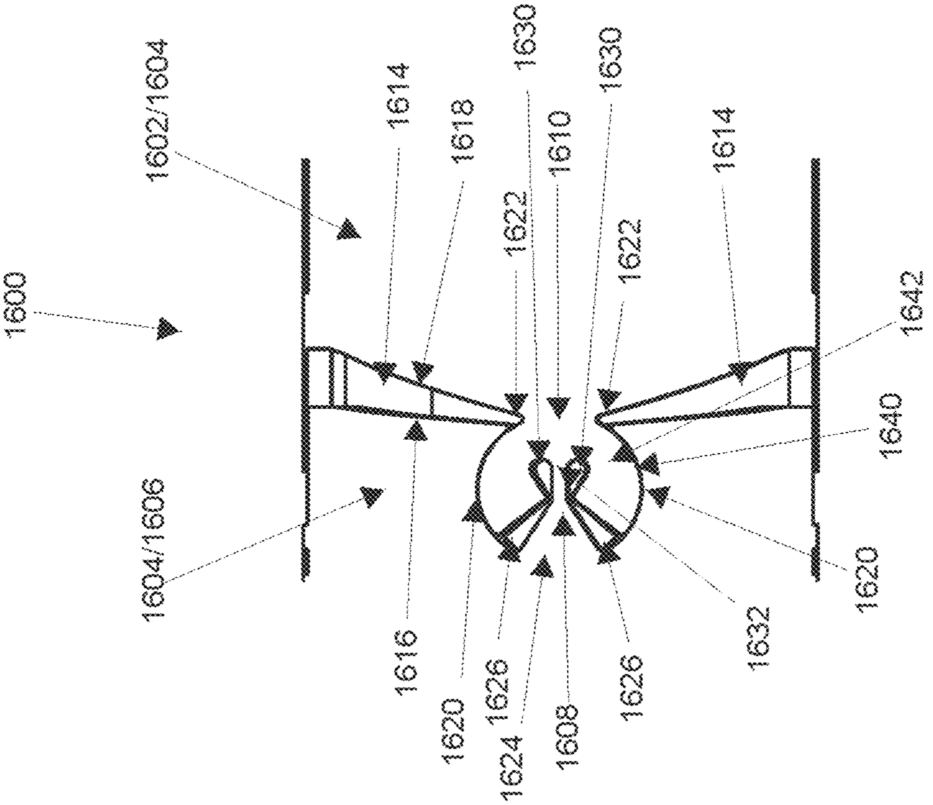
Figure 16O:
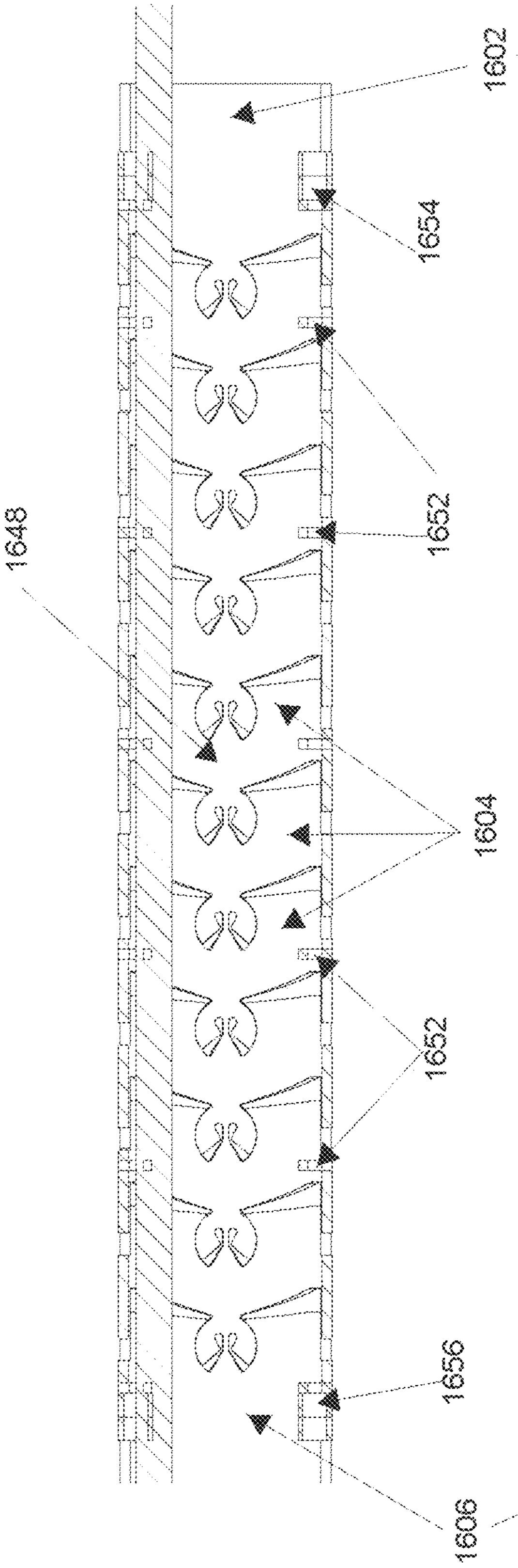
FIGS. 16O and 16P are detailed cross-sectional views of the proximal steering assembly, with and without the steering element, respectively.

Referring to FIG. 16N, in addition the pivoting movement at each opening 1640 and complementary bifid pivot head 1642, each segment 1602, 1604, 1606 also comprises a pair of notches 1644 and/or protrusions 1646 which are slidable in the notches 1644. The notches 1644 and protrusions 1646 may resist torsional forces that are acting on the proximal steering assembly 124 and/or may also provide or support the limit on the amount of flexion between each segment 1602, 1604, 1606, based on the longitudinal length of the notches 1644 and protrusions 1646. In some variations, the lengths of the notches may be in the range of 12 mm to 25 mm, 15 mm to 22 mm, or 16 mm to 20 mm, and the lengths of the protrusions may be in the range of 1.5 mm to 2.5 mm, 1.7 mm to 2.2 mm, or 1.8 mm to 2.0 mm. The widths of the notches and protrusions may be in the range of 0.8 mm to 2 mm, 1.0 mm to 1.8 mm, or 1.1 mm to 1.4 mm. The gap length between the notches and protrusions when the proximal steering assembly is in an unbent neutral position may be in the range of 0.5 mm to 1.5 mm, 0.6 mm to 1.2 mm, or 0.7 mm to 0.9 mm. This gap length may also be the maximum gap length of the larger wedge opening 1614. The number of segments 1604 in the steering assembly in FIGS. 16A and 16B is ten, but in other examples, the number may be in the range of 1 to 20, 2 to 15, 5, to 15, or 8 to 12. The average longitudinal length of segments 1604 may be in the range of 2 mm to 10 mm, 2 mm to 6 mm, 3 mm to 5 mm, or 3.5 mm to 4.5 mm. The proximal and distal segments 1602, 1606 may be longer, e.g. in the range of 2 mm to 10 mm, 4 mm to 9 mm, 5 mm to 8 mm, 4 mm to 8 mm, 4 mm to 5 mm, 3 mm to 6 mm, or 2 mm to 8 mm.

Figure 16P:
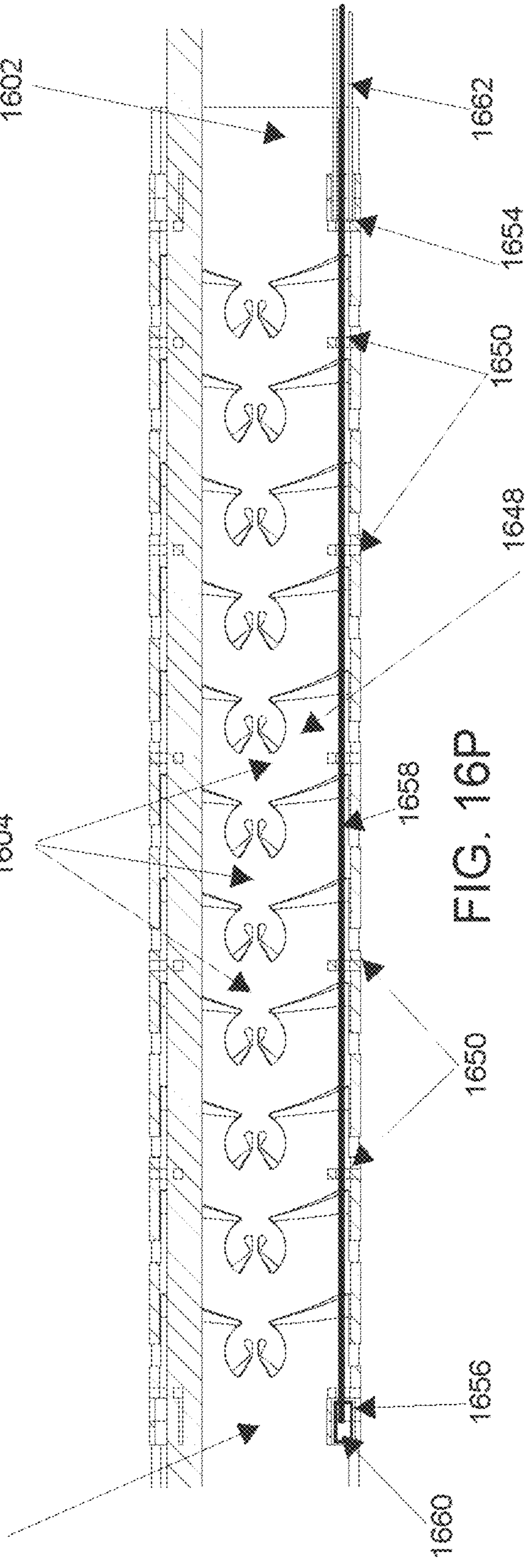
Figure 17A:
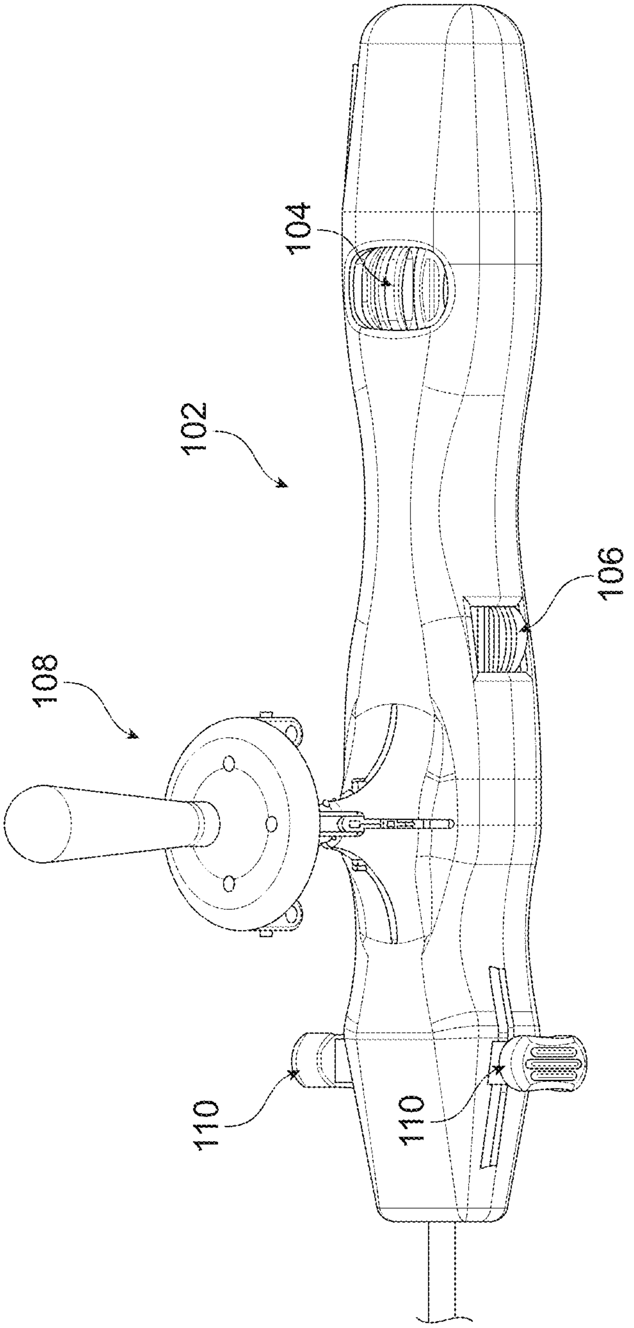
FIG. 17A is a top perspective view of the proximal handle in FIG. 1A.
Figure 17B:
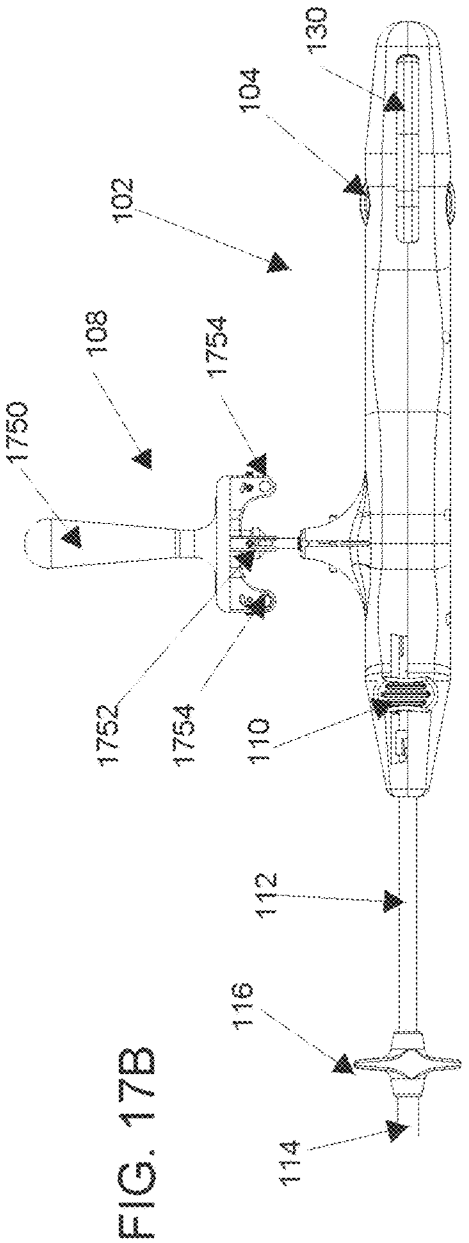
FIGS. 17B and 17C are side elevational and side cross-sectional views of the proximal handle in FIG. 17A.
Figure 17C:
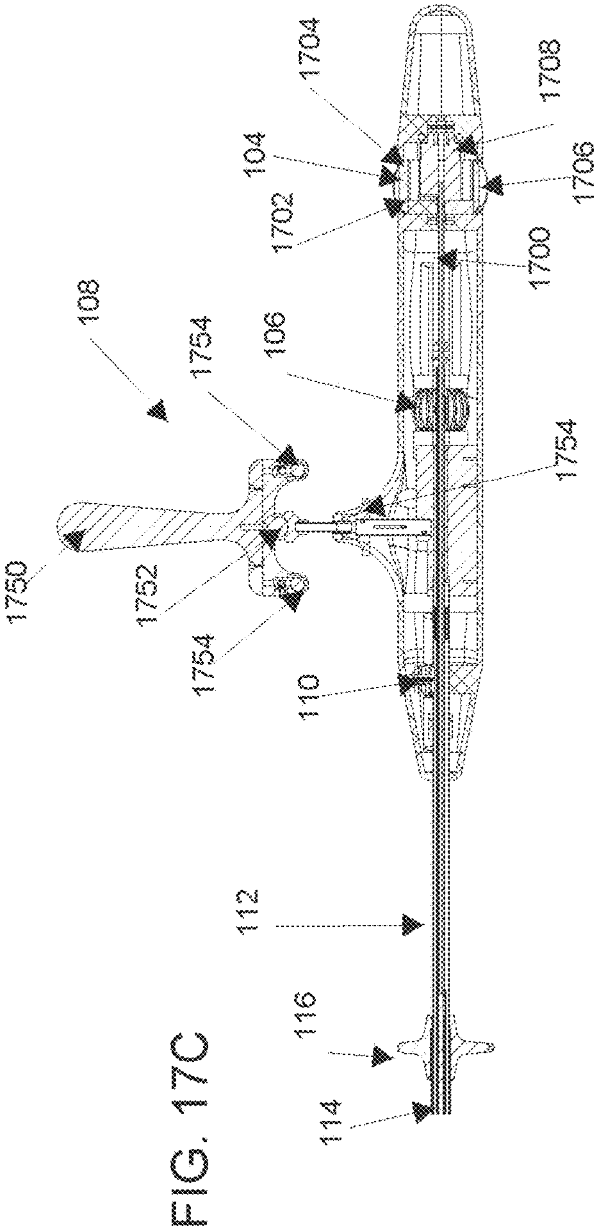
Figure 17D:
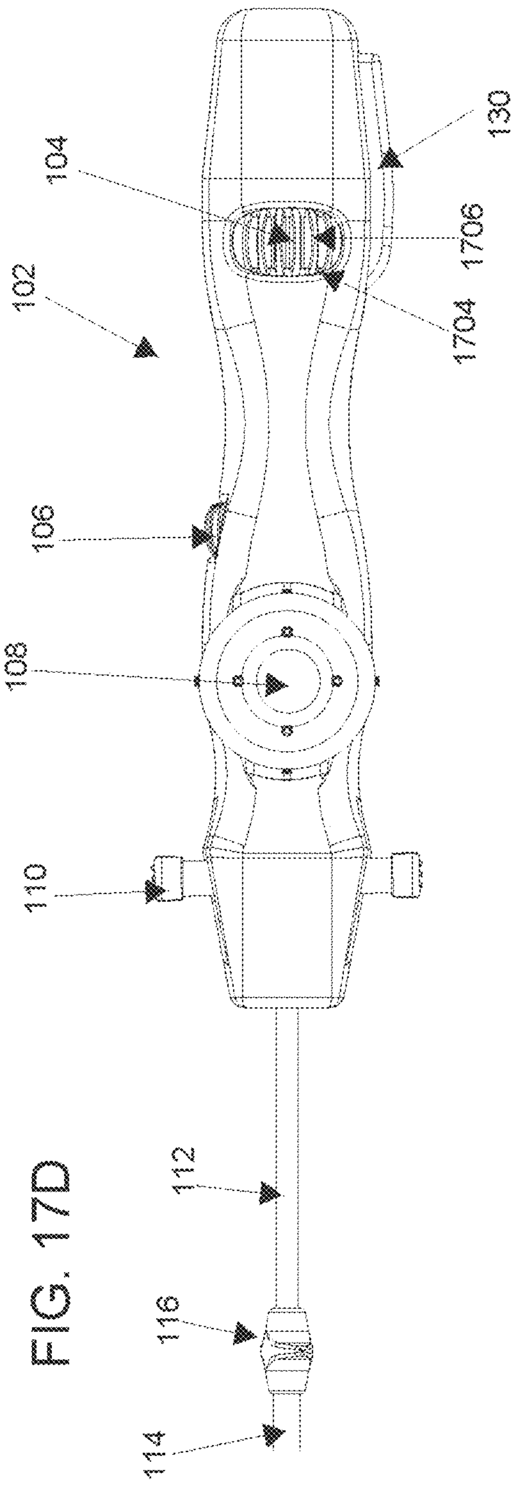
FIGS. 17D and 17E are superior plan and superior cross-sectional views of the proximal handle in FIG. 17A.
Figure 17E:
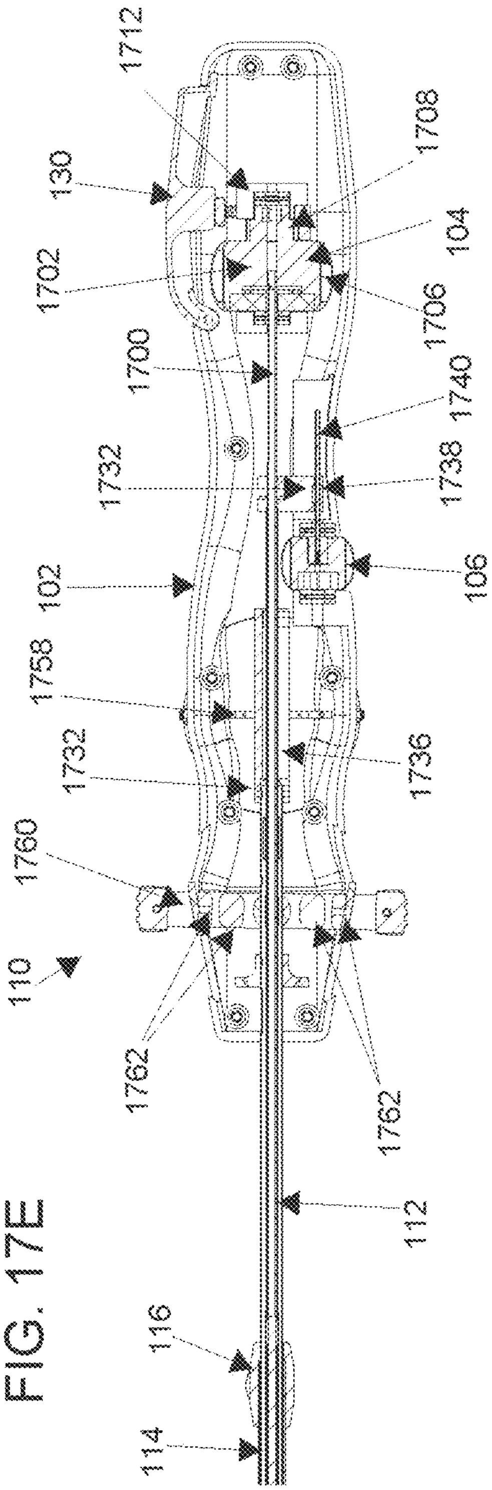
Figure 18A:
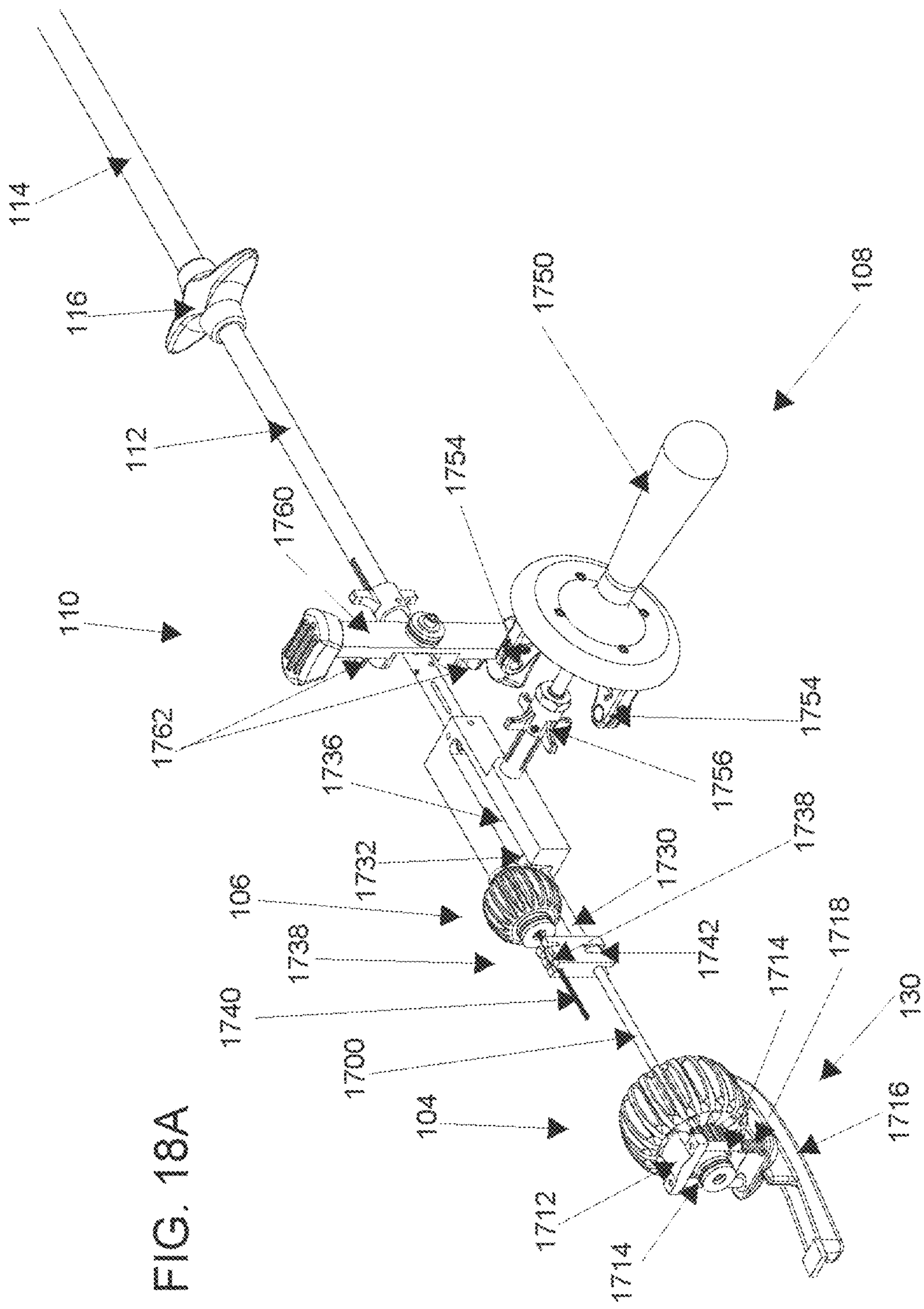
FIGS. 18A to 18C are perspective, top plan and side elevational views of the proximal handle in FIG. 17A, without the handle housing.
Figure 18B:
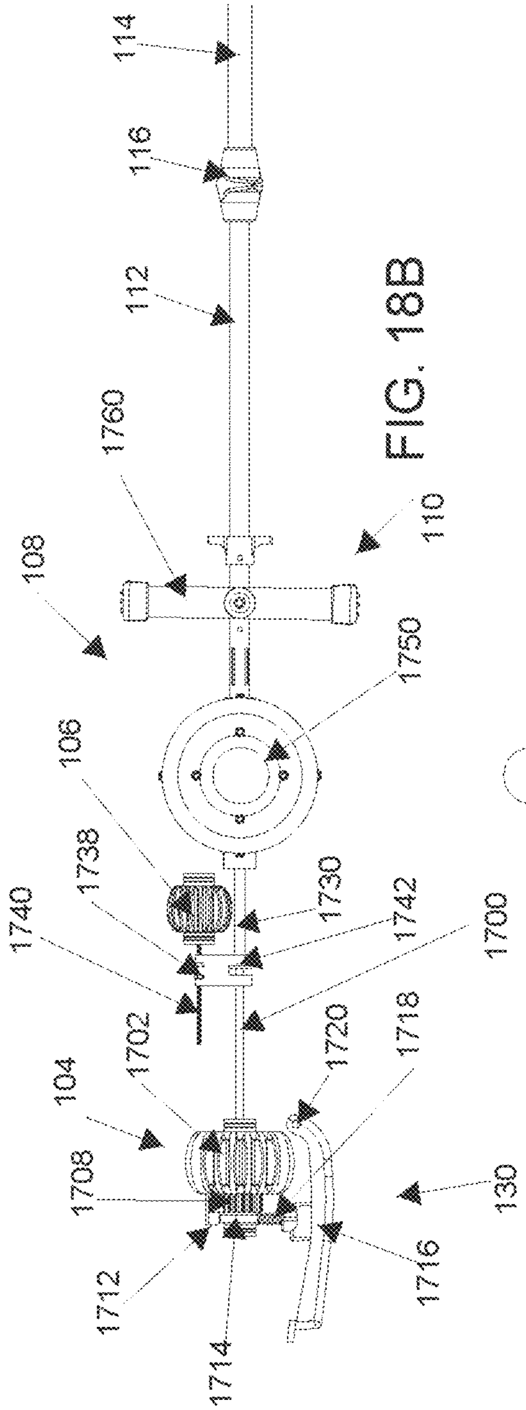
Figure 18C:
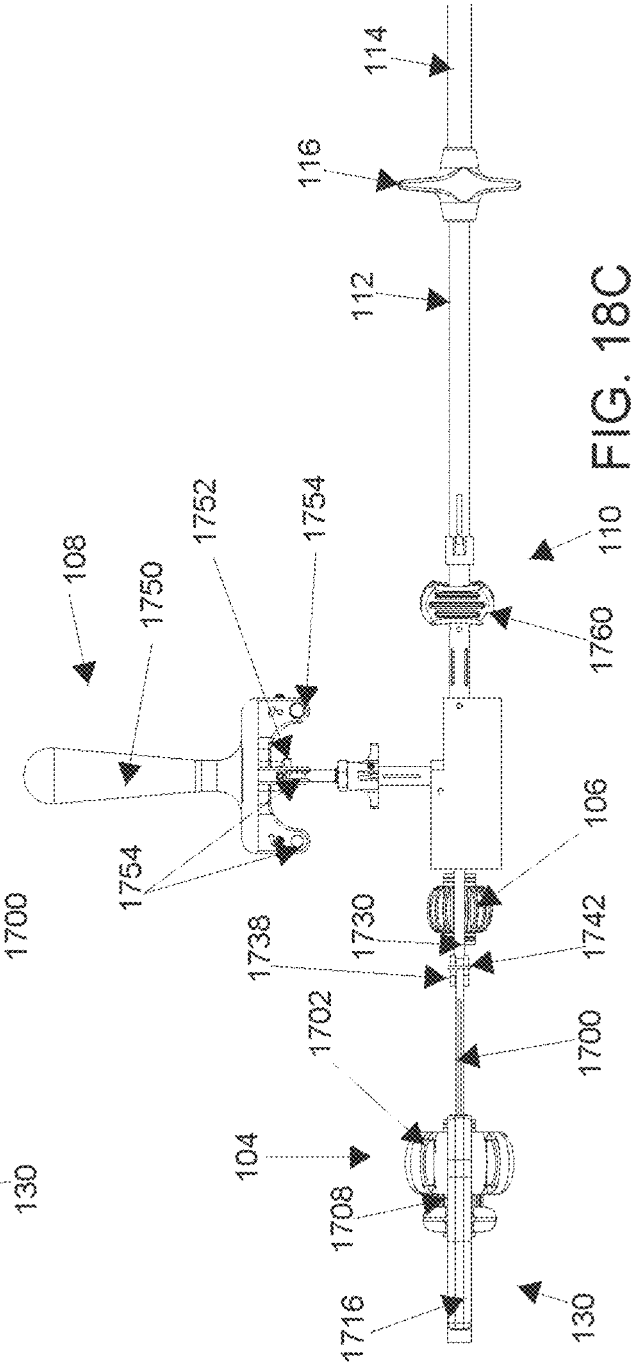

Referring to FIGS. 160 and 16P, each of the segments 1602, 1604, 1606 comprises a central or primary opening 1648, as well as steering flanges 1650 and steering openings 1652 located in the primary opening 1648 of at least some if not all of the segments 1602, 1604, 1606. The proximal and distal segments 1602, 1606 may comprise longer and/or larger steering cavities 1654, 1656. As depicted in FIG. 16P, the steering wires 1654 for the proximal steering assembly 124 slidably reside in the openings 1652 and the cavities 1654, 1656. The steering element 1658 may be attached to the distal cavity 1656 via weld, knot, crimp structure 1660 or other interference fit to the steering opening to affix. The steering element 1658 may be located in a coil sheath 1662 or other tubular structure that is attached to the steering cavity 1654 of the proximal segment 1602 of the proximal segment 1606. The steering wire may comprise a solid or multi-filament wire with a size in the range of 0.3 mm to 0.8 mm, 0.4 mm to 0.7 mm, or 0.4 mm to 0.6 mm. Proximally, the steering wires 1654 may be attached to lever 110 of the handle 102, as described in further detail below.

Referring now to the extension assembly 126 of the delivery system in FIGS. 16A to 16K, the extension assembly 126 comprises a proximal or first housing 1660 with a proximal end 1662 and a distal end 1664 and is in slidable arrangement with a distal or second housing 1666, with a proximal end 1668 and a distal end 1670. A worm gear 1672 or helically threaded shaft is rotatably coupled to a helical lumen 1674 of the proximal housing 1660. This worm gear or lead screw shaft 1672 is configured to extend and retract with rotation relative to the helical lumen 1674 and the proximal housing 1660. The distal end of the screw shaft 1672 is rotatably fixed to the proximal end 1668 of the second housing 1666 via a screw, bolt, rivet, crimp head or other fastener 1676 via an opening 1678 in the proximal end 1668. This attachment interface permits rotation of the screw shaft 1672 while also locking the extension and retraction of the screw shaft 1672 and the extension and retraction of the distal housing 1666 relative to the proximal housing 1660. To resist any torsional displacement that may occur between the proximal and distal housings 1660, 1666, a slot 1680 and grooves 1682 may be provided with one or more wall sections 1684 of the proximal and distal housings 1660, 1666. A mechanical stop structures may be provided on the worm gear or threaded shaft to provide a limit on the amount of extension. The proximal end of the worm gear or threaded shaft that controls this extension may be mechanically coupled to a rotatable knob 106 on the handle 102, which is described below.

As noted previously, control of implant expansion, steering and catheter extension may be performed using a number of controls 104, 106, 108, 110 provided on the handle 102, as depicted in FIGS. 17A to 17E. For rotation of the rotor assembly 850 900 depicted in FIGS. 8A to 9F, the rotor assembly 850, 900 may be coupled to a drive shaft 1700 in the handle 102 and attached to rotatable knob 104. The knob 104 may comprise a knob body 1702, which is exposed via one or more housing openings 1704 of the handle 102 to permit user rotation. The knob body 1702 may comprise one or more ridges 1706 to facilitate gripping of knob 104 and to resist slippage during use. The knob 104 may also comprise a secondary knob body 1708 comprises ridges or teeth that are releasably engageable by the lock assembly 130. When engaged, the locking head or structure 1712 of the lock assembly 130 engages the teeth to resist rotation of the knob 104. The locking head 1712 is attached to one or more struts 1714 to the lock lever 1716, and is biased to the engaged position by one of more springs 1718 provided on the struts 1714. To disengage the locking head 1712, the lock lever 1716 is depressed or squeezed, to thereby pivot at its housing joint 1720 and to overcome the resistance of the springs 1718 to disengage the locking head 1712.

The drive shaft 1700 is located in the tubular stator shaft 1730 located in the handle 102. To resist rotational movement of the stator shaft 1702 during manipulation of the delivery system, a stator key block 1732 is attached to or clamped to the stator shaft 1730 via a set screw or pin. The shape of the block 1704 forms a complementary interfit with the shape of the elongate block cavity 1736 resist rotational displacement while allowing longitudinal movement of the block 1704 in the cavity 1736. The longitudinal displacement permits the extension and retraction of the distal region of the delivery system as the extension assembly 126 is adjusted during the procedure. As noted previously the worm gear and threaded interface of the extension assembly 126 is configured to generate the longitudinal displacement force to extend and retract the second housing of the extension assembly, a similar threaded interface 1738 may be provided in the handle 102 to provide a second location at the proximal end of the worm gear shaft 1740 to help push or pull the stator shaft to help alleviate any resistance to the displacement of the stator shaft as it travels with the second housing of the extension assembly. The proximal threaded interface 1738 may comprise a keyed structure 1742 that permits extension and retraction of the stator shaft 1730 by exerting force on a proximal flange 1744 of the stator shaft 1730 at its proximal end during with use of the extension assembly 126.

Next, the control 108 of the 4-way distal steering assembly 128 may be provided with a joystick handle 1750. The joystick handle 1750 is configured with an articulation 1752 to pivot in at least four directions and/or a combination of the two the four directions, comprises steering element attachment structures 1754 to apply tension forces of varying amounts through the steering wire or elements (not shown) to bend the distal steering assembly 128. One or more steering wire or element guides 1756, 1758 may be provided to provide facilitate the bends in the steering wire or elements through which the tension is transferred. Similarly, the control 110 of the two-way proximal steering assembly 124 comprises a pivotable lever 1760 to which steering wires or elements are attached at attachment structures 1762 along the lever 1760. As the lever 1760 is rotated in one direction or the other direction from its neutral position, tension is generated in one of the steering wires or elements while relieving or reducing tension, if any, in the other steering wires or element. The lever 1760 may be maintained in a neutral position when not manipulated by the user either by one or more pairs of opposing springs acting on the lever 1760 or by setting a baseline balanced tension in the steering wires or elements.

Figure 19A:
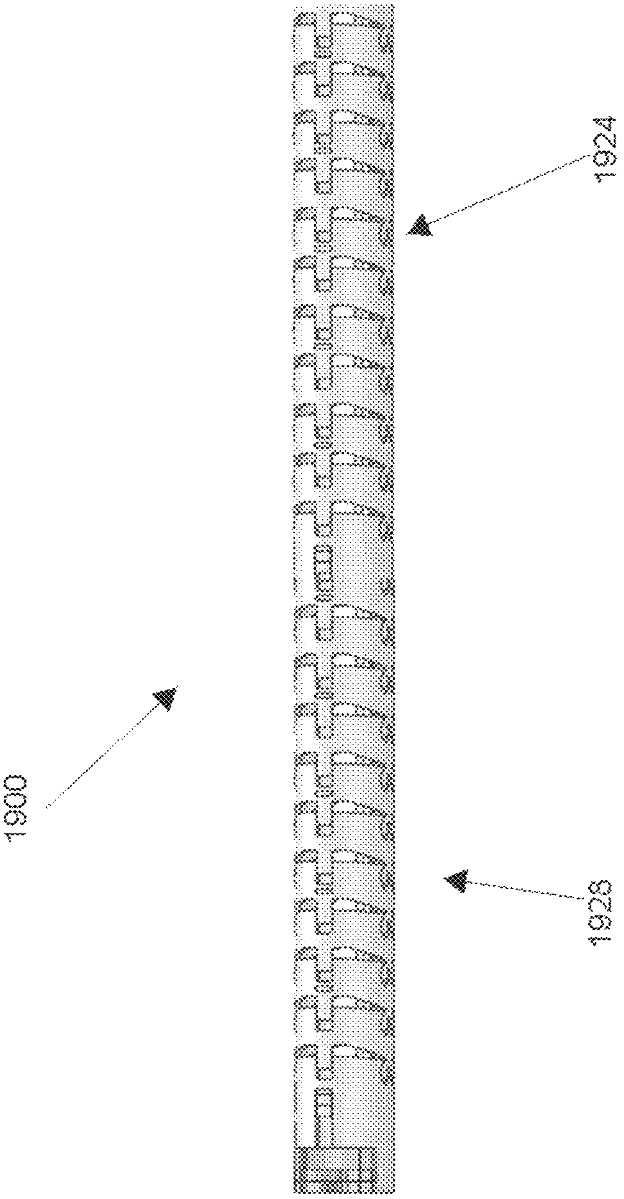
FIG. 19A depicts another embodiment of the delivery device, comprising two two-way steering assemblies.
Figure 19B:
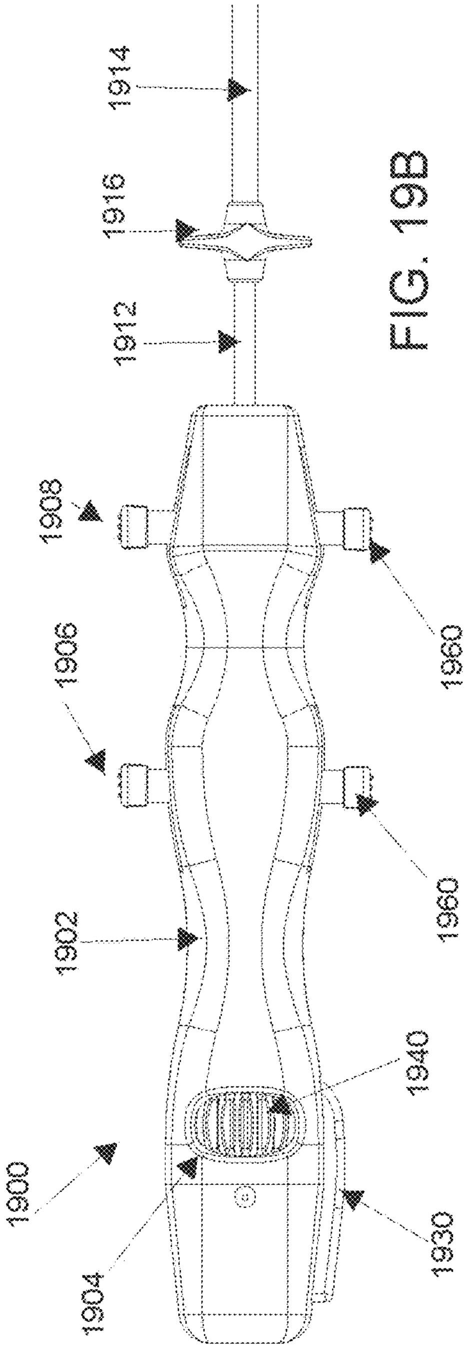
FIGS. 19B to 19E depict the handle of the delivery device of FIG. 19A.
Figure 19C:
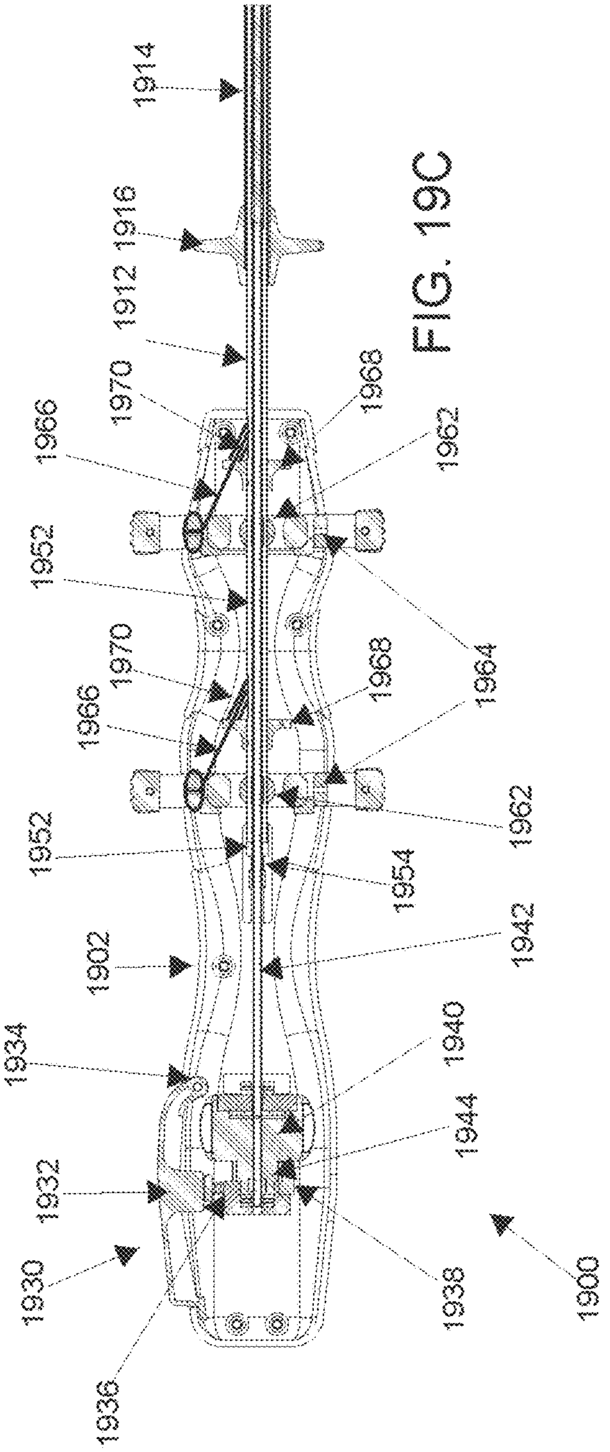
Figure 19D:
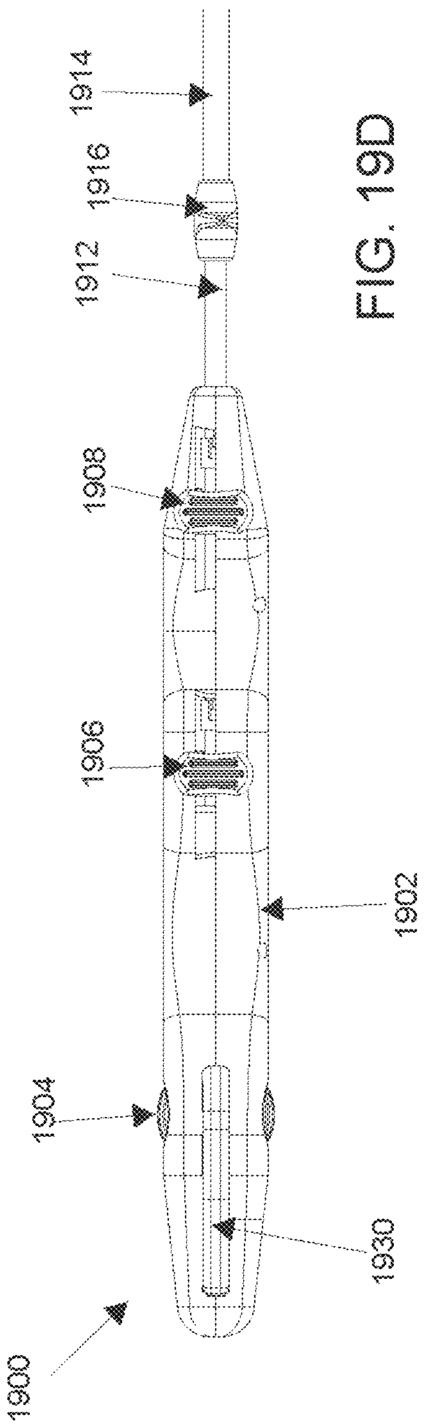
Figure 19E:
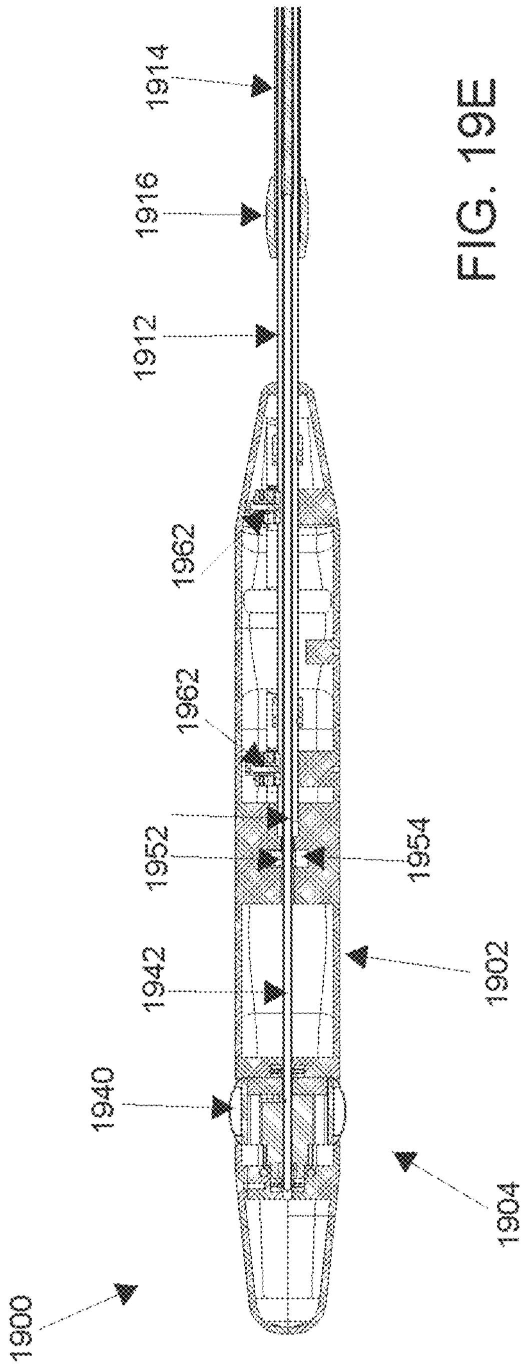

In another embodiment of a delivery device, depicted in FIG. 19A, the delivery device 1900 comprises two two-way steering assemblies 1924, 1928, without an extension assembly. In some configurations, both assemblies 1924, 1928 are configured to bend in the same bending plane, both in other configurations, the assemblies bend in different bending planes, e.g. bending planes that are orthogonal to each other. These and other components are otherwise similar to the delivery device 100 described earlier, including the rotor, stator, sheath, and adapted for this particular delivery device 1900. For example, the proximal end of the delivery device 1900 includes a handle 1902 with controls 1904, 1906, 1908 that are coupled to the catheter body 1912, along with a slidable sheath 1914 and sheath handle 1916. The control of the rotor shaft via the rotary knob 1940 of control 1904 and releasable lock 1930 are otherwise similar to the mechanism for the control 104 and releasable lock 130 of delivery device 100. The knob 1940 is fixedly attached to the rotor shaft 1942 to control the unwinding and release of the tension members in the implant delivery section of the delivery device 1900. The releasable lock 1930 comprises a lock lever 1932 that is attached to the handle 1902 via a pin joint 1934 or other articulation. The lever 1932 is maintained in a biased lock configuration via a spring 1936 that pulls the locking head 1938 into engagement with the secondary body 1944 of the knob 1940 to resist rotation. Upon depression or squeezing of the lever 1932 to overcome the spring force and to separate the locking head 1938 away from the secondary body 1944, the knob 1940 may be rotated by the user. In contrast to delivery device 100, the stator shaft 1950 of delivery device 1900 does not longitudinally displace due to the lack of an extension assembly, but may be coupled to the handle 1902 via an adhesive bond and/or a mechanical interfit or interference interface. In FIGS. 19B to 19E, for example, the stator shaft 1950 is coupled to a stator key block 1952 via a set screw or other mechanical fastener. The block 1952 is located in a block cavity 1954 with a complementary cavity shape to the outer surface of the stator key block 1952 to thereby resist rotational and longitudinal displacement.

The bending controls 1906 and 1908 may comprise a configuration similar to control 110 of delivery device 100. These controls 1906, 1908 each comprise a lever 1960 with a central pivot joint 1962 that with steering element attachment structures 1964 located on each side of the levers 1960. The steering wires or elements 1966 (depicted only on one side of the handle 1902) are coupled to the attachment structures 1964 and along steering guides 1968 and into the catheter body 1912, external to the stator shaft. Optional steering wire sheaths or compression coils 1970 may be provided to facilitate movement of the steering elements 1966. The steering elements 1966 may be routed in any of a variety of ways as shown in FIGS. 19B to 19E, but may also be routed radially inward closer to the central pivot 1962 and clamped in between the attachment structures 1964 on each side.

In one exemplary method of delivering the replacement valve, the patient is positioned on the procedure table, and the draped and sterilized in the usual fashion. Anesthesia or sedation is achieved. Percutaneous or cutdown access to the vascular or entry site is obtained, e.g. at the femoral vein, femoral artery, radial artery, subclavian artery, and an introducer guidewire is inserted. A guidewire is manipulated to reach the desired valve implantation site. Pre-shaped guidance catheters or balloon catheters may be used to facilitate the crossing of the valve implantation site Referring to FIG. 4A, the delivery system 400 with the delivery catheter 402 and valve 804 is positioned across the valve opening 406. The delivery system 400 may also be further manipulated to adjust the angle of entry through the valve opening 406 to be roughly orthogonal to the native valve opening and/or to be centered with the valve opening 406. Once the desired catheter pose is achieved, the delivery sheath 408 is withdrawn proximally, to expose the collapsed valve 404.

In FIG. 4B, the set of tension lines 428 controlling the release of the downstream end 410 of the outer wall 412 of the valve 404 are partially released, while the tension lines controlling the inner wall 416 remain tensioned. Next, in FIG. 4C, downstream end 410 of the outer wall 412 of the valve 404 is further released, allowing the downstream end, the middle region and more of the upstream end 414 of the outer wall 412 to expand further, thereby allowing the transition wall 416 of the valve 402 to at least partially expand outward. The partial expansion of the atrial end 414 and the ventricular end 410 of the valve 402 helps to further center and orient the middle region 422 of the valve 402 orthogonally prior to complete release. While the initial expansion of the atrial end 414 of the outer wall 412 in this embodiment is a secondary effect from the partial release of the ventricular end 410 of the valve 402 as longitudinal tension is released, in other examples, independent tension line control of the upstream end 414 may be provided.

In FIG. 4D, the tension lines 428 of the downstream end 410 and the tension lines 430, 432 of the upstream end 414 are further released, either simultaneously or singly in a stepwise fashion, further engaging the middle region 420 of the outer wall 412 against the valve opening 406. This further expansion of the outer wall 412 also exposes the retention barbs or projections 422 on the outer wall 412. Proper centering and orientation of the valve is reconfirmed, to make sure the valve has not been deployed in a skewed or partially disengaged pose with respect to the valve annulus. The tension lines 428, 430, 432 may be optionally re-tensioned to re-collapse the valve 404 may be performed, to facilitate re-positioning and/or re-orienting of the valve 404. Once confirmed, the tension lines of the inner wall 818 are released, as shown in FIG. 4E, which also allows the outer wall 412 to achieve its untethered expansion against the mitral valve opening 406. The tension lines 428, 430, 432 can then be separated from the valve 404 and withdrawn into the catheter and optionally out of the proximal end of the catheter 402. Alternatively, the delivery system and procedure in FIGS. 5A to 5E may be adapted for a similar delivery procedure.

In still another exemplary method of delivering the replacement valve, the patient is positioned on the procedure table, and the draped and sterilized in the usual fashion. Anesthesia or sedation is achieved, with selective ventilation of the right lung and optionally the left upper lobe of the lung to permit controlled collapse of the left lower lobe of the lung. A pursestring suture is placed at the transapical or other cardiac entry site. A trocar is inserted through a cannula or introducer with a proximal hemostasis valve, and the trocar assembly is inserted through the pursestring suture to access the cardiac chamber and the target valve.

Referring to FIG. 4A, the delivery system 400 with the delivery rigid tool 402 and valve 404 is positioned across the valve opening 406. The delivery system 400 may also be further manipulated to adjust the angle of entry through the valve opening 406 to be roughly orthogonal to the native valve opening and/or to be centered with the valve opening 406. Once the desired tool pose is achieved, the delivery sheath 408, if any, is withdrawn proximally, to expose the collapsed valve 404.

In FIG. 4B, the tension lines 438 controlling the release of the downstream end 410 of the outer wall 412 of the valve 804 are partially released, while the tension lines 430, 432 controlling the inner wall 416 remains tensioned. Next, in FIG. 4C, downstream end 410 of the outer wall 412 of the valve 404 is further released, allowing the downstream end, the middle region and more of the upstream end 414 of the outer wall 412 to expand further, thereby allowing the transition wall 416 of the valve 402 to at least partially expand outward. The partial expansion of the atrial end 414 and the ventricular end 410 of the valve 402 helps to further center and orient the middle region 422 of the valve 402 orthogonally prior to complete release. While the initial expansion of the atrial end 414 of the outer wall 412 in this embodiment is a secondary effect from the partial release of the ventricular end 410 of the valve 402 as longitudinal tension is released, in other examples, independent control of each tension line may be provided.

In FIG. 4D, the tension lines of the downstream end 410 and upstream end 414 are further released, either simultaneously or singly in a stepwise fashion, further engaging the middle region 420 of the outer wall 412 against the valve opening 406. This further expansion of the outer wall 412 also exposes the retention barbs or projections 422 on the outer wall 412. The tension lines may be optionally re-tensioned to re-collapse the valve 404 may be performed, to facilitate re-positioning and/or re-orienting of the valve 404. Proper centering and orientation of the valve is reconfirmed, to make sure the valve has not been deployed in a skewed or partially disengaged pose with respect to the valve annulus. Once confirmed, the tension lines of the inner wall 418 are released, as shown in FIG. 4E, which also allows the outer wall 412 to achieve its untethered expansion against the mitral valve opening 406. The tension lines 428, 430, 432 can then be released as shown and described for FIGS. 10G and 10H, or cut with the cut ends withdrawn into the catheter and optionally out of the proximal end of the delivery tool 402. Alternatively, the delivery system and procedure in FIGS. 5A to 5E may be adapted for a similar delivery procedure.

In some embodiments, the delivery system may be configured with an attachment interface proximal to the implant delivery section. This allows the attachment of the implant delivery section to the rest of the delivery system at the point of manufacture or at the point of use, during the assembly process or final step of the assembly procedure or preparation procedure. The attachment interface may facilitate the attachment of different handles, steering assemblies and/or different size implants during the manufacturing process or during clinical use. The attachment interface may also facilitate the separate packaging and sterilization of different components delivery system, which may have different packaging or sterilization requirements, thereby simplifying the manufacturing process, e.g. different sterilization and packaging of a pre-attached valve and/or pre-routed tension members to the stator/rotor assembly, vs. the handle and catheter body of the delivery system.

The location of the attachment interface of the delivery system may vary, depending on the features provided for the delivery system. For example, the attachment interface may be located within the distal catheter section, between a distal steering mechanism and the implant delivery section, or may be located at the proximal end of the distal catheter section, between the catheter body and the proximal end of the distal catheter section or implant delivery section, depending on whether any steering or extension assembly is provided.

Figure 20B:
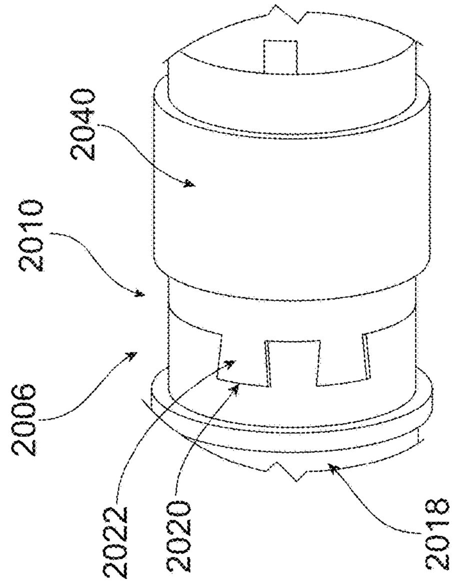
FIG. 20B is a perspective view of the engagement of the implant delivery section.
Figure 20D:
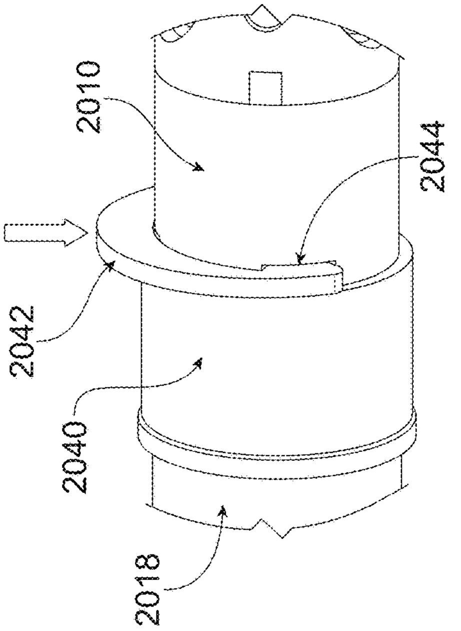
FIG. 20D is a perspective view of the securement device in the secured position.
Figure 20A:
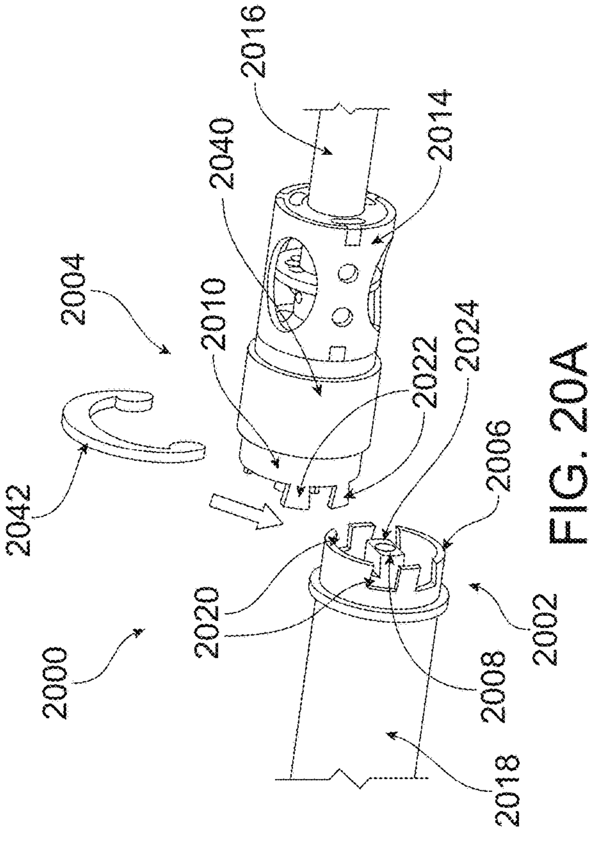
FIG. 20A is a schematic component view of another embodiment of the delivery device, comprising an attachment interface in the distal catheter section to provide attachment of the implant delivery section.
Figure 20C:
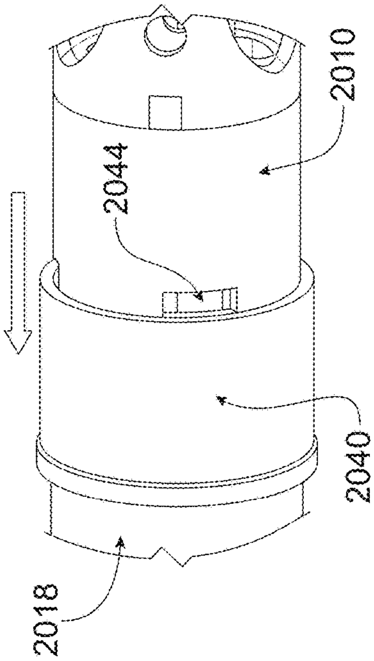
FIG. 20C is a perspective view of the locking collar in the locked position.

FIGS. 20A to 20D and 21A to 21B, for example, depicts an exemplary embodiment of the attachment interface 2000 of a delivery system that, for simplification, does not depict a steering or extension mechanism, that may be included. The attachment interface 2000 comprises a proximal attachment interface 2002 and distal attachment interface 2004. The proximal attachment interface 2002 comprises a proximal stator tube interface 2006, a drive shaft interface 2008, and the distal attachment interface 2004 comprises a stator tube interface 2010 and a rotor shaft interface 2012 (depicted in FIG. 21A), coupled to the stator housing 2014 and the rotor shaft 2016, respectively. The proximal outer tube 2006 and the stator tube interface 2010, and the drive shaft interface 2008 and the rotor shaft interface 2012, are configured to be engaged to form a mechanical interfit that resists longitudinal detachment and/or rotational separation when engaged. As illustrated in FIGS. 20A and 20B, the proximal outer tube 2006 may be attached or bonded to the end of the catheter body 2018, or steering/extension assemblies if provided. The proximal outer tube 2006 comprises a plurality of cut-outs or recesses 2020 located along the rim of the opening of the proximal outer tube 2006. These recesses 2020 form a complementary mechanical interfit with a plurality of projections 2022 of the stator tube interface 2010. Similarly, the drive shaft interface 2008 may comprise a plurality of recesses 2024, which in turn is configured to form a mechanical interfit with a plurality of projections 2026 of the rotor shaft interface 2012. Once the proximal and distal attachment interfaces 2002, 2004 are engaged, torque from the handle of the delivery system may be transmitted through the drive shaft interface 2008 and rotor shaft interface 2012 to the rotor shaft 2016, to adjust the tension members.

Once engaged, the attachment interface 2000 may be maintained in the engaged configuration with one or more locking structures or a locking assembly. For example, in FIGS. 20A to 21B, the locking interface may comprise a locking collar 2040 and a securing component 2042, where the locking collar 2040 resists transverse movement of the attachment interface 2000 when engaged and wherein the securing component 2042, which may be a pin or a resilient C-ring, resists the longitudinal displacement or disengagement of the locking collar 2040, when the securing component is engaged to one or more securing recesses 2044 located on the stator tube interface 2010.

Figure 21A:
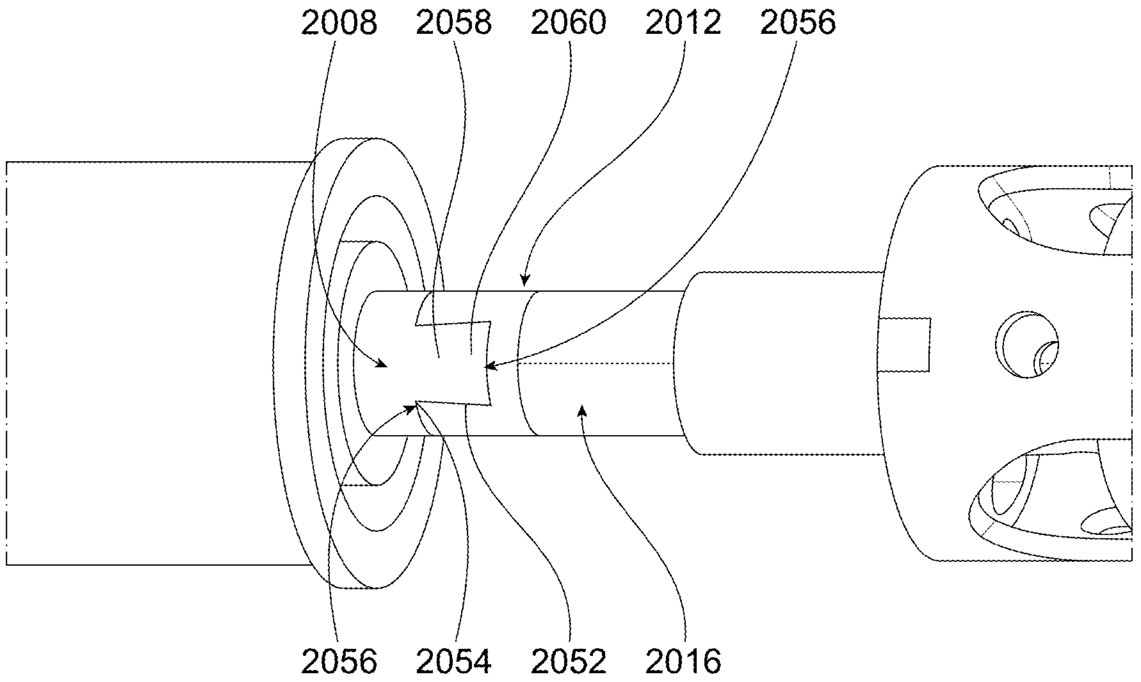
FIG. 21A depicts the engagement of the attachment interface of the drive shaft, without the stator interface.
Figure 21B:
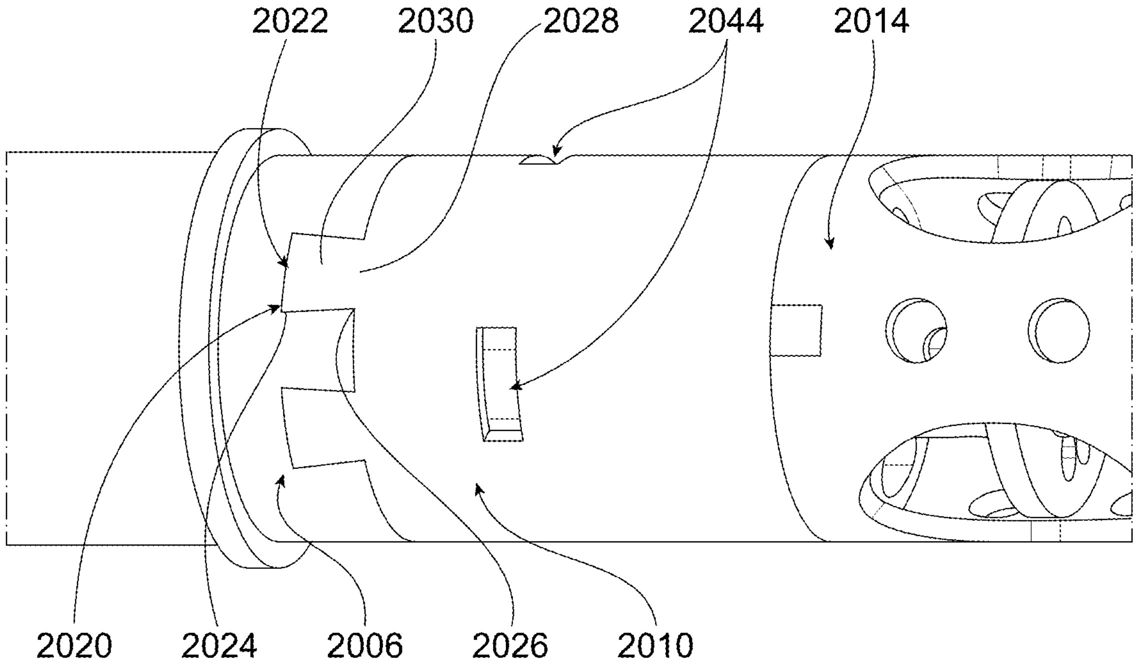
FIG. 21B depicts the engagement of the attachment interface of the stator interface.

In this particular example, as depicted best in FIG. 21B, the recesses 2020 each configured with a neck region 2024 that has a narrower width than a head region 2026, and the projections 2022 are each similarly configured with a neck region 2028 that is narrower in width than its head region 2030. The neck regions 2024 of the recesses 2020 form a complementary interfit with the head regions 2030 of the projections 2022, and the head regions 2026 of the recesses 2020 for a complementary interfit with the neck regions 2028 of the projections 2022. This configuration allows the engagement of the recesses 2018 and the projections 2024 by permitting transversely translating the recesses 2018 and 2024 into engagement, but resisting longitudinal translation once engaged, as the wider head regions 2030 of the projections 2022 resist longitudinal displacement through the narrower neck regions 2024 of the recesses 2020. When engaged, the locking collar 2040 may then be longitudinally displaced proximally from an unlock position where the attachment interface 2000 is uncovered or exposed, to a locked position where the locking collar 2040 covers the attachment interface 2000 so that transverse translation to separate the recesses 2020 and projections 2022 is resisted. In the particular example in FIGS. 20A to 21B, the head/neck configuration is a slightly angled keystone or trapezoidal shape which correspond to the larger head and narrower neck regions, with an angle in the range of 1 to 10 degrees or 2 to 5 degrees, but in other variations, a greater angle up to 20 degrees, 30 degrees or 45 degrees may be provided.

Similarly, referring to FIG. 21A, the plurality of recesses 2050 of the drive shaft interface 2008 may comprise head and neck regions 2052, 2054, respectively, that form a complementary mechanical interfit with the neck and head regions 2058, 2060, respectively of the projections 2056 of the rotor shaft interface 2012. The head and neck regions

2052, 2054, 2058, 2066 may also have angled sides so that the recesses 2032 and the projections 2038 may be engaged by transverse translation, but resist longitudinal separation once engaged.

Referring still to FIGS. 20A to 21B, to facilitate the transverse engagement of the attachment interface components, certain configurational features may be provided. Referring to the example in FIG. 22, the attachment interface 2200 comprise a proximal attachment interface 2202 on a distal end of a proximal structure of the delivery system, and a distal attachment interface 2204 on a proximal end of the corresponding distal structure of the delivery system. The proximal attachment interface 2202 comprise an outer tube interface 2206, and a drive shaft interface 2208 with a guidewire or central lumen 2210. The outer tube interface 2206 comprises four recesses 2212*a-b*, 2214*a-b*, and the drive shaft interface 2208 comprises two drive shaft engagement surfaces or recesses 2216*a-b*. The complementary distal attachment interface 2204 comprises a stator tube or housing 2218 with four projections 2220*a-b*, 2222*a-b*, and a rotor shaft interface 2224 with two projections 2226*a-b* or yoke arms. To facilitate the transverse engagement, the sides of recesses 2212*a* and 2212*b* are aligned on each side with each other along with the sides of corresponding projections 2220*a* and 2220*b*. In addition, the sides of the recesses 2212*a*, 2212*b* and projections 2220*a* and 2220*b* that are closer to the center of the delivery system are also aligned with the recess 2216*a* of the drive shaft 2208 and the engagement surface of the corresponding arm or projection 2226*a* of the rotor shaft interface 2224. The drive shaft recess 2216*a* and the arm or projection 2226*a* are also aligned with each other. Likewise, the sides of recesses 2214*a* and 2214*b* are aligned on each side with each other along with the sides of corresponding projections 2222*a* and 2222*b*, and the sides of the recesses 2214*a*, 2214*b* and projections 2222*a* and 2222*b* that are closer to the center of the delivery system are also aligned with the recess 2216*b* of the drive shaft 2208 and the corresponding arm or projection 2226*b* of the rotor shaft 2224, and where the drive shaft recess 2216*b* and the arm or projection 2226*b* are also aligned with each other. Together, the described alignments of these structures allow the transverse engagement of the proximal and distal attachment interfaces 2202, 2204 while the wider/narrower regions of the recesses and projections described earlier provide resistance to longitudinal separation once engaged.

The total gap or difference between the inner diameter of the locking collar and the outer diameter of the outer tubing interface may be in the range of 10 μm to 1000 μm, or 100 μm to 800 μm, or 200 μm to 500 μm. The gap may be selected to reduce the movement friction of the locking collar movement while limiting any play between the proximal and distal interfaces of the attachment interface that may result in partial disengagement at the attachment interface. The gap may be smaller than the radial thickness of the proximal and/or distal interfaces of the outer tubing and stator structures.

Although the embodiment depicted in FIGS. 20A to 22 is configured at both the outer tubing/stator housing and the drive shaft/rotor shaft to resist longitudinal separation, in other variations, only the outer tubing/stator housing interface may be configured to resist longitudinal separation, while the drive shaft/rotor shaft interface may not be configured to resist longitudinal separation, or where only the drive shaft/rotor shaft interface may be configured to resist longitudinal separation, but the outer tubing/stator housing interface may not be configured to resist longitudinal separation. These variations may provide greater tolerances and ease of use during transverse engagement of the attachment interface. In still other variations, the locking collar may be configured to resist longitudinal separation via barbs and recesses, such that neither the outer tubing/stator housing interface nor the drive shaft/rotor shaft interface are configured to resist longitudinal separation. In still other variations, one or more of the complementary features on the proximal attachment interface and the distal attachment interface may be reversed in their locations.

Referring back to FIG. 22, the alignments of the various structures allow the transverse engagement to be performed bi-directionally, e.g. starting with recesses 2212*a*, 2214*a* with projections 2220*b*, 2222*b*, or starting with recesses 2212*b*, 2214*b* and projections 2220*a*, 2222*a*. In other variations, as shown in FIGS. 23 and 24, the alignments and sizes of the various structures may be configured to only allow transverse engagement to performed in one direction only. A unidirectional interface may make it easier for the user or assembler to seat the projections into the recesses by providing or one or more stop surfaces to facilitate alignment during the engagement at the attachment interface, which may make alignment of the proximal and distal attachment interfaces easier and reduce the potential risk of jamming during engagement.

Referring to FIG. 23, the attachment interface 2300 comprises a proximal attachment interface 2302 on a distal end of a proximal structure of the delivery system, and a distal attachment interface 2304 on a proximal end of the corresponding distal structure of the delivery system. The proximal attachment interface 2302 comprise an outer tube interface 2306, and a drive shaft interface 2308 with a guidewire or central lumen 2310. The outer tube interface 2306 comprises four recesses 2312*a-b*, 2314*a-b* and the drive shaft interface 2308 comprises two drive shaft engagement surfaces or recesses 2316*a-b*. The complementary distal attachment interface 2304 comprises a stator tube or housing interface 2318 with four projections 2320*a-b*, 2322*a-b*, and a rotor shaft interface 2324 with two projections 2326*a-b* or yoke arms. In this embodiment, recess 2312*a* is smaller than recess 2312*b* and projection 2320*b*, with respect to their widths along the transverse translation axis, and projection 2320*a* is smaller than recess 2312*b* and projection 2320*b*, but recess 2312*a* is aligned with projection 2320*a*, and recess 2312*b* is aligned with projection 2322*b*. Recess 2316*a* of the drive shaft interface 2308 and the corresponding arm or projection 2326*a* of the rotor shaft interface 2324 remain aligned, with arm or projection 2326*a* configured by size and location to clear recess 2312*b*. Likewise, recess 2314*a* is smaller than recess 2314*b* and projection 2322*b* with respect to their widths along the transverse translation axis, and projection 2322*a* is smaller than recess 2314*b* and projection 2322*b*, but recess 2314*a* is aligned with projection 2322*a*, and recess 2314*b* is aligned with projection 2322*b*. Recess 2316*b* of the drive shaft 2308 and the corresponding arm or projection 2326*b* of the rotor shaft 2324 remain aligned with each other, with arm or projection 2326*b* configured to clear recess 2314*b*.

Figure 22:
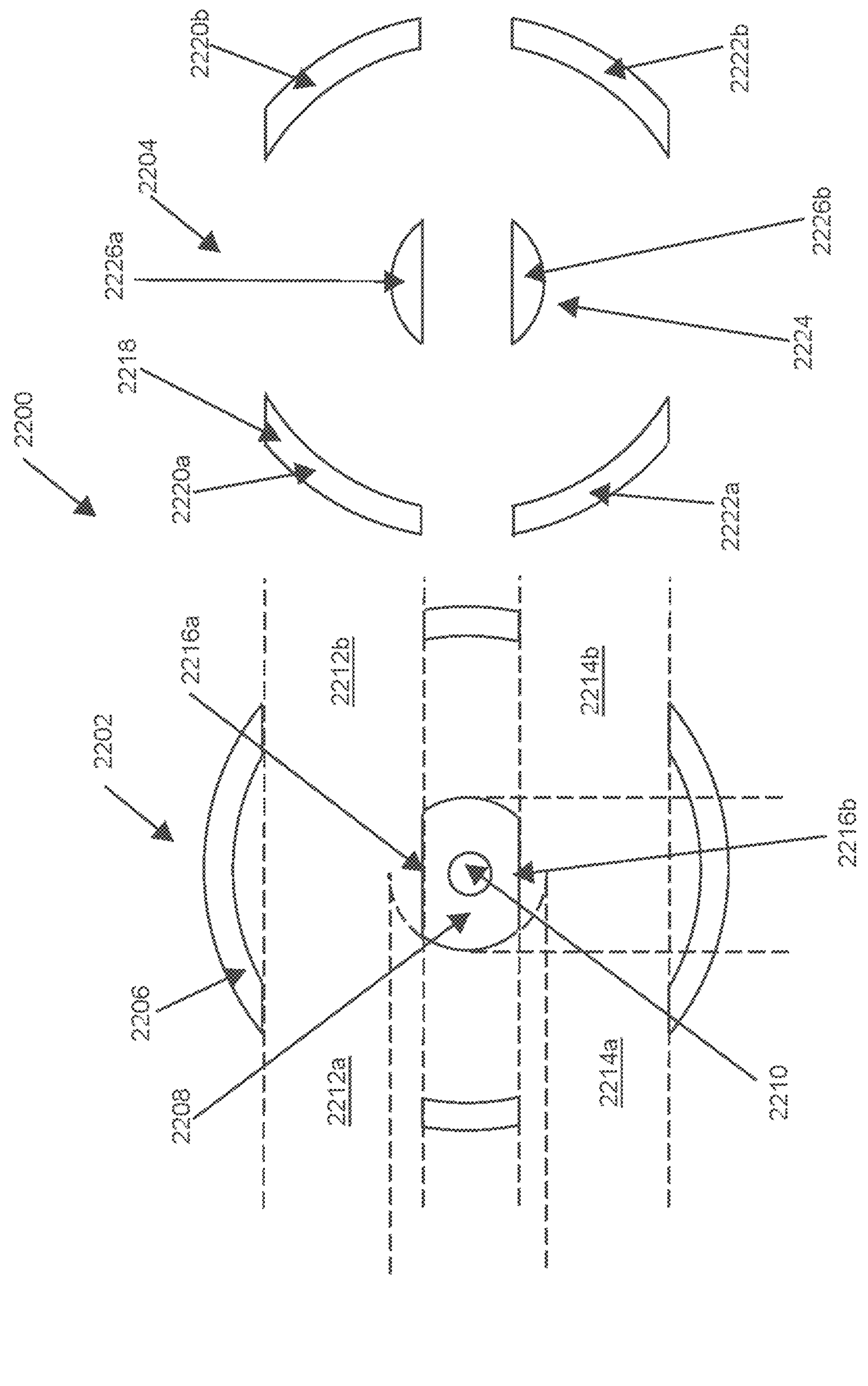
FIGS. 22 to 25 depict various exemplary configurations of the attachment interface to facilitate engagement of delivery system components.
Figure 23:
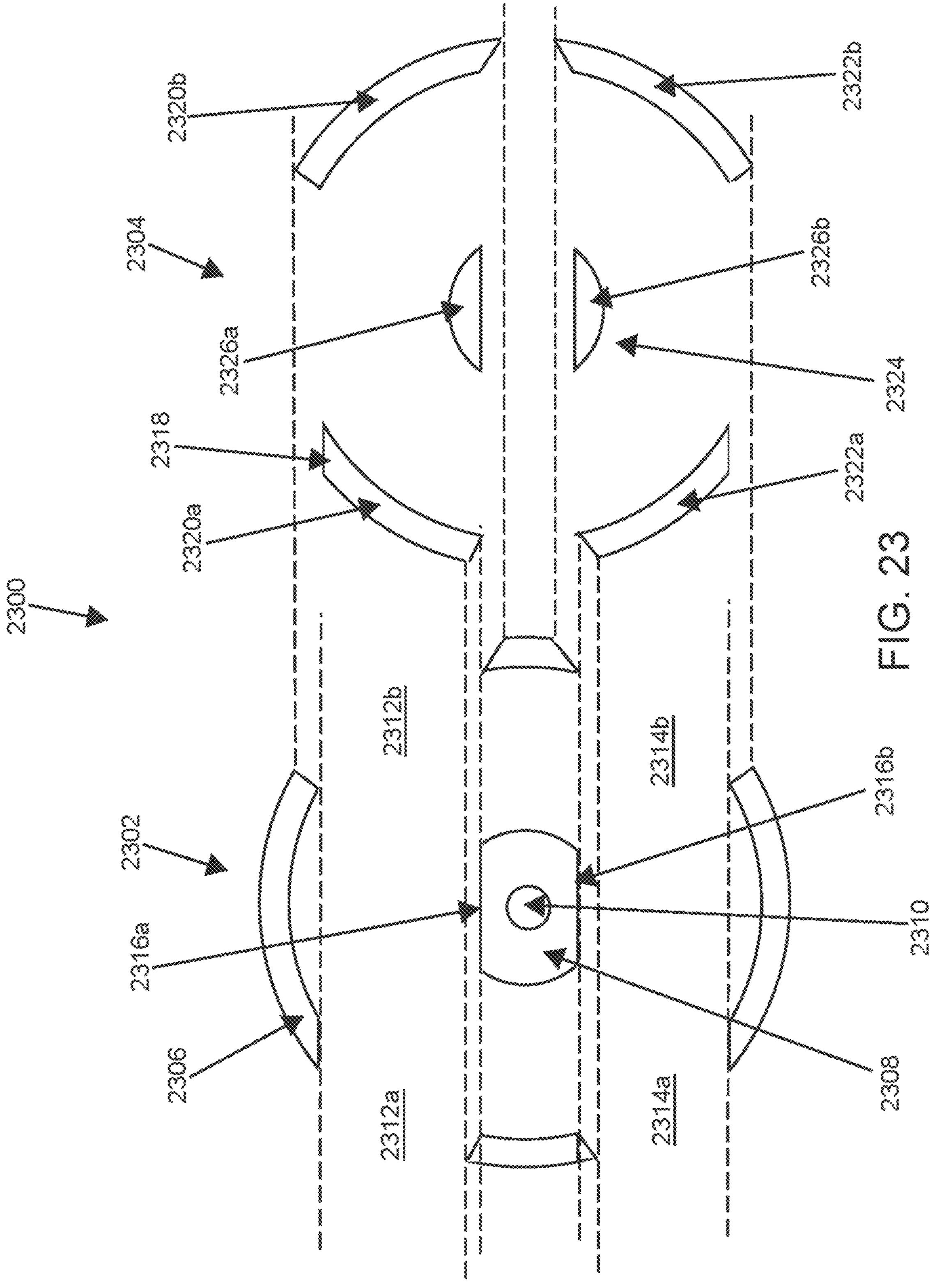
Figure 24:
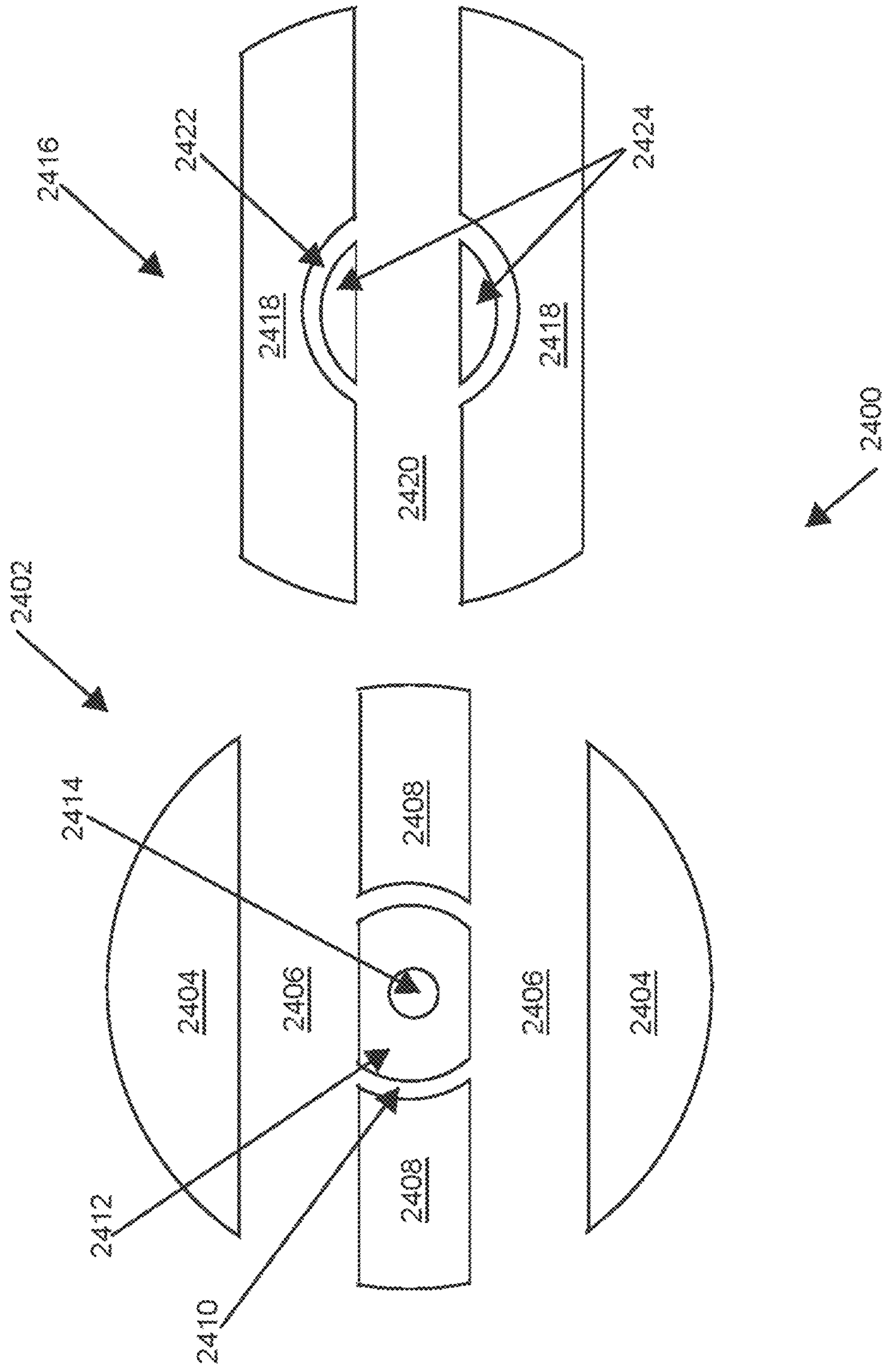

FIG. 23 depicts multiple partial alignments and size differences to facilitate the seating of the distal attachment interface 2304 into the proximal attachment interface 2302, but some of the angular and size changes between the bi-directional embodiment in FIG. 22 and the unidirectional embodiment in FIG. 23 may cause, during torqueing of the delivery system, some mechanical bias or forces that may cause the proximal and distal attachment interfaces 2302, 2304 to twist apart or out of full alignment. In other variations of the attachment interface, a subset of the alignment/seating features described in FIG. 23 may be implement, to achieve a different balance of between ease of seating, mechanical integrity and other factors.

Figure 25:
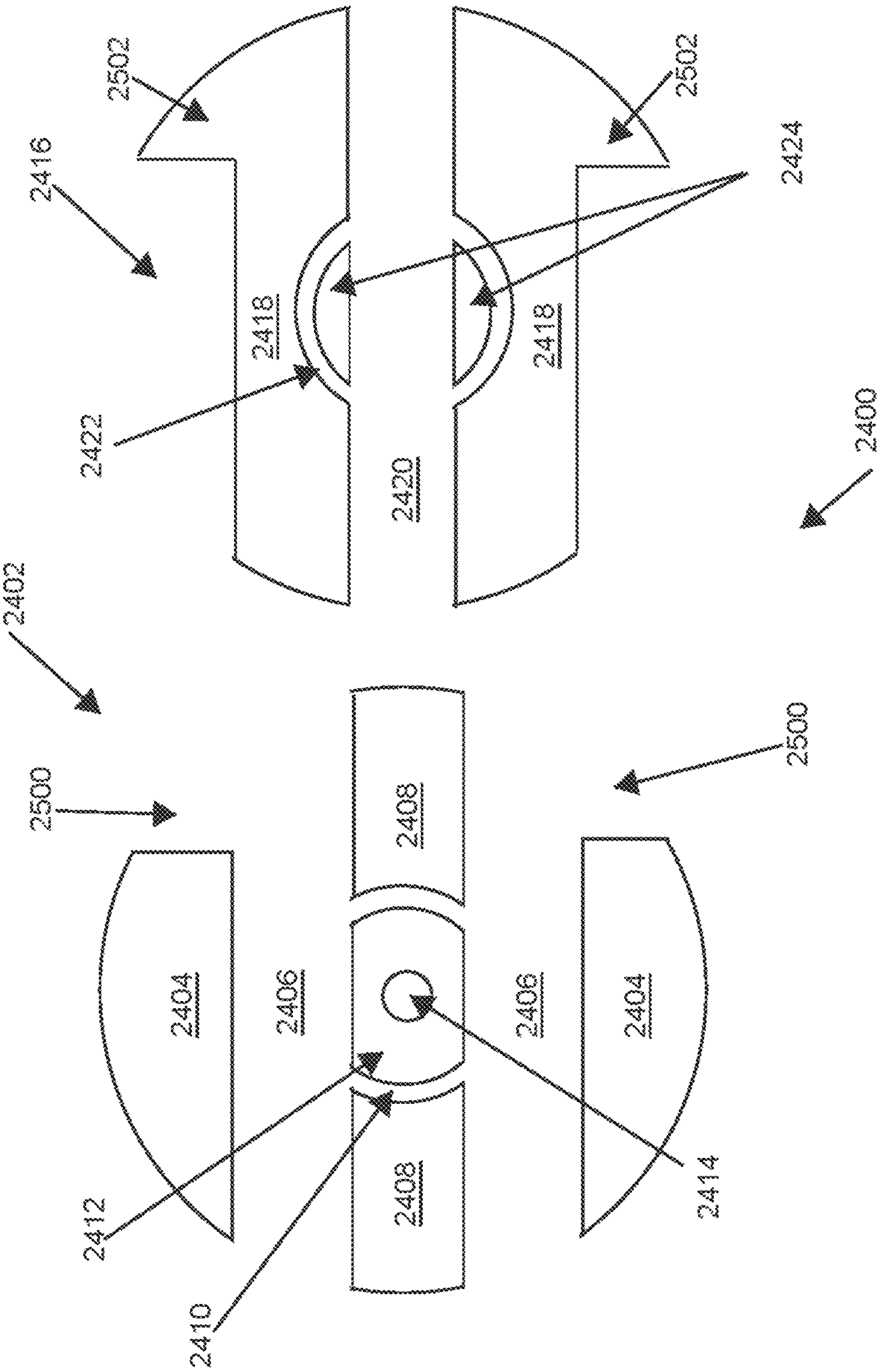

FIGS. 24 and 25 depict additional schematic variations of an attachment interface 2400 wherein the proximal attachment interface 2402 comprises two lateral alignment bodies 2404, two channels 2406, two central alignment bodies 2408 with a drive shaft cavity 2410 there between and an oblong drive shaft head 2412 and central lumen 2414. The distal attachment interface 2416 comprises two paramedial alignment bodies 2418 configured to be inserted into the channels 2406, a central channel 2420 configured to receive the two central alignment bodies 2408 and the drive shaft head 2412 a central rotor shaft cavity 2422 in which two rotor shaft arms or projections 2424 are configured to receive and engage the oblong drive shaft head 2412. Although all of the structures and surfaces of this embodiment of the engagement interface are parallel, in other variations, one or more surfaces may be angled, and or comprise additional recesses/cutouts 2500 and flanges/projections 2502, as depicted in FIG. 25.

Figure 38A:
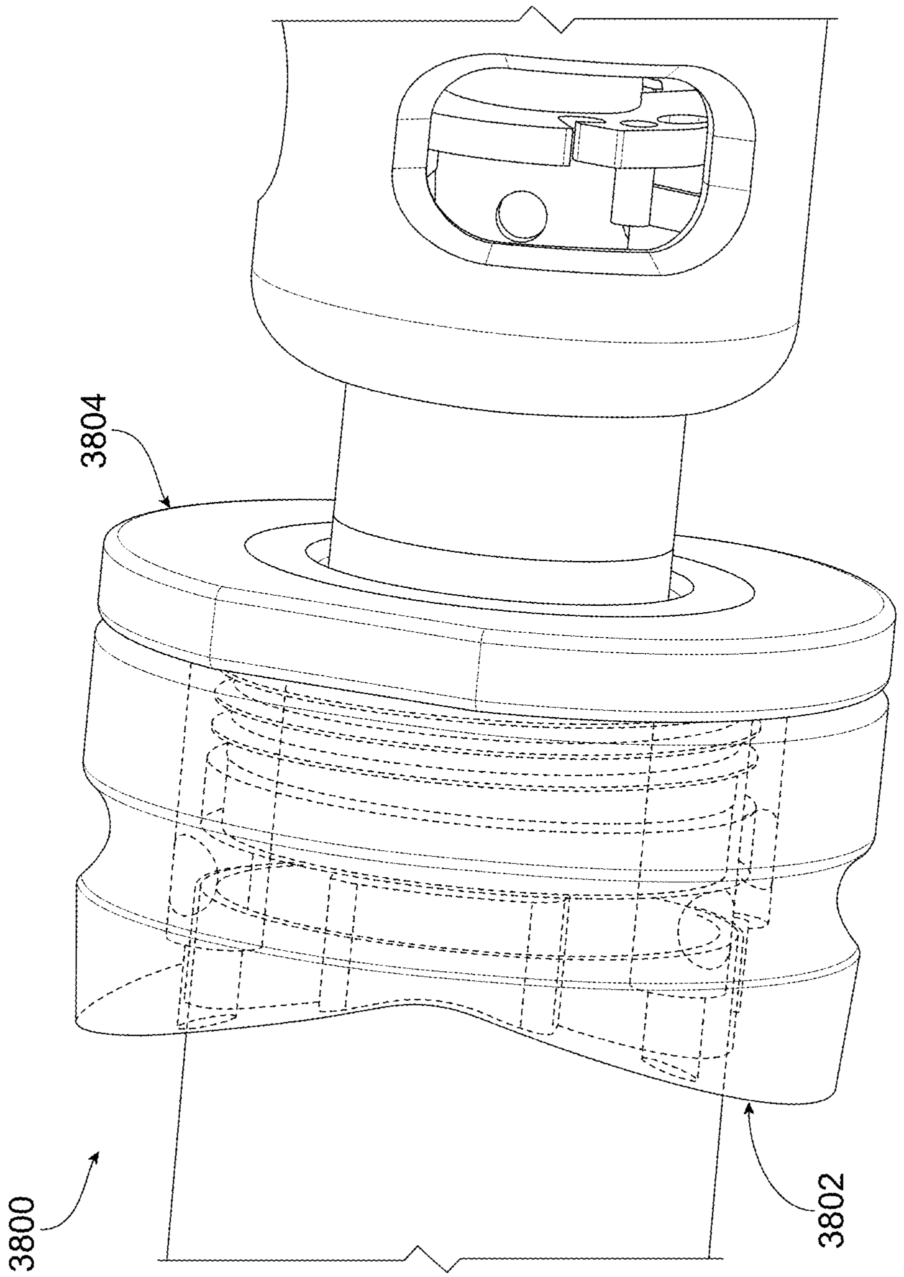
FIG. 38A is a perspective view of another embodiment of a modular interconnect assembly between the modular distal catheter section and implant delivery section of the delivery system, comprising a threaded locking mount.
Figure 38C:
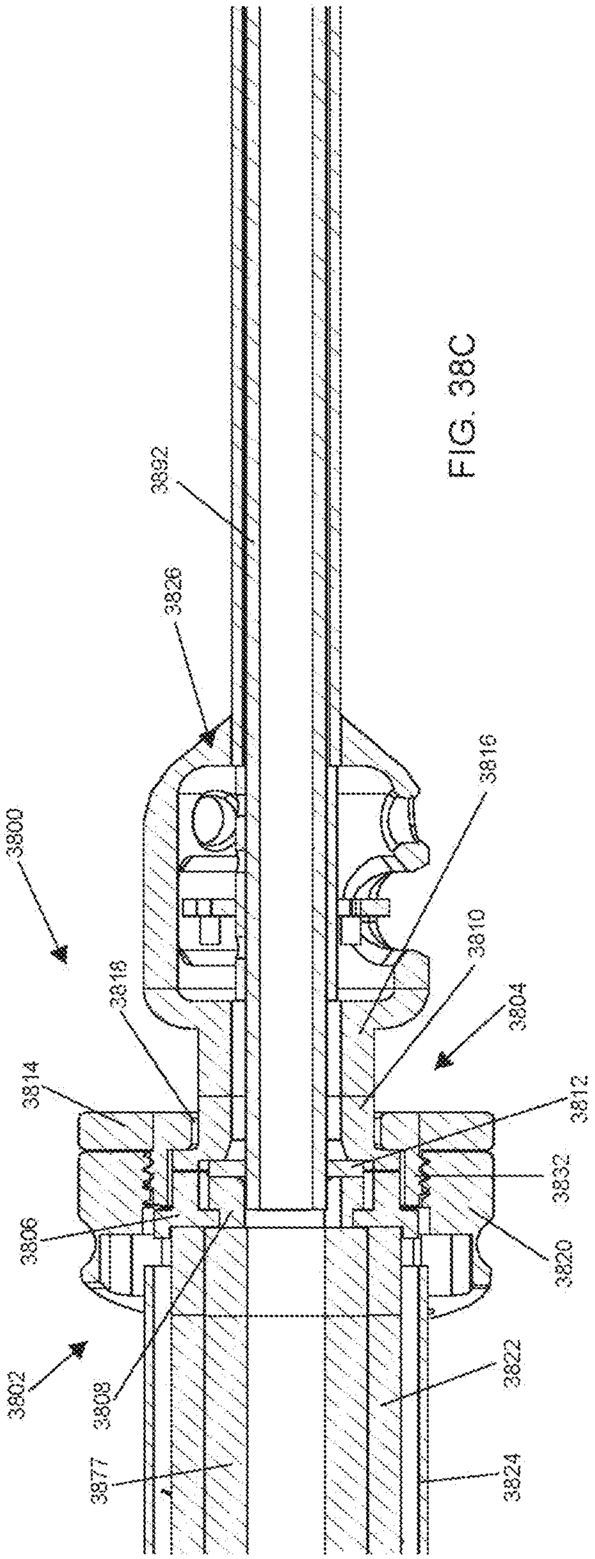
FIGS. 38B and 38C are side and longitudinal cross-sectional views of the interconnect assembly in FIG. 38A.
Figure 38B:
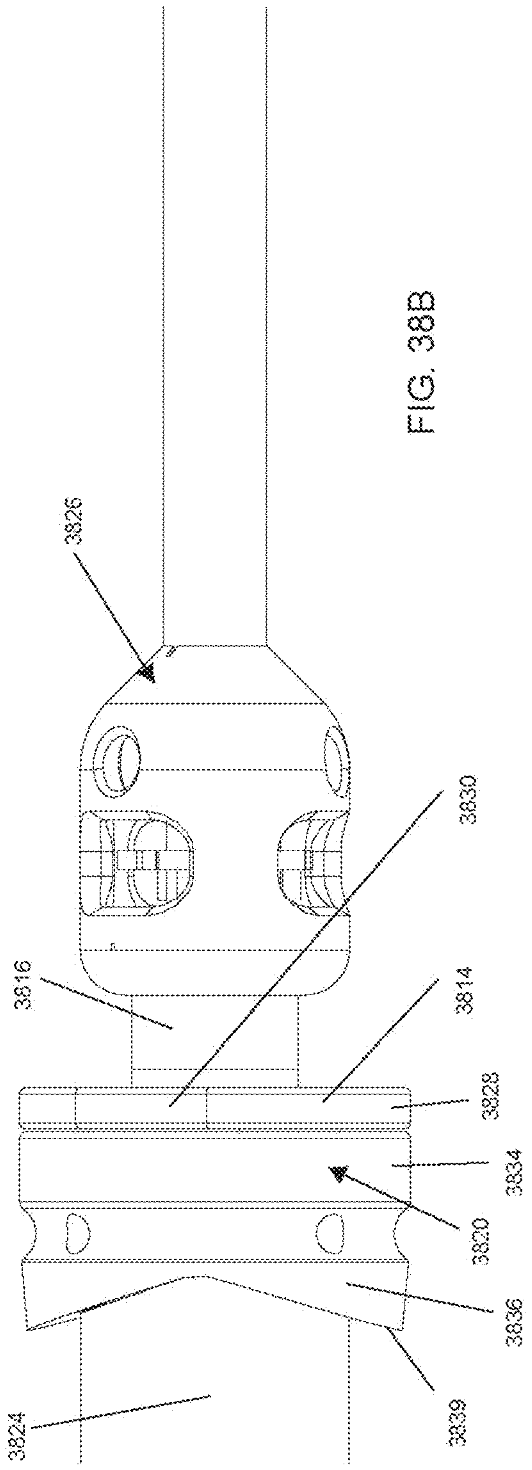
Figure 39B:
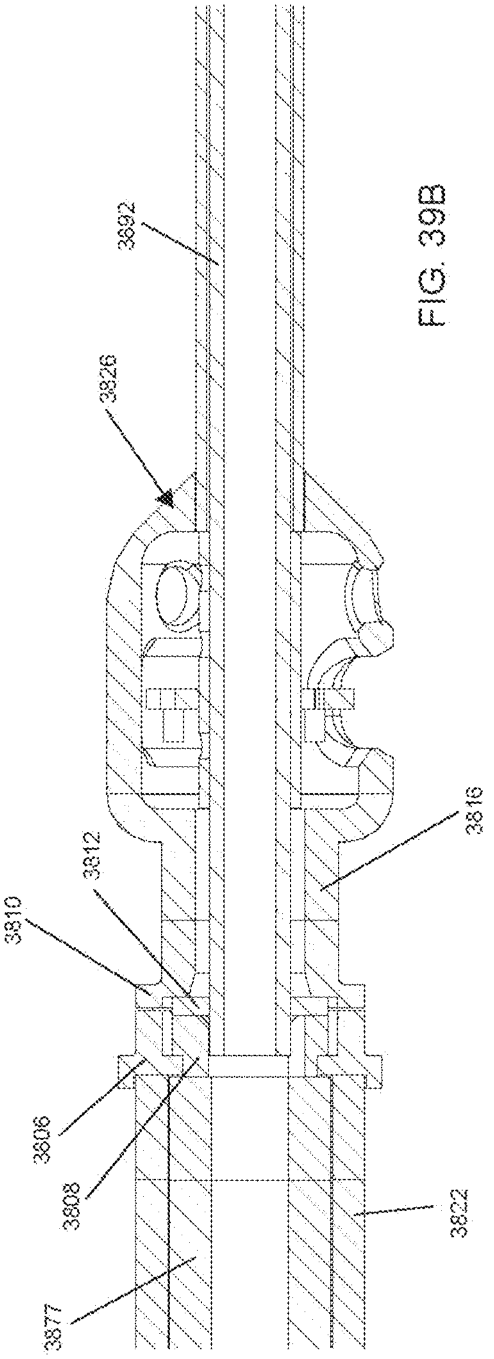
FIGS. 39A and 39B are side and longitudinal cross-sectional views of the assembly in FIGS. 38A to 38C, depicting the rotor and stator interconnect components without the lock components.
Figure 39A:
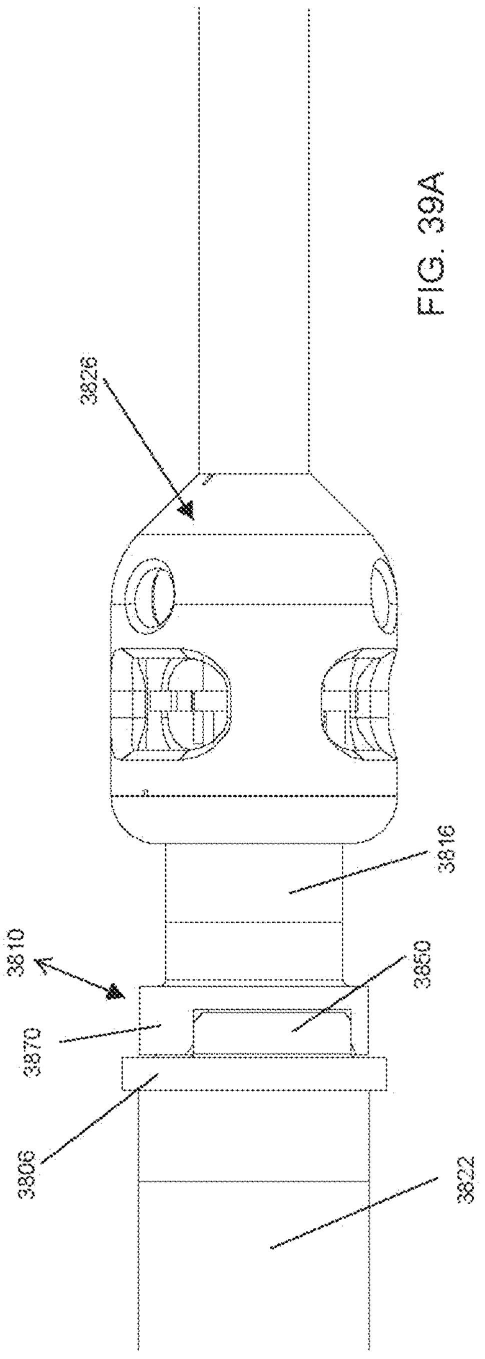
Figure 40B:
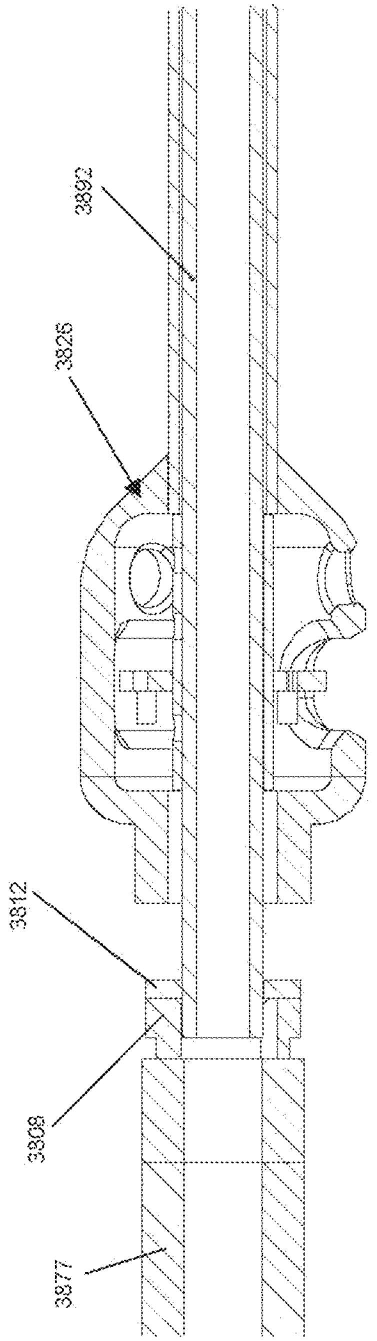
FIGS. 40A and 40B are side and longitudinal cross-sectional views of the assembly in FIGS. 38A to 39B, depicting the rotor interconnect components without the lock or stator interconnect components
Figure 40A:
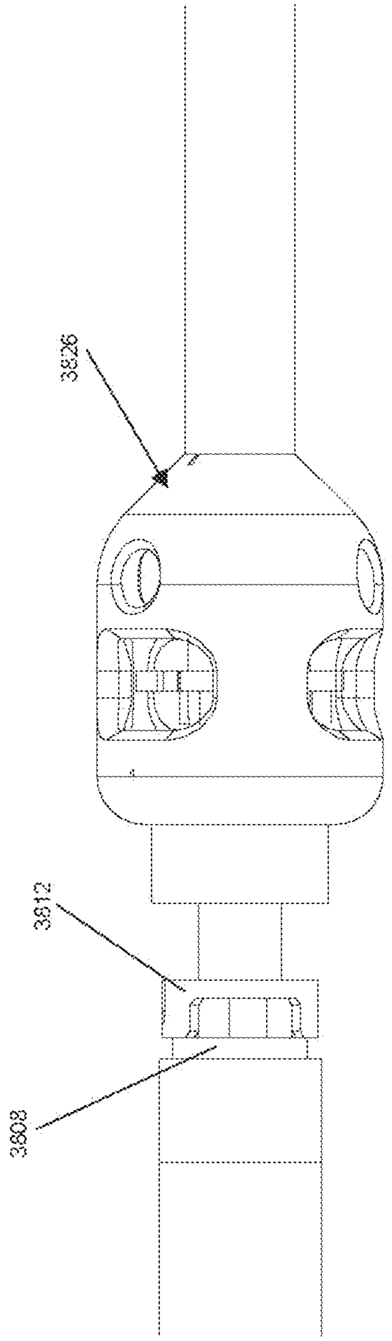
Figure 41A:
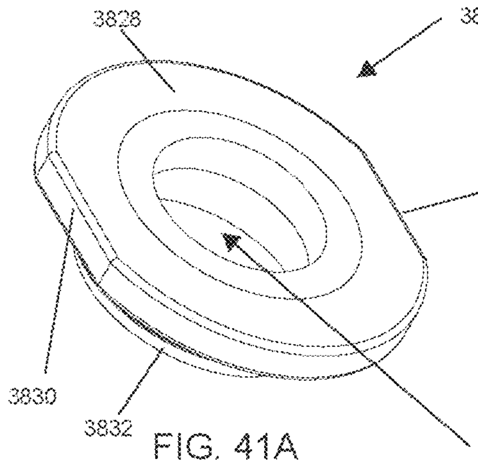
FIGS. 41A to 41E are top perspective, bottom perspective, top, cross-sectional and side views of the distal lock component.
Figure 41B:
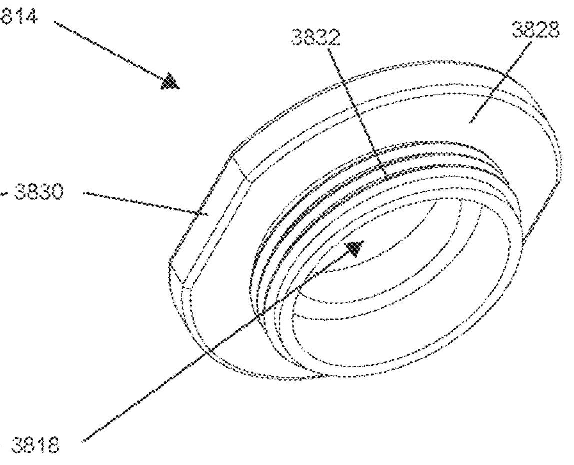
Figure 41C:
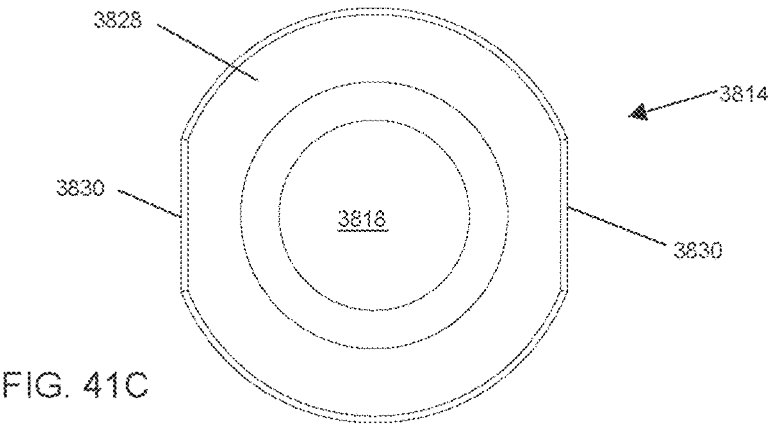
Figure 41D:
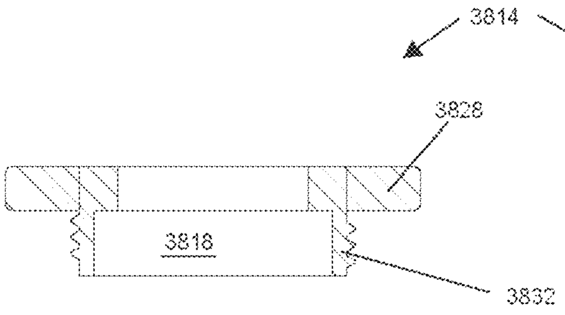
Figure 41E:
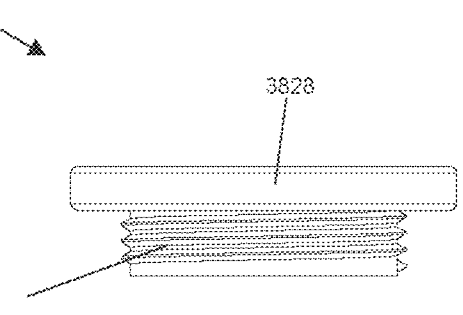
Figure 42A:
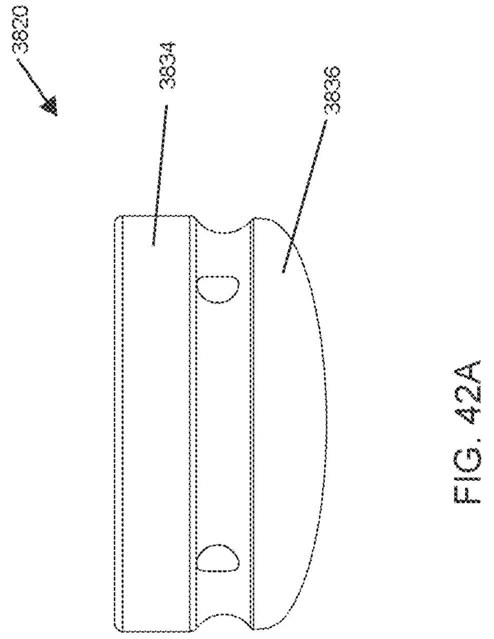
FIGS. 42A to 42D are side, perspective, cross-sectional and top views of the proximal lock component.
Figure 42B:
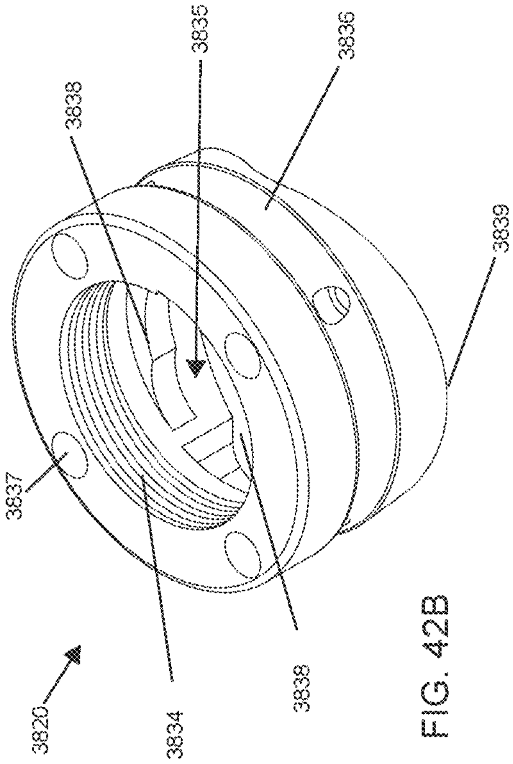
Figure 42C:
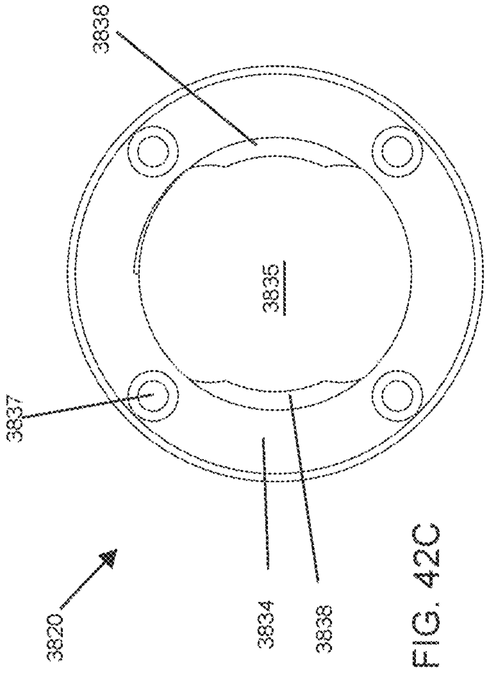
Figure 42D:
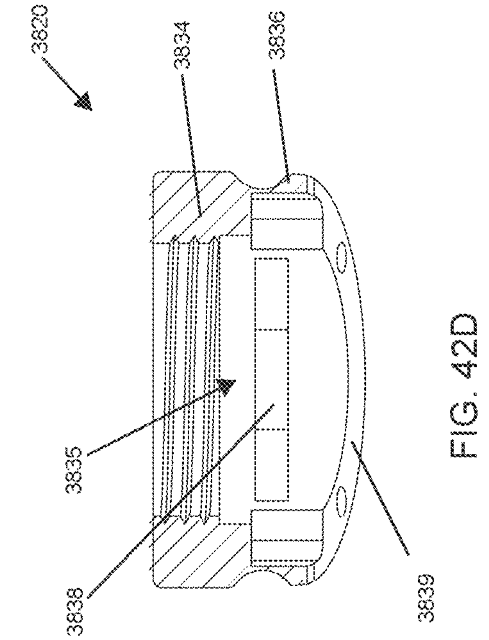

FIG. 38A to 38C depicts an alternate embodiment of the attachment interface 3800 for a delivery system, which again for simplification, does not depict a steering and/or extension mechanism that may be included. The interface 3800 comprises a proximal attachment interface 3802 and a distal attachment interface 3804. The proximal attachment interface 3802 comprises a proximal stator interface 3806, a proximal rotor interface 3808. The distal attachment interface 3804 comprise a distal stator interface 3810 that has a complementary mechanical interfit shape to the proximal stator interface 3806, and a distal rotor interface 3812, which has a complementary mechanical interfit shape to the proximal rotor interface 3808. The stator interfaces 3806, 3810 are configured to be engageable in an axial direction, concurrently with the rotor interfaces 3808, 3812 configured to be engageable in an axial direction. When engaged, the stator interfaces 3806, 3810 is configured to resist rotation while the rotor interfaces 3808, 3812 are configured to transmit rotational force and movement. To maintain the engagement of the stator interfaces 3806, 3810 and rotor interfaces 3808, 3812, a distal locking component, such as a threaded locking washer 3814, may be is coupled to the distal stator shaft 3816 via the washer opening 3818 can be engaged to a proximal locking component, such as a corresponding threaded locking housing 3820 that is fixed to the proximal stator shaft 3822, and/or proximal outer tube 3824 in which the stator shaft 3822 resides. The threaded locking washer 3814 may be restrained from separation from the delivery system by the diameter or width of the distal stator interface 3810 and the proximal stator housing 3826, but is otherwise free to rotate and axially translate along the stator shaft 3816. This allows the engagement of the washer 3814 to the locking housing 3820 without interference with the stator or rotor interfaces 3806, 3810, 3808, 3812. Referring to FIGS. 41A to 41E, the locking washer 3814 includes disc body 3828 which optionally has flat opposing ends 3830 to facilitate rotation of the locking washer 3814 by tool or by hand. The washer opening 3818 is in communication with the lumen of the tubular threaded body 3832 of the locking washer 3814. In some variations, the number of rotations of the tubular threaded body 3832 may include 2-10 thread rotations, 3-5 rotations, or 3-4 rotations. The thread pitch may be in the range of 0.2 mm to 3 mm, 0.4 mm to 2 mm, or 0.5 mm to 1.5 mm. Referring to FIGS. 42A to 42D, the locking housing 3820 may comprise a lumen with a distal threaded locking portion 3834 configured to engage the locking washer 3814, and a proximal mounting portion 3836 configured to receive and to be affixed to the proximal stator shaft 3822 or outer tube 3824 of the delivery system. One or more internal flanges 3838 may be provided in the mounting portion 3836 of the lumen 3835 to facilitate the desired insertion distance of the stator shaft 3822 and/or outer tube 3824. Of course, in other variations, the locking washer may be placed on the proximal side of the locking assembly, and the locking housing may be located on the distal side of the locking assembly. This particular example of the locking housing 3820 also comprises several mount openings 3837 for a steering mechanism, as well as angled pivot surfaces 3839 to interface with a steering mechanism, if provided.

Figure 43A:
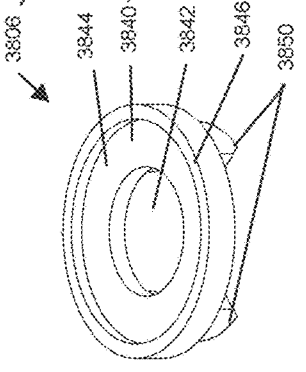
FIGS. 43A to 43D are various perspective views of the distal stator connector.
Figure 43B:
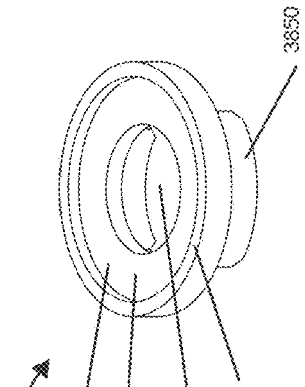
Figure 43C:
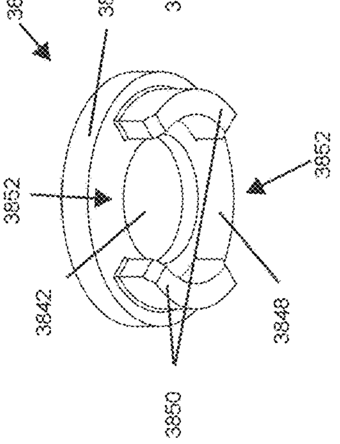
Figure 43D:
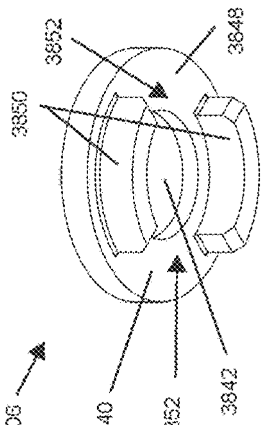
Figure 44A:
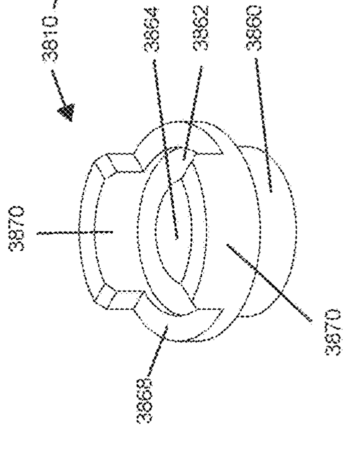
FIGS. 44A to 44D are various perspective views of the proximal stator connector.
Figure 44B:
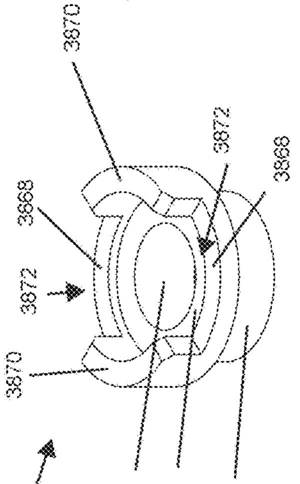
Figure 44C:
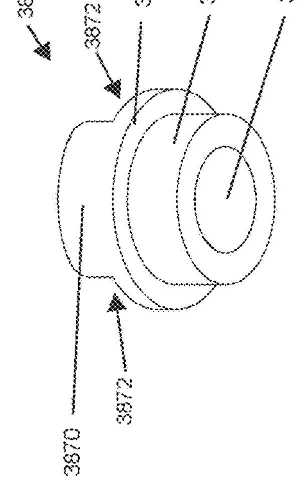
Figure 44D:
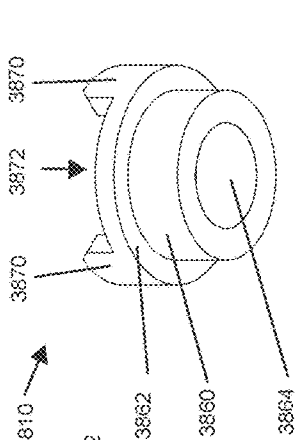
Figure 47A:
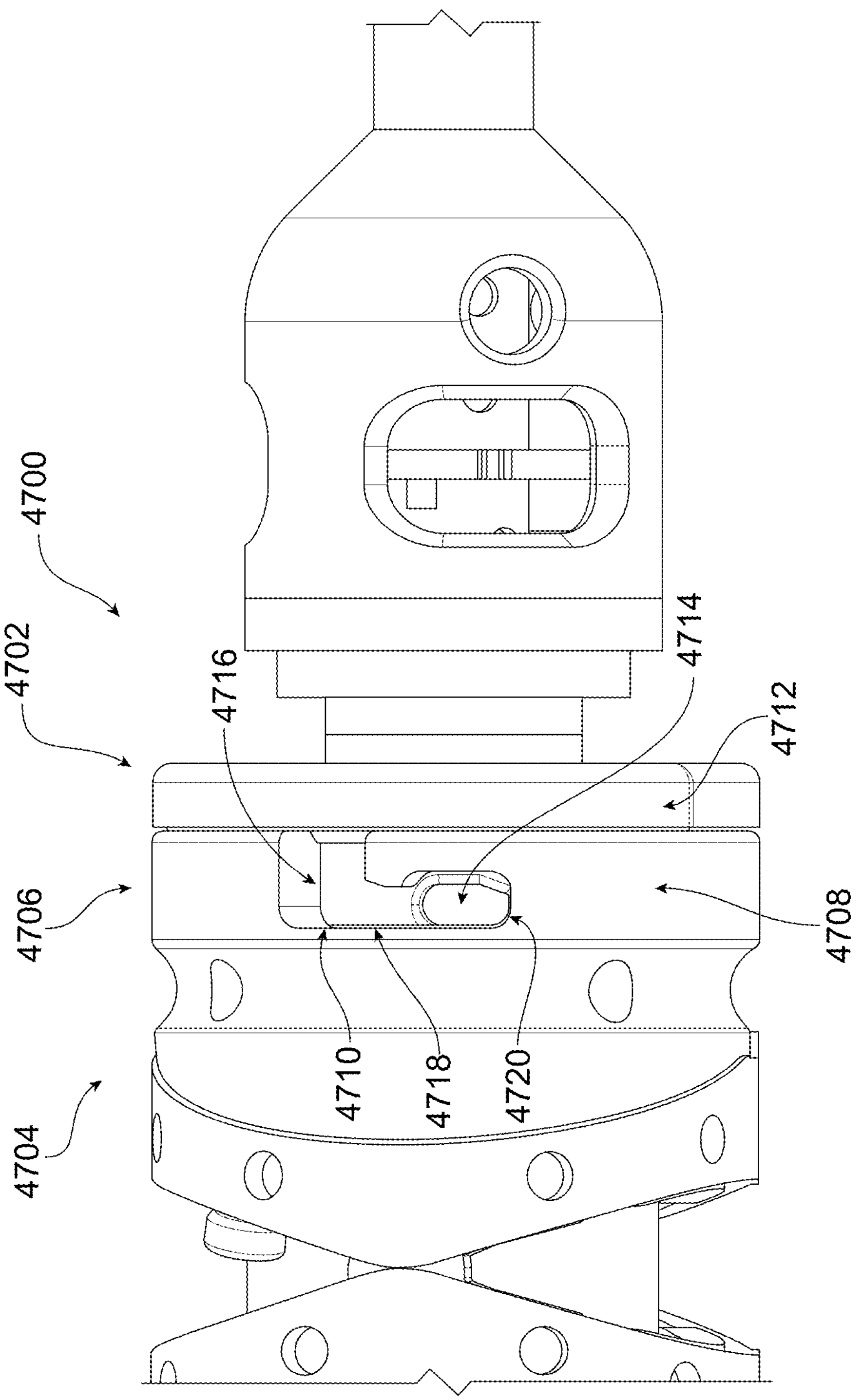
FIGS. 47A and 47B are side and top views of another embodiment of a modular interconnect assembly between the modular distal catheter section and implant delivery section of the delivery system, comprising a bayonet mount.
Figure 47B:
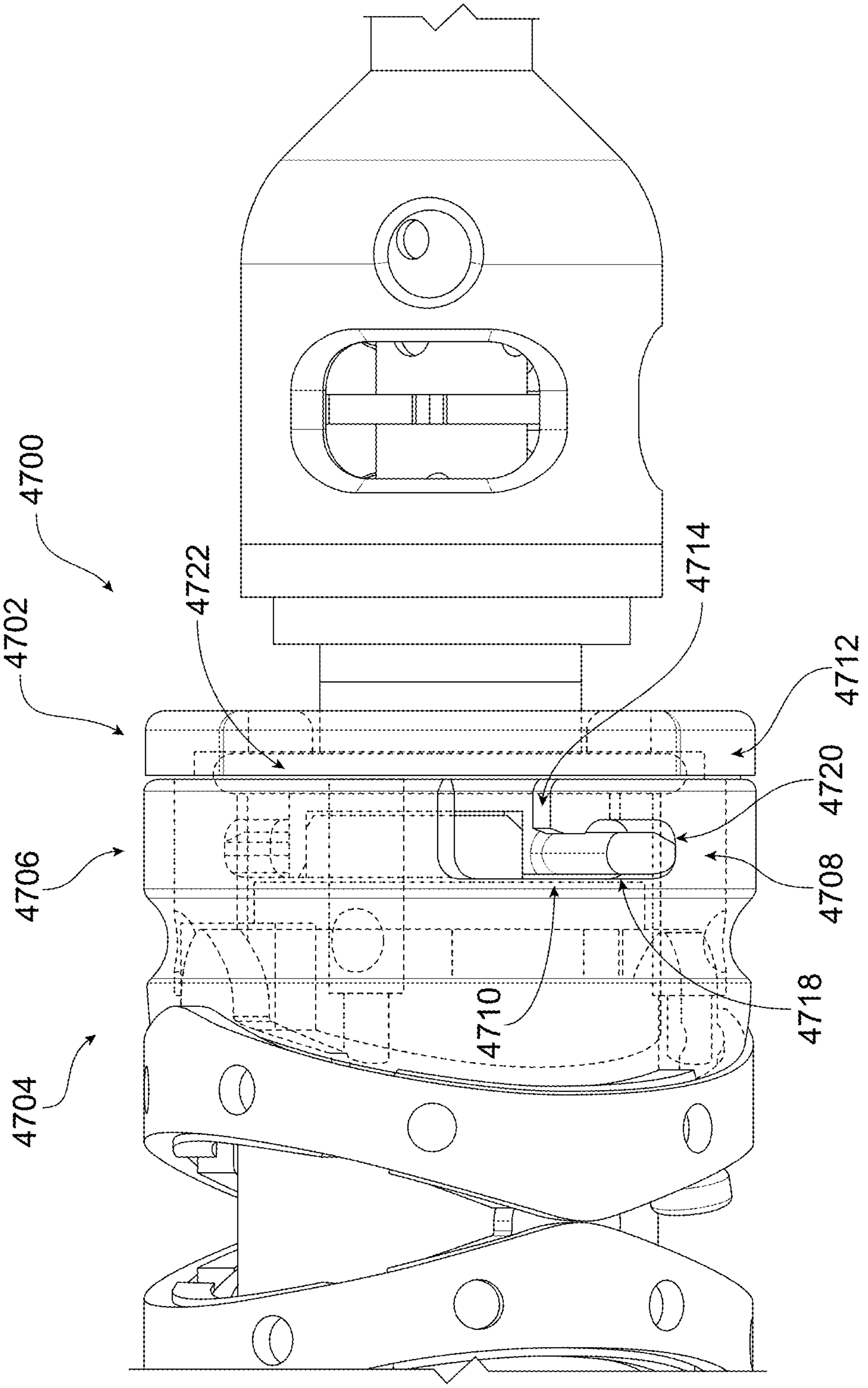
Figure 48A:
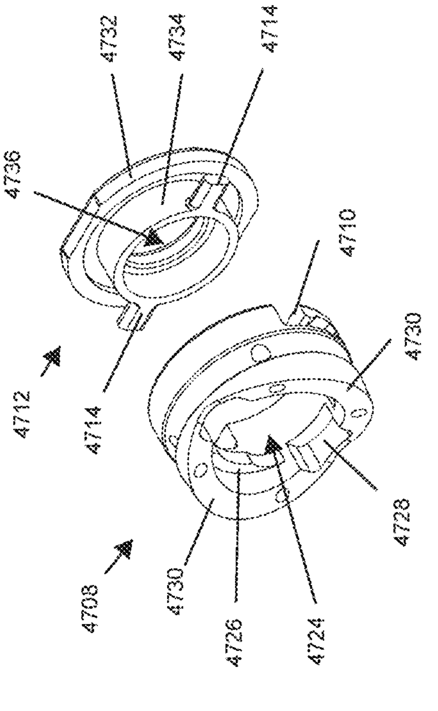
FIGS. 48A to 48D are various exploded components views of the proximal and distal locking components of the bayonet mount assembly in FIGS. 47A and 47B.
Figure 48B:
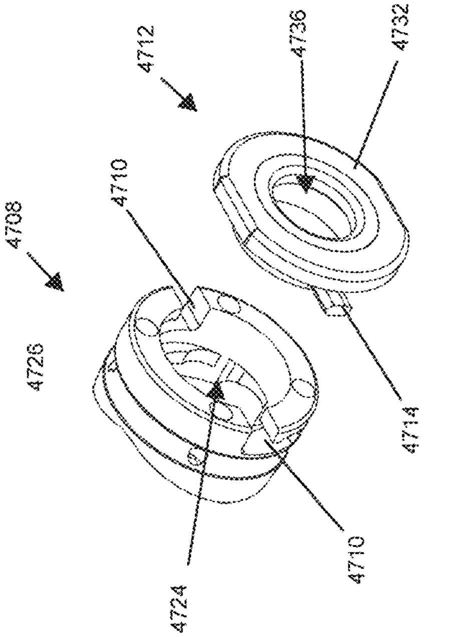
Figure 48C:
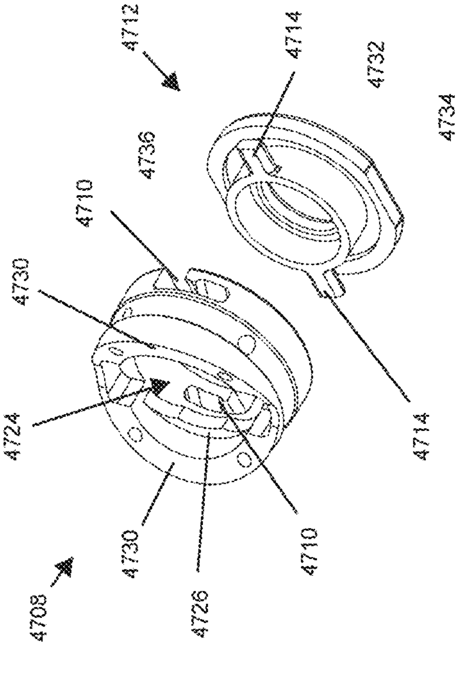
Figure 48D:
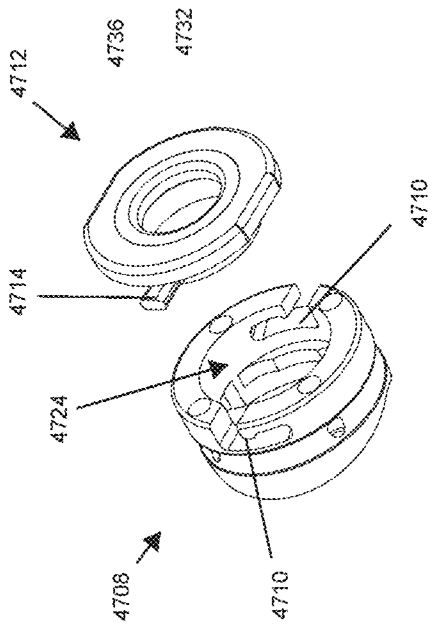
Figure 49B:
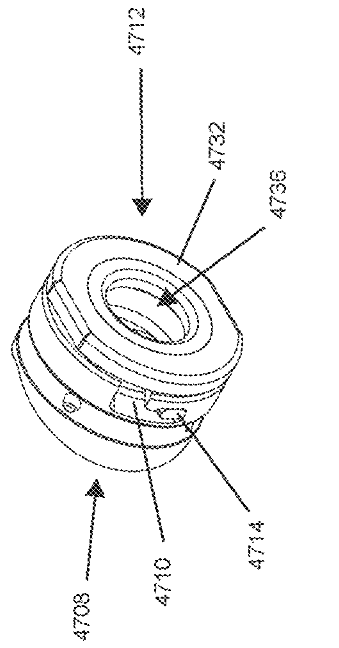
FIGS. 49A to 49D are various perspective views of the proximal and distal locking components in an engaged position.
Figure 49D:
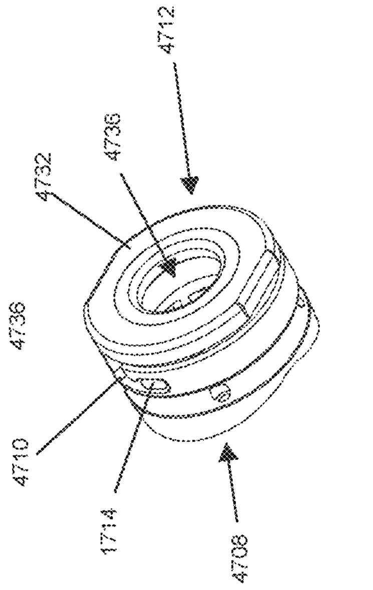
Figure 49A:
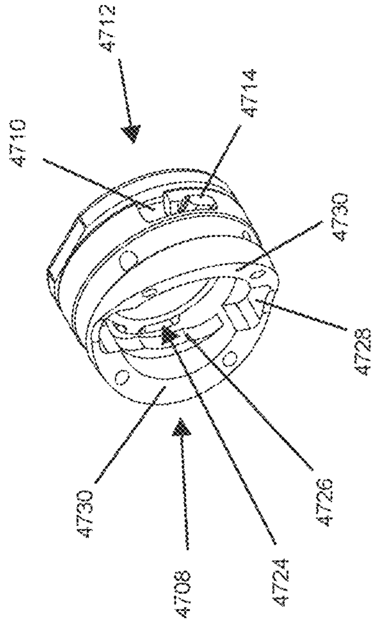
Figure 49C:
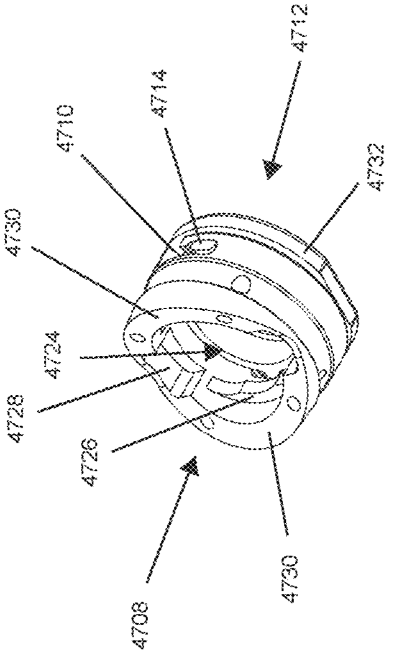
Figure 49G:
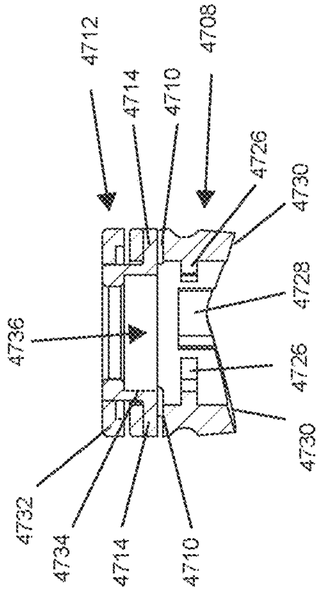
FIG. 49G is a cross-sectional view of the components in FIG. 49F.
Figure 49E:
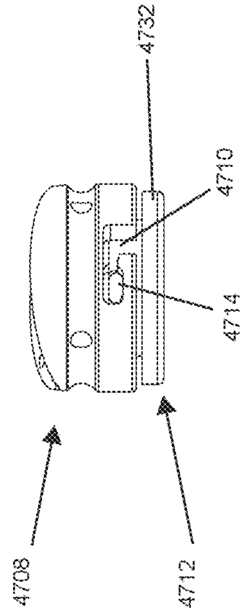
FIGS. 49E and 49F are side and front views of the components in FIGS. 49A to 49D.
Figure 49F:
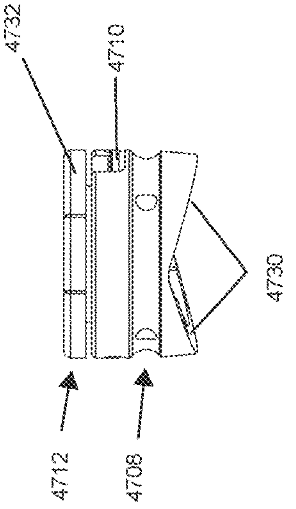
Figure 50A:
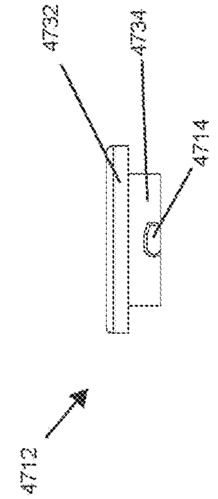
FIGS. 50A to 50C are side, front and cross-sectional views of the distal locking component in FIGS. 47A to 49D.
Figure 50B:
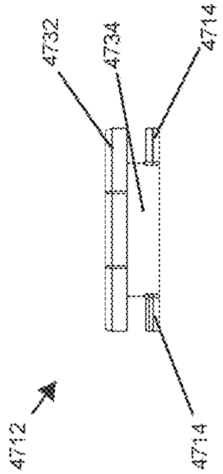
Figure 50C:
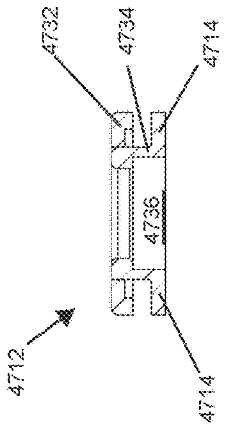
Figure 51A:
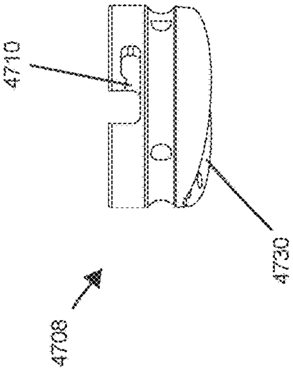
FIGS. 51A and 51C are side, front and cross-sectional views of the distal locking component in FIGS. 47A to 49D.
Figure 51B:
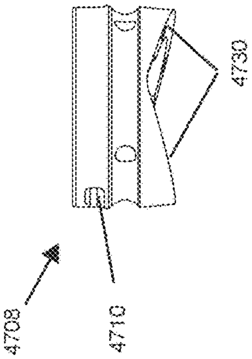
Figure 51C:
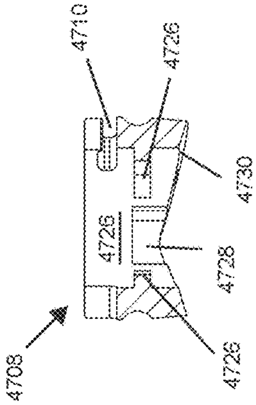

FIGS. 43A to 43D and 44A to 44D depict exemplary embodiments of the proximal and distal stator interfaces 3806, 3810, respectively. The proximal stator interface 3806 comprises an annular disc or base 3840 with a central aperture 3842 therethrough, through with the proximal rotor interface and/or proximal rotor shaft resides. The proximal surface 3844 of the base 3840, depicted in FIGS. 43A and 43B, may include an annular or perimeter lip 3846 extending in the proximal axial direction and configured to receive and/or to facilitate positioning and mounting the proximal stator interface 3806 to the proximal stator shaft and/or proximal outer tube. Although the lip 3846 depicted in FIGS. 43A and 43B is contiguous along the entire circumference of the interface 3806, in other variations, the lip may be a series of partial, discontiguous lip structures. Extending axially from the distal surface 3848 of the base 3840 are one or more teeth 3850, which in turn delineate receiving spaces or gaps 3852 therebetween the teeth 3850. The teeth 3850 and gaps 3852 will form a complementary interfit with the corresponding gaps and teeth on the distal stator interface. Referring still to FIGS. 43C and 43D, the teeth 3850 may comprise an angled or arcuate shape that may be flush with the perimeter of the base, or spaced in from the perimeter of the base 3840. In other variations, however, these or other teeth described herein may comprise linear shapes or an elongate axial shapes that otherwise form a mechanical interfit with a complementary interface. Typically, each tooth 3850 may comprise an arcuate length that is a percentage of the 360 degree interface, typically equal to 100 divided by twice the number of teeth. Thus, for the two teeth 3850 configuration of the stator interface 3806 in FIGS. 43C and 43D, each tooth 3850 is 25% or 90 degrees of the interface. In other variations, however, the teeth and gaps may not be uniform, and may have different shapes or sizes while still having a complementary interfit with the distal stator interface. The teeth of the interface may comprise one or more chamfered edges to facilitate engagement with the distal interface, and may have a maximum height in the range of 2 mm to 15 mm, 3 mm to 10 mm, or 3 mm to 6 mm, which in turn may delineate the depth of the gaps 3852 between the teeth 3850. Referring now to FIGS. 44A to 44D, the distal stator interface 3810 comprises distal ring or tubular body 3860 with a proximal base 3862 with a lumen 3864. On the opposite side of the base 3862 from the tubular body 3860 comprises an annular or perimeter lip 3868 from which the angled or arcuate complementary teeth projecting axially in the proximal direction, and in turn delineating receiving gaps 3872 bound by the adjacent lip 3868 and teeth 3870. The interior space 3874 that is radially inward from the teeth 3870 and the gaps 3872 may be configured to receive one or more rotatable structures of the rotor interface, which is described in greater detail below. In contrast to the proximal stator interface 3806, the teeth 3870 of the distal interface 3810 are flush with the perimeter of the interface 3810, but in other variations, may also be set in from the perimeter of the interface. The arcuate shape and size of the teeth 3870 and gaps 3872 may otherwise be similar to the teeth and gaps as described for the teeth and gaps of the proximal stator interface 3806, so that a complementary mechanical interfit may be achieved.

FIGS. 45A to 45D and 46A to 46D depict exemplary embodiments of the proximal and distal rotor interfaces 3808, 3812, respectively, that may be provided in the delivery system. Referring first to FIGS. 45A to 45D, the proximal rotor interface 3808 comprises a proximal rotor ring or base 3876 with a central lumen 3878 to receive either the proximal rotor shaft 3877, or the distal rotor shaft 3892 in embodiments there the distal rotor shaft extends proximally from the distal rotor interface. One or more axial channels 3880 may be provided along the lumen 3878 which may facilitate attachment of the proximal rotor interface 3808 to other components of the delivery system, such as the distal rotor shaft 3892, by providing additional space for welding or adhesives in areas with tight tolerances between components. Referring to FIGS. 45C and 45D, extending axially from the distal surface of the base 3876 are two angled or arcuate teeth 3884 and gaps 3886 there between. In contrast to the teeth of the proximal and distal stator interfaces, the teeth of the proximal rotor interface extend radially beyond the perimeter of the base 3876. Because the rotor interface 3808, 3812 resides within the stator interface 3806, 3810, this teeth configuration may help with the mechanical reliability and torque transfer of the rotor interface while maintaining an overall reduced size to the attachment interface. In addition, the teeth and gaps of the rotor interface will have a height or depth that is the same or smaller than the teeth and gaps of the stator interface, but are otherwise similar to the range of characteristics as described for the teeth and gaps of the stator interface. In some variations, the height and depth of the rotor teeth and gaps is smaller by a size that is in the range of about 0 mm to 4 mm smaller, 1 mm to 3 mm, or 1.5 mm to 2.5 mm.

Referring now to FIGS. 46A to 46D, the distal rotor interface 3812 comprises distal rotor ring 3888 with a distal rotor lumen 3890 configured to receive and to be mounted onto the distal rotor shaft 3892. On the proximal surface of the ring 3888 are two angled or arcuate teeth 3896 with two arcuate gaps 3898 there between, which are configured to form a mechanical interfit with the corresponding gaps and teeth on the proximal rotor interface 3808 when axially engaged. As depicted, the angled or arcuate teeth 3896 are flush with the perimeter of the ring 3888 but the arcuate length and height/depth of the teeth 3896 and gaps 3898 may otherwise be the same those on the proximal rotor interface 3808, as that a complementary mechanical interfit may be achieved. The distal rotor interface 3812 may also further comprise a transverse channel or recess 4000 across the distal surface 4002 the mounting of the ring 3888 to the distal rotor shaft 3892, which may facilitate attachment of the distal rotor interface 3812 to other components of the system.

In still another embodiment, depicted in FIGS. 47A to 51C, the attachment interface 4700 of the delivery system between the distal catheter section 4702 and the implant delivery section 4704 comprises a locking assembly 4706 comprising a bayonet or pin lock assembly. Except for the locking assembly, the other components and/or configuration of components may be the same or similar to the range of embodiments and features exemplified by the delivery system depicted in FIG. 38A to 46D. Referring back to FIGS. 47A to 51C, the locking assembly 4706 comprises a proximal locking interface 4708 with one or more generally L-shaped slot 4710 that is configured to receive a complementary radial pin or protrusion 4714 on the distal locking interface 4712. Of course, in other variation, the features on the proximal and distal locking interfaces may be reversed. The L-shaped slot 4710 comprises an axially oriented slot segment 4716 configured to axially receive the radial protrusion 4714. The axially oriented slot segment 4716 is confluent with a circumferential or transverse slot segment 4718, so that when the radial pin 4714 is fully inserted or seated in the axial slot segment 4716, the distal locking interface 4712 may be rotated so that the radial pin 4714 rotate to the end 4720 of the transverse slot segment 4718. The end 4720 of the transverse slot segment 4718 may comprise a larger width along the axial direction so that the radial pin 4714 can resist inadvertent rotation back toward the axial slot segment 4716. As shown in FIG. 47B, a bias member, such as a resilient o-ring 4722, split lock washer, resilient bumper or spring may also be provided in in the locking assembly 4706, so that the proximal and distal locking interfaces 4708, 4710 may be biased apart when fully engaged, to further resist inadvertent disengagement. Although the axial and transverse slot segments 4716, 4718 as depicted have a 90 degree or orthogonal orientation relative to each other, in other variations, the angle may be in the range of 75 degrees or 105 degrees, 80 degrees to 100 degrees, 85 degrees to 100 degrees, 90 degrees to 95 degrees, or 92 degrees to 97 degrees, for example. Also, in this particular example, the locking assembly 4706 comprises two L-shaped slots 4710 and two radial pins 4714 that are each configured 180 degrees apart on their respective locking interfaces 4708, 4710, respectively, and have the same size, shape and configuration. In other variations, each set of slots and each set of pins may not have a uniform size, shape or configuration.

Referring to FIGS. 48A to 51C, the proximal locking interface 4708 comprises a short tube or ring structure with a central lumen 4724 that is in communication with the L-shaped slots 4710. The central lumen 4724 is configured to receive the distal locking interface 4712 and the pins 4714. The pins 4714 may comprise a length in the range of about 1 mm to 10 mm, 2 mm to 8 mm, or 3 mm to 5 mm, and a width or diameter in the range of about 0.5 mm to 10 mm, 1 mm to 8 mm, or 2 mm to 5 mm. The width of the L-shaped slots 4710 may be sized similarly to the width or diameter of the pin 4714, or slightly larger, e.g. 0.05 mm to 1 mm. or 0.10 mm to 0.5 mm. The central lumen 4724 may also comprise one or more internal flanges 4726 which may act as an insertion stop for the distal locking interface 4712. In some variations, the bias member, e.g. the resilient o-ring 4722, may be provided in the central lumen 4724, against the internal flanges 4726. This may also reduce the risk that the pins 4714 are not bent or damaged during engagement. The central lumen 4724 may also comprise other recesses 4728 and interface surfaces 4730 that are complementary to the distal components of a steering assembly as described elsewhere herein.

Referring still to FIGS. 48A to 51C, the distal locking interface 4710 may comprise a distal annular disc-shaped base 4732 with a proximal tube or ring 4734 from which the radial protrusions or pins 4714 extend. The ring 4734 is configured to be received in the central lumen 4724 of the proximal locking interface 4708 to allow the pins 4714 to axially enter and traverse the axial slot segment 4716 and then to be rotated through the transverse slot segment 4718.

The distal locking interface 4710 also comprises its own lumen 4736, in which the stator/rotor components are configured to reside.

While the embodiments herein have been particularly shown and described with references to embodiments thereof, it will be understood by those skilled in the art that various changes in form and details may be made therein without departing from the scope of the embodiments. For all of the embodiments described above, the steps of the methods need not be performed sequentially.

What is claimed is:

1. A delivery system, comprising:

a proximal handle comprising a handle housing and a first actuator;

a catheter body coupled to the handle, the catheter body comprising a distal section, a proximal section and a middle section therebetween;

a rotatable drive shaft coupled to the first actuator and located in the catheter body;

a first stator housing attached to the catheter body, the first stator housing comprising an internal opening and an external opening;

a first rotor attached to the rotatable drive shaft and located in the first stator housing, the first rotor comprising at least one tension line attachment site; a self-expanding implant, the implant comprising a contracted configuration and an expanded configuration; and a first tensioning member releasably coupled to the self-expanding implant and fixedly coupled to the attachment site of the first rotor and a movable sheath located over the catheter body.

2. The delivery system of claim 1, wherein the first tensioning member is further wound around the first rotor.

3. The delivery system of claim 2, wherein the first tensioning member is wound around the first rotor at least three times.

4. The delivery system of claim 1, wherein the self-expanding implant further comprises:

a stent frame, the stent frame comprising:

a non-foreshortening tubular valve support;

a fixation support comprising a fixation ring and a fixation brim.

5. The delivery system of claim 1, wherein the self-expanding implant comprises a first opening, and a first attachment ring located in the first opening, and wherein the first tensioning member is looped through the first attachment ring.

6. The delivery system of claim 5, wherein the first attachment ring is movable in the first opening.

7. The delivery system of claim 5, wherein the first attachment ring is a metal ring.

8. The delivery system of claim 5, wherein the first opening is aligned with a first longitudinal strut of the self-expanding implant.

9. The delivery system of claim 1, further comprising:

a second stator housing attached to the catheter body and spaced apart from the first stator housing, the second stator housing comprising an internal opening and an external opening;

a second rotor attached to the rotatable drive shaft and located in the second stator housing, the second rotor comprising at least one tension line attachment site.

10. The delivery system of claim 9, further comprising:

a third stator housing attached to the catheter body and spaced apart from the first and second stator housings, the third stator housing comprising an internal opening and an external opening;

a third rotor attached to the rotatable drive shaft and located in the third stator housing, the third rotor comprising at least one tension line attachment site.

11. The delivery system of claim 10, wherein the first stator housing is larger than the second stator housing and the first rotor is larger than the second rotor.

12. The delivery system of claim 10, wherein the first stator housing is larger than both the second and third stator housings and the first rotor is larger than the second and third rotors.

13. The delivery system of claim 1, wherein the proximal handle further comprise a first actuator lock, wherein the first actuator lock comprises locked and unlocked configurations and is biased to the lock configuration.

14. The delivery system of claim 1, further comprising a catheter extension assembly configured to reversibly adjust a longitudinal spacing between the distal section and the middle section of the catheter body.

15. The delivery system of claim 14, wherein the catheter extension assembly comprises a proximal housing with a proximal threaded lumen, a distal housing and a threaded extension shaft located in the proximal threaded lumen and coupled to the distal housing.

16. The delivery system of claim 15, wherein the proximal housing and distal housing comprise a slotted interface therebetween to resist rotational displacement therebetween.

17. The delivery system of claim 15, wherein the proximal handle further comprises a second actuator coupled to the threaded extension shaft.

18. The delivery system of claim 14, further comprising a first steering assembly comprising a first segmented tubular body and a first plurality of elongate steering wires.

19. The delivery system of claim 18, wherein the first steering assembly is located proximal to the catheter extension assembly.

20. The delivery system of claim 18, wherein the first segmented tubular body comprises a laser-cut tubular body.

21. The delivery system of claim 18, further comprising a second steering assembly comprising a second segmented tubular body and a second plurality of steering wires.

22. The delivery system of claim 21, wherein the first steering assembly and second steering assembly comprise different bending configurations.

23. The delivery system of claim 21, wherein the first steering assembly comprises a two-way steering assembly and the second steering assembly comprises a four-way steering assembly.

24. The delivery system of claim 21, wherein the first segmented tubular body comprises segments attached by living hinges.

25. The delivery system of claim 24, wherein the second segmented tubular body comprises a plurality of discrete segments.

26. The delivery system of claim 25, wherein each of the plurality of discrete segments comprises one or two non-planar end openings.

27. The delivery system of claim 26, wherein the non-planar end openings comprise a hyperbolic paraboloid shape.

28. The delivery system of claim 27, wherein the each of the plurality of discrete segments comprises a perimeter bumper.

29. The delivery system of claim 18, wherein the second steering assembly is located distal to the catheter extension assembly.

30. The delivery system of claim 1, wherein the first stator housing comprises at least one routing ring attached to an outer surface of the first stator housing.

31. The delivery system of claim 30, wherein the at least one routing ring is attached along a perimeter of the first stator housing.

32. The delivery system of claim 30, wherein the at least one routing ring comprises at least three routing rings attached to an end wall of the first a stator housing.

33. The delivery system of claim 1, further comprising a first guide structure located on the first stator housing.

34. The delivery system of claim 33, wherein the first guide structure is a first guide ring.

35. The delivery system of claim 1, further comprising a second guide structure located on the catheter body.

36. The delivery system of claim 35, wherein the second guide structure comprises a second guide ring and a ring support.

37. The delivery system of claim 36, wherein the first guide ring and the second guide ring have the same inner diameter.

38. A delivery system, comprising:

a proximal handle comprising a handle housing and a first actuator;

a catheter body coupled to the handle, comprising;

a first rotatable drive shaft coupled to the first actuator and located in the catheter body, the first rotatable drive shaft comprising a first mechanical interfit interface at a distal end of the first rotatable drive shaft; and a first locking structure coupled to the catheter body;

an implant delivery body, comprising:

a first stator housing attached to the implant delivery body, the first stator housing comprising an internal opening and an external opening; and a second rotatable drive shaft located in the implant delivery body, the second rotatable drive shaft comprising a second mechanical interfit interface at a proximal end of the second rotatable drive shaft and configured to form a mechanical interfit with the first mechanical interfit interface of the first rotatable drive shaft;

a first rotor attached to the second rotatable drive shaft and located in the first stator housing, the first rotor comprising at least one tension line attachment site; and a second locking structure coupled to the implant delivery body, the second locking structure configured to attach to the first locking structure; and a movable sheath located over the catheter body.

39. The delivery system of claim 38, wherein the first and second locking structures are configured to attach via a threaded interface.

40. The delivery system of claim 39, wherein the first locking structure comprises a threaded lumen, and the second locking structure comprises a complementary threaded tubular body.

41. The delivery system of claim 38, wherein the first and second locking structure configured to attach via a bayonet mount interface.

42. The delivery system of claim 41, wherein the first locking structure comprises an L-shape slot, and the second locking structure comprises a radial pin configured to movably reside in the L-shape slot.

43. The delivery system of claim 38, wherein the first rotor is a rotor plate.

44. The delivery system of claim 43, wherein the rotor plate comprises at least one elongate projection.

45. The delivery system of claim 43, wherein the rotor plate comprises a plurality of identical groups of attachment structures comprising at least one projection and at least one aperture.

* * * * *